United States Patent
Crawley et al.

(10) Patent No.: US 6,806,274 B1
(45) Date of Patent: Oct. 19, 2004

(54) QUINAZOLINE DERIVATIVES

(75) Inventors: Graham C Crawley, Macclesfield (GB); Laurent F A Hennequin, Reims (FR); Darren McKerrecher, Macclesfield (GB); Patrick Ple, Reims (GB); Jeffrey Philip Poyser, Macclesfield (GB); Christine M P Lambert, Reims (GB)

(73) Assignee: AstraZeneca UK Limited, London (GB)

( * ) Notice: Subject to any disclaimer, the term of this patent is extended or adjusted under 35 U.S.C. 154(b) by 224 days.

(21) Appl. No.: 10/019,945

(22) PCT Filed: Jul. 4, 2000

(86) PCT No.: PCT/GB00/02566

§ 371 (c)(1),
(2), (4) Date: Jan. 7, 2002

(87) PCT Pub. No.: WO01/04102

PCT Pub. Date: Jan. 18, 2001

(30) Foreign Application Priority Data

Jul. 7, 1999 (EP) ............................................. 99401692
May 4, 2000 (EP) ............................................. 00401221

(51) Int. Cl.$^7$ .................... A61K 31/517; C07D 419/00; C07D 239/72
(52) U.S. Cl. ................. 514/266.2; 514/266.4; 544/284; 544/285; 544/286; 544/287; 544/288; 544/289; 544/291; 544/292; 544/293
(58) Field of Search .......................... 514/266.2, 266.4; 544/284–289, 291–293

(56) References Cited

U.S. PATENT DOCUMENTS

| | | | | |
|---|---|---|---|---|
| 4,659,736 A | * | 4/1987 | Schluter et al. | 514/452 |
| 5,073,558 A | * | 12/1991 | Obata et al. | 514/266.23 |
| 5,773,459 A | | 6/1998 | Tang et al. | 514/445 |
| 5,886,044 A | * | 3/1999 | Widdowson et al. | 514/596 |
| 6,204,267 B1 | * | 3/2001 | Tang et al. | 514/252.17 |
| 6,492,393 B1 | * | 12/2002 | Breitfelder et al. | 514/319 |
| 2003/0158198 A1 | * | 8/2003 | Lee et al. | 514/241 |

FOREIGN PATENT DOCUMENTS

| | | |
|---|---|---|
| WO | WO 97/03069 | 1/1997 |
| WO | WO 98/38984 | 9/1998 |
| WO | WO 98/50047 | 11/1998 |
| WO | WO 98/50370 | 11/1998 |
| WO | WO 98/52558 | 11/1998 |
| WO | WO 99/09024 | 2/1999 |
| WO | WO 02/00644 | 1/2002 |

OTHER PUBLICATIONS

Gibson et al.; "Epidermal Growth Factor Receptor Tyrosine Kinase: Structure–Activity Relationships and Antitumour Activity of Novel Quinazolines"; Bioorganic & Medicinal Chemistry Letters, 1997, vol. 7, No. 21, pp. 2723–2728.

Hong et al.; "Synthesis and Billogical Activities of Some $N^4$–Substituted 4–Aminopyrazolo[3,4–d–pyrimidines"; Journal of Medicinal Chemistry, 1976, vol. 19, No. 4, pp. 555–558.

Myers et al.; "The Preparation and SAR of 4–(Anilino), 4–(Phenoxy), and 4–(Thiophenoxy)–Quinazolines: Inhibitors of p56lck and EGF–R Tyrosine Kinase Activity", Bioorganic & Medicinal Chemistry Letters, 1997, vol. 7, No. 4, pp. 417–420.

van Muijlwijk–Koezen et al.; "Isoquinoline and Quinazoline Urea Analogues as Antagonists for the Human Adenosine $A_3$ Receptor"; J. Med. Chem., 2000, vol. 43, pp. 2227–2238.

* cited by examiner

Primary Examiner—Richard L. Raymond
Assistant Examiner—Tamthom N. Truong
(74) Attorney, Agent, or Firm—Morgan, Lewis & Bockius LLP

(57) ABSTRACT

The invention concerns quinazoline derivatives of Formula (I) wherein $Q^1$ includes a quinazoline ring optionally substituted with a group such as halogeno, trifluoromethyl and cyano, or a group of the formula: $Q^3$—$X^1$— wherein $X^1$ includes a direct bond and O and $Q^3$ includes aryl, aryl-(1–6C)alkyl, heterocyclyl and heterocyclyl-(1–6C)alkyl; each of $R^2$ and $R^3$ is hydrogen or (1–6C)alkyl; Z includes O, S and NH; and $Q^2$ includes aryl and aryl-(1–3C)alkyl or a pharmaceutically-acceptable salt thereof; processes for their preparation, pharmaceutical compositions containing them and their use in the manufacture of a medicament for use in the prevention or treatment of T cell mediated diseases or medical conditions in a warm-blooded animal.

7 Claims, No Drawings

QUINAZOLINE DERIVATIVES

CROSS REFERENCE TO RELATED APPLICATIONS

This application is the National Phase of International Application No. PCT/GB00/02566, filed Jul. 4, 2000, which designated the United States, and which further claims priority from European Patent Application No. 99401692.1, filed Jul. 7, 1999, and European Patent Application No. 00401221.7, filed May 4, 2000. The priority applications are incorporated herein by reference.

This invention concerts certain novel quinazoline derivatives which possess pharmacological properties of use in the treatment of autoimmune diseases or medical conditions, for example T cell mediated disease such as transplant rejection or rheumatoid arthritis. The invention also concerns processes for the manufacture of the quinazoline derivatives of the invention, pharmaceutical compositions containing them and their use in therapeutic methods, for example by virtue of inhibition of T cell mediated disease.

A critical requirement of the immune system is the ability to differentiate between "self" and "non-self" (i.e. foreign) antigens. This discrimination is required to enable the immune system to mount a response to foreign proteins such as those on the surface of pathogens whilst maintaining tolerance to endogenous proteins and thereby preventing damage to normal tissues. An autoimmune disease results when self-tolerance breaks down and the immune system reacts against tissues such as the joints in rheumatoid arthritis or nerve fibres in multiple sclerosis. Stimulation of the human immune response is dependent on the recognition of protein antigens by T cells. However T cells do not become activated by and respond to antigen alone but are only triggered into action when the antigen is complexed with major histocompatibility complex (MHC) molecules on the surface of an antigen-presenting cell such as a B cell, macrophage or dendritic cell. Thus T cell activation requires the docking into the T cell receptor of the peptide/MHC complex expressed on an antigen-presenting cell. This interaction, which confers the antigen specificity to the T cell response, is essential for full activation of T lymphocytes. Subsequent to this docking, some of the earliest signal transduction events leading to full T cell activation are mediated through the action of multiple tyrosine-specific protein kinases (E. Hsi et al., *J. Biol. Chem.*, 1989, 264, 10836) including $p56^{lck}$ and ZAP-70. The tyrosine kinase $p56^{lck}$ is a lymphocyte specific member of the src family of non-receptor protein tyrosine kinases (J. D. Marth et al., *Cell*, 1985, 43, 393). The enzyme is associated with the inner surface of the plasma membrane where it binds to the T cell receptor associated glycoproteins CD4 (in helper T cells) and CD8 (in cytotoxic or killer T cells) (C. E. Rudd et al., *Proc. Natl. Acad. Sci. USA*, 1988, 85, 5190 and M. A. Campbell et al., *EMBO J*, 1990, 9, 2125).

It is believed that $p56^{lck}$ tyrosine kinase plays an essential role in T cell activation as, for example, the loss of $p56^{lck}$ expression in a human Jurkat T cell line prevents the normal T cell response to stimulation of the T cell receptor (D. B. Straus et al., *Cell*, 1992, 70, 585) and a deficiency in $p56^{lck}$ expression causes severe immune deficiency in humans (F. D. Goldman et al., *J. Clin. Invest.*, 1998, 102, 421).

Certain autoimmune conditions or diseases such as inflammatory diseases (for example rheumatoid arthritis, inflammatory bowel disease, glomerulonephritis and lung fibrosis), multiple sclerosis, psoriasis, hypersensitivity reactions of the skin, atherosclerosis, restenosis, allergic asthma and insulin-dependent diabetes are believed to be associated with inappropriate T cell activation (see, for example, J. H. Hanke et al., *Inflamm. Res.*, 1995, 44, 357). In addition the acute rejection of transplanted organs can also be interpreted as a consequence of inappropriate T cell activation. Therefore, compounds which modulate T cell activation by way of inhibition of one or more of the multiple tyrosine-specific protein kinases which are involved in the early signal transduction steps which lead to full T cell activation, for example by way of inhibition of $p56^{lck}$ tyrosine kinase, are expected to provide therapeutic agents for such pathological conditions.

Without wishing to imply that the compounds disclosed in the present invention possess pharmacological activity only by virtue of an effect on a single biological process, it is believed that the compounds modulate T cell activation by way of inhibition of one or more of the multiple tyrosine-specific protein kinases which are involved in the early signal transduction steps which lead to full T cell activation, for example by way of inhibition of $p56^{lck}$ tyrosine kinase.

In particular, the quinazoline derivatives of the invention are expected to be useful as immunoregulation or immunosuppressive agents for the prevention or treatment of organ rejection following transplant surgery.

Agents of this kind would offer therapy for transplant rejection and autoimmune diseases whilst avoiding toxicities associated with the commonly used, less selective immunosuppressants. The leading agent for the prevention or treatment of transplant rejection is cyclosporin A which, although effective, is often associated with side-effects such as renal damage and hypertension which results in kidney failure in a substantial number of patients. It is contemporary practice to treat rheumatoid arthritis initially with symptom relief agents such as NSAIDs, which do not have any beneficial effect on disease progression and are often associated with unwanted side-effects. A rationally based, disease modifying agent, without such deleterious side-effects, would therefore offer significant benefits in the prevention or treatment of transplant rejection or autoimmune conditions such as rheumatoid arthritis.

As stated above, the present invention is based, in particular, on the discovery that the quinazoline derivatives of the invention modulate T cell activation by way of inhibition of one or more of the multiple tyrosine-specific protein kinases which are involved in the early signal transduction steps which lead to full T cell activation. Accordingly compounds of the present invention possess higher inhibitory potency against particular non-receptor tyrosine kinases such as $p56^{lck}$ tyrosine kinase than against other non-receptor tyrosine kinases or against receptor tyrosine kinases (RTKs) such as epidermal growth factor (EGF) RTX. In general, the quinazoline derivatives of the invention possess sufficient potency in inhibiting non-receptor tyrosine kinases such as $p56^{lck}$ tyrosine kinase that they may be used in an amount sufficient to inhibit, for example, $p56^{lck}$ tyrosine kinase whilst demonstrating reduced potency, preferably whilst demonstrating no significant activity, against RTKs such as EGF RTK. Thus the quinazoline derivatives of the invention can be used in the clinical management of those particular diseases which are sensitive to inhibition of such non-receptor tyrosine kinases, for example autoimmune diseases or medical conditions, for example T cell mediated disease such as transplant rejection or rheumatoid arthritis.

It is disclosed by K. H. Gibson et al., *Bioorganic & Medicinal Chemistry Letters*, 1997, 7, 2723–2728 that certain-4-anilinoquioline derivatives possess useful EGF RTK inhibitory properties. It is also disclosed that 1-(6,7-dimethoxyquinazolin-4-yl)-3-phenylurea is inactive as an EGF RTK inhibitor.

It is disclosed in International Patent Application WO 98/50370 that certain 5-substituted quinazoline derivatives may be useful as inhibitors of serine/threonine protein kinases. Whilst most of the examples are 4-amino-5-phenoxyquinazolines, there is the disclosure of three 4-ureido-5-phenoxyquinazolines, namely of:

1-[5-(4-methoxyphenoxy)quinazolin-4-yl]-3-phenylurea,

1-[5-(4-methoxyphenoxy)quinazolin-4-yl]-3-(3-bromophenyl)urea and

1-[5-(4-methoxyphenoxy)quinazolin-4-yl]-3-(3-methoxyphenyl)urea.

It is disclosed by C. I. Hong et al, *J. Med. Chem.*, 1976, 19, 555–558 that certain 4-aminopyrazolo[3,4-d]pyrimidine derivatives possess growth inhibitory activity against cultured L1210 leukaemia cells. The disclosed compounds include:

1-phenyl-3-(pyrazolo[3,4-d]pyrimidin-4-yl)urea, 1-(2-chlorophenyl)-3-(pyrazolo[3,4-d]pyrimidin-4-yl)urea, 1-(3-chlorophenyl)-3-(pyrazolo[3,4-d]pyrimidin-4-yl)urea, 1-(4-chlorophenyl)-3-(pyrazolo[3,4-d]pyrimidin-4-yl)urea, 1-(2-fluorophenyl)-3-(pyrazolo[3,4-d]pyrimidin-4-yl)urea, 1-benzyl-3-(pyrazolo[3,4-d]pyrimidin-4-yl)urea and 1-(3-phenylpropyl)-3-(pyrazolo[3,4-d]pyrimidin-4-yl)urea.

It is disclosed in International Patent Application WO 97/03069 that certain quinoline and quinazoline derivatives may be useful as protein tyrosine kinase inhibitors. All of the disclosed examples are 4-heteroarylaminoquinazoline derivatives and none of them are 1-heteroaryl-3-(quinazolin-4-yl)urea derivatives.

It is disclosed in International Patent Application WO 98/43960 that certain 3-cyanoquinoline derivatives may be useful as protein tyrosine kinase inhibitors. Almost all of the 398 disclosed examples were 3-cyano-4-anilinoquinoline or 3-cyano-4-benzylaminoquinoline derivatives. There is no disclosure of any (3-cyanoquinolin-4-yl)urea derivatives.

It is disclosed in International Patent Application WO 99/69024 that certain 1-phenyl-3-(quinolin-4-yl)urea derivatives may be useful as antagonists of the human HFGAN72 receptor, a G-protein coupled neuropeptide receptor, and hence may be of potential use in the treatment of obesity. There is no disclosure as examples of any 1-phenyl-3-(quinazolin-4-yl)urea or 1-phenyl-3-(3-cyanoquinolin-4-yl)urea compounds.

According to one aspect of the invention there is provided a quinazoline derivative of the Formula I

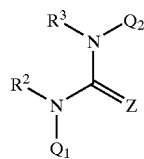

wherein $Q^1$ is a quinazoline-like ring such as a group of the formula Ia, Ib, Ic or Id

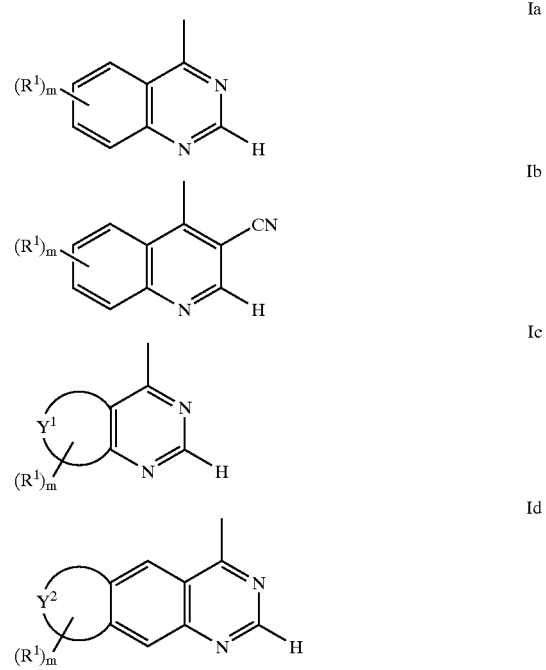

wherein:

$Y^1$ together with the carbon atoms to which it is attached forms a 5- or 6-membered aromatic or partially unsaturated ring comprising 1 to 3 heteroatoms selected from O, N and S provided that the group of formula Ic so formed is not a purine ring;

$Y^2$ together with the carbon atoms to which it is attached forms a 5- or 6-membered aromatic or partially unsaturated ring comprising 1 to 3 heteroatoms selected from O, N and S;

m is 0, 1, 2, 3 or 4;

each $R^1$ group, which may be the same or different, is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)akenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$Q^3$—$X^1$— wherein $X^1$ is a direct bond or is selected from O, S, SO, $SO_2$, $N(R^4)$, CO, $CH(OR^4)$, $CON(R^4)$, $N(R^4)CO$, $SO_2N(R^4)$, $N(R^4)SO_2$, $OC(R^4)_2$, $SC(R^4)_2$ and $N(R^4)C(R^4)_2$, wherein $R^4$ is hydrogen or (1–6C)alkyl, and $Q^3$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or $(R^1)_m$ is (1–3C)alkylenodioxy, and wherein adjacent carbon atoms in any (2–6C)alkylene chain within a $R^1$ substituent are optionally separated by the insertion into the chain of a group selected from O, S, SO, $SO_2$, $N(R^5)$, CO, $CH(OR^5)$, $CON(R^5)$, $N(R^5)$CO, $SO_2N(R^5)$, $N(R^5)SO_2$, CH=CH and C≡C wherein $R^5$ is hydrogen or (1–6C)alkyl, and wherein any $CH_2$=CH— or HC≡C— group within a $R^1$ substituent optionally bears at the terminal $CH_2$= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^4$—$X^2$— wherein $X^2$ is a direct bond or is selected from CO and $N(R^6)CO$, wherein $R^6$ is hydrogen or (1–6C)alkyl, and $Q^4$ is aryl, aryl-(1–6C)alkyl, heteroaryl, heteroaryl-(1–6C)alkyl, heterocyclyl or heterocyclyl-(1–6C)alkyl, and wherein any $CH_2$ or $CH_3$ group within a $R^1$ substituent optionally bears on each said $CH_2$ or $CH_3$ group one or more halogeno substituents or a substituent selected from hydroxy, cyano, amino, carboxy, carbamoyl, (1–6C)alkyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^3$—$Q^5$ wherein $X^3$ is a direct bond or is selected from O, S, SO, $SO_2$, $N(R^7)$, CO, $CH(OR^7)$, $CON(R^7)$, $N(R^7)CO$, $SO_2N(R^7)$, $N(R^7)SO_2$, $C(R^7)_2O$, $C(R^7)_2S$ and $N(R^7)C(R^7)_2$, wherein $R^7$ is hydrogen or (1–6C)alkyl, and $Q^5$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(4C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl)sulphamoyl, (1–6C)alkanesulphonylamino and N-(1–6C)alkyl-(1–6C)alkanesulphonylamino, or from a group of the formula:

—$X^4$—$R^8$ wherein $X^4$ is a direct bond or is selected from O and $N(R^9)$, wherein $R^9$ is hydrogen or (1–6C)alkyl, and $R^8$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, or from a group of the formula:

—$X^5$—$Q^6$ wherein $X^5$ is a direct bond or is selected from O and $N(R^{10})$, wherein $R^{10}$ is hydrogen or (1–6C)alkyl, and $Q^6$ is aryl, aryl-(1–6C)alkyl, heteroaryl, heteroaryl-(1–6C)alkyl, heterocyclyl or heterocyclyl-(1–6C)alkyl, and any $Q^6$ group optionally bears 1 or 2 substituents, which may be the same or different, selected from halogeno, (1–6C)alkyl and (1–6C)alkoxy, and wherein any heterocyclyl group within a substituent on $R^1$ optionally bears 1 or 2 oxo or thioxo substituents;

$R^2$ is hydrogen or (1–6C)alkyl and $R^1$ is hydrogen or (1–6C)alkyl, or $R^2$ and $R^3$ together form a $CH_2$, $(CH_2)_2$ or $(CH_2)_3$ group;

Z is O, S, N(C≡N) or $N(R^{11})$, wherein $R^{11}$ is hydrogen or (1–6C)alkyl; and $Q^2$ is aryl, aryl-(1–3C)alkyl, aryl-(3–7C)cycloalkyl, heteroaryl, heteroaryl-(1–3C)alkyl or heteroaryl-(3–7C)cycloalkyl wherein each aryl group is phenyl or naphthyl and each heteroaryl group is a 5- or 6-membered monocyclic or a 9- or 10-membered bicyclic heteroaryl ring containing 1 or 2 nitrogen heteroatoms and optionally containing a further heteroatom selected from nitrogen, oxygen and sulphur, and $Q^2$ is optionally substituted with 1, 2, 3 or 4 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl (1–6C)alkylamino, di-[(1–6C)alkyl]amino, (1–6C)alkoxycarbonyl, N-(1–6C)alkylcarbamoyl, N,N di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^6$—$R^{12}$ wherein $X^6$ is a direct bond or is selected from O and $N(R^{13})$, wherein $R^{13}$ is hydrogen or (1–6C)alkyl, and $R^{12}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^7$—$Q^7$ wherein $X^7$ is a direct bond or is selected from O, S, SO, $SO_2$, $N(R^{14})$, CO, $CH(OR^{14})$, $CON(^{14})$, $N(R^{14})CO$, $SO_2N(R^{14})$, $N(R^{14})SO_2$, $C(R^{14})_2O$, $C(R^{14})_2S$ and $C(R^{14})_2N(R^{14})$, wherein each $R^{14}$ is hydrogen or (1–6C)alkyl, and Q⁷ is aryl, aryl-(1–6C)alkyl, heteroaryl, heteroaryl-(1–6C)alkyl, heterocyclyl or heterocyclyl-(1–6C)alkyl, or Q² is optionally substituted with a (1–3C)alkylenedioxy group, and wherein any aryl, heteroaryl or heterocyclyl group within a substituent on Q² optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl (1–6C)alkoxy, (2–6C) alkenyloxy, (2–6C)alkynyloxy, (1–6C)alkylthio, (1–6C)alkylsulphinyl, (1–6C)alkylsulphonyl, (1–6C) alkylamino, di-[(1–6C)alkyl]amino, (1–6C) alkoxycarbonyl, N-(1–6C)alkylcarbamoyl, N,N-di-[(1–6C)alkyl]carbamoyl, (2–6C)alkanoyl, (2–6C) alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C) alkanesulphonylamino and N-(1–6C)alkyl-(1–6C)alkanesulphonylamino, or from a group of the formula:

wherein X⁸ is a direct bond or is selected from O and N(R¹⁶), wherein R¹⁶ is hydrogen or (1–6C)alkyl, and R¹⁵ is halogeno-(1–6C)alkyl, hydroxy-(1–6C)alkyl, (1–6C)alkoxy-(1–6C)alkyl, cyano-(1–6C)alkyl, amino-(1–6C)alkyl-(1–6C)alkylamino-(1–6C)alkyl or di-[(1–6C)alkyl]amino-(1–6C)alkyl, and wherein any heterocyclyl group within a substituent on Q² optionally bears 1 or 2 oxo or thioxo substituents;
or a pharmaceutically-acceptable salt thereof;
provided that the compounds:

1-(6,7-dimethoxyquinazolin-4-yl)-3-phenylurea,

1-[-(4-methoxyphenoxy)quinazolin-4-yl]-3-phenylurea,

1-[5-(4-methoxyphenoxy)quinazolin-4-yl]-3-(3-bromophenyl)urea,

1-[5-(4-methoxyphenoxy)quinazolin-4-yl]-3-(3-methoxyphenyl)urea, 1-phenyl-3-(pyrazolo[3,4-d]pyrimidin-4-yl)urea, 1-(2-chlorophenyl)-3-(pyrazolo[3,4-d]pyrimidin-4-yl) urea, 1-(3-chlorophenyl)-3-(pyrazolo[3,4-d]pyrimidin-4-yl) urea, 1-(4-chlorophenyl)-3-(pyrazolo[3,4-d]pyrimidin-4-yl) urea, 1-(2-fluorophenyl)-3-(pyrazolo[3,4-d]pyrimidin-4-yl) urea, 1-benzyl-3-(pyrazolo[3,4-d]pyrimidin-4-yl)urea and 1-(3-phenylpropyl)-3-(pyrazolo[3,4-d]pyrimidin-4-yl) urea are excluded.

In this specification the genetic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art for example by synthesis from optically active starting materials or by resolution of a racemic form. Similarly, the above-mentioned activity may be evaluated using the standard laboratory techniques referred to hereinafter.

It is to be understood that the hydrogen atom which is shown at the 2-position in each of the part structures of the formulae Ia, Ib, Ic and Id indicates that position remains unsubstituted by any R¹ group.

Suitable values for the generic radicals referred to above include those set out below.

A suitable value for any one of the 'Q' groups (Q² to Q⁷) when it is aryl or for the aryl group within a 'Q' group is, for example, phenyl or naphthyl, preferably phenyl.

A suitable value for a (3–7C)cycloalkyl group within Q² or for Q³ or Q⁴ when it is (3–7C)cycloalkyl is, for example, cyclopropyl, cyclobutyl, cyclopentyl, cyclohexyl, cycloheptyl or bicyclo[2.2.1]heptyl and a suitable value for Q³ or Q⁴ when it is (3–7C)cycloalkenyl is, for example, cyclobutenyl, cyclopentenyl, cyclohexenyl or cycloheptenyl.

A suitable value for Q² when it is a 5- or 6-membered monocyclic or a 9- or 10-membered bicyclic heteroaryl ring containing 1 or 2 nitrogen heteroatoms and optionally containing a further heteroatom selected from nitrogen, oxygen and sulphur is, for example, pyrrolyl, oxazolyl, isoxazolyl, imidazolyl, pyrazolyl thiazolyl, isothiazolyl, oxadiazolyl, thiadiazolyl, triazolyl, pyridyl, pyridazinyl, pyrimidinyl, pyrazinyl, 1,3,5-triazenyl, indolyl, benzoxazolyl, benzimidazolyl, benzothiazolyl, indazolyl, benzofurazanyl, quinolyl, isoquinolyl, quinazolinyl, quinoxalinyl, cinnolinyl or naphthyridinyl, preferably isoxazolyl, 1,2,3-triazolyl, pyridyl, benzothiazolyl, quinolyl or quinazolinyl.

A suitable value for any one of the 'Q' groups, Q³ to Q⁷,when it is heteroaryl or for the heteroaryl group within a 'Q' group is, for example, an aromatic 5- or 6-membered monocyclic ring or a 9- or 10-membered bicyclic ring with up to five ring heteroatoms selected from oxygen, nitrogen and sulphur, for example furyl, pyrrolyl, thienyl, oxazolyl, isoxazolyl, imidazolyl, pyrazolyl, thiazolyl, isothiazolyl, oxadiazolyl, thiadiazolyl triazolyl, tetrazolyl, pyridyl, pyridazinyl, pyrimidinyl pyrazinyl, 1,3,5-triazenyl, benzofuranyl, indolyl, benzothienyl, benzoxazolyl, benzimidazolyl, benzothiazolyl, indazolyl, benzofurazanyl quinolyl, isoquinolyl, quinazolinyl, quinoxalinyl, cinnolinyl or naphthyridinyl, preferably thienyl, 1,2,3-triazolyl, pyridyl, quinolyl, quinazolinyl or quinoxalinyl.

A suitable value for any one of the 'Q' groups, Q³ to Q⁷, when it is heterocyclyl or for the heterocyclyl group within a 'Q' group is, for example, a non-aromatic saturated or partially saturated 3 to 10-membered monocyclic or bicyclic ring with up to five heteroatoms selected from oxygen, nitrogen and sulphur, for example oxiranyl, oxetanyl, tetrahydrofyranyl, tetrahydropyranyl, pyrrolinyl, pyrrolidinyl, morpholinyl, tetrahydro-1,4-thiazinyl, 1,1-dioxotetrahydro-1,4-thiazinyl, piperidinyl, homopiperidinyl, piperazinyl, homopiperazinyl, dihydropyridinyl, hydropyridinyl, dihydropyrimidinyl or tetrahydropyrimidinyl, preferably pyrrolidin-1-yl, pyrrolidin-2-yl, morpholino, 1,1-dioxotetrahydro-4H-1,4-thiazin-4-yl, piperidino, piperidin-3-yl, piperidin-4-yl, homopiperidin-1-yl, piperazin-1-yl or homopiperazin-1-yl, more preferably piperidinyl. A suitable value for such a group which bears 1 or 2 oxo or thioxo substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl.

A suitable value for a 'Q' group when it is heteroaryl-(1–6C)alkyl is, for example, heteroarylmethyl, 2-heteroarylethyl and 3-heteroarylpropyl. The invention comprises corresponding suitable values for 'Q' groups when, for example, rather than a heteroaryl-(1–6C)alkyl group, an aryl-(1–6C)alkyl, (3–7C)cycloalkyl-(1–6C)alkyl, (3–7C)cycloalkenyl-(1–6C)alkyl or heterocyclyl-(1–6C) alkyl group is present.

When, as defined hereinbefore, $Y^1$ together with the carbon atoms to which it is attached forms a 5- or 6-membered aromatic or partially unsaturated ring comprising 1 to 3 heteroatoms selected from O, N and S (provided that the group of formula Ic so formed is not a purine ring), ring $Y^1$ is suitably unsaturated or partially unsaturated wherein a —$CH_2$— group can optionally be replaced by a —CO— group and a ring nitrogen atom may optionally bear a (1–6C)alkyl group. Diradicals of suitable fused $Y^1$ rings include thiendiyl, furandiyl, pyrazolediyl, oxazolediyl, isoxazolediyl, thiazolediyl, isothiazolediyl, 1,2,3-oxadiazolediyl, 1,2,3-triazolediyl, pyridinediyl pyrimidinediyl, pyrazinediyl, pyridazinediyl and 1,3,4-triazinediyl. Examples of suitable bicyclic rings of formula Ic formed by the fusion of ring $Y^1$ to the adjacent pyrimidine ring include fluropyrimidinyl, thienopyrimidinyl, pyrrolopyimidinyl, pyrrolinopyrimidinyl, oxopyrrolinopyrimidinyl, oxazolopyrimidinyl, oxazolinopyrimidinyl, oxooxazolinopyrimidinyl, isoxazolopyrimidinyl, thiazolopyrimidinyl, thiazolinopyrimidinyl, oxothazolinopyrimidinyl, isothiazolopyrimidinyl, oxoimidazolinopyrimidinyl, pyrazolopyrimidinyl, pyrazolinopyrimidinyl, oxopyrazolinopyrimidinyl, pyridopyrimidinyl, pyrimidopyrimidinyl and pteridinyl. Preferably the bicyclic ring of formula Ic is furo[3,2-d]pyrimidinyl, furo[2,3-d]pyrimidinyl, thieno[3,2-d]pyrimidinyl, thieno[2,3-d]pyrimidinyl, pyrrolo[3,2-d]pyrimidinyl, pyrrolo[2,3-d]pyrimidinyl, oxazolo[5,4-d]pyrimidinyl, oxazolo[4,5-d]pyrimidinyl, thiazolo[5,4-d]pyrimidinyl, thiazolo[4,5-d]pyrimidinyl, pyrido[2,3-d]pyrimidinyl, pyrido[3,4-d]pyrimidinyl, pyrido[4,5-d]pyrimidinyl, pyrido[3,2-d]pyrimidinyl, pyrimido[4,5-d]pyrimidinyl, pyrimido[5,6-d]pyrimidinyl or pteridinyl. More specifically the bicyclic ring of formula Ic is 6-oxopyrrolino[2,3-d]pyrimidin-4-yl, 6-oxopyrrolino[3,2-d]pyrimidin-4-yl, 2-oxooxazolino[5,4-d]pyrimidin-7-yl, 2-oxothiazolino[5,4-d]pyrimidin-7-yl, 2-oxooxazolino[4,5-d]pyrimidin-7-yl, 2-oxothiazolino[4,5-d]pyrimidin-7-yl, 2-oxoimidazolino[4,5-d]pyrimidin-7-yl, 3-oxopyrazolino[3,4-d]pyrimidinyl or 3-oxopyrazolino[4,3-d]pyrimidin-7-yl. Further preferred bicyclic rings of formula Ic include thieno[3,2-d]pyrimidinyl, thieno[2,3-d] pyrimidinyl, thiazolo[5,4-d]pyrimidinyl, pyrido[2,3-d]pyrimidinyl, pyrido[3,4-d]pyrimidinyl, pyrido[4,3-d]pyrimidinyl, pyrido[3,2-d]pyrimidinyl and pteridinyl, more specifically thieno[3,2-d]pyrimidin-4-yl, thieno[2,3-d]pyrimidin-4-yl, thiazolo[5,4-d]pyrimidin-7-yl, pyrido[2,3-d]pyrimidin-4-yl, pyrido[3,4-d]pyrimidin-4-yl, pyrido[4,3-d]pyrimidin-4-yl, pyrido[3,2-d]pyrimidin-4-yl and pteridine-4-yl.

When, as defined hereinbefore, $Y^2$ together with the carbon atoms to which it is attached forms a 5- or 6-membered aromatic or partially unsaturated ring comprising 1 to 3 heteroatoms selected from O, N and S, ring $Y^2$ is suitably unsaturated or partially unsaturated wherein a —$CH_2$— group can optionally be replaced by a —CO— group and a ring nitrogen atom may optionally bear a (1–6C)alkyl group. Diradicals of suitable fused $Y^2$ rings include thiendiyl, furandiyl, imidazolediyl, pyrazolediyl, oxazolediyl, isoxazolediyl, thiazolediyl, isothiazolediyl, 1,2,3-oxadiazolediyl, 1,2,3-triazolediyl, pyridinediyl, pyrimidinediyl, pyraziediyl, pyridazinediyl and 1,3,4-triazinediyl. Examples of suitable tricyclic rings of formula Id formed by the fusion of ring $Y^2$ to the adjacent quinazoline ring include imidazoquinazolinyl, oxazoloquinazolinyl, thiazoloquinazolinyl, [1,2,3]triazoloquinazolinyl, pyrazoloquinazolinyl, pyrroloquinazolinyl oxoimidazolinoquinazolinyl, oxooxazolinoquinazolinyl, oxothiazolinoquinazolinyl and oxopyrazolinoquinazolinyl. Preferably the tricyclic ring of formula Id is 3H-imidazo[4,5-g]quinazolinyl, oxazolo[4,5-g]quinazolinyl, thiazolo[4,5-g]quinazolinyl, 3H-[1,2,3]triazolo[4,5-g]quinazolinyl, 1H-pyrazolo[3,4-g]quinazolinyl, 6H-pyrrolo[2,3-g] quinazolinyl, 2-oxo-1,2-dihydro-3H-imidazo[4,5-g] quinazolinyl, 2-oxo-1,2-dihydrooxazolo[4,5-g]quinazolinyl, 2-oxo-1,2-dihydrothiazolo[4,5-g]quinazolinyl, 3-oxo-2,3-dihydro-1H-pyrazolo[3,4-g]quinazolinyl, pyrido[2,3-g] quinazolinyl, pyrimidino[4,5-g]cinnolinyl, pyrimidino[4,5-g]quinazolinyl, pyrazino[2,3-g]quinazolinyl, 7-oxo-6,7-dihydropyrido[2,3-g]quinazolinyl, pyrazino[2,3-g] quinazolinyl and 8-oxo-8,9-dihydropyrazino[2,3-g] quinazolinyl. More specifically the tricyclic ring of formula Id is 3H-imidazo[4,5-g]quinazolin-8-yl, oxazolo[4,5-g]quinazolin-8-yl, thiazolo[4,5-g]quinazolin-8-yl, 3H-[1,2,3] triazolo[4,5-g]quinazolin-8-yl, 1H-pyrazolo[3,4-g]quinazolin-8-yl, 6H-pyrrolo[2,3-g]quinazolin-4-yl, 2-oxo-1,2-dihydro-3H-imidazo[4,5-g]quinazolin-8-yl, 2-oxo-1,2-dihydrooxazolo[4,5-g]quinazolin-8-yl, 2-oxo-1,2-dihydrothiazolo[4,5-g]quinazolin-8-yl, 3-oxo-2,3-dihydro-1H-pyrazolo[3,4-g]quinazolin-8-yl, pyrido[-2,3-g]quinazolin-4-yl, pyrimidino[4,5-g]cinnolin-9-yl, pyrimidino[4,5-g]quinazolin-4-yl, pyrazino[2,3-g]quinazolin-4-yl, 7-oxo-6,7-dihydropyrido[2,3-g]quinazolin-4-yl, pyrazino[2,3-g]quinazolin-4-yl or 8-oxo-8,9-dihydropyrazino[2,3-g]quinazolin-4-yl. Further preferred tricyclic rings of formula Id include 3-methyl-3H-imidazo[4,5-g]quinazolin-8-yl, 3-methyl-3H-1,2,3]triazolo[4,5-g]quinazolin-8-yl, 3-methyl-2-oxo-1,2-dihydro-3H-imidazo[4,5-g]quinazolin-8-yl, pyrazino[2,3-g]quinazolin-4-yl and 9-methyl-8-oxo-8,9-dihydropyrazino[2,3-g]quinazolin-4-yl.

Suitable values for any of the 'R' groups ($R^1$ to $R^{16}$), or for various groups within an $R^1$ substituent, or within a substituent on $Q^2$ include:

for halogeno fluoro, chloro, bromo and iodo;

for (1–6C)alkyl: methyl, ethyl, propyl, isopropyl and tert-butyl;

for (2–8C)alkenyl: vinyl, allyl and but-2-enyl;

for (2–8C)alkynyl: ethynyl, 2-propynyl and but-2-ynyl;

for (1–6C)alkoxy: methoxy, ethoxy, propoxy, iopropoxy and butoxy;

for (2–6C)alkenyloxy: vinyloxy and allyloxy;

for (2–6C)alkynyloxy: ethynyloxy and 2-propynyloxy;

for (1–6C)alkylthio: methylthio, ethylthio and propylthio;

for (1–6C)alkylsulphinyl: methylsulphinyl and ethylsulphinyl;

for (1–6C)alkylsulphonyl: methylsulphonyl and ethylsulphonyl;

for (1–6C)alkylamino: methylamino, ethylamino, propylamino, isopropylamino and butylamino;

for di-[(1–6C)alkyl]amino: dimethylamino, diethylamino, N-ethyl-N-methylamino and diisopropylamino;

for (1–6C)alkoxycarbonyl: methoxycarbonyl, ethoxycarbonyl, propoxycarbonyl and tert-butoxycarbonyl;

for N-(1–6C)alkylcarbamoyl: N-methylcarbamoyl, N-ethylcarbamoyl and N-propylcarbamoyl;

for N,N-di-[(1–6C)alkyl]carbamoyl: N,N-dimethylcarbamoyl, N-ethyl-N-methylcarbamoyl and N,N-diethylcarbamoyl;

for (2–6C)alkanoyl: acetyl and propionyl;

for (2–6C)alkanoyloxy: acetoxy and propionyloxy;

for (2–6C)alkanoylamino: acetamido and propionamido;

for N-(1–6C)alkyl-(2–6C)alkanoylamino: N-methylacetamido and N-methylpropionamido;

for N-(1–6C)alkylsulphamoyl: N-methylsulphamoyl and N-ethylsulphamoy);

for N,N-di-[(1–6C)alkyl]sulphamoyl: N,N-dimethylsulphamoyl;

for (1–6C)alkanesulphonylamino: methanesulphonylamino and ethanesulphonylamino;

for N-(1–6C)alkyl-(1–6C)alkanesulphonylamino: N-methylmethanesulphonylamino and N-methylethanesulphonylamino;

for (3–6C)alkenoylamino: acrylamido, methacrylamido and crotonamido;

for N-(1–6C)alkyl-(3–6C)alkenoylamino: N-methylacrylamido and N-methylcrotonamido;

for (3–6C)alkynoylamino: propionamido;

for N-(1–6C)alkyl-(3–6C)alkynoylamino: N-methylpropionamido;

for amino-(1–6C)alkyl: aminomethyl, 2-aminoethyl, 1-aminoethyl and 3-aminopropyl;

for (1–6C)alkylamino-(1–6C)alkyl: methylaminomethyl, ethylaminomethyl, 1-methylaminoethyl, 2-methylaminoethyl, 2-ethylaminoethyl and 3-methylaminopropyl;

for di-[(1–6C)alkyl]amino-(1–6C)alkyl: dimethylaminomethyl, diethylaminomethyl, 1-dimethylaminoethyl, 2-dimethylaminoethyl and 3-dimethylaminopropyl;

for halogeno-(1–6C)alkyl: chloromethyl, 2-chloroethyl, 1-chloroethyl and 3-chloropropyl;

for hydroxy-(1–6C)alkyl: hydroxymethyl, 2-hydroxyethyl, 1-hydroxyethyl and 3-hydroxypropyl;

for (1–6C)alkoxy-(1–6C)alkyl: methoxymethyl, ethoxymethyl, 1-methoxyethyl, 2-methoxyethyl, 2-ethoxyethyl and 3-methoxypropyl;

for cyano-(1–6C)alkyl: cyanomethyl, 2-cyanoethyl, 1-cyanoethyl and 3-cyanopropyl;

for (2–6C)alkanoylamino-(1–6C)alkyl: acetamidomethyl, propionamidomethyl and 2-acetamidoethyl; and for (1–6C)alkoxycarbonylamino-(1–6C)alkyl: methoxycarbonylaminomethyl, ethoxycarbonylaminomethyl, tert-butoxycarbonylaminomethyl and 2-methoxycarbonylaminoethyl.

A suitable value for $(R^1)_m$ or for a substituent on $Q^2$ when it is (1–3C)alkylenedioxy is, for example, methylenedioxy or ethylenedioxy and the oxygen atoms thereof occupy adjacent ring positions.

When, as defined hereinbefore, an $R^1$ group forms a group of the formula $Q^3$—$X^1$— and, for example, $X^1$ is a $OC(R^4)_2$ linking group, it is the carbon atom, not the oxygen atom, of the $OC(R^4)_2$ linking group which is attached to the quinazoline-like ring such as the ring of formula Ia and the oxygen atom is attached to the $Q^3$ group. Similarly, when, for example a $CH_3$ group within a $R^1$ substituent bears a group of the formula —$X^3$—$Q^5$ and, for example, $X^3$ is a $C(R^7)_2O$ linking group, it is the carbon atom, not the oxygen atom, of the $C(R^7)_2O$ linking group which is attached to the $CH_3$ group and the oxygen atom is linked to the $Q^5$ group. A similar convention applies to the attachment of the groups of the formulae $Q^4$—$X^2$— and —$X^7$—$Q^7$.

As defined hereinbefore, adjacent carbon atoms in any (2–6C)alkylene chain within a $R^1$ substituent may be optionally separated by the insertion into the chain of a group such as O, CON($R^5$) or C≡C. For example, insertion of a C≡C group into the ethylene chain within a 2-morpholinoethoxy group gives rise to a 4-morpholinobut-2-ynyloxy group and, for example, inspection of a CONH group into the ethylene chain within a 3-methoxypropoxy group gives rise to, for example, a 2-(2-methoxyacetamido)ethoxy group.

When, as defined hereinbefore, any $CH_2$=CH— or HC≡C— group within a $R^1$ substituent optionally bears at the terminal $CH_2$= or HC≡ position a substituent such as a group of the formula $Q^4$—$X^2$— wherein $X^2$ is, for example, NHCO and $Q^4$ is a heterocyclyl-(1–6C)alkyl group, suitable $R^1$ substituents so formed include, for example, N-[heterocyclyl-(1–6C)alkyl]carbamoylvinyl groups such as N-(2-pyrrolidin-1-ylethyl)carbamoylvinyl or N-[heterocyclyl-(1–6C)alkyl]carbamoylethynyl groups such as N-(2-pyrrolidin-1-ylethyl)carbamoylethynyl.

When, as defined hereinbefore, any $CH_2$ or $CH_3$ group within a $R^1$ substituent optionally bears on each said $CH_2$ or $CH_3$ group one or more halogeno substituents, there are suitably 1 or 2 halogeno substituents present on each said $CH_2$ group and there are suitably 1, 2 or 3 halogeno substituents present on each said $CH_3$ group.

When, as defined hereinbefore, any $CH_2$ or $CH_3$ group within a $R^1$ substituent optionally bears on each said $CH_2$ or $CH_3$ group a substituent as defined hereinbefore, suitable $R^1$ substituents so formed include, for example, hydroxy-substituted heterocyclyl- (1–6C)alkoxy groups such as 2-hydroxy-3-piperidinopropoxy and 2-hydroxy-3-morpholinopropoxy, hydroxy-substituted amino-(2–6C)alkoxy groups such as 3-amino-2-hydroxypropoxy, hydroxy-substituted (1–6C)alkylamino-(2–6C)alkoxy groups such as 2-hydroxy-3-methylaminopropoxy, hydroxy-substituted di-[(1–6C)alkyl]amino-(2–6C)alkoxy groups such as 3-dimethylamino-2-hydroxypropoxy, hydroxy-substituted heterocyclyl-(1–6C)alkylamino groups such as 2-hydroxy-3-piperidinopropylamino and 2-hydroxy-3-morpholinopropylamino, hydroxy-substituted amino-(2–6C)alkylamino groups such as 3-amino-2-hydroxypropylamino, hydroxy-substituted (1–6C) alkylamino-(2–6C)alkylamino groups such as 2-hydroxy-3-methylaminopropylamino, hydroxy-substituted di-[(1–6C) alkyl]amino-(2–6C)alkylamino groups such as 3-dimethylamino-2-hydroxypropylamino, hydroxy-substituted (1–6C)alkoxy groups such as 2-hydroxyethoxy, (1–6C)alkoxy-substituted (1–6C)alkoxy groups such as 2-methoxyethoxy and 3-ethoxypropoxy, (1–6C) alkylsulphonyl-substituted (1–6C)alkoxy groups such as 2-methylsulphonylethoxy and heterocyclyl-substituted (1–6C)alkylamino-(1–6C)alkyl groups such as 2-morpholinoethylaminomethyl, 2-piperazin-1-ylethylaminomethyl and 3-morpholinopropylaminomethyl.

A suitable pharmaceutically-acceptable salt of a compound of the Formula I is, for example, an acid-addition salt of a compound of the Formula I, for example an acid-addition salt with an inorganic or organic acid such as hydrochloric, hydrobromic, sulphuric, trifluoroacetic, citric or maleic acid; or, for example, a salt of a compound of the Formula I which is sufficiently acidic, for example an alkali or alkaline earth metal salt such as a calcium or magnesium salt, or an ammonium salt, or a salt with an organic base such as methylamine, dimethylamine, trimethylamine, piperidine, morpholine or tris-(2-hydroxyethyl)amine.

According to a further aspect of the invention there is provided a quinazoline derivative of the Formula I

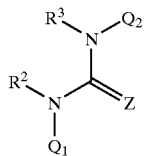

wherein $Q^1$ is a quinazoline-like ring such as a group of the formula Ia, Ib, Ic or Id

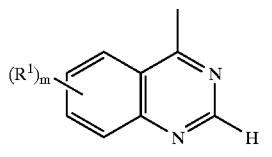

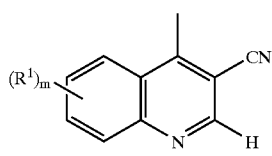

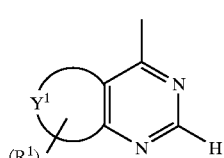

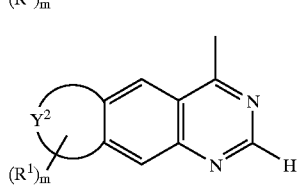

wherein:
$Y^1$ together with the carbon atoms to which it is attached forms 5- or 6-membered aromatic or partially unsaturated ring comprising 1 to 3 heteroatoms selected from O, N and S provided that the group of formula Ic so formed is not a purine ring;
$Y^2$ together with the carbon atoms to which it is attached forms a 5- or 6-membered aromatic or partially unsaturated ring comprising 1 to 3 heteroatoms selected from O, N and S;
m is 0, 1, 2, 3 or 4;
each $R^1$ group, which may be the same or different, is selected from halogeno, trifluoromethyl cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$Q^3-X^1-$ wherein $X^1$ is a direct bond or is selected from O, S, SO, $SO_2$, $N(R^4)$, CO, $CH(OR^4)$, $CON(R^4)$, $N(R^4)CO$, $SO_2N(R^4)$, $N(R^4)SO_2$, $OC(R^4)_2$, $SC(R^4)_2$ and $N(R^4)C(R^4)_2$, wherein $R^4$ is hydrogen or (1–6C)alkyl, and $Q^3$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or $(R^1)_m$ is (1–3C)alkylenedioxy,
and wherein adjacent carbon atoms in any (2–6C)alkylene chain within a $R^1$ substituent are optionally separated by the insertion into the chain of a group selected from O, S, SO, $SO_2$, $N(R^5)$, CO, $CH(OR^5)$, $CON(R^5)$, $N(R^5)CO$, $SO_2N(R^5)$, $N(R^5)SO_2$, CH=CH and C≡C wherein $R^5$ is hydrogen or (1–6C)alkyl,
and wherein any $CH_2$=CH— or HC≡C— group within a $R^1$ substituent optionally bears at the terminal $CH_2$= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^4-X^2-$ wherein $X^2$ is a direct bond or is selected from CO and $N(R^6)CO$, wherein $R^6$ is hydrogen or (1–6C)alkyl, and $Q^4$ is aryl, aryl-(1–6C)alkyl, heteroaryl, heteroaryl-(1–6C)alkyl, heterocyclyl or heterocyclyl-(1–6C)alkyl,
and wherein any $CH_2$ or $CH_3$ group within a $R^1$ substituent optionally bears on each said $CH_2$ or $CH_3$ group one or more halogeno substituents or a substituent selected from hydroxy, cyano, amino, carboxy, carbamoyl, (1–6C)alkyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$-X^3-Q^5$ wherein $X^3$ is a direct bond or is selected from O, S, SO, $SO_2$, $N(R^7)$, CO, $CH(OR^7)$, $CON(R^7)$, $N(R^7)CO$, $SO_2N(R^7)$, $N(R^7)SO_2$, $C(R^7)_2O$, $C(R^7)_2S$ and $N(R^7)C(R^7)_2$, wherein $R^7$ is hydrogen or (1–6C)alkyl and $Q^5$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl,
and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X$^4$—Q$^8$ wherein X$^4$ is a direct bond or is selected from O and N(R$^9$), wherein R$^9$ is hydrogen or (1–6C)alkyl, and R$^8$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—X$^5$—Q$^6$ wherein X$^5$ is a direct bond or is selected from O and N(R$^{10}$), wherein R$^{10}$ is hydrogen or (1–6C)alkyl, and Q$^6$ is aryl, aryl-(1–6C)alkyl, heteroaryl, heteroaryl-(1–6C)alkyl, heterocyclyl or heterocyclyl-(1–6C)alkyl, and wherein any heterocyclyl group within a substituent on R$^1$ optionally bears 1 or 2 oxo or thioxo substituents;

R$^2$ is hydrogen or (1–6C)alkyl and R$^3$ is hydrogen or (1–6C)alkyl, or R$^2$ and R$^3$ together form a CH$_2$, (CH$_2$)$_2$ or (CH$_2$)$_3$ group;

Z is O, S, N(C≡N) or N(R$^{11}$), wherein R$^{11}$ is hydrogen or (1–6C)alkyl; and Q$^2$ is aryl, aryl-(1–3C)alkyl, aryl-(3–7C)cycloalkyl, heteroaryl, heteroaryl-(1–3C)alkyl or heteroaryl-(3–7C)cycloalkyl wherein each aryl group is phenyl or naphthyl and each heteroaryl group is a 5- or 6-membered monocyclic or a 9- or 10-membered bicyclic heteroaryl ring containing 1 or 2 nitrogen heteroatoms and optionally containing a further heteroatom selected from nitrogen, oxygen and sulphur, and Q$^2$ is optionally substituted with 1, 2, 3 or 4 substituents, which may be the same or different, selected from halogeno, trifluoromethyl cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X$^6$—R$^{12}$ wherein X$^6$ is a direct bond or is selected from O and N(R$^{13}$), wherein R$^{13}$ is hydrogen or (1–6C)alkyl, and R$^{12}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—X$^7$—Q$^7$ wherein X$^7$ is a direct bond or is selected from O, S, SO, SO$_2$, N(R$^{14}$), CO, CH(OR$^{14}$), CON(R$^{14}$), N(R$^{14}$)CO, SO$_2$N(R$^{14}$), N(R$^{14}$)SO$_2$, C(R$^{14}$)$_2$O, C(R$^{14}$)$_2$S and C(R$^{14}$)$_2$N(R$^{14}$), wherein each R$^{14}$ is hydrogen or (1–6C)alkyl, and Q$^7$ is aryl, aryl-(1–6C)alkyl, heteroaryl, heteroaryl-(1–6C)alkyl, heterocyclyl or heterocyclyl-(1–6C)alkyl, or Q$^2$ is optionally substituted with a (1–3C)alkylenedioxy group, and wherein any aryl, heteroaryl or heterocyclyl group within a substituent on Q$^2$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X$^8$—R$^{15}$ wherein X$^8$ is a direct bond or is selected from O and N(R$^{16}$), wherein R$^{16}$ is hydrogen or (1–6C)alkyl, and R$^{15}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, and wherein any heterocyclyl group within a substituent on Q$^2$ optionally bears 1 or 2 oxo or thioxo substituents;

or a pharmaceutically-acceptable salt thereof;

provided that the compounds:

1-(6,7-dimethoxyquinazolin-4-yl)-3-phenylurea,

1-[5-(4-methoxyphenoxy)quinazolin-4-yl]-3-phenylurea,

1-[5-(4-methoxyphenoxy)quinazolin-4-yl]-3-(3-bromophenyl)urea,

1-[5-(4-methoxyphenoxy)quinazolin-4-yl]-3-(3-methoxyphenyl)urea.

1-phenyl-3-(pyrazolo[3,4-d]pyrimidin-4-yl)urea, 1-(2-chlorophenyl)-3-(pyrazolo[3,4-d]pyrimidin-4-yl)urea, 1-(3-chlorophenyl)-3-(pyrazolo[3,4-d]pyrimidin-4-yl)urea, 1-(4-chlorophenyl)-3-(pyrazolo[3,4-d]pyrimidin-4-yl)urea, 1-(2-fluorophenyl)-3-(pyrazolo[3,4-d]pyrimidin-4-yl)urea, 1-benzyl-3-(pyrazolo[3,4-d]pyrimidin-4-yl)urea and 1-(3-phenylpropyl)-3-(pyrazolo[3,4-d]pyrimidin-4-yl)urea are excluded.

Particular novel compounds of the invention include, for example,
(i) quinazoline derivatives of the Formula II

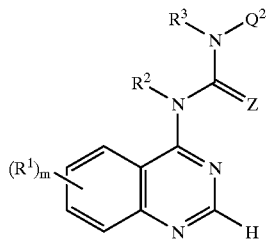

wherein each of m R¹, R², R³, Z and Q² has any of the meanings defined hereinbefore;
(ii) quinoline derivatives of the Formula III

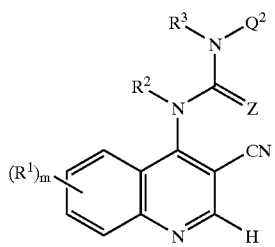

wherein each of m, R¹, R², R³, Z and Q² has any of the meanings defined hereinbefore;
(iii) pyrimidine derivatives of the Formula IV

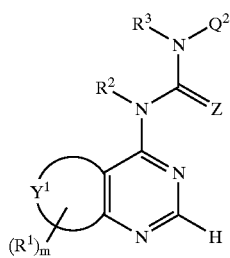

wherein each of m, R¹, Y¹, R², R³, Z and Q² has any of the meanings defined hereinbefore; and
(iv) quinazoline derivatives of the Formula V

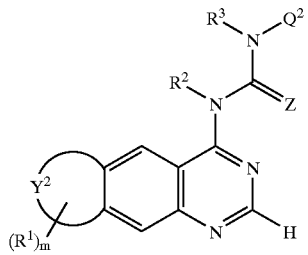

wherein each of m, R¹, Y², R², R³, Z and Q² has any of the meanings defined hereinbefore.
Subject to the provisos described hereinbefore, further particular novel compounds of the invention include, for example, quinazoline derivatives of the Formula II, or pharmaceutically-acceptable salts thereof, wherein, unless otherwise stated, each of m, R¹, R², R³, Z and Q² has any of the meanings defined hereinbefore or in paragraphs (a) to (o) hereinafter:

(a) m is 1, 2 or 3, and each R¹ group, which may be the same or different, is selected from halogeno, trifluoromethyl, hydroxy, amino, carbamoyl, (1–6C)alkyl, (2–8C)alkenyl, (2–8C)alkynyl, (1–6C)alkoxy, (1–6C)alkylamino, di-[(1–6C)alkyl]amino, N-(1–6C)alkylcarbamoyl, N,N-di-[(1–6C)alkyl]carbamoyl, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino and N-(1–6C)alkyl-(3–6C)alkynoylamino, or from a group of the formula:

Q³—X¹— wherein X¹ is a direct bond or is selected from O, N(R⁴), CON(R⁴), N(R⁴)CO and OC(R⁴)₂ wherein R⁴ is hydrogen or (1–6C)alkyl, and Q³ is aryl, aryl-(1–6C)alkyl, cycloalkyl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within a R¹ substituent are optionally separated by the insertion into the chain of a group selected from O, N(R⁵), CON(R⁵), N(R⁵)CO, CH=CH and C≡C wherein R⁵ is hydrogen or (1–6C)alkyl, and wherein any CH₂=CH— or HC≡C— group within a R¹ substituent optionally bears at the terminal CH₂= or HC≡ position a substituent selected from carbamoyl N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

Q⁴—X²— wherein X² is a direct bond or is CO or N(R⁶)O, wherein R⁶ is hydrogen or (1–6C)alkyl, and Q⁴ is heteroaryl, heteroaryl-(1–6C)alkyl, heterocyclyl or heterocyclyl-(1–6C)alkyl, and wherein any CH₂ or CH₃ group within a R¹ substituent optionally bears on each said CH₂ or CH₃ group a substituent selected from hydroxy, amino, (1–6C)alkoxy, (1–6C)alkylsulphonyl, (1–6C)alkylamino and di-[(1–6C)alkyl]amino, or from a group of the formula:

—X³—Q⁵ wherein X³ is a direct bond or is selected from O, N(R⁷), CON(R⁷), N(R⁷)CO and C(R⁷)₂O, wherein R⁷ is hydrogen or (1–6C)alkyl, and Q⁵ is heteroaryl, heteroaryl-(1–6C)alkyl, heterocyclyl or heterocyclyl-(1–6C)alkyl, and wherein any aryl, heteroaryl or heterocyclyl group within a substituent on R¹ optionally bears 1, 2 or 3 substituents, which may be the same or different, selected from halogeno, trifluoromethyl, hydroxy, amino, carbamoyl, (1–6C)alkyl, (1–6C)alkoxy, N-(1–6C)alkylcarbamoyl, N,N-di-[(1–6C)alkyl]carbamoyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl and (1–6C)alkoxycarbonylamino-(1–6C)alkyl, and wherein any heterocyclyl group within a substituent on R¹ optionally bears 1 or 2 oxo substituents;
(b) m is 1, 2 or 3, and each R¹ group, which may be the same or different, is selected from halogeno, trifluoromethyl, hydroxy, amino, carbamoyl, (1–6C)alkyl, (2–8C)alkenyl, (2–8C)alkynyl, (1–6C)alkoxy, (1–6C)alkylamino, di-[(1–6C)alkyl]amino, N-(1–6C)alkylcarbamoyl, N,N-di-

[(1–6C)alkyl]carbamoyl, (2–6C)alkanoylamino, N-(1–6C)alkyl-(2–6C)alkanoylamino, (3–6C)alkenoylamino, N-di-(1–6C)alkyl-(3–6C)alkenoylamino, (3–6C)alkynoylamino and N-(1–6C)alkyl-(3 6C)alkynoylamino, or from a group of the formula:

$Q^3-X^1-$ wherein $X^1$ is a direct bond or is selected from O, N($R^4$), CON($R^4$), N($R^4$)CO and OC($R^4$)$_2$ wherein $R^4$ is hydrogen or (1–6C)alkyl, and $Q^3$ is aryl, aryl-(1–6C)alkyl, heteroaryl, heteroaryl-(1–6C)alkyl, heterocyclyl or heterocyclyl-(1–6C)alkyl, and wherein adjacent carbon atoms in any (2–6C)alkylene chain within a $R^1$ substituent are optionally separated by the insertion into the chain of a group selected from O, N($R^5$), CON($R^5$), N($R^5$)CO, CH=CH and C≡C wherein $R^5$ is hydrogen or (1–6C)alkyl, and wherein any CH$_2$=CH— or HC≡C— group within a $R^1$ substituent optionally bears at the terminal CH$_2$= or HC≡ position a substituent selected from carbamoyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$Q^4-X^2-$ wherein $X^2$ is a direct bond or is CO or N($R^6$)CO, wherein $R^6$ is hydrogen or (1–6C)alkyl, and $Q^4$ is heteroaryl, heteroaryl-(1–6C)alkyl, heterocyclyl or heterocyclyl-(1–6C)alkyl, and wherein any CH$_2$ or CH$_3$ group within a $R^1$ substituent optionally bears on each said CH$_2$ or CH$_3$ group a substituent selected from hydroxy, amino, (1–6C)alkoxy, (1–6C)alkylsulphonyl, (1–6C)alkylamino and di-[(1–6C)alkyl]amino, or from a group of the formula:

$-X^3-Q^5$ wherein $X^3$ is a direct bond or is selected from O, N($R^7$), CON($R^7$), N($R^7$)CO and C($R^7$)$_2$O, wherein $R^7$ is hydrogen or (1–6C)alkyl, and $Q^5$ is heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, hydroxy, amino, (1–6C)alkyl and (1–6C)alkoxy, and wherein any heterocyclyl group within a substituent on $R^1$ optionally bears 1 or 2 oxo substituents;

(c) m is 1, 2 or 3, and each $R^1$ group, which may be the same or different, is selected from fluoro, chloro, trifluoromethyl, hydroxy, amino, carbamoyl, methyl, ethyl, propyl, vinyl, ethynyl, methoxy, ethoxy, propoxy, methylamino, ethylamino, propylamino, dimethylamino, diethylamino, dipropylamino, N-methylcarbamoyl, N,N-dimethylcarbamoyl, acetamido, propionamido, acrylamido and propionamido, or from a group of the formula:

$Q^3-X^1-$ wherein $X^1$ is a direct bond or is selected from O, NH, CONH, NHCO and OCH$_2$ and $Q^3$ is phenyl, benzyl, cyclopropylmethyl, thienyl, 1-imidazolyl, 1,2,3-triazolyl, pyridyl, 2-imidazol-1-ylethyl, 3-imidazol-1-ylpropyl, 2-(1,2,3-triazolyl)ethyl, 3-(1,2,3-triazolyl)propyl, pyridylmethyl, 2-pyridylethyl, 3-pyridylpropyl, pyrrolidin-1-yl, pyrrolidin-2-yl, morpholino, 1,1-dioxotetrahydro-4H-1,4-thiazin-4-yl, piperidino, piperidin-3-yl, piperidin-4-yl, homopiperidin-1-yl, piperazin-1-yl, homopiperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-(1,1-dioxotetrahydro-4H-1,4-thiazin-4-yl)ethyl, 3-(1,1-dioxotetrahydro-4H-1,4-thiazin-4-yl)propyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-homopiperidin-1-ylethyl, 3-homopiperidin-1-ylpropyl, 2-piperazin-1-ylethyl, 3-piperazin-1-ylpropyl, 2-homopiperazin-1-ylethyl or 3-homopiperazin-1-ylpropyl, and wherein adjacent carbon atoms in any (2–6C)alkylene chain within a $R^1$ substituent are optionally separated by the insertion into the chain of a group selected from O, NH, CONH, NHCO, CH=CH and C≡C, and wherein any CH$_2$=CH— or HC≡C— group within a $R^1$ substituent optionally bears at the terminal CH$_2$= or HC≡ position a substituent selected from carbamoyl, N-methylcarbamoyl, N-ethylcarbamoyl, N-propylcarbamoyl, N,N-dimethylcarbamoyl, aminomethyl, 2-aminoethyl, 3-aminopropyl, 4-aminobutyl, methylaminomethyl, 2-methylaminoethyl, 3-methylaminopropyl, 4-methylaminobutyl, dimethylaminomethyl, 2-dimethylaminoethyl, 3-methylaminopropyl or 4-dimethylaminobutyl, or from a group of the formula:

$Q^4-X^2-$ wherein $X^2$ is a direct bond or is CO, NHCO or N(Me)CO and $Q^4$ is pyridyl, pyridylmethyl, 2-pyridylethyl, pyrrolidin-1-yl, pyrrolidin-2-yl, morpholino, piperidino, piperidin-3-yl, piperidin-4-yl, piperazin-1-yl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidin-4-ylethyl, piperazin-1-ylmethyl, 2-piperazin-1-ylethyl, 3-piperazin-1-ylpropyl or 4-piperazin-4-ylbutyl, and wherein any CH$_2$ or CH$_3$ group within a $R^1$ substituent optionally bears on each said CH$_2$ or CH$_3$ group a substituent selected from hydroxy, amino, methoxy, methylsulphonyl, methylamino and dimethylamino, or from a group of the formula:

$-X^3-Q^5$ wherein $X^3$ is a direct bond or is selected from O, NH, CONH, NHCO and CH$_2$O and $Q^5$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin- 3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on $R^1$ optionally bears 1, 2 or 3 substituents, which may be the same or different, selected from fluoro, chloro, trifluoromethyl hydroxy, amino, carbamoyl, methyl, ethyl, methoxy, aminomethyl, methylaminomethyl, dimethylaminomethyl, acetamidomethyl, methoxycarbonylaminomethyl, ethoxycarbonylaminomethyl and tert-butoxycarbonylaminomethyl, and wherein any heterocyclyl group within a substituent on $R^3$ optionally bears 1 or 2 oxo substituents;

(d) m is 1, 2 or 3, and each $R^1$ group, which may be the same or different, is selected from fluoro, chloro, trifluoromethyl, hydroxy, amino, carbamoyl, methyl, ethyl, propyl, vinyl, ethynyl, methoxy, ethoxy, propoxy, methylamino, ethylamino, propylamino, dimethylamino, diethylamino, dipropylamino, N-methylcarbamoyl, N,N-dimethylcarbamoyl, acetamido, propionamido, acrylamido and propionamido, or from a group of the formula:

$$Q^3-X^1-$$

wherein $X^1$ is a direct bond or is selected from O, NH, CONH, NHCO and $OCH_2$ and $Q^3$ is phenyl, benzyl, thienyl, 1,2,3-triazolyl, pyridyl, 2-(1,2,3-triazolyl)ethyl, 3-(1,2,3-triazolyl)propyl, pyridylmethyl, 2-pyridylethyl, 3-pyridylpropyl, pyrrolidin-1-yl, pyrrolidin-2-yl, morpholino, 1,1-dioxotetrahydro-4H-1,4-thiazin-4-yl, piperidino, piperidin-3-yl, piperidin-4-yl, homopiperidin-1-yl, piperazin-1-yl, homopiperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-(1,1-dioxotetrahydro-4H-1,4-thiazin-4-yl)ethyl, 3-(1,1-dioxotetrahydro-4H-1,1-thiazin-4-yl)propyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-homopiperidin-1-ylethyl, 3-homopiperidin-1-ylpropyl, 2-piperazin-1-ylethyl, 3-piperazin-1-ylpropyl, 2-homopiperazin-1-ylethyl or 3-homopiperazin-1-ylpropyl, and wherein adjacent carbon atoms in any (2–6C)alkylene chain within a $R^1$ substituent are optionally separated by the insertion into the chain of a group selected from O, NH, CONH, NHCO, CH=CH and C≡C, and wherein any $CH_2$=CH— or HC≡C— group within a $R^1$ substituent optionally bears at the terminal $CH_2$= or HC≡ position a substituent selected from carbamoyl, N-methylcarbamoyl, N-ethylcarbamoyl, N-propylcarbamoyl, N,N-dimethylcarbamoyl, aminomethyl, 2-aminoethyl, methylaminomethyl, 2-methylaminoethyl, dimethylaminomethyl or 2-dimethylaminoethyl, or from a group of the formula:

$$Q^4-X^2-$$

wherein $X^2$ is a direct bond or is CO, NHCO or N(Me)CO and $Q^4$ is pyridyl, pyridylmethyl, 2-pyridylethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino and dimethylamino, or from a group of the formula:

$$-X^3-Q^5$$

wherein $X^3$ is a direct bond or is selected from O, NH, CONH, NHCO and $CH_2O$ and $Q^5$ is pyridyl, pyridylmethyl, pyrrolidin-1-yl, pyrrolidin-2-yl, morpholino, piperidino, piperidin-3-yl, piperidin-4-yl, piperazin-1-yl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any aryl, heteroaryl or heterocyclyl group within a substituent on $R^1$ optionally bears 1, 2 or 3 substituents, which may be the same or different, selected from fluoro, chloro, trifluoromethyl, hydroxy, amino, methyl, ethyl and methoxy, and wherein any heterocyclyl group within a substituent on $R^1$ optionally bears 1 or 2 oxo substituents;

(e) m is 1 or 2 and the $R^1$ groups, which may be the same or different, are located at the 6- and/or 7-positions and arm selected from hydroxy, amino, methyl, ethyl, propyl, vinyl, ethynyl, methoxy, ethoxy, propoxy, methylamino, ethylamino, dimethylamino, diethylamino, acetamido, propionamido, benzyloxy, cyclopropylmethoxy, 2-imidazol-1-ylethoxy, 3-imidazol-1-ylpropoxy, 2-(1,2,3-triazol-1-yl)ethoxy, 3-(1,2,3-triazol-1-yl)propoxy, pyrid-2-ylmethoxy, pyrid-3-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, pyrrolidin-1-yl, morpholino, piperidino, piperazin-1-yl, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy, 3-homopiperazin-1-ylpropoxy, 2-pyrrolidin-1-ylethylamino, 3-pyrrolidin-1-ylpropylamino, pyrrolidin-3-ylamino, pyrrolidin-2-ylmethylamino, 2-pyrrolidin-2-ylethylamino, 3-pyrrolidin-2-ylpropylamino, 2-morpholinoethylamino, 3-morpholinopropylamino, 2-(1,1-dioxotetrahydro-4H-1,4-thiazin-4-yl)ethylamino, 3-(1,1-dioxotetrahydro-4H-1,4-thiazin-4-yl)propylamino, 2-piperidinoethylamino, 3-piperidinopropylamino, piperidin-3-ylamino, piperidin-4-ylamino, piperidin-3-ylmethylamino, 2-piperidin-3-ylethylamino, piperidin-4-ylmethylamino, 2-piperidin-4-ylethylamino, 2-homopiperidin-1-ylethylamino, 3-homopiperidin-1-ylpropylamino, 2-piperazin-1-ylethylamino, 3-piperazin-1-ylpropylamino, 2-homopiperazin-1-ylethylamino or 3-homopiperazin-1-ylpropylamino, and wherein adjacent carbon atoms in any (2–6C)alkylene chain within a $R^1$ substituent are optionally separated by the insertion into the chain of a group selected from O, NH, CH=CH and C≡C, and when $R^1$ is a vinyl or ethynyl group, the $R^1$ substituent optionally bears at the terminal $CH_2$= or HC≡ position a substituent selected from N-(2-dimethylaminoethyl)carbamoyl, N-(3-diethylaminopropyl)carbamoyl, methylaminomethyl, 2-methylaminoethyl, 3-methylaminopropyl, 4-methylaminobutyl, dimethylaminomethyl, 2-dimethylaminoethyl, 3-dimethylaminopropyl and 4-dimethylaminobutyl, or from a group of the formula:

$$Q^4-X^2-$$

wherein $X^2$ is a direct bond or is NHCO or N(Me)CO and $Q^4$ is imidazolylmethyl, 2-imidazolylethyl, 3-imidazolylpropyl, pyridylmethyl, 2-pyridylethyl, 3-pyridylpropyl, pyrrolidin-1-ylmethyl, 2-pyrrolidin-1-ylethyl, 3-pyrrolidin-1-ylpropyl, 4-pyrrolidin-1-ylbutyl, pyrrolidin-2-ylmethyl, 2-pyrrolidin-2-ylethyl, 3-pyrrolidin-2-ylpropyl, morpholinomethyl, 2-morpholinoethyl, 3-morpholinopropyl, 4-morpholinobutyl, piperidinomethyl, 2-piperidinoethyl, 3-piperidinopropyl, 4-piperidinobutyl, piperidin-3-ylmethyl, 2-piperidin-3-ylethyl, piperidin-4-ylmethyl, 2-piperidinylethyl, piperazin-1-ylmethyl, 2-piperazin-1-ylethyl, 3-piperazin-1-ylpropyl or 4-piperazin-1-ylbutyl, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino and dimethylamino, and wherein any phenyl, pyridyl or heterocyclyl group within a substituent on $R^1$ optionally bears 1 or 2 substituents, which may be the same or different, selected from fluoro, chloro, trifluoromethyl, hydroxy, amino, carbamoyl, methyl, ethyl, methoxy, aminomethyl, acetamidomethyl and tert-butoxycarbonylaminomethyl, and wherein any heterocyclyl group within a substituent on $R^1$ optionally bears 1 or 2 oxo substituents;

(f) m is 1 or 2 and the $R^1$ groups, which may be the same or different, are located at the 6- and/or 7-positions and are selected from hydroxy, amino, methyl, ethyl, propyl, vinyl, ethynyl, methoxy, ethoxy, propoxy, methylamino, ethylamino, dimethylamino, diethylamino, acetamido, propionamido, benzyloxy, 2-(1,2,3-triazol-1-yl)ethoxy, 3-(1,2,3-triazol-1-yl)propoxy, pyrid-2-ylmethoxy, pyrid-3-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, 2-pyrrolidin-1-ylethoxy, 3-pyrrolidin-1-ylpropoxy, pyrrolidin-3-yloxy, pyrrolidin-2-ylmethoxy, 2-pyrrolidin-2-ylethoxy, 3-pyrrolidin-2-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, piperidin-3-ylmethoxy, 2-piperidin-3-ylethoxy, piperidin-4-ylmethoxy, 2-piperidin-4-ylethoxy, 2-homopiperidin-1-ylethoxy, 3-homopiperidin-1-ylpropoxy, 2-piperazin-1-ylethoxy, 3-piperazin-1-ylpropoxy, 2-homopiperazin-1-ylethoxy or 3-homopiperazin-1-ylpropoxy, and wherein adjacent carbon atoms in any (2–6C)alkylene chain within a $R^1$ substituent are optionally separated by the insertion into the chain of a group selected from O, NH, CH=CH and C≡C, and when $R^1$ is a vinyl or ethynyl group, the $R^1$ substituent optionally bears at the terminal $CH_2$= of HC≡ position a substituent selected from N-(2-dimethylaminoethyl)carbamoyl or N-(3-dimethylaminopropyl)carbamoyl, or from a group of the formula:

$$Q^4-X^2-$$

wherein $X^2$ is NHCO or N(Me)CO and $Q^4$ is imidazolylmethyl, 2-imidazolylethyl, 3-imidazolylpropyl, pyridylmethyl, 2-pyridylethyl, 3-pyridylpropyl, 2-pyrrolidin-1-ylethyl, 3-pyrrolidin-1-ylpropyl, pyrrolidin-2-ylmethyl, 2-pyrrolidin-2-ylethyl, 3-pyrrolidin-2-ylpropyl, 2-morpholinoethyl, 3-morpholinopropyl, 2-piperidinoethyl, 3-piperidinopropyl, piperidin-3-ylmethyl, 2-piperidin-3-ylethyl, piperidin-4-ylmethyl, 2-piperidin-4-ylethyl, 2-piperazin-1-ylethyl or 3-piperazin-1-ylpropyl, and wherein any $CH_2$ or $CH_3$ group within a $R^1$ substituent optionally bears on each said $CH_2$ or $CH_3$ group a substituent selected from hydroxy, amino, methoxy, methylsulphonyl, methylamino and dimethylamino, and wherein any phenyl, pyridyl or heterocyclyl group within a substituent on $R^1$ optionally bears 1 or 2 substituents, which may be the same or different, selected from fluoro, chloro, trifluoromethyl, hydroxy, amino, methyl, ethyl and methoxy, and wherein any heterocyclyl group within a substituent on $R^1$ optionally bears 1 or 2 oxo substituents;

(g) each of $R^2$ and $R^3$ is hydrogen or methyl;

(h) each of $R^2$ and $R^3$ is hydrogen;

(i) Z is O, S or $N(R^{11})$, wherein $R^{11}$ is hydrogen or (1–6C)alkyl;

(j) Z is O, S, $N(R^{11})$, wherein $R^{11}$ is hydrogen, methyl, ethyl or propyl;

(k) Z is O;

(l) $Q^2$ is phenyl, benzyl, t-methylbenzyl phenethyl, naphthyl, 1-(1-naphthyl)ethyl or 2-phenylcyclopropyl which is optionally substituted with 1, 2 or 3 substituents, which may be the same or different, selected from halogeno, trifluoromethyl cyano, nitro, hydroxy, amino, carbamoyl, (1–6C)alkyl, (2–8C)alkenyl, (2–8C)alkynyl, (1–6C)alkoxy, (1–6C)alkylamino, di-[(1–6C)alkyl]amino, N-(1–6C)alkylcarbamoyl, N,N-di-[(1–6C)alkyl]carbamoyl, (2–6C)alkanoylamino, or from a group of the formula:

$$-X^6-R^{12}$$

wherein $X^6$ is a direct bond or is selected from O and $N(R^{13})$, wherein $R^{13}$ is hydrogen or (1–6C)alkyl, and $R^{12}$ is hydroxy-(1–6C)alkyl, (1–6C)alkoxy-(1–6C)alkyl, amino-(1–6C)alkyl, (1–6C)alkylamino-(1–6C)alkyl or di-[(1–6C)alkyl]amino-(1–6C)alkyl, or from a group of the formula:

$$-X^7-Q^7$$

wherein $X^7$ is a direct bond or is selected from O, $N(R^{14})$, CO, $CON(R^{14})$, $N(R^{14})CO$ and $C(R^{14})_2O$, wherein each $R^{14}$ is hydrogen or (1–6C)alkyl, and $Q^7$ is phenyl, benzyl, heteroaryl or heteroaryl-(1–6C)alkyl, and wherein any phenyl or heteroaryl group within a substituent on $Q^2$ optionally bears 1, 2 or 3 substituents, which may be the same or different, selected from halogeno, trifluoromethyl, hydroxy, amino, (1–6C) alkyl and (1–6C)alkoxy;

(m) $Q^2$ is phenyl, benzyl, α-methylbenzyl or phenethyl which is optionally substituted with 1, 2 or 3 substituents, which may be the same or different, selected from fluoro, chloro, bromo, trifluoromethyl, cyano, nitro, hydroxy, methyl, ethyl, propyl, tert-butyl, vinyl, ethynyl and methoxy, or from a group of the formula:

$$-X^7-Q^7$$

wherein $X^7$ is a direct bond or is selected from O and CO, and $Q^7$ is phenyl, benzyl, pyridyl or pyridylmethyl, and wherein any phenyl or pyridyl group within a substituent on $Q^2$ optionally bears 1 or 2 substituents, which may be the same or different, selected from fluoro, chloro, trifluoromethyl hydroxy, amino, methyl and methoxy;

(n) $Q^2$ is phenyl, benzyl or phenethyl which is substituted with 1, 2 or 3 substituents, which may be the same or different, selected from fluoro, chloro, bromo, trifluoromethyl, cyano, nitro, hydroxy, methyl, ethyl, propyl, tert-butyl, vinyl, ethynyl and methoxy provided that at least one substituent is located at an ortho position (for example the 2-position on a phenyl group); and (o) $Q^2$ is phenyl, benzyl or phenethyl which is substituted with 2 or 3 substituents, which may be the same or different, selected from fluoro, chloro, bromo, trifluoromethyl, cyano, nitro, hydroxy, methyl, ethyl, propyl, tert-butyl, vinyl, ethynyl and methoxy provided that two substituents are located at ortho positions (for example the 2- and 6-positions on a phenyl group).

Further particular novel compounds of the invention include, for example, quinoline derivatives of the Formula III, or pharmaceutically-acceptable salts thereof, wherein, unless otherwise stated, each of m, $R^1$, $R^2$, $R^3$, Z and $Q^2$ has any of the meanings defined hereinbefore or in any of the paragraphs (a) to (o) immediately hereinbefore.

Further particular novel compounds of the invention include, for example, pyrimidine derivatives of the Formula IV, or pharmaceutically-acceptable salts thereof, wherein, unless otherwise stated, each of m, $R^1$, $R^2$, $R^3$, Z and $Q^2$ has any of the meanings defined hereinbefore or in any of the paragraphs (a) to (o) immediately hereinbefore and $Y^1$ has any of the meanings defined hereinbefore or in paragraphs (a) to (c) hereinafter:

(a) bicyclic rings formed by the fusion of ring $Y^1$ to the adjacent pyrimidine ring include thieno[3,2-d]pyrimidin-4-yl, thieno[2,3-d]pyrimidin-4-yl, thiazolo[5,4-d]pyrimidin-7-yl, pyrido[2,3-d]pyrimidin-4-yl, pyrido[3,4-d]pyrimidin-4-yl, pyrido[4,3-d]pyrimidin-4-yl and pyrido[3,2-d]pyrimidin-4-yl;

(b) bicyclic rings formed by the fusion of ring $Y^1$ to the adjacent pyrimidine ring include thieno[3,2-d]pyrimidin-4-yl, pyrido[3,4-d]pyrimidin-4-yl, pyrido[4,3-d]pyrimidin-4-yl and pyrido[3,2-d]pyrimidin-4-yl; and (c) the bicyclic ring formed by the fusion of ring $Y^1$ to the adjacent pyrimidine ring is thieno[3,2-d]pyrimidin-4-yl.

Further particular novel compounds of the invention include, for example, quinazoline derivatives of the Formula V, or pharmaceutically-acceptable salts thereof, wherein, unless otherwise stated, each of m, $R^1$, $R^2$, $R^3$, Z and $Q^2$ has any of the meanings defined hereinbefore or in any of the paragraphs (a) to (o) immediately hereinbefore and $Y^2$ has any of the meanings defined hereinbefore or in paragraphs (a) and (b) hereinafter:

(a) tricyclic rings formed by the fusion of ring $Y^2$ to the adjacent quinazoline ring include 3H-imidazo[4,5-g]quinazolin-8-yl and 2-oxo-1,2-dihydro-3H-imidazo[4,5-g]quinazolin-8-yl; and (b) tricyclic rings formed by the fusion of ring $Y^2$ to the adjacent quinazoline ring include 3-methyl-3H-imidazo[4,5-g]quinazolin-8-yl and 3-methyl-2-oxo-1,2-dihydro-3H-imidazo[4,5-g]quinazolin-8-yl.

A preferred compound of the invention is a quinazoline derivative of the Formula II wherein:

m is 1 and the $R^1$ group is located at the 6- or 7-position and is selected from methoxy, benzyloxy, cyclopropylmethoxy, 2-dimethylaminoethoxy, 2-diethylaminoethoxy, 3-dimethylaminopropoxy, 3-diethylaminopropoxy, 2-(1,2,3-triazol-1-yl)ethoxy, 3-(1,2,3-triazol-1-yl)propoxy, pyrid-2-ylmethoxy, pyrid-3-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, 2-pyrrolidin-1-ylethoxy, 3-pyrrolidin-1-ylpropoxy, pyrrolidin-3-yloxy, N-methylpyrrolidin-3-yloxy, pyrrolidin-2-ylmethoxy, N-methylpyrrolidin-2-ylmethoxy, 2-pyrrolidin-2-ylethoxy, 2-(N-methylpyrrolidin-2-yl)ethoxy, 3-pyrrolidin-2-ylpropoxy, 3-(N-methylpyrrolidin-2-yl)propoxy, 2-(2-oxoimidazolidin-1-yl)ethoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, N-methylpiperidin-4-yloxy, piperidin-3-ylmethoxy, N-methylpiperidin-3-ylmethoxy, 2-piperidin-3-ylethoxy, 2-(N-methylpiperidin-3-yl)ethoxy, piperidin-4-ylmethoxy, N-methylpiperidin-4-ylmethoxy, 2-piperidin-4-ylethoxy, 2-(N-methylpiperidin-4-yl)ethoxy, 3-(4-aminomethylpiperidin-1-yl)propoxy, 3-(4-tert-butoxycarbonylaminopiperidin-1-yl)propoxy, 3-(4-carbamoylpiperidin-1-yl)propoxy, 2-piperazin-1-ylethoxy, 3-piperazin-1-ylpropoxy, 2-(4-methylpiperazin-1-yl)ethoxy, 3-(4-methylpiperazin-1-yl)propoxy, 4-morpholinobut-2-en-1-yloxy, 4-morpholinobut-2-yn-1-yloxy, 2-(2-morpholinoethoxy)ethoxy, 2-methylsulphonylethoxy, 3-methylsulphonylpropoxy, 2-[N-(2-methoxyethyl)-N-methylamino]ethoxy, 3-[N-(2-methoxyethyl)-N-methylamino]propoxy, 2-(2-methoxyethoxy)ethoxy, 3-methylamino-1-propynyl, 3-dimethylamino-1-propynyl, 3-diethylamino-1-propynyl, 6-methylamino-1-hexynyl, 6-dimethylamino-1-hexynyl, 3-(pyrrolidin-1-yl)-1-propynyl, 3-(piperidino)-1-propynyl, 3-(morpholino)-1-propynyl, 3-(4-methylpiperazin-1-yl)-1-propynyl, 6-(pyrrolidin-1-yl)-1-hexynyl, 6-(piperidino)-1-hexynyl, 6-(morpholino)-1-hexynyl, 6-(4-methylpiperazin-1-yl, 1-hexynyl, piperazin-1-yl, 4-methylpiperazin-1-yl, 3-imidazol-1-ylpropylamino, 3-pyrrolidin-1-ylpropylamino, 3-morpholinopropylamino, 3-piperidinopropylamino and 3-piperazin-1-ylpropylamino, or m is 2 and the $R^1$ groups are located at the 6 and 7-positions, one $R^1$ group is located at the 6 or 7-position and is selected from the groups defined immediately hereinbefore and the other $R^1$ group is a methoxy group;

$R^2$ is hydrogen or methyl;

$R^3$ is hydrogen;

Z is O, S, NH or N(Et); and $Q^2$ is phenyl, benzyl or phenethyl which optionally bears 1, 2 or 3 substituents, which may be the same or different, selected from fluoro, chloro, bromo, trifluoromethyl, nitro, methyl, ethyl and methoxy provided that al least one substituent is located at an ortho position;

or a pharmaceutically-acceptable acid-addition salt thereof; and provided that 1-(6,7-dimethoxyquinazolin-4-yl)-3-phenylurea is excluded.

A further preferred compound of the invention is a quinazoline derivative of the Formula II wherein:

m is 1 or 2 and the $R^1$ groups, which may be the same or different, are located at the 6- and/or 7-positions and are selected from methoxy, benzyloxy, 2-(1,2,3-triazol-1-yl)ethoxy, 3-(1,2,3-triazol-1-yl)propoxy, pyrid-2-ylmethoxy, pyrid-3-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, 2-pyrrolidin-1-ylethoxy, 3-pyrrolidin-1-ylpropoxy, pyrrolidin-3-yloxy, 1-methylpyrrolidin-3-yloxy, pyrrolidin-2-ylmethoxy, 1-methylpyrrolidin-2-ylmethoxy, 2-pyrrolidin-2-ylethoxy, 2-(1-methylpyrrolidin-2-yl)ethoxy, 3-pyrrolidin-2-ylpropoxy, 3-(1-methylpyrrolidin-2-yl)propoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-pipridinoethoxy, 3-piperidinopropoxy, piperidin-3-yloxy, piperidin-4-yloxy, 1-methylpiperidin-4-yloxy, piperidin-3-ylmethoxy, 1-methylpiperidin-3-ylmethoxy, 2-piperidin-3-ylethoxy, 2-(1-methylpiperidin-3-yl)ethoxy, piperidin-4-ylmethoxy, N-methylpiperidin-4-ylmethoxy, 2-piperidin-4-ylethoxy, 2-(N-methylpiperidin-4-yl)ethoxy, 2-piperazin-1-ylethoxy, 3-piperazin-1-ylpropoxy, 2-(4-methylpiperazin-1-yl)ethoxy, 3-(4-methylpiperazin-1-yl)propoxy, 4-morpholinobut-2-en-1-yloxy, 4-morpholinobut-2-yn-1-yloxy, 2-methylsulphonylethoxy, 3-methylsulphonylpropoxy, 2-[N-(2-methoxyethyl)-N-methylamino]ethoxy and 3-[N-(2-methoxyethyl)-N-methylamino]propoxy;

$R^2$ is hydrogen or methyl;

$R^3$ is hydrogen;

Z is O; and $Q^2$ is phenyl, benzyl or phenethyl which optionally bears 1, 2 or 3 substituents, which may be the same or different, selected from fluoro, chloro, bromo, trifluoromethyl and methyl;

or a pharmaceutically-acceptable acid-addition salt thereof; provided that 1-(6,7-dimethoxyquinazolin-4-yl)-3-phenylurea is excluded.

A further preferred compound of the invention is a quinazoline derivative of the Formula II wherein:

m is 1 and the $R^1$ group is located at the 7-position and is selected from 3-(1,2,3-triazol-1-yl)propoxy, 2-pyrid-4-ylethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-ylethoxy, 3-(1,1-dioxotetrahydro-4H-1,4-thiazin-4-yl)propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, 2-(4-methylpiperazin-1-yl,ethoxy, 3-(4-methylpiperazin-1-yl)propoxy, 4-pyrrolidin-1-ylbut-2-en-1-yloxy, 4-morpholinobut-2-en-1-yloxy, 4-morpholinobut-2-yn-1-yloxy, 3-methylsulphonylpropoxy and 2-[N-(2-methoxyethyl)-N-methylamino]ethoxy;

or m is 2 and one $R^1$ group is located at the 7-position and is selected from the groups defined immediately hereinbefore and the other $R^1$ group is a 6-methoxy group;

$R^2$ is hydrogen or methyl;

$R^3$ is hydrogen;

Z is O, S, NH or N(Et); and $Q^2$ is phenyl which bears 1, 2 or 3 substituents, which may be the sane or different, selected from fluoro, chloro, bromo, trifluoromethyl, nitro, methyl, ethyl and methoxy provided that at least one substituent is located at an ortho position;

or a pharmaceutically-acceptable acid-addition salt thereof.

A further preferred compound of the invention is a quinazoline derivative of the Formula II wherein:

m is 1 and the $R^1$ group is located at the 7-position and is selected from 3-(1,2,3-triazol-1-yl)propoxy, 2-pyrid-4-ylethoxy, 3-pyrrolidin-1-ylpropoxy, 3-morpholinopropoxy, 3-(1,1-dioxotetrahydro-4H-1,4-thiazin-4-yl)propoxy, 2-piperidinoethoxy, 3-piperidinopropoxy, N-methylpiperidin-4-ylmethoxy, 3-(4-methylpiperazin-1-yl)propoxy, 4-morpholinobut-2-en-1-yloxy, 4-morpholinobut-2-yn-1-yloxy, 3-methylsulphonylpropoxy and 2-[N-2-methoxyethyl)-N-methylamino]ethoxy;

or m is 2 and one $R^1$ group is located at the 7-position and is selected from the groups defined immediately hereinbefore and the other $R^1$ group is a 6-methoxy group;

$R^2$ is hydrogen or methyl;

$R^3$ is hydrogen;

Z is O; and $Q^2$ is phenyl which bears 1, 2 or 3 substituents, which may be the same or different, selected from fluoro, chloro, bromo and trifluoromethyl provided that at least one substituent is located at an ortho position;

or a pharmaceutically-acceptable acid-addition salt thereof.

A particular preferred compound of the invention is, for example, a quinazoline derivative of the Formula II selected from:

1-(2,6-dichlorophenyl)-3-[7-(3-morpholinopropoxy)quinazolin-4-yl]urea and 1-(2,6-dichlorophenyl)-3-{7-[3-(1,1-dioxotetrahydro-4H-1,4-thiazin-4-yl)propoxy]quinazolin-4-yl}urea;

or a pharmaceutically-acceptable acid-addition salt thereof.

A further particular preferred compound of the invention is, for example, a quinazoline derivative of the Formula II selected from:

1-benzyl-3-[6-methoxy-7-(1-methylpiperidin-4-ylmethoxy)quinazolin-4-yl]urea and 1-phenethyl-3-[6-methoxy-7-(1-methylpiperidin-4-ylmethoxy)quinazolin-4-yl]urea;

or a pharmaceutically-acceptable acid-addition salt thereof.

A further particular preferred compound of the invention is, for example, a quinazoline derivative of the Formula II selected from:

1-(2,6-dichlorophenyl)-3-[6-methoxy-7-(1-methylpiperidin-4-ylmethoxy)quinazolin-4-yl]urea and 1-(2,6-difluorophenyl)-3-[6-methoxy-7-(1-methylpiperidin-4-ylmethoxy)quinazolin-4-yl]urea;

or a pharmaceutically-acceptable acid-addition salt thereof.

A further particular preferred compound of the invention is, for example, a quinazoline derivative of the Formula II selected from:

1-(2,6-dimethylphenyl)-3-[6-methoxy-7-(N-methylpiperidin-4-ylmethoxy)quinazolin-4-yl]urea, 1-(2-chloro-6-methylphenyl)-3-[6-methoxy-7-(N-methylpiperidin-4-ylmethoxy)quinazolin-4-yl]urea;

1-(2,6-difluorophenyl)-3-[6-methoxy-7-(3-morpholinopropoxy)quinazolin-4-yl]urea;

1-(2,6-difluorophenyl)-3-[6-methoxy-7-[3-(4-methylpiperazin-1-yl)propoxy]quinazolin-4-yl]urea;

1-(2,6-dimethylphenyl)-3-[6-methoxy-7-[3-(4-methylpiperazin-1-yl)propoxy]quinazolin-4-yl]urea;

1-(2,6-dimethylphenyl)-3-[6-methoxy-7-(3-piperidinopropoxy)quinazolin-4-yl]urea;

1-(2,6-dimethylphenyl)-3-[6-methoxy-7-(N-methylpiperidin-4-ylmethoxy)quinazolin-4-yl]thiourea and 1-(2-chloro-6-methylphenyl)-3-[6-methoxy-7-(3-pyrrolidin-1-ylpropoxy)quinazolin-4-yl]guanidine;

or a pharmaceutically-acceptable acid-addition salt thereof.

A further preferred compound of the invention is a pyrimidine derivative of the Formula IV wherein the fusion of ring $Y^1$ to the adjacent pyrimidine ring forms a thieno[3,2-d]pyrimidin-4-yl group;

m is 0, or m is 1 and the $R^1$ group is a methyl, ethyl, vinyl or ethynyl group which is located at the 6-position and bears a substituent selected from carboxy, carbamoyl, N-(2-methylaminoethyl)carbamoyl, N-(2-dimethylaminoethyl)carbamoyl, N-(3-methylaminopropyl)carbamoyl or N-(3-dimethylaminopropyl)carbamoyl, or from a group of the formula:

$Q^4$—$X^2$— wherein $X^2$ is NHCO or N(Me)CO and $Q^4$ is 2-imidazol-1-ylethyl, 3-imidazol-1-ylpropyl, 2-pyridylmethyl, 4-pyridylmethyl, 2-pyrid-2-ylethyl, 2-pyrrolidin-1-ylethyl, 2-(2-oxopyrrolidin-1-yl)ethyl, 3-pyrrolidin-1-ylpropyl, 3-(2-oxopyrrolidin-1-yl)propyl, pyrrolidin-2-ylmethyl, 1-methylpyrrolidin-2-ylmethyl, 2-pyrrolidin-2-ylethyl, 2-(1-methylpyrrolidin-2-yl)ethyl, 3-pyrrolidin-2-ylpropyl, 3-(1-methylpyrrolidin-2-yl)propyl, 2-morpholinoethyl, 3-morpholinopropyl, 2-piperidinoethyl, 3-piperidinopropyl, piperidin-3-ylmethyl, 1-methylpiperidin-3-ylmethyl, 2-piperidin-3-ylethyl, 2-(1-methylpiperidin-3-yl)ethyl, piperidinylmethyl, 1-methylpiperidin-4-ylmethyl, 2-piperidin-4-ylethyl, 2-(1-methylpiperidin-4-yl)ethyl, 2-piperazin-1-ylethyl, 2-(4-methylpiperazin-1-yl)ethyl, 3-piperazin-1-ylpropyl or 3-(4-methylpiperazin-1-yl)propyl, $R^2$ is hydrogen or methyl;

$R^3$ is hydrogen;

Z is O; and $Q^2$ is phenyl, benzyl or phenethyl which optionally bears 1, 2 or 3 substituents, which may be the same or different, selected from fluoro, chloro, bromo, trifluoromethyl and methyl;

or a pharmaceutically-acceptable acid-addition salt thereof.

A further preferred compound of the invention is a pyrimidine derivative of the Formula IV wherein the fusion of ring $Y^1$ to the adjacent pyrimidine ring forms a thieno[3,2-d]pyrimidin-4-yl group;

m is 0, or m is 1 and the $R^1$ group is a vinyl group located at the 6-position which bears at the terminal $CH_2$= position a substituent selected from N-(2-dimethylaminoethyl)carbamoyl or N-(3-dimethylaminopropyl)carbamoyl, or from a group of the formula:

$Q^4$—$X^2$— wherein $X^2$ is NHCO or N(Me)CO and $Q^4$ is 2-pyridylmethyl, 4-pyridylmethyl, 2-pyrid-2-ylethyl, 2-pyrrolidin-1-ylethyl, 3-(2-oxopyrrolidin-1-yl)propyl, 3-morpholinopropyl, 2-piperidinoethyl or 3-(4-methylpiperazin-1-yl)propyl, $R^2$ is hydrogen or methyl;

$R^3$ is hydrogen;

Z is O; and $Q^2$ is phenyl which bears 1, 2 or 3 substituents, which may be the same or different, selected from fluoro, chloro, bromo and trifluoromethyl provided that at least one substituent is located at the ortho position;

or a pharmaceutically-acceptable acid-addition salt thereof.

A particular preferred compound of this aspect of the invention is, for example, a pyrimidine derivative of the Formula II selected from:

1-(2,6-dichlorophenyl)-3-(thieno[3,2-d]pyrimidin-4-yl)urea and (E)-3-{4-[3-(2,6-dichlorophenyl)ureido]thieno[3,2-d]pyrimidin-6-yl}-N-(3-dimethylaminopropyl)acrylamide;

or a pharmaceutically-acceptable acid-addition salt thereof.

A quinazoline derivative of the Formula I, or a pharmaceutically-acceptable salt thereof, may be prepared by any process known to be applicable to the preparation of chemically-related compounds. Such processes, when used to prepare a quinazoline derivative of the Formula I are provided as a further feature of the invention and are illustrated by the following representative process variants in which, unless otherwise stated, $Q^1$, $R^2$, Z, $R^3$ and $Q^2$ have any of the meanings defined hereinbefore. Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

(a) For those compounds of the Formula I wherein $R^3$ is hydrogen and Z is oxygen the reaction, conveniently in the presence of a suitable base, of an amine of the Formula VI $Q^1$—NHR$^2$               VI wherein $Q^1$ and $R^2$ have any of the meanings defined hereinbefore except that any functional group is protected if necessary, with an isocyanate of the Formula VII, or a conventional chemical equivalent thereof or a conventional chemical precusor thereof,

O=C=N—$Q^2$               VII wherein $Q^2$ has any of the meanings defined hereinbefore except that any functional group is protected if necessary, whereafter any protecting group that is present is removed by conventional means.

A suitable base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate, alkoxide or hydroxide, for example sodium carbonate, potassium carbonate, calcium carbonate, sodium ethoxide, potassium tert-butoxide, sodium hydroxide or potassium hydroxide, or, for example, an alkali metal hydride, for example sodium hydride or potassium hydride, or an organometallic base such as an alkyl-lithium, for example n-butyl-lithium or a dialkylamino-lithium, for example lithium di-isopropylamide.

The reaction is conveniently carried out in the presence of a suitable inert solvent or diluent, for example a halogenated solvent such as methylene chloride, chloroform or carbon tetrachloride, an ether such as tetrahydrofuran or 1,4-dioxan, or a dipolar aprotic solvent such as acetonitrile, N,N-dimethylformamide, N,N-dimethylacetamide, N-methylpyrrolidin-2-one or dimethylsulphoxide. The reaction is conveniently carried out at a temperature in the range, for example, 10 to 150° C., preferably in the range 20 to 75° C.

A suitable conventional chemical equivalent of an isocyanate of the Formula VII is, for example, a compound of the Formula VIII

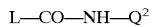 VIII wherein $Q^2$ has any of the meanings defined hereinbefore except that any functional group is protected if necessary, and L is a suitable displaceable or leaving group. On treatment with a suitable base as defined hereinbefore, the compound of the Formula VIII reacts to form the desired isocyanate of the Formula VII.

A suitable displaceable or leaving group L is, for example, a halogeno, alkoxy, aryloxy or sulphonyloxy group, for example a chloro, bromo, methoxy, phenoxy, methanesulphonyloxy or toluene-4-sulphonyloxy group.

A suitable conventional chemical precursor of an isocyanate of the Formula VII is, for example, an acyl azide of the Formula IX

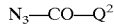 IX wherein $Q^2$ has any of the meanings defined hereinbefore except that any functional group is protected if necessary. On thermal or photolytic treatment the acyl azide of the Formula IX decomposes and rearranges to form the desired isocyanate of the Formula VII.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1–20 carbon atoms). Examples of carboxy protecting groups include straight or branched chain (1–12C) alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl) silyl groups (for example triethylsilyl and tert-butyldimethylsilyl); tri(lower alkyl)silyl-lower alkyl groups (for example trimethylsilylethyl); and (2–6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

The reader is referred to Advanced Organic Chemistry, 4th Edition, by J. March, published by John Wiley & Sons 1992, for general guidance on reaction conditions and reagents and to Protective Groups in Organic Synthesis, $2^{nd}$ Edition, by T. Green et al., also published by John Wiley & Son, for general guidance on protecting groups.

When L is, for example, a chloro group, the compound of the Formula VIII may be prepared by, for example, the reaction, conveniently in the presence of a suitable base as defined hereinbefore, of phosgene with an amine of the Formula X.

 X

The compound of the Formula IX may be prepared by, for example, the reaction of a metal azide such as sodium azide with a compound of the Formula XI.

 XI (b) For those compounds of the Formula I wherein $R^3$ is hydrogen and Z is sulphur, the reaction, conveniently in the presence of a suitable base as defined hereinbefore, of an amine of the Formula VI

    VI wherein $Q^1$ and $R^2$ have any of the meanings defined hereinbefore except that any functional group is protected if necessary, with an isothiocyanate of the Formula XII, or a conventional chemical equivalent thereof or a conventional chemical precusor thereof,

    XII wherein $Q^2$ has any of the meanings defined hereinbefore except that any functional group is protected if necessary, whereafter any protecting group that is present is removed by conventional means.

A suitable conventional chemical equivalent of an isothiocyanate of the Formula XII is, for example, a compound of the Formula XIII

    XIII wherein $Q^2$ has any of the meanings defined hereinbefore except that any functional group is protected if necessary, and L is a suitable displaceable group as defined hereinbefore. On treatment with a suitable base as defined hereinbefore, the compound of the Formula XIII reacts to form the desired isothiocyanate of the Formula XII.

A suitable conventional chemical precursor of an isothiocyanate of the Formula XII is, for example, an acyl azide of the Formula XIV

    XIV wherein $Q^2$ has any of the meanings defined hereinbefore except that any functional group is protected if necessary. On thermal or photolytic treatment the thioacyl azide of the Formula XIV decomposes and rearranges to form the desired isothiocyanate of the Formula XII.

When L is, for example, a chloro group, the compound of the Formula XIII may be prepared by, for example, the reaction, conveniently in the presence of a suitable base as defined hereinbefore, of thiophosgene with an amine of the Formula X.

    X

The compound of the Formula XIV may be prepared by, for example, the reaction of a metal azide such as sodium azide with a compound of the Formula XV.

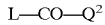    XV (c) For those compounds of the Formula I wherein $R^2$ is hydrogen and Z is oxygen, the reaction, conveniently in the presence of a suitable base, of an amine of the Formula XVI

    XVI wherein $Q^2$ and $R^3$ have any of the meanings defined hereinbefore except that any functional group is protected if necessary, with an isocyanate of the Formula XVII, or a conventional chemical equivalent thereof or a conventional chemical precusor thereof,

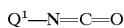    XVII wherein $Q^1$ has any of the meanings defined hereinbefore except that any functional group is protected if necessary, whereafter any protecting group that is present is removed by conventional means.

A suitable conventional chemical equivalent of an isocyanate of the Formula XVII is, for example, a compound of the Formula XVIII

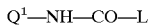    XVIII wherein $Q^1$ has any of the meanings defined hereinbefore except that any functional group is protected if necessary, and L is a suitable displaceable group as defined hereinbefore. On treatment with a suitable base as defined hereinbefore, the compound of the Formula XVIII reacts to form the desired isocyanate of the Formula XVII.

A suitable conventional chemical precursor of an isocyanate of the Formula XVII is, for example, an acyl azide of the Formula XIX

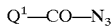    XIX wherein $Q^1$ has any of the meanings defined hereinbefore except that any functional group is protected if necessary. On thermal or photolytic treatment the thioacyl azide of the Formula XIX decomposes and rearranges to form the desired isocyanate of the Formula XVII.

When L is, for example, a chloro group, the compound of the Formula XVIII may be prepared by, for example, the reaction, conveniently in the presence of a suitable base as defined hereinbefore, of phosgene with an amine of the Formula XX.

    XX

The compound of the Formula XIX may be prepared by, for example, the reaction of a metal azide such as sodium azide with a compound of the Formula XXI.

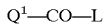    XXI (d) For those compounds of the Formula I wherein $R^2$ is hydrogen and Z is sulphur, the reaction, conveniently in the presence of a suitable base, of an amine of the Formula XVI

    XVI wherein $Q^2$ and $R^3$ have any of the meanings defined hereinbefore except that any functional group is protected if necessary, with an isothiocyanate of the Formula XXII, or a conventional chemical equivalent thereof or a conventional chemical precusor thereof,

    XXII wherein $Q^1$ has any of the meanings defined hereinbefore except that any functional group is protected if necessary, whereafter any protecting group that is present is removed by conventional means.

A suitable conventional chemical equivalent of an isothiocyanate of the Formula XXII is, for example, a compound of the Formula XXIII

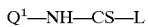    XXIII wherein $Q^1$ has any of the meanings defined hereinbefore except that any functional group is protected if necessary, and L is a suitable displaceable group as defined hereinbefore. On treatment with a suitable base as defined hereinbefore, the compound of the Formula XXIII reacts to form to desired isothiocyanate of the Formula XXII.

A suitable conventional chemical precursor of an isothiocyanate of the Formula XXII is, for example, an acyl azide of the Formula XXIV $$Q^1\text{—}CS\text{—}N_3 \qquad\qquad XXIV$$

wherein $Q^1$ has any of the meanings defined hereinbefore except that any functional group is protected if necessary. On thermal or photolytic treatment the thioacyl azide of the Formula XXIV decomposes and rearranges to form the desired isothiocyanate of the Formula XXII.

When L is, for example, a chloro group, the compound of the Formula XXIII may be prepared by, for example, the reaction, conveniently in the presence of a suitable base as defined hereinbefore, of thiophosgene with an amine of the Formula XX.

$$Q^1\text{—}NH_2 \qquad\qquad XX$$

The compound of the Formula XXIV may be prepared by, for example, the reaction of a metal azide such as sodium azide with a compound of the Formula XXV.

$$Q^1\text{—}CS\text{—}L \qquad\qquad XXV$$

(e) For those compounds of the Formula I wherein a substituent on $Q^1$ or $Q^2$ contains an alkylcarbamoyl group or a substituted alkylcarbamoyl group, the reaction of the corresponding compound of Formula I wherein a substituent on $Q^1$ or $Q^2$ is a carboxy group, or a reactive derivative thereof, with an amine or substituted amine as appropriate.

A suitable reactive derivative of a compound of Formula I wherein a substituent on $Q^1$ or $Q^2$ is a carboxy group is, for example, an acyl halide, for example an acyl chloride formed by the reaction of the acid and an inorganic acid chloride, for example thionyl chloride; a mixed anhydride, for example an anhydride formed by the reaction of the acid and a chloroformate such as isobutyl chloroformate; an active ester, for example an ester formed by the reaction of the acid and a phenol such as pentafluorophenol, an ester formed by the reaction of the acid and an ester such as pentafluorophenyl trifluoroacetate or an ester formed by the reaction of the acid and an alcohol such as N-hydroxybenzotriazole; an acyl azide, for example an azide formed by the reaction of the acid and an azide such as diphenylphosphoryl azide; an acyl cyanide, for example a cyanide formed by the reaction of an acid and a cyanide such as diethylphosphoryl cyanide; or the product of the reaction of the acid and a carbodiimide such as dicyclohexylcarbodiimide or 1-(3-dimethylaminopropyl)-3-ethylcarbodiimide.

The reaction is conveniently carried out in the presence of a suitable base as defined hereinbefore and in the presence of a suitable inert solvent or diluent as defined hereinbefore.

Typically a carbodiimide coupling reagent is used in the presence of an organic solvent (preferably an anhydrous polar aprotic organic solvent) at a non-extreme temperature, for example in the region −10 to 40° C., typically at ambient temperature of about 20° C.

A compound of Formula I wherein a substituent on $Q^1$ or $Q^2$ is a carboxy group may conveniently be prepared by the cleavage of the corresponding ester such as a (1–12C)alkyl ester, for example by acid-, base- metal- or enzymatically-catalysed cleavage.

(f) For those compounds of the Formula I wherein a substituent on $Q^1$ or $Q^2$ contains an amino-(1–6C)alkyl group, the cleavage of the corresponding compound of Formula I wherein a substituent on $Q^1$or $Q^2$ is a protected amino-(1–6C)alkyl group.

Suitable protecting groups for an amino-(1–6C)alkyl group are, for example, any of the protecting groups disclosed hereinbefore for an amino group. Suitable methods for the cleavage of such amino protecting groups are also disclosed hereinbefore. In particular, a suitable protecting group is a lower alkoxycarbonyl group such as a tert-butoxycarbonyl group which may be cleaved under conventional reaction conditions such as under acid-catalysed hydrolysis.

(g) For those compounds of the Formula I wherein Z is a $N(R^{11})$ group wherein $R^{11}$ is hydrogen or (1–6C)alkyl, the reaction, conveniently in the presence of a suitable metallic salt catalyst, of a thiourea of the Formula I wherein $Q^1$, $Q^2$, $R^2$ and $R^3$ have any of the meanings defined hereinbefore except that any functional group is protected if necessary and Z is sulphur, with an amine of formula $R^{11}NH_2$, whereafter any protecting group that is present is removed by conventional means.

A suitable metallic salt catalyst is, for example, a mercuric salt such as mercuric(II) oxide and the reaction is conveniently carried out in the presence of a suitable inert solvent or diluent as defined hereinbefore.

(h) For those compounds of the Formula I wherein a substituent on $Q^1$ or $Q^2$ contains an amino group, the reduction of a corresponding compound of Formula I wherein a substituent on $Q^1$ or $Q^2$ contains a nitro group.

Typical reaction conditions include the use of ammonium formate or hydrogen gas in the presence of a catalyst, for example a metallic catalyst such as palladium-on-carbon. Alternatively a dissolving metal reduction may be carried out, for example using iron in the presence of an acid, for example an inorganic or organic acid such as hydrochloric, hydrobromic, sulphuric or acetic acid. The reaction is conveniently carried out in the presence of an organic solvent (preferably a polar protic solvent) and preferably with heating, for example to about 60° C. Any functional groups are protected and deprotected as necessary.

When a pharmaceutically-acceptable salt of a quinazoline derivative of the Formula I is required, for example an acid-addition salt, it may be obtained by, for example, reaction of said quinazoline derivative with a suitable acid using a conventional procedure.

Biological Assays

The following assays can be used to measure the effects of the compounds of the present invention as $p56^{lck}$ inhibitors, as inhibitors of T cell activation, as inhibitors of cytokine production in mice and as inhibitors of transplant rejection.

(a) In Vitro Enzyme Assay

The ability of test compounds to inhibit phosphorylation by the enzyme $p56^{lck}$ of a tyrosine-containing polypeptide substrate was assessed using a conventional Elisa assay.

The following conventional procedure was used to obtain $p56^{lck}$ enzyme. An EcoRI/NotI fragment containing the entire coding sequence of $p56^{lck}$ was generated by the technique of polymers chain reaction (PCR) from Incyte clone No. 2829606. A 6-His tag was added to the sequence at the N-terminus during the PCR stage. Conventional sequence, analysis identified a number of changes compared to the published sequence and this were found also to have been present in the original Incyte template. To achieve expression of the enzyme, the PCR fragment was inserted downstream of the polyhedrin promotor of pFASTBAC1 (Life Techinologies Limited, Paisley, UK, Catalogue No. 10360-014). A recombinant Baculovirus was constructed using the Bac-to-Bac system (Life Technologies Limited).

High Five insect cells (Invitrogen BV, PO Box 2312, 9704 CH Groningen, The Netherlands, Catalogue No. B855-02) were infected with the recombinant Baculovirus at a multiplicity of infection of 1 and incubated for 48 hours. The cells were harvested. Groups of $1.6 \times 10^9$ cells were lysed by incubation in 20 mM Hepes pH7.5 buffer containing 10% glycerol, 1% Triton-X-100, magnesium chloride (1.5 mM), ethylene glycol bisthaminoethyl ether N,N,N',N'-tetraactic acid) (EGTA, 1 mM), sodium vanadate (1 mM), sodium fluoride (10 mM), imidazole (5 mM), sodium chloride (150 mM), phenylmethanesulphonyl fluoride (0.1 mM), pepstatin (1 mg/ml) and leupeptin (1 mg/ml). A soluble fraction was obtained by centrifugation and His-p56$^{lck}$ was purified by column chromatography on a 1 ml Ni-NTA agarose column (Qiagen Limited, Crawley, West Sussex, UK). The protein was eluted using the above-mentioned buffer except that imidazole (100 mM) was also present. The p56$^{lck}$ enzyme so obtained was stored at −80° C.

Substrate solution [100 µl of a 24 µg/ml solution of the polyamino acid Poly(Glu, Ala, Tyr) 6:3:1 (Sigma Catalogue No. P3899) in phosphate buffered salin (PBS)] was added to each well of a Nunc 96-well immunoplate (Catalogue No. 439454) and the plate was sealed and stored at 4° C. for 16 hours. The process of substrate solution was discarded, the substrate-coated wells were washed with Hepes pH7.4 buffer (50 mM, 300 µl) and blotted dry. Each test compound was dissolved in DMSO and diluted to give a series of dilutions (from 100 µM to 0.0001 µM) of the compound in a 10:1 mixture of water and DMSO. Portions (25 µl) of each dilution of test compound were transferred to the 96-well assay plate. Aliquots (25 µl) of a 10:1 mixture of water and DMSO were added followed by aliquots (25 µl) of a mixture of adenosine triphosphate (ATP; 24 µl of a 1 mM aqueous solution) and manganese chloride (3 ml of a 40 mM aqueous solution).

p56$^{lck}$ enzyme (0.3 µl of a 0.5 mg/ml stock solution) was diluted in a mixture of Hepes pH 7.4 buffer (200 mM, 3 ml), sodium orthovanadate (2 mM, 0.6 ml), 1% Triton X-100 (0.6 ml), dithiothreitol (25 mM, 48 µl) and distilled water (1.8 ml). Aliquots (50 µl) of the resultant solution were transferred to each well in the assay plate and the plate was incubated at ambient temperature for 8 minutes. The wells were washed sequentially with two aliquots (300 µl) of phosphate-buffered saline (PBS) containing 0.1% Tween 20 (hereinafter PBS/T).

Aliquots (100 µl) were added to each well of a mixture of antiphosphotyrosine-4G10 monoclonal IgG2bk antibody (UBI Catalogue No. 05-321; 30 µl of a 50 µg/ml solution of the antibody in PBS/T), PBS/T (11 ml) and bovine serum albumin (BSA; Sigma Catalogue No. A6793; 55 mg) and the plate was incubated at ambient temperature for 1 hour. The wells were washed sequentially with two aliquots (300 µl) of PBS/T and blotted dry. Aliquots (100 µl) were added to each well of a mixture of sheep anti-mouse IgG-peroxidase antibody (Amersham Catalogue No. NXA931; 20µl), PBS/T (11 ml) and BSA (55 mg) and the plate was incubated at ambient temperature for 1 hour. The wells were washed sequentially with two aliquots (300 µl) of PBS/T and blotted dry.

Aliquots (100 µl) were added to each well of an ABTS solution [prepared by adding an 2,2'-azinobis(3-ethylbenzothiazolinesulphonic acid) (ABTS) tablet (50 mg; Boehringer Catalogue No. 1204521) to a mixture (50 mM) of phosphate-citrate pH5.0 buffer and 0.03% sodium perforate (obtained by adding a PCSB capsule (Sigma Catalogue No. P-4922) to distilled water (100 ml)]. The plate was incubated at ambient temperature for 1.5 hours and the absorbance at 405 nm was determined.

The extent of inhibition of the phosphorylation reaction at a range of concentrations of each test compound was determined and an $IC_{50}$ value was calculated.

(b) In Vitro T Cell Proliferation Assays

The ability of test compounds to inhibit T cell proliferation was assessed by using human peripheral blood mononuclear cells and stimulation of the T cells by way of the T cell receptor or other than by way of the T cell receptor.

Peripheral blood mononuclear cells (PBMC) were isolated from heparinised (10 units/ml heparin) human blood by density centrifugation (Lymphoprep™; Nycomed) spinning initially at 2000 rpm at ambient temperature for 20 minutes. Cells at the interphase were transferred to clean tubes, diluted 1:1 with RPMI 1640 medium (Gibco) and spun at 2000 rpm at ambient temperature for 10 minutes. The cell pellet was resuspended in RPMI 1640 medium and spun at 1400 rpm at ambient temperature for 10 minutes. The cell pellet was resuspended in RPMI 1640 medium and spun at 90 rpm at ambient temperature for 10 minutes to remove platelets. The prepared mononuclear cells were resuspended in an assay medium comprising RPMI 1640 culture medium supplemented with 50 units/ml penicillin, 50 µg/ml streptomycin, 1 mM glutamine and 10% beat-inactivated human AB serum.

Test compounds were solubilities in DMSO at a concentration of 10 mM and diluted 1:83.3 in assay medium. Aliquots (75 µl) were added to each well of a 96 well flat-bottomed tissue culture plate and subsequently serial 1 to 3 dilutions were made into assay medium giving final test concentrations in the range 0.1 to 30 µM. Control wells contained assay medium (50 µl) containing 1.2% DMSO. PBMCs (100 µl of a suspension of $2 \times 10^6$ cell/ml in assay medium) were added to each well and incubated for 1 hour at 37° C. in a humidified (5% CO2/95% air) incubator.

The extent of inhibition of T cell proliferation at a range of concentrations of each test compound was determined and an $IC_{50}$ value was calculated.

(b)(i) T Cell Receptor Stimulation

Aliquots (50 µl) of the T cell receptor stimulatory anti-CD3 antibody (Pharmingen Catalogue No. 30100D; 40 ng/ml in assay medium) were added to each well and the cells were incubated for 24 hours at 37° C. in a humidified (5% $CO_2$/95% air) incubator. Triturated thymidine (1 µCi per well) was added and the cells were incubated for up to a further 24 hours at 37° C. The cells were harvested onto a filter mat and radioactivity was counted using a Wallac 1450 Microbeta Plus liquid scintillation counter.

(b)(ii) Non T Cell Receptor Stimulation

Aliquots (50 µl) of a mixture of the cell stimulants PMA (phorbol-12-myrstate-13-acetate, Sigma Catalogue No. P8139; 40 ng/ml) and Ionomycin (Sigma Catalogue No. 10684; 1.2 µM) were added to each well and the cells were incubated and analysed as described in paragraph (b)(i).

(c) In Vivo Skin Graft Rejection Test

The ability of test compounds to inhibit rodent skin allograft rejection was assessed using analogous procedures to those disclosed by J. Magae et al., *Cellular Immunology*, 1996, 173, 276–281 and R. Tsuji et al., *J. Antibiot.*, 1992, 45, 1295 to assess the effect of cyclosporin A on T cell properties in vivo.

(d) Test as Anti-arthritic Agent

Activity of a test compound as an anti-arthritic agent was assessed as follows. Acid soluble native type II collagen has been shown to be arthritogenic in rats causing polyarthritis when administered in Freunds incomplete adjuvant by (D. E. Trentham et al. *J. Exp. Med.*, 1977, 146, 857). This is now known as collagen-induced arthritis (CIA) and similar conditions can be induced in mice and primates. CIA in DBA/1 mice as described by R. O. Williams et al., *Proc Natl. Acad Sci.* 1992, 89, 9784 and *Immunology*, 1995, 84, 433 is a tertiary model which can be used to demonstrate the anti-arthritic activity of a test compound.

Although the pharmacological properties of the compounds of the Formula I vary with structural change as expected, in general activity possessed by compounds of the Formula I, including those compounds excluded by way of one of the provisos in the definition hereinbefore, may be demonstrated at the following concentrations or doses in one or more of the above tests (a), (b), (c) and (d):

Test (a): $IC_{50}$ in the range, for example, 0.0001–5 $\mu$M;

Test (b)(i): $IC_{50}$ in the range, for example, 0.001–10 $\mu$M;

Test (b)(ii): $IC_{50}$ in the range, for example, 0.5→30 $\mu$M;

Test (c): activity in the range, for example, 0.1–100 mg/kg;

Test (d): activity in the range, for example, 1–100 mg/kg;

No physiologically-unacceptable toxicity was observed at the effective dose for compounds tested of the present invention. Accordingly no untoward toxicological effects are expected when a compound of Formula I, or a pharmaceutically-acceptable salt thereof, as defined hereinbefore but without the proviso that the group of formula Ic so formed is not a purine ring and including the compounds:

1-(6,7-dimethoxyquinazolin-4-yl)-3-phenylurea,

1-[5-(4-methoxyphenoxy)quinazolin-4-yl]-3-phenylurea,

1-[5-(4-methoxyphenoxy)quinazolin-4-yl]-3-(3-bromophenyl)urea,

1-[5-(4-methoxyphenoxy)quinazolin-4-yl]-3-(3-methoxyphenyl)urea, 1-phenyl-3-pyrazolo[3,4-d]pyrimidin-4-yl)urea, 1-(2-chlorophenyl)-3-(pyrazolo[3,4-d]pyrimidinyl)urea, 1-(3-chlorophenyl)-3-(pyrazolo[3,4-d]pyrimidin-4-yl)urea, 1-(4-chlorophenyl)-3-(pyrazolo[3,4-d]pyrimidin-4-yl)urea, 1-(2-fluorophenyl)-3-(pyrazolo[3,4-d]pyrimidin-4-yl)urea, 1-benzyl-3-(pyrazolo[3,4-d]pyrimidin-4-yl)urea and 1-(3-phenylpropyl)-3-(pyrazolo[3,4-d]pyrimidin-4-yl)urea, is administered at the dosage ranges defined hereinafter.

According to a further aspect of the invention there is provided a pharmaceutical composition which comprises a quinazoline derivative of the Formula I, or a pharmaceutically-acceptable thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insulation (for example as a finely divided powder) or for parent administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the Formula I for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration is however preferred, particularly in tablet form. Typically, unit dosage forms will contain about 0.5 mg to 0.5 g of a compound of this invention.

According to a further aspect of the invention there is provided a quinazoline derivative of the Formula I, or a pharmaceutically-acceptable salt thereof, as defined hereinbefore for use in a method of treatment of the human or animal body by therapy.

We have found that the compounds of the present invention are of use in the prevention or treatment of autoimmune diseases or medical conditions, for example T cell mediated disease such as transplant rejection, rheumatoid arthritis or multiple sclerosis. We have further found that these effects are believed to arise by virtue of inhibition of one or more of the multiple tyrosine-specific protein kinases which are involved in the early signal transduction steps which lead to full T cell activation, for example by way of inhibition of the enzyme $p56^{lck}$. Accordingly the compounds of the present invention are expected to be useful in the prevention or treatment of T cell mediated diseases or medical conditions. In particular the compounds of the present invention are expected to be useful in the prevention or treatment of those pathological conditions which are sensitive to inhibition of one or more of the multiple tyrosine-specific protein kinases which are involved in the early signal transduction steps which lead to T cell activation, for example by way of inhibition of $p56^{lck}$ tyrosine kinase. Further, the compounds of the present invention are expected to be useful in the prevention or treatment of those diseases or medical conditions which are mediated alone or in part by inhibition of the enzyme $p56^{lck}$, i.e. the compounds may be used to produce a $p56^{lck}$ enzyme inhibitory effect in a warm-blooded animal in need of such treatment. Specifically, the compounds of the present invention are expected to be useful in the prevention or treatment of autoimmune conditions or diseases such as inflammatory diseases (for example rheumatoid arthritis, inflammatory bowel disease, glomerulonephritis and lung fibrosis), multiple sclerosis, psoriasis, hypersensitivity reactions of the skin, atherosclerosis, restenosis, allergic asthma and insulin-dependent diabetes. In particular the compounds of the present invention are expected to be useful in the prevention or treatment of the acute rejection of transplanted tissue or organs.

Thus according to this aspect of the invention there is provided the use of a quinazoline derivative of the Formula I, or a pharmaceutically-acceptable salt thereof, as defined hereinbefore but without the proviso that the group of formula Ic so formed is not a purine ring and including the compounds:

1-(6,7-dimethoxyquinazolin-4-yl)-3-phenylurea,

1-[5-(4-methoxyphenoxy)quinazolin-4-yl]-3-phenylurea,

1-[5-(4-methoxyphenoxy)quinazolin-4-yl]-3-(3-bromophenyl)urea,

1-[5-(4-methoxyphenoxy)quinazolin-4-yl]-3-(3-methoxyphenyl)urea, 1-phenyl-3-(pyrazolo[3,4-d]pyrimidin-4-yl)urea, 1-(2-chlorophenyl)-3-(pyrazolo[3,4-d]pyrimidin-4-yl)urea, 1-(3-chlorophenyl)-3-(pyrazolo[3,4-d]pyrimidin-4-yl)urea, 1-(4-chlorophenyl)-3-(pyrazolo[3,4-d]pyrimidin-4-yl)urea, 1-(2-fluorophenyl)-3-(pyrazolo[3,4-d]pyrimidin-4-yl)urea, 1-benzyl-3-(pyrazolo[3,4-d]pyrimidin-4-yl)urea and 1-(3-phenylpropyl)-3-(pyrazolo[3,4-d]pyrimidin-4-yl)urea, in the manufacture of a medicament for use in the prevention or treatment of T cell mediated diseases or medical conditions in a warm-blooded animal such as man.

According to a further feature of this aspect of the invention them is provided a method for the prevention or treatment of T cell mediated diseases or medical conditions in a warm-blooded animal, such as man, in need of such treatment which comprises administering to said animal an effective amount of a quinazoline derivative of the Formula I, or a pharmaceutically-acceptable salt thereof, as defined hereinbefore but without the proviso that the group of formula Ic so formed is not a purine ring and including the compounds:

1-(6,7-dimethoxyquinazolin-4-yl)-3-phenylurea,

1-[5-(4-methoxyphenoxy)quinazolin-4-yl]-3-phenylurea,

1-[5-(4-methoxyphenoxy)quinazolin-4-yl]-3-(3-bromophenyl)urea,

1-[5-(4-methoxyphenoxy)quinazolin-4-yl]-3-(3-methoxyphenyl)urea, 1-phenyl-3-(pyrazolo[3,4-d]pyrimidin-4-yl)urea, 1-(2-chlorophenyl)-3-(pyrazolo[3,4-d]pyrimidin-4-yl)urea, 1-(3-chlorophenyl)-3-(pyrazolo[3,4-d]pyrimidin-4-yl)urea, 1-(4-chlorophenyl)-3-(pyrazolo[3,4-d]pyrimidin-4-yl)urea, 1-(2-fluorophenyl)-3-(pyrazolo[3,4-d]pyrimidin-4-yl)urea, 1-benzyl-3-(pyrazolo[3,4-d]pyrimidin-4-yl)urea and 1-(3-phenylpropyl)-3-(pyrazolo[3,4-d]pyrimidin-4-yl)urea.

According to a further feature of the invention there is provided the use of a quinazoline derivative of the Formula I, or a pharmaceutically-acceptable salt thereof, as defined immediately hereinbefore in the manufacture of a medicament for use in the prevention or treatment of those pathological conditions which are sensitive to inhibition of one or more of the multiple tyrosine-specific protein kinases which are involved in the early signal transduction steps which lead to T cell activation.

According to a further feature of the invention there is provided a method for the prevention or treatment of those pathological conditions which are sensitive to inhibition of one or more of the multiple tyrosine-specific protein kinases which are involved in the early signal transduction steps which lead to T cell activation which comprises administering to said animal an effective amount of a quinazoline derivative of the Formula I, or a pharmaceutically-acceptable salt thereof, as defined immediately hereinbefore.

As stated above the size of the dose required for the therapeutic or prophylactic treatment of T cell mediated disease will necessarily be varied depending on the host treated, the route of administration and the severity of the illness being treated. A unit dose in the range, for example, 0.1 mg/kg to 75 mg/kg body weight, preferably 0.1 mg/g to 30 mg/kg body weight, is envisaged, given if required in divided doses.

The compounds of this invention may be used in combination with other drugs and therapies used in the treatment of T cell mediated disease. For example, the compounds of the Formula I could be used in combination with drugs and therapies used in the treatment of autoimmune conditions or diseases such as inflammatory diseases (for example rheumatoid arthritis, inflammatory bowel disease, glomerulonephritis and lung fibrosis), multiple sclerosis, psoriasis, hypersensitivity reactions of the skin, atherosclerosis, restenosis, allergic asthma and insulin-dependent diabetes. In particular the compounds of the Formula I could be used in combination with drugs and therapies such as cyclosporin A used in the prevention or treatment of the acute rejection of transplanted organs.

For example, the compounds of the Formula I are of value in the treatment of certain inflammatory and non-inflammatory diseases which are currently treated with a cyclooxygenase-inhibitory non-steroidal anti-inflammatory drug (NSAID) such as indomethacin, ketorolac, acetylsalicyclic acid, ibuprofen, sulindac, tolmetin and piroxicam. Co-adminstration of a compound of the Formula I with a NSAID can result in a reduction of the quantity of the latter agent needed to produce a therapeutic effect. Thereby the likelihood of adverse side-effects from the NSAID such as gastrointestinal effects are reduced. Thus according to a further feature of the invention there is provided a pharmaceutical composition which comprises a compound of the Formula I, or a pharmaceutically-acceptable salt thereof, in conjunction or admixture with a cyclooxygenase inhibitory non-steroidal anti-inflammatory agent, and a pharmaceutically-acceptable diluent or carrier.

The compounds of the invention may also be used with anti-inflammatory agents such as an inhibitor of the enzyme 5-lipoxygenase. The compounds of the invention may also be used with anti-inflammatory agents such as an inhibitor of the enzyme COX-2 such as celecoxib or rofecoxib.

The compounds of the Formula I may also be used in the treatment of conditions such as rheumatoid arthritis in combination with antiarthritic agents such as gold, methotrexate, steroids and penicillinamine, and in conditions such as osteoarthritis in combination with steroids.

The compounds of the present invention may also be administered in degradative diseases, for example osteoarthritis, with chondroprotective, anti-degradative and/ or reparative agents such as Diacerhein, hyaluronic acid formulations such as Hyalan, Rumalon, Arteparon and glucosamine salts such as Antril.

The compounds of the Formula I may be used in the treatment of asthma in combination with antiasthmatic agents such as bronchodilators and leukotnene antagonists.

If formulated as a fixed dose such combination products employ the compounds of this invention within the dosage range described herein and the other pharmaceutically-active agent within its approved dosage range. Sequential use is contemplated when a combination formulation is inappropriate.

Although the compounds of the Formula I are primarily of value as therapeutic agents for use in warm-blooded animals (including man), they are also useful whenever it is required to inhibit the effects of T cell activation. Thus, they are useful as pharmacological standards for use in the development of new biological tests and in the search for new pharmacological agents.

The invention will now be illustrated in the following non-limiting Examples in which, unless otherwise stated:

(i) operations were carried out at ambient temperature, it, in die range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck. Darmstadt, Germany or high pressure liquid chromatography (HPLC) was performed on C18 reverse phase silica, for example on a Dynamax C-18 60Å preparative reversed-phase column;

(iv) yields, where present, arm given for illustration only and are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Jeol JNM EX 400 spectrometer operating at a field strength of 400 MHz, a Varian Gemini 2000 spectrometer operating at a field strength of 300 MHz or a Bruker AM300 spectrometer operating at a field strength of 300 MHz]; the following abbreviations have been used: s, singlet; d, doublet; t, triplet; q, quartet; m, multiplet; br, broad;

(vi) intermediates were not generally fully characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture; and (viii) the following abbreviations have been used:
DMF N,N-dimethylformamide
DMSO dimethylsulphoxide
THF tetrahydrofuran

EXAMPLE 1

1-(2,6-dichlorophenyl)-3-[6-methoxy-7-(N-methylpiperidin-4-ylmethoxy)quinazolin-4-yl]urea 2,6-Dichlorophenyl isocyanate (0.075 g) was added to a solution of 4-amino-6-methoxy-7-(methylpiperidin-4-ylmethoxy)quinazoline (0.093 g) in a mixture of methylene chloride (2 ml) and DMF (0.1 ml) and the reaction mixture was stirred at ambient temperature for 16 hours. The resultant solid was isolated, redissolved in a 20:1 mixture of methylene chloride and methanol and purified by column chromatography on silica using increasingly polar mixtures of methylene chloride, methanol and a 1% aqueous ammonium hydroxide solution as eluent. There was thus obtained the title compound as a white solid (0.029 g); NMR Spectrum: (DMSOd$_6$) 1.3–1.4 (m, 2H), 1.7–1.8 (m, 4H), 1.85 (t, 1H), 2.1 (s, 3H), 2.8 (d, 2H), 3.9 (s, 3H), 4.0 (br d, 2H), 7.3 (br s, 1H), 7.4 (d, 1H), 7.5 (s, 1H), 7.6 (s, 1H), 8.0 (br s, 1H), 8.7 (s, 1H); Mass Spectrum: M+H$^+$ 490, 492 and 494.

The 4-amino-6-methoxy-7-(N-methylpiperidinylmethoxy)quinazoline used as a starting material was prepared as follows:

A solution of di-tert-butyl dicarbonate (41.7 g) in ethyl acetate (75 ml) was added dropwise to a stirred solution of ethyl piperidinecarboxylate (30 g) in ethyl acetate (150 ml) which had been cooled to 0 to 5° C. in an ice-bath. The resultant mixture was stirred at ambient temperature for 48 hours. The mixture was poured into water (300 ml). The organic layer was separated, washed in turn with water (200 ml), 0.1N aqueous hydrochloric acid solution (200 ml), a saturated aqueous sodium bicarbonate solution (200 ml) and brine (200 ml), dried over magnesium sulphate and evaporated. There was thus obtained ethyl N-tert-butoxycarbonylpiperidine-4-caboxylate (48 g); NMR Spectrum: (CDCl$_3$) 1.25 (t, 3H), 1.45 (s, 9H), 1.55–1.7 (m, 2H), 1.8–2.0 (d, 2H), 2.35–2.5 (m, 1H), 2.7–2.95 (t, 2H), 3.9–4.1 (br s, 2H), 4.15 (q, 2H).

A solution of the material so obtained in THF (180 ml) was cooled at 0° C. and lithium aluminium hydride (1M solution in THF; 133 ml) was added dropwise. The mixture was stirred at 0° C. for 2 hours. Water (30 ml) and 2N aqueous sodium hydroxide solution (10 ml) were added in turn and the mixture was stirred for 15 minutes. The resultant mixture was filtered through diatomaceous earth and the solids were washed with ethyl acetate. The filtrate was washed in turn with water and with brine, dried over magnesium sulphate and evaporated. There was thus obtained N-tert-butoxycarbonyl-4-hydroxymethylpiperidine (36.3 g); NMR Spectrum: (CDCl$_3$) 1.05–1.2 (m, 2H), 1.35–1.55 (m, 10H), 1.6–1.8 (m, 2H), 2.6–2.8 (t, 2H), 3.4–3.6 (t, 2H), 4.0–4.2 (br s, 2H).

1,4-Diazabicyclo[2.2.2]octane (42.4 g) was added to a solution of N-tert-butoxycarbonyl-4-hydroxymethylpiperidine (52.5 g) in tert-butyl methyl ether (525 ml) and the mixture was stirred at ambient temperature for 15 minutes. The mixture was then cooled in an ice-bath to 5° C. and a solution of 4-toluenesulphonyl chloride (62.8 g) in tert-butyl methyl ether (525 ml) was added dropwise over 2 hours while maintaining the reaction temperature at approximately 0° C. The resultant mixture was allowed to warm to ambient temperature and was stirred for 1 hour. Petroleum ether (b.p. 60–80° C., 1 L) was added and the precipitate was removed by filtration. The filtrate was evaporated to give a solid residue which was dissolved in diethyl ether. The organic solution was washed in turn with 0.5N aqueous hydrochloric acid solution, water, a saturated aqueous sodium bicarbonate solution and brine, dried over magnesium sulphate and evaporated. There was thus obtained N-tert-butoxycarbonyl-4-(4-toluenesulphonyloxymethyl)piperidine (76.7 g), NMR Spectrum: (CDCl$_3$) 1.0–1.2 (m, 2H), 1.45 (s, 9H), 1.65 (d, 2H), 1.75–1.9 (m, 2H), 2.45 (s, 3H), 2.55–2.75 (m, 2H), 3.85 (d, 1H), 4.0–4.2 (br s, 2H), 7.35 (d, 2H), 7.8 (d, 2H).

A portion (40 g) of the material so obtained was added to a suspension of ethyl 4-hydroxy-3-methoxybenzoate (19.6 g) and potassium carbonate (28 g) in DMF (200 ml) and the resultant mixture was stirred and heated to 95° C. for 2.5 hours. The mixture was cooled to ambient temperature and partitioned between water and a mixture of ethyl acetate and diethyl ether. The organic layer was washed in turn with water and brine, dried over magnesium sulphate and evaporated. The resulting oil was crystallised from petroleum ether (b.p. 60–80° C.) and the suspension was stored overnight at 5° C. The resultant solid was collected by filtration, washed with petroleum ether and dried under vacuum. There was thus obtained ethyl 4(N-tert-butoxycarbonylpiperidin-4-ylmethoxy)-3-methoxybenzoate (35 g), m.p. 81–83° C.; NMR Spectrum: (CDCl$_3$) 1.2–1.35 (m, 2H), 1.4 (t, 3H), 1.48 (s, 9H), 1.8–1.9 (d, 2H), 2.0–2.15 (m, 2H), 2.75 (t, 2H), 3.9 (d, 2H), 3.95 (s, 3H), 4.05–4.25 (br s, 2H), 4.35 (q, 2H), 6.85 (d, 1H), 7.55 (s, 1H), 7.65 (d, 1H).

The material so obtained was dissolved in formic acid (35 ml), formaldehyde (12M, 37% in water, 35 ml) was added and the mixture was stirred and heated to 95° C. for 3 hours. The resultant mixture was evaporated. The residue was dissolved in methylene chloride and hydrogen chloride (3M solution in diethyl ether, 40 ml) was added. The mixture was diluted with diethyl ether and the mixture was triturated until a solid was formed. The solid was collected, washed with diethyl ether and dried under vacuum overnight at 50° C. The was thus obtained ethyl 3-methoxy-4-(N-methylpiperidin-4-ylmethoxy)benzoate (30.6 g), NMR Spectrum: (DMSOd$_6$) 1.29 (t, 3H), 1.5–1.7 (m, 2H), 1.95 (d, 2H), 2.0–2.15 (br s, 1H), 2.72 (s, 3H), 2.9–3.1 (m, 2H), 3.35–3.5 (br s, 2H), 3.85 (s, 3H), 3.9–4.05 (br s, 2H), 4.3 (q, 2H), 7.1 (d, 1H), 7.48 (s, 1H), 7.6 (d, 1H).

The material so obtained was dissolved in methylene chloride (75 ml) and the solution was cooled in an ice-bath to 0–5° C. Trifluoroacetate acid (37.5 ml) was added followed by the dropwise addition over 15 minutes of a solution of fuming nitric acid (24M; 7.42 ml) in methylene chloride (15 ml). The resultant solution was allowed to warm to ambient temperature and was stirred for 2 hours. Volatile materials were evaporated. The residue was dissolved in methylene chloride (50 ml) and the solution was cooled in an ice-bath to 0–5° C. Diethyl ether was added and the resultant precipitate was collected and dried under vacuum at 50° C. The solid was dissolved in methylene chloride (500 ml) and hydrogen chloride (3M solution in diethyl ether; 30 ml) was added followed by diethyl ether (500 ml). The resultant solid was collected and dried under vacuum at 50° C. There was thus obtained ethyl 5-methoxy-4-(N-methylpiperidin-4-ylmethoxy)-2-nitrobenzoate (28.4 g), NMR Spectrum: (DMSO$_6$) 1.3 (t, 3H), 1.45–1.65 (m, 2H), 1.75–2.1 (m, 3H), 2.75 (s, 3H), 29–3.05 (m, 2H), 3.4–3.5 (d, 2H), 3.95 (s, 3H), 4.05 (d, 2H), 4.3 (q, 2H), 7.32 (s, 1H), 7.66 (s, 1H).

A mixture of a portion (3.89 g) of the material so obtained, 10% platinum-on-activated carbon (50% wet, 0.389 g) and methanol (80 ml) was stirred under 1.8 atmospheres pressure of hydrogen until uptake of hydrogen processed. The mixture was filtered and the filtrate was evaporated. The residue was dissolved in water (30 ml) and basified to pH10 by the addition of a saturated aqueous sodium bicarbonate solution. The mixture was diluted with a 1:1 mixture of ethyl acetate and diethyl ether and the organic layer was separated. The aqueous layer was further extracted with a 1:1 mixture of ethyl acetate and diethyl ether and the organic extracts were combined, washed in turn with water and brine dried over magnesium sulphate and evaporated. The residue was triturated under a mixture of petroleum ether (b.p. 60–80° C.) and diethyl ether. The solid so obtained was isolated, washed with petroleum ether and dried under vacuum at 60° C. There was thus obtained ethyl 2-amino-5-methoxy-4-(N-methylpiperidinylmethoxy)benzoate (258 g), m.p. 111–112° C.; NMR Spectrum: (CDCl$_3$) 1.35 (t, 3H), 1.4–1.5 (m, 2H), 1.85 (m, 3H), 1.95 (t, 2H), 2.29 (s, 3H), 2.9 (d, 2H), 3.8 (s, 3H), 3.85 (d, 2H), 4.3 (q, 2H), 5.55(br s, 2H), 6.13 (s, 1H), 7.33 (s, 1H).

A mixture of ethyl 2-aminomethoxy-4-methylpiperidin-4-ylmethoxy)benzoate (16.1 g), formamidine acetic acid salt (5.2 g) and 2-methoxyethanol (160 ml) was stirred and heated at 115° C. for 2 hours. Further formamidine acetic acid salt (10.4 g) was added in portions every 30 minutes during 4 hours, and heating was continued for 30 minutes after the last addition. The resultant mixture was evaporated. The solid residue was stirred under a mixture of methylene chloride (50 ml) and ethanol (100 ml). The precipitate was removed by filtration and the filtrate was concentrated to a final volume of 100 ml. The resultant suspension was cooled to 5° C. The solid so obtained was collected, washed with cold ethanol and with diethyl ether and dried under vacuum at 60° C. There was thus obtained 6-methoxy-7-(N-methylpiperidin-4-ylmethoxy)-3,4-dihydroquinazolin-4-one (12.7 g); NMR Spectrum: (DMSOd$_6$) 1.25–1.4 (m, 2H), 1.75 (d, 2H), 1.9 (t, 1H), 1.9 (s, 3H), 2.16 (s, 2H), 2.8 (d, 2H), 3.9 (s, 3H), 4.0 (d, 2H), 7.11 (s, 1H), 7.44 (s, 1H), 7.97 (s, 1H).

A mixture of a portion (2.8 g) of the material so obtained, thionyl chloride (28 ml) and DMF (0.28 ml) was heated to reflux for 1 hour. The mixture was evaporated and the precipitate was triturated under diethyl ether. The resultant solid was isolated and washed with diethyl ether. The solid was then dissolved in methylene chloride and the solution was washed with a saturated aqueous sodium bicarbonate solution. The organic layer was washed in turn with water and brine, dried over magnesium sulphate and evaporated. There was thus obtained 4-chloro-6-methoxy-7-(N-methylpiperidin-4-ylmethoxy)quinazoline (2.9 g,), NMR Spectrum: (DMSOd$_6$) 1.3–1.5 (m, 2H), 1.75–1.9 (m, 4H), 2.0 (t, 1H), 2.25 (s, 3H), 2.85 (d, 2H), 4.02 (s, 3H), 4.12 (d, 2H), 7.41 (s, 1H), 7.46 (s, 1H), 8.9 (s, 1H).

A mixture of 4-chloro-6-methoxy-7-(N-methylpiperidinylmethoxy)quinazoline (11.17 g), 4-bromo-2-fluorophenol (4.57 ml), potassium carbonate (7.19 g) and DMF (110 ml) was stirred and heated at 100° C. for 2.5 hours. The mixture was allowed to cool to ambient temperature and was poured into a mixture (1 L) of ice and water. The precipitate was collected, washed with water and dried. The solid was purified by column chromatography on silica using increasingly polar mixtures of methylene chloride, methanol and a 1% aqueous ammonium hydroxide solution (20:1:0 to 10:1:0 to 10:1:1) as eluent. There was thus obtained 4-(4-bromo-2-fluorophenoxy)-6-methoxy-7-(N-methylpiperidin-4-ylmethoxy)quinazoline (13.1 g), NMR Spectrum: (DMSOd$_6$) 1.3–1.4 (m, 2H), 1.7–1.8 (m, 4H), 1.9 (t, 1H), 2.15 (s, 3H), 2.5 (br s, 2H), 4.0 (s, 3H), 4.1 (d, 2H), 7.4 (s, 1H), 7.45–7.6 (m, 3H), 7.8 (d, 1H), 8.5 (s, 1H); Mass Spectrum: M+H$^+$ 476 and 478.

A portion (9.4 g) of the material so obtained was dissolved in a 2M solution of ammonia in isopropanol (150 ml).

Liquid ammonia (10 ml) was added and the reaction mixture was sealed in a Carius tube. The reaction mixture was heated to 130° C. for 16 hours. The Carius tube was cooled and opened and the reaction mixture was evaporated. The residue was stirred under a 2N aqueous sodium hydroxide solution for 1 hour. The resultant solid was isolated and washed in turn with water and methyl tert-butyl ether. There was thus obtained 4-amino-6-methoxy-7-(N-methylpiperidin-4-ylmethoxy)quinazoline (5.55 g); NMR Spectrum: (DMSOd$_6$) 1.2–1.4 (m, 2H), 1.7–1.8 (m, 4H), 1.85 (t, 1H), 2.1 (s, 3H), 2.8 (d, 2H), 3.8 (s, 3H), 3.9 (d, 2H), 7.0 (s, 1H), 7.3 (br s, 2H), 7.5 (s, 1H), 8.2 (s, 1H); Mass Spectrum: M+H$^+$ 303.

EXAMPLE 2

Using an analogous procedure to that described in Example 1, except that, unless otherwise stated, chloroform was used in place of methylene chloride as the reaction solvent, the appropriate 4-aminoquinazoline was, reacted with the appropriate isocyanate to give the compounds described in Table I. In general, unless otherwise stated, the appropriate isocyanates were commercially available. Alternatively appropriate isocyanates could be prepared by the reaction of the appropriate aniline with di-tert-butyl dicarbonate in the presence of 4-dimethylaminopyridine and a solvent such as methylene chloride.

TABLE I

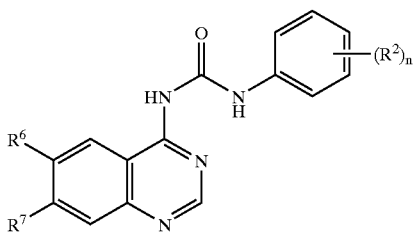

| No. | R$^6$ | R$^7$ | (R$^2$)$_n$ | Note |
|---|---|---|---|---|
| 1 | methoxy | N-methylpiperidin-4-ylmethoxy | 2-chloro | [1] |
| 2 | methoxy | N-methylpiperidin-4-ylmethoxy | 2,3-dichloro | [2] |
| 3 | methoxy | N-methylpiperidin-4-ylmethoxy | 2,4-dichloro | [3] |
| 4 | methoxy | N-methylpiperidin-4-ylmethoxy | 2-fluoro | [4] |
| 5 | methoxy | N-methylpiperidin-4-ylmethoxy | 2,6-difluoro | [5] |
| 6 | methoxy | N-methylpiperidin-4-ylmethoxy | 2-bromo | [6] |
| 7 | methoxy | N-methylpiperidin-4-ylmethoxy | 2-trifluoromethyl | [7] |
| 8 | methoxy | N-methylpiperidin-4-ylmethoxy | 2-methyl | [8] |
| 9 | methoxy | N-methylpiperidin-4-ylmethoxy | 2,6-dimethyl | [9] |
| 10 | methoxy | N-methylpiperidin-4-ylmethoxy | 2-tert-butyl | [10] |
| 11 | methoxy | 3-piperidinopropoxy | 2,6-dimethyl | [11] |
| 12 | hydrogen | 3-morpholinopropoxy | 2,6-dichloro | [12] |
| 13 | hydrogen | 3-(1,1-dioxotetrahydro-4H-1,4-thiazin-4-yl)propoxy | 2,6-dichloro | [13] |
| 14 | hydrogen | 4-morpholinobut-2-ynyloxy | 2,6-dichloro | [14] |
| 15 | hydrogen | (E)-4-morpolinobut-2-enyloxy | 2,6-dichloro | [15] |
| 16 | methoxy | 2-piperidinoethoxy | 2,6-dichloro | [16] |
| 17 | methoxy | 3-morpholinopropoxy | 2,6-dichloro | [17] |
| 18 | methoxy | 3-(4-methylpiperazin-1-yl)propoxy | 2,6-dichloro | [18] |
| 19 | methoxy | 3-pyrrolidin-1-ylpropoxy | 2,6-dichloro | [19] |
| 20 | methoxy | 3-(1,1-dioxotetrahydro-4H-1,4-thiazin-4-yl)propoxy | 2,6-dichloro | [20] |
| 21 | methoxy | 2-[N-(2-methoxyethyl)-N-methylamino)ethoxy | 2,6-dichloro | [21] |
| 22 | methoxy | 3-mesylpropoxy | 2,6-dichloro | [22] |
| 23 | methoxy | 3-(1,2,3-triazol-1-yl)propoxy | 2,6-dichloro | [23] |
| 24 | methoxy | 2-(4-pyridyl)ethoxy | 2,6-dichloro | [24] |
| 25 | methoxy | N-methylpiperidin-4-ylmethoxy | 2,4,6-trichloro | [25] |
| 26 | methoxy | N-methylpiperidin-4-ylmethoxy | 2,5-dichloro | [26] |
| 27 | methoxy | N-methylpiperidin-4-ylmethoxy | 2,4-difluoro | [27] |
| 28 | methoxy | N-methylpiperidin-4-ylmethoxy | 2,5-dimethoxy | [28] |
| 29 | methoxy | N-methylpiperidin-4-ylmethoxy | 2,4-dimethoxy | [29] |
| 30 | methoxy | N-methylpiperidin-4-ylmethoxy | 2,6-di-isopropyl | [30] |
| 31 | methoxy | N-methylpiperidin-4-ylmethoxy | 2,4,6-trimethyl | [31] |
| 32 | methoxy | N-methylpiperidin-4-ylmethoxy | 2,5-dimethyl | [32] |
| 33 | methoxy | N-methylpiperidin-4-ylmethoxy | 2,5-diethyl | [33] |
| 34 | methoxy | N-methylpiperidin-4-ylmethoxy | 2-ethyl-6-methyl | [34] |
| 35 | methoxy | N-methylpiperidin-4-ylmethoxy | 4-bromo-2,6-dimethyl | [35] |
| 36 | methoxy | N-methylpiperidin-4-ylmethoxy | 2-chloro-6-methyl | [36] |
| 37 | methoxy | 3-pyrrolidin-1-ylpropoxy | 2,4,6-trichloro | [37] |
| 38 | methoxy | 3-(4-methylpiperazin-1-yl)propoxy | 2,4,6-trichloro | [38] |
| 39 | methoxy | 3-piperidinopropoxy | 2,6-difluoro | [39] |
| 40 | methoxy | 3-pyrrolidin-1-ylpropoxy | 2,6-difluoro | [40] |
| 41 | methoxy | 3-piperidinopropoxy | 2,6-difluoro | [41] |
| 42 | methoxy | 3-morpholinopropoxy | 2,6-difluoro | [42] |
| 43 | methoxy | 3-(4-methylpiperazin-1-yl)propoxy | 2,6-difluoro | [43] |
| 44 | methoxy | 2-piperidinoethoxy | 2,6-difluoro | [44] |
| 45 | methoxy | 2-piperidinoethoxy | 2,4,6-trichloro | [45] |
| 46 | methoxy | 3-pyrrolidin-1-ylpropoxy | 2-fluoro-6-trifluoromethyl | [46] |
| 47 | methoxy | 2-dimethylaminoethoxy | 2,6-difluoro | [47] |
| 48 | methoxy | 2-dimethylaminoethoxy | 2,6-dichloro | [48] |
| 49 | methoxy | 2-(2-oxoimidazolidin-1-yl)ethoxy | 2,6-difluoro | [49] |
| 50 | methoxy | 2-(2-oxoimidazolidin-1-yl)ethoxy | 2,6-dichloro | [50] |
| 51 | methoxy | 2-pyrrolidin-1-ylethoxy | 2,6-dichloro | [51] |
| 52 | methoxy | 2-pyrrolidin-1-ylethoxy | 2,6-difluoro | [52] |
| 53 | methoxy | 2-morpholinoethoxy | 2,6-dichloro | [53] |
| 54 | methoxy | 2-morpholinoethoxy | 2,6-difluoro | [54] |
| 55 | methoxy | 3-pyrrolidin-1-ylpropoxy | 2,6-dimethyl | [55] |
| 56 | methoxy | 3-morpholinopropoxy | 2,6-dimethyl | [56] |
| 57 | methoxy | 3-(4-methylpiperazin-1-yl)propoxy | 2,6-dimethyl | [57] |
| 58 | methoxy | 2-pyrrolidin-1-ylethoxy | 2,6-dimethyl | [58] |
| 59 | methoxy | 2-piperidinoethoxy | 2,6-dimethyl | [59] |
| 60 | methoxy | 2-morpholinoethoxy | 2,6-dimethyl | [60] |
| 61 | methoxy | 2-(2-oxoimidazolidin-1-yl)ethoxy | 2,6-dimethyl | [61] |
| 62 | methoxy | 2-dimethylaminoethoxy | 2,6-dimethyl | [62] |
| 63 | methoxy | 3-pyrrolidin-1-ylpropoxy | 4-bromo-2,6-dimethyl | [63] |
| 64 | methoxy | 3-piperidinopropoxy | 4-bromo-2,6-dimethyl | [64] |
| 65 | methoxy | 3-morpholinopropoxy | 4-bromo-2,6-dimethyl | [65] |
| 66 | methoxy | 3-(4-methylpiperazin-1-yl)propoxy | 4-bromo-2,6-dimethyl | [66] |
| 67 | methoxy | 2-piperidinoethoxy | 4-bromo-2,6-dimethyl | [67] |
| 68 | methoxy | 2-morpholinoethoxy | 4-bromo-2,6-dimethyl | [68] |

TABLE I-continued

| No. | R⁶ | R⁷ | (R²)ₙ | Note |
|---|---|---|---|---|
| 69 | methoxy | 2-(2-oxoimidazolidin-1-yl)ethoxy | 4-bromo-2,6-dimethyl | [69] |
| 70 | methoxy | 2-(2-methoxyethoxy)ethoxy | 2,6-dichloro | [70] |
| 71 | methoxy | 2-(2-methoxyethoxy)ethoxy | 2,6-difluoro | [71] |
| 72 | methoxy | 2-(2-methoxyethoxy)ethoxy | 2,6-dimethyl | [72] |
| 73 | methoxy | N-methylpiperidin-4-ylmethoxy | 2-fluoro-6-trifluoromethyl | [73] |
| 74 | hydrogen | 2-pyrrolidin-1-ylethoxy | 2,6-dichloro | [74] |
| 75 | hydrogen | 2-pyrrolidin-1-ylethoxy | 2-chloro-6-methyl | [75] |
| 76 | hydrogen | 2-pyrrolidin-1-ylethoxy | 2-chloro | [76] |
| 77 | hydrogen | 2-pyrrolidin-1-ylethoxy | 2,4,6-trichloro | [77] |
| 78 | hydrogen | 2-piperidinoethoxy | 2,6-dichloro | [78] |
| 79 | hydrogen | 2-piperidinoethoxy | 2,6-difluoro | [79] |
| 80 | hydrogen | 2-piperidinoethoxy | 2-chloro-6-methyl | [80] |
| 81 | hydrogen | 2-piperidinoethoxy | 2-chloro | [81] |
| 82 | hydrogen | 2-piperidinoethoxy | 2,4,6-trichloro | [82] |
| 83 | hydrogen | 2-(4-methylpiperazin-1-yl)ethoxy | 2,6-dichloro | [83] |
| 84 | hydrogen | 2-(4-methylpiperazin-1-yl)ethoxy | 2-chloro-6-methyl | [84] |
| 85 | hydrogen | 2-(4-methylpiperazin-1-yl)ethoxy | 2-chloro | [85] |
| 86 | hydrogen | 2-(4-methylpiperazin-1-yl)ethoxy | 2,4,6-trichloro | [86] |
| 87 | hydrogen | N-methylpiperidin-3-ylmethoxy | 2,6-dichloro | [87] |
| 88 | hydrogen | N-methylpiperidin-3-ylmethoxy | 2,6-difluoro | [88] |
| 89 | hydrogen | N-methylpiperidin-3-ylmethoxy | 2-chloro-6-methyl | [89] |
| 90 | hydrogen | N-methylpiperidin-3-ylmethoxy | 2-chloro | [90] |
| 91 | hydrogen | N-methylpiperidin-3-ylmethoxy | 2,4,6-trichloro | [91] |
| 92 | hydrogen | 3-pyrrolidin-1-ylpropoxy | 2,6-dichloro | [92] |
| 93 | hydrogen | 3-pyrrolidin-1-ylpropoxy | 2,6-difluoro | [93] |
| 94 | hydrogen | 3-pyrrolidin-1-ylpropoxy | 2-chloro-6-methyl | [94] |
| 95 | hydrogen | 3-pyrrolidin-1-ylpropoxy | 2-chloro | [95] |
| 96 | hydrogen | 3-pyrrolidin-1-ylpropoxy | 2,5,6-trichloro | [96] |
| 97 | hydrogen | 3-morpholinopropoxy | 2,6-difluoro | [97] |
| 98 | hydrogen | 3-morpholinopropoxy | 2-chloro-6-methyl | [98] |
| 99 | hydrogen | 3-morpholinopropoxy | 2,4,6-trichloro | [99] |
| 100 | hydrogen | 3-(4-methylpiperazin-1-yl)propoxy | 2,6-dichloro | [100] |
| 101 | hydrogen | 3-(4-methylpiperazin-1-yl)propoxy | 2-chloro | [101] |
| 102 | hydrogen | 3-(4-methylpiperazin-1-yl)propoxy | 2,4,6-trichloro | [102] |
| 103 | hydrogen | 3-(1,1-dioxotetrahydro-4H-1,4-thiazin-4-yl)propoxy | 2,6-difluoro | [103] |
| 104 | hydrogen | 3-(1,1-dioxotetrahydro-4H-1,4-thiazin-4-yl)propoxy | 2-chloro-6-methyl | [104] |
| 105 | hydrogen | 3-(1,1-dioxotetrahydro-4H-1,4-thiazin-4-yl)propoxy | 2,4,6-trichloro | [105] |
| 106 | hydrogen | 3-(1,2,3-triazol-1-yl)propoxy | 2,4,6-trichloro | [106] |
| 107 | hydrogen | (E)-4-pyrrolidin-1-ylbut-2-enyloxy | 2,6-difluoro | [107] |
| 108 | hydrogen | (E)-4-pyrrolidin-1-ylbut-2-enyloxy | 2-chloro-6-methyl | [108] |
| 109 | hydrogen | (E)-4-pyrrolidin-1-ylbut-2-enyloxy | 2-chloro | [109] |
| 110 | methoxy | 3-(4-carbamoylpiperidin-1-yl)propoxy | 2,6-dichloro | [110] |
| 111 | methoxy | 3-(4-carbamoylpiperidin-1-yl)propoxy | 2,6-difluoro | [111] |
| 112 | methoxy | 3-(4-carbamoylpiperidin-1-yl)propoxy | 2,6-dimethyl | [112] |
| 113 | methoxy | 3-(4-carbamoylpiperidin-1-yl)propoxy | 2-chloro-6-methyl | [113] |
| 114 | hydrogen | 3-(pyrrolidin-1-yl)-1-propynyl | 2,6-dichloro | [114] |
| 115 | methoxy | 3-(pyrrolidin-1-yl)-1-propynyl | 2,6-dichloro | [115] |
| 116 | methoxy | 6-morpholino-1-hexynyl | 2,6-dichloro | [116] |
| 117 | methoxy | 6-morpholino-1-hexynyl | 2,6-difluoro | [117] |
| 118 | methoxy | 6-(2-methylimidazol-1-yl)-1-hexynyl | 2,6-dichloro | [118] |
| 119 | methoxy | 6-(2-methylimidazol-1-yl)-1-hexynyl | 2,6-difluoro | [119] |
| 120 | methoxy | 3-dimethylamino-1-propynyl | 2,6-difluoro | [120] |
| 121 | methoxy | N-methylpiperidin-4-ylmethoxy | 2-nitro | [121] |
| 122 | methoxy | N-methylpiperidin-4-ylmethoxy | 2-methyl-3-fluoro | [122] |
| 123 | methoxy | N-methylpiperidin-4-ylmethoxy | 2,5-dichloro | [123] |
| 124 | methoxy | N-methylpiperidin-4-ylmethoxy | 2-methyl-5-nitro | [124] |
| 125 | methoxy | N-methylpiperidin-4-ylmethoxy | 2-chloro-5-trifluoromethyl | [125] |
| 126 | methoxy | N-methylpiperidin-4-ylmethoxy | 5-chloro-2-methoxy | [126] |
| 127 | methoxy | N-methylpiperidin-4-ylmethoxy | 2-methoxy-5-methyl | [127] |
| 128 | methoxy | N-methylpiperidin-4-ylmethoxy | 5-chloro-2-methyl | [128] |
| 129 | methoxy | N-methylpiperidin-4-ylmethoxy | 2-methyl-5-fluoro | [129] |
| 130 | methoxy | N-methylpiperidin-4-ylmethoxy | 2-chloro-5-methyl | [130] |
| 131 | methoxy | 3-pyrrolidin-1-ylpropoxy | 2,5-difluoro | [131] |
| 132 | methoxy | 3-pyrrolidin-1-ylpropoxy | 2,5-dichloro | [132] |
| 133 | methoxy | 3-pyrrolidin-1-ylpropoxy | 5-chloro-2-methyl | [133] |
| 134 | methoxy | 3-pyrrolidin-1-ylpropoxy | 5-fluoro-2-methyl | [134] |
| 135 | methoxy | 3-pyrrolidin-1-ylpropoxy | 2-methyl-5-nitro | [135] |
| 136 | methoxy | 3-pyrrolidin-1-ylpropoxy | 2-chloro-5-methyl | [136] |
| 137 | methoxy | 6-(N-methylpiperazin-1-yl)-1-hexynyl | 2,6-dichloro | [137] |
| 138 | methoxy | benzyloxy | 3-dimethylcarbamoyl-2,6-dimethyl | [138] |
| 139 | methoxy | cyclopropylmethoxy | 2,6-dimethyl | [139] |
| 140 | methoxy | 6-(N-methylpiperazin-1-yl)hexyl | 2,6-dichloro | [140] |
| 141 | methoxy | 3-(pyrrolidin-1-yl)propyl | 2,6-dichloro | [141] |
| 142 | methoxy | N-[3-(N-methylpiperazin-1-yl)propyl]carbamoyl | 2,6-dichloro | [142] |
| 143 | methoxy | N-[3-(imidazol-1-yl)propyl]carbamoyl | 2,6-dichloro | [143] |
| 144 | methoxy | N-methylpiperazin-1-yl | 2,6-dichloro | [144] |
| 145 | methoxy | N-(tert-butoxycarbonyl)piperazin-1-yl | 2,6-dichloro | [145] |

TABLE I-continued

[Structure: quinazoline with R6, R7 substituents linked via urea to phenyl-(R²)n group]

| No. | R⁶ | R⁷ | (R²)ₙ | Note |
|---|---|---|---|---|
| 146 | methoxy | 3-morpholinopropylamino | 2,6-dichloro | [146] |
| 147 | methoxy | 3-imidazol-1-ylpropylamino | 2,6-dichloro | [147] |
| 148 | methoxy | N-methylpiperidin-4-ylmethoxy | 3-dimethylcarbamoyl-2,6-dimethyl | [148] |
| 149 | methoxy | 3-pyrrolidin-1-ylpropoxy | 2-chloro-6-methyl | [149] |
| 150 | methoxy | 3-methoxypropylamino | 2,6-dichloro | [150] |
| 151 | methoxy | 2-aminoethylamino | 2,6-dichloro | [151] |
| 152 | methoxy | N-(2-diethylaminoethyl)-N-methylamino | 2,6-dichloro | [152] |

Notes

[1] The product gave the following data: NMR Spectrum: (DMSOd₆) 1.36 (m, 2H), 1.74 (d, 3H), 1.86 (t, 2H), 2.14 (s, 3H), 2.87 (d, 2H), 3.96 (s, 3H), 4.03 (d, 2H), 7.11 (t, 1H), 7.29 (s, 3H), 7.38 (t, 1H), 7.56 (d, 1H), 8.08 (s, 1H), 8.41 (d, 1H), 8.73 (s, 1H), 10.59 (s, 1H), 13.2 (s, 1H); Mass Spectrum: M+H⁺ 456 and 458.

[2] The product gave the following data: NMR Spectrum: (CDCl₃) 1.87 (m, 2H), 2.11 (m, 3H), 2.78 (m, 2H), 2.78 (s, 3H), 3.68 (d, 2H), 4.07 (s, 3H), 4.1 (s, 2H), 7.12 (m, 2H) 7.43 (s, 1H), 7.78 (s, 1H), 8.28 (m, 1H), 8.75 (s, 1H), 13.2 (s, 1H); Mass Spectrum: M+H⁺ 490 and 492.

[3] The product gave the following data: NMR Spectrum: (DMSOd₆) 1.83 (m, 2H), 2.1 (m, 3H), 2.63 (m, 2H), 2.7 (s, 3H), 3.6 (d, 2H), 4.08 (s, 3H), 4.1 (d, 2H), 7.23 (m, 1H), 7.33 (s, 1H), 7.46 (s, 1H), 7.72 (s, 1H), 8.31 (d, 1H), 8.74 (s, 1H), 13.3 (s, 1H); Mass Spectrum: M+H⁺ 490 and 492.

[4] Methylene chloride was used as the reaction solvent. The product gave the following data: NMR Spectrum: (DMSOd₆) 1.34 (q, 2H), 1.74 (d, 3H), 1.86 (t, 2H), 2.15 (s, 3H), 2.78 (d, 2H), 3.96 (s, 3H), 4.02 (d, 2H), 7.08–7.16 (m, 1H), 7.19–7.36 (m, 3H), 8.06 (s, 1H), 8.27 (s, 1H), 8.69 (s, 1H), 10.56 (s, 1H), 12.81 (s, 1H); Mass Spectrum: M+H⁺ 440.

[5] DMF was used as the reaction solvent. The product gave the following data: NMR Spectrum: (DMSOd₆) 1.35 (m, 2H), 1.8 (m, 5H), 2.15 (s, 3H), 2.79 (d, 2H), 2.94 (s, 3H), 4.03 (d, 2H), 7.1–7.35 (m, 5H), 8.03 (s, 1H), 8.66 (s, 1H), 10.6 (s, 1H); Mass Spectrum: M+H⁺ 458.

[6] DMF was used as the reaction solvent. The product gave the following data: NMR Spectrum: (DMSOd₆) 1.3–1.5 (m, 2H), 1.7–1.8 (m, 4H), 1.85 (t, 1H), 2.2 (s, 3H), 2.8 (d, 2H), 3.9 (s, 3H), 4.1 (br d, 2H), 7.0 (t, 1H), 7.3 (br s, 1H), 7.4 (t, 1H), 7.7 (d, 1H), 8.1 (br s, 1H), 8.4 (d, 1H), 8.8 (s, 1H), 10.5 (br s, 1H); Mass Spectrum: M+H⁺ 500 and 502.

[7] The product gave the following data: NMR Spectrum: (CDCl₃) 1.47 (m, 2H), 1.97 (m, 5H), 2.3 (s, 3H), 2.88 (d, 2H), 3.61 (s, 3H), 4.01 (d, 2H), 7.24 (s, partially obscured by CHCl₃ peak), 7.25 (t, partially obscured by CHCl₃ peak), 7.37 (s, 1H), 7.56 (t, 1H), 7.7 (d, 1H), 8.17 (d, 1H), 8.7 (s, 1H), 9.36 (s, 1H), 13.2 (s, 1H); Mass Spectrum: M+H⁺ 490.

[8] The product gave the following data: NMR Spectrum: (CDCl₃) 1.38–1.55 (m, 2H), 1.84–2.04 (m, 5H), 2.3 (s, 3H), 2.47 (s, 3H), 2.91 (d, 2H), 3.66 (s, 3H), 4.01 (d, 2H), 7.05–7.14 (m, 1H), 7.17–7.28 (m, 4H), 7.4 (s, 1H), 7.96 (d, 1H), 8.7 (s, 1H), 9.24 (s, 1H), 12.34 (s, 1H); Mass Spectrum: M+H⁺ 436.

[9] The product gave the following data: NMR Spectrum: (DMSOd₆ and CD₃COOH) 1.5–1.67 (q, 2H), 1.93–2.17 (m, 3H), 2.24 (s, 6H), 2.71 (s, 3H), 2.93 (t, 2H), 3.37 (d, 2H), 3.95 (s, 3H), 4.09 (d, 2H), 7.1 (s, 3H), 7.31 (s, 1H), 8.07 (s, 1H), 8.66 (d, 1H); Mass Spectrum: M+H⁺ 450.

[10] The product gave the following data: NMR Spectrum: (CDCl₃) 1.43 (m, 2H), 1.5 (s, 9H), 1.82 (m, 5H), 2.28 (s, 3H), 2.89 (d, 2H), 3.32 (s, 3H), 4.0 (d, 2H), 7.2 (m, 3H), 7.5 (m, 2H), 7.57 (s, 1H), 8.62 (s, 1H), 9.9 (s, 1H), 12.35 (s, 1H); Mass Spectrum: M+H⁺ 478.

[11] The product gave the following data: NMR Spectrum: (CDCl₃) 1.45 (m, 2H), 1.59 (m, 4H), 2.11 (m, 2H), 2.33 (s, 6H), 2.4 (br s, 4H), 2.5 (t, 2H), 3.23 (s, 3H), 4.22 (t, 2H), 7.14 (m, 3H), 7.28 (s, 1H), 7.62 (s, 1H), 8.66 (s, 1H), 10.16 (s, 1H), 12.08 (s, 1H); Mass Spectrum: M+H⁺ 513.

The 4-amino-6-methoxy-7-(3-piperidinopropoxy) quinazoline used as a starting material was prepared as follows:

Sodium hydride (60% suspension in mineral oil, 1.44 g) was added portionwise during 20 minutes to a solution of 7-benzyloxy-6-methoxy-3,4-dihydroquinazolin-4-one (International Patent Application WO 97/22596, Example 1 thereof; 8.46 g) in DMF (70 ml). The mixture was stirred at ambient temperature for 1.5 hours. Chloromethyl pivalate (5.65 g) was added dropwise and the mixture was stirred at ambient temperature for 2 hours. The mixture was diluted with ethyl acetate (100 ml) and poured onto a mixture (400 ml) of ice and water containing 2N aqueous hydrochloric acid (4 ml). The organic layer was separated and the aqueous layer was extracted with ethyl acetate. The combined extracts were washed with brine, dried over magnesium sulphate and evaporated. The residue was triturated under a mixture of diethyl ether and petroleum ether (b.p. 60–80° C.) and the resultant solid was collected and dried under vacuum. There was thus obtained 7-benzyloxy-6-methoxy-3-pivaloyloxymethyl-3,4-dihydroquinazolin-4-one (10 g); NMR Spectrum: (DMSOd₆) 1.11 (s, 9H), 3.89 (s, 3H), 5.3 (s, 2H), 5.9 (s, 2H), 7.27 (s, 1H), 7.35 (m, 1H), 7.47 (t, 2H), 7.49 (d, 2H), 7.51 (s, 1H), 8.34 (s, 1H).

A mixture of a portion (7 g) of the material so obtained, 10% palladium-on-charcoal catalyst (0.7 g), DMF (50 ml), methanol (50 ml), acetic acid (0.7 ml) and ethyl acetate (250 ml) was stirred under an atmosphere pressure of hydrogen for 40 minutes. The catalyst was removed by friction and the solvent was evaporated. The residue was triturated under diethyl ether and the resultant solid was collected and dried under vacuum. There was thus obtained 7-hydroxy-6-methoxy-3-pivaloyloxymethyl-3,4-dihydroquinazolin-4-one (4.36 g); NMR Spectrum: (DMSOd₆) 1.1 (s, 9H), 3.89 (s, 3H), 5.89 (s, 2H), 7.0 (s, 1H), 7.48 (s, 1H), 8.5 (s, 1H).

Diethyl azodicarboxylate (3.9 ml) was added dropwise to a stirred mixture of 7-hydroxy-6-methoxy-3-pivaloylaxymethyl-3,4-dihydroquinazolin-4-one (5 g), 3-bromopropanol (2.21 ml), triphenylphosphine (6.42 g) and methylene chloride (50 ml) and the mixture was stirred at ambient temperature for 2 hours. The mixture was evaporated and the residue was purified by column chromatography on silica using a 19:1 mixture of methylene chloride and methanol as eluent. There was thus obtained 7-(3-bromopropoxy)-6-methoxy-3-pivaloyloxymethyl-3,4-dihydroquinazolin-4-one (6 g); NMR Spectrum: (DMSOd₆)

1.12 (s, 9H), 2.32 (t, 2H), 3.7 (t, 2H), 3.9 (s, 3H), 4.25 (t, 2H), 5.9 (s, 2H), 7.20 (s, 1H), 7.61 (s, 1H), 8.36 (s, 1H).

A mixture of a portion (2.89 g) of the material so obtained and piperidine (10 ml) was stirred and heated to 100° C. for 1 hour. The mixture was evaporation and the residue was partitioned between methylene chloride and a saturated aqueous ammonium chloride solution. The organic phase was washed with brine, dried over magnesium sulphate and evaporated. There was thus obtained 6-methoxy-7-(3-piperidinopropoxy)-3-pivaloyloxymethyl-3,4-dihydroquinazolin-4-one (2.4 g); NMR Spectrum: (DMSOd$_6$) 1.15 (s, 9H), 1.35–1.5 (m, 1H), 1.6–1.8 (m, 3H), 1.8–1.9 (d, 2H), 2.2–2.3 (m, 2H), 2.95 (t, 2H), 3.25 (t, 2H), 3.55 (d, 2H), 3.95 (s, 3H), 4.25 (t, 2H), 5.94 (s, 2H), 7.24 (s, 1H), 7.56 (s, 1H), 8.36 (s, 1H).

A mixture of the material so obtained and a 7N solution of ammonia in methanol (50 ml) was stirred at ambient temperature for 16 hours. The mixture was evaporated and the residue was triturated under diethyl ether. The resultant solid was isolated, washed in turn with diethyl ether and a 1:1 mixture of diethyl ether and methylene chloride and dried under vacuum. There was thus obtained 6-methoxy-7-(3-piperidinopropoxy)-3,4-dihydroquinazolin-4-one (1.65 g); NMR Spectrum: (DMSOd$_6$) 1.3–1.4 (m, 2H), 1.4–1.55 (m, 4H), 1.85–1.95 (m, 2H), 2.35 (br s, 4H), 2.4 (t, 2H), 3.9 (s, 3H), 4.15 (t, 2H), 7.11 (s, 1H), 7.44(s, 1H), 7.9 (s, 1H).

A mixture of the material so obtained, thionyl chloride (15 ml) and DMF (1.5 ml) was heated to reflux for 3 hours. The mixture was evaporated. Toluene was added and the mixture was again evaporated. The residue was partitioned between methylene chloride and a saturated aqueous sodium bicarbonate solution (the basicity of which was adjusted to pH10 by adding 6N aqueous sodium hydroxide). The organic layer was separated, washed with brine, dried over magnesium sulphate and evaporated. There was thus obtained 4-chloro-6-methoxy-7-(3-piperidinopropoxy)quinazoline (1.2 g); NMR Spectrum: (DMSOd$_6$) 1.35–1.45 (m, 2H), 1.5–1.6 (m, 4H), 1.9–2.05 (m, 2H), 2.4 (br s, 4H), 2.45 (t, 2H), 4.0 (s, 3H), 4.29 (t, 2H), 7.41 (s, 1H), 7.46 (s, 1H), 8.9 (s, 1H).

A portion (0.5 g) of the material so obtained was dissolved in a 1M solution of ammonia in isopropanol (10 ml). Liquid ammonia (1 ml) was added and the reaction mixture was sealed in a Carius tube. The reaction mixture was heated to 120° C. for 16 hours. The Carius tube was cooled and opened and the reaction mixture was evaporated. The residue was stirred under a 2N aqueous sodium hydroxide solution for 1 hour. The resultant solid was isolated and washed in turn with water and methyl tert-butyl ether. There was thus obtained 4-amino-6-methoxy-7-(3-piperidinopropoxy)quinazoline (0.225 g); NMR Spectrum: (DMSOd$_6$) 1.37 (d, 2H), 1.49 (t, 4H), 1.91 (m, 2H), 2.3 (s, 4H), 2.37 (t, 2H), 3.86 (s, 3H), 4.1 (t, 2H), 7.04 (s, 1H), 7.38 (s, 2H), 7.54 (s, 1H), 8.22 (s, 1H); Mass Spectrum: M+H$^+$ 317.

[12] Acetontile was used as the reaction solvent. The product gave the following data: NMR Spectrum: (CDCl$_3$) 2.1 (m, 2H), 2.5 (br s, 4H), 2.7 (t, 2H), 3.75 (t, 4H), 4.25 (t, 2H), 7.15 (d, 1H), 7.3 (m, 2), 7.5 (d, 2H), 8.1 (d, 1H), 8.85 (s, 1H), 9.05 (s, 1H), 12.1 (s, 1H); Mass Spectrum: M+H$^+$ 476 and 478.

The 4-amino-7-(3-morpholinopropoxy)quinazoline used as a starting material was prepared as follows:

A solution of 2-amino-4-fluorobenzoic acid (3 g) in formamide (30 ml) was heated to 150° C. for 6 hour. The reaction mixture was poured onto a 1:1 mixture of ice and water (250 ml) and the precipitated solid was collected, washed with water and dried to give 7-fluoro-3,4-dihydroquinazolin-4-one (2.6 g).

Sodium metal (4.4 g) was added to benzyl alcohol (100 ml) and the resultant mixture was stirred at ambient temperature for 30 minutes and then and heated to 80° C. for 1 hour. The mixture was cooled to 40° C. and 7-fluoro-3,4-dihydroquinazolin-4-one (7.8 g) was added. The reaction mixture was stirred and heated to 130° C. for 4 hours. The mixture was allowed to cool to ambient temperature and was stirred for a further 18 hours. The solution was quenched with water (800 ml) and acidified to pH3 by the addition of concentrated hydrochloric acid. The resultant precipitate was collected, washed in turn with water and diethyl ether and dried under vacuum for 4 hours at 60° C. There was thus obtained 7-benzyloxy-3,4-dihydroquinazolin-4-one (7.02 g).

A mixture of the material so obtained, phosphorus pentasulphide (12.5 g) and pyridine (350 ml) was stirred and heated to reflux for 8 hours. After cooling, the mixture was poured into water (1 L). The precipitate was collected and washed with water. The solid so obtained was dissolved in 6N aqueous sodium hydroxide solution and the solution was filtered. The filtrate was acidified to pH2 by the addition of 6N aqueous hydrochloric acid. The resultant precipitate was collected, washed with water and dried under vacuum at 60° C. There was thus obtained 7-benzyloxy-3,4-dihydroquinazolin-4-thione (7.42 g); NMR Spectrum: (DMSOd$_6$) 5.32 (s, 2H), 7.25 (d, 1H), 7.32 (m, 1H), 7.4 (m, 1H), 7.45 (t, 2H), 7.55 (d, 2H), 8.15 (s, 1H), 8.5 (d, 1H).

A portion (3.45 g) of the material so obtained was dissolved in THF (13 ml) and 1N aqueous sodium hydroxide solution (25.7 ml) was added. Methyl iodide (0.97 ml) was added dropwise and the mixture was stirred at ambient temperature for 30 minus. The mixture was neutralised by the addition of 2N aqueous hydrochloric acid and the mixture was diluted by the addition of water. The resultant solid was collect washed with water and dried under vacuum to give 7-benzyloxy-4-methylthioquinazolin (3.3 g); NMR Spectrum: (DMSOd$_6$) 2.67 (s, 3H), 5.32 (s, 2H), 7.3–7.45 (m, 5H), 7.5 (d, 2H), 8.05 (d, 1H), 8.9 (s, 1H).

A mixture of a portion (3 g) of the material so obtained and trifluoroacetic acid (30 ml) was heated to reflux for 5 hours. The mixture was evaporated. The residue was suspended in water and solid sodium bicarbonate was added until complete dissolution. The solution was extracted with diethyl ether. The aqueous layer was acidified to pH2 by the addition of 2N aqueous hydrochloric acid and the resultant precipitate was collected, washed in turn with water and diethyl ether and dried under vacuum. The was thus obtained 7-hydroxy-4-methylthioquinazoline (2 g); NMR Spectrum: (DMSOd$_6$) 2.7 (s, 3H), 7.15 (d, 1H), 7.25 (m, 1H), 8.0 (d, 1H), 8.9 (s, 1H).

Diethyl azodicarboxylate (2.92 g) was added dropwise to a stirred mixture of 7-hydroxy-4-methylthioquinazoline (2.5 g), 4-(3-hydroxypropyl)morpholine (*Bull. Soc. Chim. Fr.* 1962, 1117; 2.47 g), triphenylphosphine (4.45 g) and methylene chloride (65 ml). The reaction mixture was stirred at ambient temperature for 1 hour. The mixture was evaporated and the residue was partitioned between a 1:1 mixture of ethyl acetate and diethyl ether and a 1N aqueous hydrochloric acid solution. The aqueous layer was separated, basified to pH9 by the addition of solid sodium bicarbonate and extracted with methylene chloride. The organic layer was separated washed with water and brine, dried over magnesium sulphate and evaporated. The residue was purified by column chromatography on silica using increasingly polar mixtures of methylene chloride, ethyl acetate and methanol (from 6:3:1 to 5:3:2 to 75:0:25) as eluent. There was thus obtained 4-methylthio-7-(3-morpholinopropoxy)

quinazoline (2.03 g); NMR Spectrum: (DMSOd$_6$, and CF$_3$COOD) 2.2–2.3 (m, 2H), 2.7 (s, 3H), 3.05–3.25 (m, 2H), 3.35 (t, 2H), 3.55 (d, 2H), 3.7 (t, 2H), 4.05 (d, 2H), 4.32 (t, 2H), 7.38 (d, 1H), 7.4 (s, 1H), 8.1 (d, 1H), 9.05 (d, 1H); Mass Spectrum: M+H$^+$ 320.

A mixture of a portion (0.5 g) of the material so obtained and a solution of ammonia gas in methanol (7M; 50 ml) was sealed in a pressure vessel and heated to 120° C. for 16 hours. The mixture was cooled to ambient temperature and evaporated. The residue was purified by column chromatography on silica using increasingly polar mixtures of methylene chloride, methanol and a 1% aqueous ammonium hydroxide solution as eluent. The material so obtained was triturated under diethyl ether and the resultant solid was isolated, washed with diethyl ether and dried under vacuum. There was thus obtained 4-amino-7-(3-morpholinopropoxy) quinazoline (0.35 g); NMR Spectrum: (CDCl$_3$) 2.0–2.15 (m, 2H), 2.5 (br s, 4H), 2.6 (t, 2H), 3.75 (br s, 4H), 4.2 (t, 2H), 5.65 (br s, 2H), 7.1 (d, 1H), 7.2 (s, 1H), 7.65 (d, 1H), 8.55 (s, 1H); Mass Spectrum: M+H$^+$ 280.

[13] Acetonitrile was used as the reaction solvent. The product gave the following data: NMR Spectrum: (CDCl$_3$) 2.05 (m, 2H), 2.75 (t, 2H), 3.0–3.15 (m, 8H), 4.2 (t, 2H), 7.1 (d, 1H). 7.2–7.35 (m, 2H), 7.5 (d, 2H), 8.2 (d, 1H), 8.8 (s, 1H), 9.45 (s, 1H); Mass Spectrum: M+H$^+$ 524 and 526; Elemental Analysis: Found C, 50.0; H, 4.4; N, 13.3; C$_{22}$H$_{23}$N$_5$O$_4$Cl$_2$S requires C, 50.39; H, 4.42; N, 13.35%.

The 4-amino-7-[3-(1,1-dioxotetrahydro-4H-1,4-thiazin-4-yl)propoxy]quinazoline used as a starting material was prepared as follows:

A mixture of 3-aminopropan-1-ol (0.650 ml) and divinyl sulphone (1 g) was heated to 110° C. for 45 minutes. The mixture was allowed to cool to ambient temperature and was purified by column chromatography on silica using a 19:1 mixture of methylene chloride and methanol as eluent. There was thus obtained 3-(1,1-dioxotetrahydro-4H-1,4-thiazin-4-yl)propan-1-ol (0.8 g); NMR Spectrum: (CDCl$_3$) 1.7–1.8 (m, 2H), 2.73 (t, 2H), 3.06 (br s, 8H), 3.25 (s, 1H), 3.78 (t, 2H); Mass Spectrum: M+H$^+$ 194.

Diethyl azodicarboxylate (3.3 ml) was added dropwise to a stirred mixture of 7-hydroxy-4-methylthioquinazoline (1.34 g), 3-(1,1-dioxotetrahydro-4H-1,4-thiazin-4-yl) propan-1-ol (2.03 g), triphenylphosphine (5.51 g) and methylene chloride (100 ml). The reaction mixture was stirred at ambient temperature for 4 hours. The mixture was evaporated and the residue was purified by column chromatography on silica using initially ethyl acetate and then a 24:1 mixture of ethyl acetate and ethanol as eluent. There was thus obtained 7-[3-(1,1-dioxotetrahydro-4H-1,4-thiazin-4-yl)propoxy]-4-methylthioquinazoline (1.79 g); NMR Spectrum: (CDCl$_3$) 2.05 (m, 2H), 2.7 (s, 3H), 2.73 (t, 2H), 3.05 (m, 8H), 4.2 (t, 2H), 7.15 (m, 1H), 7.2 (d, 1H), 8.0 (d, 1H), 8–9 (s, 1H); Mass Spectrum: M+H$^+$ 368.

Using an analogous procedure to that described in the last paragraph of Note [12] immediately above, a portion (0.5 g) of the material so obtained was reacted with anmonia gas in methanol. The reaction product was purified by column chromatography on silica using increasingly polar mixtures of chloroform and methanol as eluent. There was thus obtained 4-amino-7-[3-(1,1-dioxotetrahydro-4H-1,4-thiazin-4-yl)propoxy]quinazoline (0.45 g); NMR Spectrum (CDCl$_3$) 2.05 (m, 2H), 2.75 (t, 2H), 3.0–3.1 (m, 8H), 4.2 (t, 2H), 5.5 (br s, 2H), 7.15 (m, 1H), 7.2 (s, 1H), 7.65 (d, 1H), 8.6 (s, 1H); Mass Spectrum: M+H$^+$ 337.

[14] Acetonitrile was used as the reaction solvent. The product gave the following data: NMR Spectrum: (DMSOd$_6$ and CF$_3$COOD) 3.0–3.4 (m, 2H), 3.4 (br d, 2H), 3.6–3.7 (m, 2H), 3.95 (br d, 2H), 4.25 (s, 2H), 5.2 (s, 2H), 7.32 (t, 1H), 7.5 (d, 2H), 7.5–7.6 (m, 2H), 8.9 (d, 1H), 9.2 (s, 1H); Mass Spectrum: M+H$^+$ 486 and 488; Elemental Analysis: Found C, 55.4; H, 4.3; N, 14.1; C$_{23}$H$_{21}$N$_5$O$_3$Cl$_2$0.6H$_2$O requires C, 55.57; H, 4.50; N, 14.09%.

The 4-amino-7-(4-morpholinobut-2-yn-1-yloxy) quinazoline used as a starting material was prepared as follows:

Diethyl azodicarboxylate (2.46 ml) was added dropwise to a stirred mixture of 7-hydroxy-4-methylthioquinazoline (1.2 g), 4-morpholinobut-2-yn-1-ol (J. Amer. Chem. Soc., 1957, 79, 6184; 1.26 g), triphenylphosphine (4.09 g) and methylene chloride (35 ml). The reaction mixture was stirred at ambient temperature for 3 hours. The mixture was evaporated and the residue was purified by column chromatography on silica using initially methylene chloride and then a 19:1 mixture of methylene chloride and methanol as eluent. The material so obtained was triturated under diethyl ether. The resultant solid was collected and dried under vacuum. There was thus obtained 4-methylthio-7-(4-morpholinobut-2-yn-1-yloxy)quinazoline (1.3 g); NMR Spectrum: (CDCl$_3$) 2.5 (t, 4H), 2.7 (s, 3H), 3.32 (t, 2H), 3.7 (t, 4H), 4.9 (t, 2H), 7.2 (d, 1H), 7.35 (d, 1H), 8.0 (d, 1H), 8.9 (s, 1H); Mass Spectrum: M+H$^+$ 330.

Using an analogous procedure to that described in the last paragraph of Note [12] above, a portion (0.5 g) of the material so obtained was reacted with a saturated solution of ammonia gas in methanol. The reaction product was purified by column chromatography on silica using increasingly polar mixtures of methylene chloride, methanol and a 1% aqueous ammonium hydroxide solution as eluent. There was thus obtained 4-amine-7-(4-morpholinobut-2-yn-1-yloxy) quinazoline (0.283 g); NMR Spectrum: (DMSOd$_6$) 2.4 (m, 4H), 3.3 (t, 2H), 3.5 (m, 4H), 5.0 (s, 2H), 7.15 (m, 1H), 7.18 (d, 1H), 7.6 (br s, 2H), 8.15 (d, 1H), 8.32 (s, 1H); Mass Spectrum: M+Na$^+$ 321; Elemental Analysis: Found C, 63.8; H, 6.1; N, 18.7; C$_{16}$H$_{18}$N$_4$O$_2$0.2H$_2$O requires C, 63.65; H, 6.14; N, 18.55%.

[15] Acetonitrile was used as the reaction solvent. The product gave the following data: NMR Spectrum (DMSOd$_6$ and CF$_3$COOD) 3.0–3.1 (m, 2H), 3.4 (d, 2H), 3.65 (t, 2H), 3.85 (d, 2H), 4.0 (d, 2H), 4.95 (br s, 2H), 6.0 (m, 1H), 6.3 (m, 1H), 7.4 (t, 1H), 7.45 (s, 1H), 7.55 (m, 1H), 7.6 (d, 2H), 8.85 (d, 1H), 9.17 (s, 1H); Mass Spectrum: M+Na$^+$ 510 and 512; Elemental Analysis: Found C, 56.2; H, 4.7; N, 14.2; C$_{23}$H$_{23}$N$_5$O$_3$Cl$_2$ requires C, 56.57; H, 4.75; N, 14.34%.

The 4-amino-7-[(E)-4-morpholinobut-2-en-1-yloxy] quinazoline used as a starting material was prepared as follows:

Using an analogous procedure to that described in the second last paragraph of Note [12] above, (E)-4-morpholinobut-2-en-1-ol (J. Med. Chem., 1972, 15, 110–112; 1.27 g), was reacted with 7-hydroxy-4-methylthioquinazoline (1.2 g) to give 4-methylthio-7-[(E)-4-morpholinobut-2-en-1-yloxy]quinazolin (1.15 g); NMR Spectrum: (CDCl$_3$) 2.45 (br s, 4H), 2.7 (s, 3H), 3.05 (d, 2H), 3.7 (t, 4H), 4.7 (d, 2H), 5.9 (m, 2H), 7.15–7.25 (m, 2H), 7.95 (d, 1H), 8.9 (d, 1H); Mass Spectrum: M+H$^+$ 332.

Using an analogous procedure to that described in the last paragraph of Note [12] above, 4-methylthio-7-[(E)-4-morpholinobut-2-en-1-yloxy]quinazoline (0.5 g) was reacted with a saturated solution of ammonia gas in methanol. The reaction product was purified by column chromatography on silica using increasingly polar mixtures of methylene chloride, methanol and a 1% aqueous ammonium hydroxide solution as eluent. There was thus obtained 4-amino-7-[(E)-4-morpholinobut-2-en-1-yloxy]quinazoline (0.372 g); NMR Spectrum: (DMSOd$_6$) 2.35 (br s, 4H), 3.0 (br s, 2H), 3.56 (t, 4H), 4.7 (br s, 2H), 5.9 (br s, 2H), 7.05 (s, 2H), 7.1 (m, 1H), 7.6 (br s, 2H), 8.12 (d, 1H), 8.3 (s, 1H); Mass Spectrum: M+Na$^+$ 323; Elemental Analysis: Found C, 63.1; H, 6.7; N, 18.4; C$_{16}$H$_{20}$N$_4$O$_2$0.2H$_2$O requires C, 63.22; H, 6.76; N, 18.51%.

[16] Acetonitrile was used as the reaction solvent and the reaction mixture was heated to 35° C. for 7 hours and then to 50° C. for 5 hours. The resultant precipitate was collected, washed in turn with acetonitrile and diethyl ether and dried. The product gave the following data: NMR Spectrum: (DMSOd$_6$ and CF$_3$COOD) 1.4 (m, 1H), 1.7 (m, 3H), 1.9 (m, 2H), 3.1 (t, 2H), 3.65 (m, 4H), 4.05 (s, 3H), 4.65 (t, 2H), 7.45 (t, 1H), 7.52 (s, 1H), 7.62 (d, 2H), 8.3 (s, 1H), 9.05 (s, 1H); Mass Spectrum: M+H$^+$ 490 and 492.

The 4-amino-6-methoxy-7-(2-piperidinoethoxy) quinazoline used as a starting material was prepared as follows:

A mixture of 7-benzyloxy-6-methoxy-3,4-dihydroquinazolin-4-one (25.1 g), thionyl chloride (450 ml) and DMF (1 ml) was stirred and heated to reflux for 2 hours. The mixture was evaporated and the residue was dissolved in toluene and the solution was evaporated. The resultant solid was suspended in methylene chloride (500 ml), solid potassium carbonate (39 g) was added and the mixture was stirred for 10 minutes. Water (500 ml) was added and the mixture stirred for another 10 minutes. The methylene chloride layer was separated, dried over magnesium sulphate and evaporated. The residue was purified by column chromatography on silica using increasingly polar mixtures of methylene chloride and ethyl acetate as eluent. There was thus obtained 7-benzyloxy-4-chloro-6-methoxyquinazoline (21.54 g); NMR Spectrum: (DMSOd$_6$) 4.0 (s, 3H), 5.36 (s, 2H), 7.31–7.46 (m, 4H), 7.51 (d, 2H), 7.58 (s, 1H), 8.88 (s, 1H).

A portion (3 g) of the material so obtained was dissolved in 1M solution of ammonia in isopropanol (50 ml). Liquid ammonia (5 ml) was added and the reaction mixture was sealed in a Carius tube. The reaction mixture was heated to 120° C. for 16 hours. The Carius tube was cooled and opened and the reaction mixture was evaporated. The residue was under a 2N aqueous sodium hydroxide solution for 1 hour. The resultant solid was isolated and washed in turn with water and methyl tert-butyl ether. There was thus obtained 4-amino-7-benzyloxy-6-methoxyquinazoline (2.65 g); NMR Spectrum: (DMSOd$_6$) 3.88 (s, 3H), 3.9 (s, 3H), 7.2 (s, 1H), 7.63 (s, 2H), 7.69 (s, 1H), 8.38 (s, 1H); Mass Spectrum: M+H$^+$ 230.

A mixture of 4-amino-7-benzyloxy-6-methoxyquinazoline (4.15 g) and trifluoroacetic acid (35 ml) was stirred and heated to reflux for 1 hour. The solvent was evaporated, the residue was redissolved in a mixture of methylene chloride and toluene and the solvent was evaporated. The solid so obtained was suspended in water and basified to pH11 by the addition of 2N aqueous sodium hydroxide solution. The mixture was then neutralised to pH7 by the addition of 1N aqueous hydrochloric acid solution. The resultant solid was collected, washed in turn with water and acetonitrile and dried under vacuum over phosphorus pentoxide. There was thus obtained 4-amino-7-hydroxy-6-methoxyquinazoline (255 g); NMR Spectrum: (DMSOd$_6$) 3.9 (s, 3H), 7.05 (s, 1H), 7.65 (s, 1H), 8.0 (br s, 2H), 8.35 (s, 1H), 10.0–11.0 (br s, 1H).

A portion (0.15 g) of the material so obtained and triphenylphosphine (0.31 g) were dissolved in DMF (3 ml). THF (3 ml) was added causing partial precipitation of the starting material. A solution of N-(2-hydroxyethyl)piperidine (0.111 g) in THF (1 ml) was added followed by diethyl azodicarboxylate (0.186 ml) and the reaction mixture was stirred at ambient temperature for 30 minutes. Further portions of triphenylphosphine (0.105 g), N-(2-hydroxyethyl)piperidine (0.02 g) and diethyl azodicarboxylate (0.062 ml) were added and reaction mixture was stirred at ambient temperature for a further 30 minutes. The mixture was evaporated and the residue was purified by column chromatography on silica using increasingly polar mixtures of methylene chloride and methanol as eluent. There was thus obtained the required starting material (0.18 g); NMR Spectrum: (DMSOd$_6$ and CF$_3$COOD) 1.4 (m, 1H), 1.7 (m, 3H), 1.8 (m, 2H), 3.15 (m, 2H), 3.65 (m, 4H), 3.95 (s, 3H), 4.55 (t, 2H), 7.3 (s, 1H), 7.9 (s, 1H), 8.75 (s, 1H), 9.45 (br s, 1H); Mass Spectrum: M+H$^+$ 303.

[17] Acetonitrile was used as the reaction solvent and the reaction mixture was heated to 35° C. for 7 hours and then to 50° C. for 5 hours. The resultant precipitate was collected, washed in turn with acetonitrile and diethyl ether and dried. The product gave the following data: NMR Spectrum: (DMSOd$_6$ and CF$_3$COOD) 2.3 (m, 2H), 3.15 (m, 2H), 3.35 (m, 2H), 3.55 (m, 2H), 3.7 (t, 2H), 4.0 (s, 3H), 4.05 (m, 2H), 4.35 (t, 2H), 7.45 (t, 1H), 7.63 (d, 2H), 8.25 (s, 1H), 8.3 (s, 1H), 8.95 (s, 1H); Mass Spectrum: M+H$^+$ 506 and 508.

The 4-amino-6-methoxy-7-(3-morpholinopropoxy) quinazoline used as a starting material was prepared by the reaction of 4-amino-7-hydroxymethoxy)quinazoline and N-(3-hydroxypropyl)morpholine using an analogous procedure to that described in the last paragraph of Note [16] above. There was thus obtained the required starting material; NMR Spectrum: (DMSOd$_6$ and CF$_3$COOD) 2.25 (m, 2H), 3.15 (m, 2H), 3.35 (m, 2H), 3.55 (m, 2H), 3.7 (t, 2H), 3.95 (s, 3H), 4.05 (m, 2H), 4.3 (t, 2H), 7.35 (s, 1H), 7.85 (s, 1H), 8.75 (s, 1H), 9.4 (br s, 1H); Mass Spectrum: M+H$^+$ 319.

[18] Acetonitrile was used as the reaction solvent and the reaction mixture was heated to 35° C. for 7 hours and then to 50° C. for 5 hours. The resultant precipitate was collected, washed in turn with acetonitrile and diethyl ether and dried. The product gave the following data: NMR Spectrum: (DMSOd$_6$ and CF$_3$COOD) 2.3 (m, 2H), 2.95 (s, 3H), 3.2–3.8 (br s, 8H), 3.45 (m, 2H), 4.05 (s, 3H), 4.35 (t, 2H), 7.45 (t, 1H), 7.47 (s, 1H), 7.62 (d, 2H), 8.3 (s, 1H), 9.05 (s, 1H); Mass Spectrum: M+H$^+$ 519 and 521.

The 4-amino-6-methoxy-7-[3-(4-methylpiperazin-1-yl) propoxy]quinazoline used as a starting material was prepared by the reaction of 4-amino-7-hydroxy-6-methoxyquinazoline and 1-(3-hydroxypropyl-4-methylpiperazine using an analogous procedure to that described in the last paragraph of Note [16] above. There was thus obtained the required starting material; NMR Spectrum: (DMSOd$_6$ and CF$_3$COOD) 2.3 (m, 2H), 2.95 (s, 3H), 3.2–3.8 (br s, 8H), 3.4 (m, 2H), 3.95 (s, 3H), 4.3 (t, 2H), 7.25 (s, 1H), 7.85 (s, 1H), 8.75 (s, 1H), 9.4 (br s, 1H); Mass Spectrum: M+H$^+$ 332.

[19] Acetonitrile was used as the reaction solvent and the reaction mixture was heated to 35° C. for 7 hours and then to 50° C. for 5 hours. The resultant precipitate was collected, washed in turn with acetonitrile and diethyl ether and dried. The product gave the following data: NMR Spectrum: (DMSOd$_6$, and CF$_3$COOD) 1.9 (m, 2H), 2.05 (m, 2H), 2.25 (m, 2H), 3.1 (m, 2H), 3.35 (m, 2H), 3.65 (m, 2H), 4.05 (s, 3H), 4.35 (t, 2H), 7.45 (t, 1H), 7.47

(s, 1H), 7.63 (d, 2H), 8.3 (s, 1H), 9.1 (s, 1H); Mass Spectrum: M+H$^+$ 490 and 492.

The 4-amino-6-methoxy-7-(3-pyrrolidin-1-ylpropoxy) quinazoline used as a starting material was prepared by the reaction of 4-amino-7-hydroxy-6-methoxyquinazoline and N-(3-hydroxypropyl)pyrrolidine using an analogous procedure to that described in the last paragraph of Note [16] above. There was thus obtained the required starting material; NMR Spectrum: (DMSOd$_6$ and CF$_3$COOD) 1.9 (m, 2H), 2.05 (m, 2H), 2.25 (m, 2H), 3.05 (m, 2H), 3.35 (m, 2H), 3.65 (m, 2H), 3.95 (s, 3H), 4.3 (t, 2H), 7.25 (s, 1H), 7.85 (s, 1H), 8.75 (s, 1H), 9.4 (br s, 1H); Mass Spectrum: M+H$^+$ 303.

[20] Acetonitrile was used as the reaction solvent and the reaction mixture was heated to 35° C. for 7 hours and then to 50° C. for 5 hours. The resultant precipitate was collected, washed in turn with acetonitrile and diethyl ether and dried. The product gave the following data: NMR Spectrum: (DMSOd$_6$, and CF$_3$COOD) 2.3 (m, 2H), 3.5 (t, 2H), 3.65 (m, 4H), 3.85 (m, 4H), 4.05 (s, 3H), 4.35 (t, 2H), 7.43 (t, 1H), 7.46 (s, 1H), 7.65 (d, 2H), 8.3 (s, 1H), 9.05 (s, 1H); Mass Spectrum: M+H$^+$ 554 and 556.

The 4-amino-7-[3-(1,1-dioxotetrahydro-4H-1,4-thiazin-4-yl)propoxy]-6-methoxyquinazoline used as a starting material was prepared by the reaction of 4-amino-7-hydroxy-6-methoxyquinazoline and N-(3-hydroxypropyl)-1,1-dioxotetrahydro-4H-1,4-thiazine using an analogous procedure to that described in the last paragraph of Note [16] above. There was thus obtained the required starting material; NMR Spectrum: (DMSOd$_6$ and CF$_3$COOD) 2.3 (m, 2H), 3.5 (m, 2H), 3.65 (m, 4H), 3.85 (m, 4H), 3.95 (s, 3H), 4.25 (t, 2H), 7.25 (s, 1H), 7.85 (s, 1H), 8.75 (s, 1H), 9.4 (br s, 1H); Mass Spectrum: M+H$^+$ 367.

[21] Acetonitrile was used as the reaction solvent and the reaction mixture was heated to 35° C. for 7 hours and then to 50° C. for 5 hours. The resultant precipitate was collected, washed in turn with acetonitrile and diethyl ether and dried. The product gave the following data: NMR Spectrum: (DMSOd$_6$, and CF$_3$COOD) 2.95 (s, 3H), 3.35 (s, 3H), 3.4 (m, 1H), 3.55 (m, 1H), 3.75 (m, 4H), 4.05 (s, 3H), 4.65 (t, 2H), 7.45 (t, 1H), 7.50 (s, 1H), 7.65 (d, 2H), 8.3 (s, 1H), 9.05 (s, 1H); Mass Spectrum: M+H$^+$ 494 and 496.

The 4-amino-6-methoxy-7-{2-[N-(2-methoxyethyl)-N-methylamino]ethoxy}quinazoline used as a starting material was prepared by the reaction of 4-amino-7-hydroxy-6-methoxyquinazoline and 2-[N-(2-methoxyethyl)-N-methylamino]ethanol using an analogous procedure to that described in the last paragraph of Note [16] above. There was thus obtained the required starting material; NMR Spectrum: (DMSOd$_6$ and CF$_3$COOD) 2.95 (s, 3H), 3.35 (s, 3H), 3.4 (m, 1H), 3.55 (m, 1H), 3.75 (br m, 4H), 3.95 (s, 3H), 4.55 (t, 2H), 7.25 (s, 1H), 7.85 (s, 1H), 8.75 (s, 1H), 9.45 (br s, 1H); Mass Spectrum: M+H$^+$ 307.

The 2-[N-(2-methoxyethyl)-N-methylamino]ethanol used as a starting material was prepared as follows:

A mixture of 2-methylaminoethanol (5.4 g), 2-bromoethyl methyl ether (10 g), triethylamine (10 ml) and acetonitrile (70 ml) was stirred and heated to reflux for 16 hours. The mixture was cooled to ambient temperature and filtered. The filtrate was evaporated and the residue was triturated under diethyl ether. The organic solution was separated and evaporated to give 2-[N-(2-methoxyethyl)-N-methylamino] ethanol (3 g, 31%); NMR Spectrum: (CDCl$_3$) 2.35 (s, 3H), 2.6 (t, 2H), 2.65 (t, 2H), 3.35 (s, 3H), 3.5 (t, 2H), 3.6 (t, 2H).

[22] Acetonitrile was used as the reaction solvent and the reaction mixture was heated to 35° C. for 7 hours and then to 50° C. for 5 hours. The resultant precipitate was collected, washed in turn with acetonitrile and diethyl ether and dried. The product gave the following data: NMR Spectrum: (DMSOd$_6$ and CF$_3$COOD) 2.3 (m, 2H), 3.05 (s, 3H), 3.35 (t, 2H), 4.05 (s, 3H), 4.4 (t, 2H), 7.45 (m, 2H), 7.65 (d, 2H), 8.29 (s, 1H), 9.1 (s, 1H); Mass Spectrum: M+H$^+$ 499 and 501.

The 4-amino-6-methoxy-7-(3-mesylpropoxy)quinazoline used as a starting material was prepared by the reaction of 4-amino-7-hydroxy-6-methoxyquinazoline and 3-mesylpropanol using an analogous procedure to that described in the last paragraph of Note [16] above. There was thus obtained the required starting material; NMR Spectrum: (DMSOd$_6$ and CF$_3$COOD) 2.3 (m, 2H), 3.05 (s, 3H), 3.3 (t, 2H), 3.95 (s, 3H), 4.3 (t, 2H), 7.2 (s, 1H), 7.85 (s, 1H), 8.75 (s, 1H), 9.45 (br s, 1H); Mass Spectrum: M+H$^+$ 312.

The 3-mesylpropanol used as a starting material was prepared as follows:

3-Chloroperoxybenzoic acid (25 g) was added in portions to a solution of 3-methylthiopropanol (5 ml) in methylene chloride (100 ml) while maintaining the reaction temperature at 25° C. The mixture was stirred at ambient temperature for 1 hour. The mixture was filtered and the filtrate was diluted with an aqueous solution of sodium sulphate (6.5 g) in water (200 ml). The organic layer was separated and evaporated. The white residue was triturated under acetone and the resultant solution was evaporated to give a solid which was dissolved in methylene chloride. Aluminum oxide (90 Å mesh) was added and the mixture was allowed to stand for 15 minutes. The mixture was filtered and the filtrate was evaporated to give 3-mesylpropanol as a colourless oil (4.46 g); NMR Spectrum: (CDCl$_3$) 1.9–2.1 (br s, 1H), 2.15 (m, 2H), 2.95 (s, 3H), 3.2 (t, 2H), 3.85 (t, 2H).

[23] Acetonitrile was used as the reaction solvent and the reaction mixture was heated to 35° C. for 7 hours and then to 50° C. for 5 hours. The resultant precipitate was colleted, washed in turn with acetonitrile and diethyl ether and dried. The product gave the following data: NMR Spectrum: (DMSOd$_6$, and CF$_3$COOD) 2.45 (m, 2H), 4.0 (s, 3H), 4.25 (t, 2H), 4.6 (t, 2H), 7.38 (s, 1H), 7.43 (t, 1H), 7.63 (d, 2H), 7.77 (s, 1H), 8.22 (s, 1H), 8.26 (s, 1H), 9.03 (s, 1H); Mass Spectrum: M+H$^+$ 488 and 490.

The 4-amino-6-methoxy-7-[3-(1,2,3-triazol-1-yl)propoxy]quinazoline used as a starting material was prepared by the reaction of 4-amino-7-hydroxy-6-methoxyquinazine and N$^1$-(3-hydroxypropyl)-1,2,3-triazole (see Note [16] hereinafter) using an analogous procedure to that described in the last paragraph of Note [16] above. There was thus obtained the required starting material; NMR Spectrum: (DMSOd$_6$ and CF$_3$COOD) 2.4 (m, 2H), 3.95 (s, 3H), 4.15 (t, 2H), 4.6 (t, 2H), 7.15 (s, 1H), 7.75 (s, 1H), 7.85 (s, 1H), 8.2 (s, 1H), 8.75 (s, 1H), 9.45 (br s, 1H); Mass Spectrum: M+H$^+$ 301.

[24] Acetonitrile was used as the reaction solvent and the reaction mixture was heated to 35° C. for 7 hours and then to 50° C. for 5 hours. The resultant precipitate was collected, washed in turn with acetonitrile and diethyl ether and dried. The product gave the following data: NMR Spectrum: (DMSOd$_6$ and CF$_3$COOD) 3.55 (t, 2H), 4.0 (s, 3H), 4.65 (t, 2H), 7.45 (t, 1H), 7.5 (s, 1H), 7.65 (d, 2H), 8.15 (d, 2H), 8.3 (s, 1H), 8.95 (d, 2H), 9.1 (s, 1H); Mass Spectrum: M+H$^+$ 484 and 486.

The 4-amino-6-methoxy-7-[2-(4-pyridyl)ethoxy] quinazoline used as a starting material was prepared by die reaction of 4-amino-7-hydroxy-6-methoxyquinazoline and 4-(2-hydroxyethyl)pyridine (*Zhur. Obshchei. Khim.*, 1958, 28, 103–110) using an analogous procedure to that described in the last paragraph of Note [16] above. There was thus obtained the required starting material; NMR Spectrum: (DMSOd$_6$ and CF$_3$COOD) 3.5 (t, 2H), 3.9 (s, 3H), 4.6 (t, 2H), 7.3 (s, 1H), 7.85 (s, 1H), 8.15 (d, 2H), 8.75 (s, 1H), 8.95 (d, 2H), 9.4 (br s, 1H); Mass Spectrum: M+H$^+$ 297.

[25] The product gave the following data: NMR Spectrum: (CDCl$_3$+CD$_3$CO$_2$D) 1.78–1.9 (m, 2H), 2.05–2.3 (m, 3H), 2.64 (t, 2H), 2.7 (s, 3H), 3.59 (d, 2H), 4.04 (s, 3H), 4.1 (d, 2H), 7.25 (s, 1H), 7.44 (s, 2H), 7.74 (s, 1H), 8.2–8.6 (m, partially obscured by CD$_3$CO$_2$H), 8.71 (s, 1H), 12.4 (s, 1H); Mass Spectrum: M+H$^+$ 524 and 526.

[26] The product gave the following data: NMR Spectrum: (CDCl$_3$) 1.41–1.56 (m, 2H), 1.85–2.05 (m, 5H), 2.3 (s, 3H), 2.91 (d, 2H), 3.96 (s, 3H), 4.03 (d, 2H), 6.74 (m, 1H), 7.1 (m, 1H), 7.18 (s, 1H), 7.28 (s, 1H), 8.11 (m, 1H), 8.46 (s, 1H), 8.88 (s, 1H), 12.86 (s, 1H); Mass Spectrum: M+H$^+$ 458.

[27] The product gave the following data: NMR Spectrum: (CDCl$_3$) 1.42–1.58 (m, 2H), 1.87–2.08 (m, 5H), 2.31 (s, 3H), 2.93 (d, 2H), 3.84 (s, 3H), 4.02 (d, 2H), 6.9 (m, 2H), 7.28 (m, 2H), 8.16 (m, 1H), 8.76 (s, 1H), 8.86 (s, 1H), 12.65 (s, 1H); Mass Spectrum: M+H$^+$ 458.

[28] Methylene chloride was used as the reaction solvent. The product was obtained as a 1:1 adduct with DMF and gave the following data: NMR Spectrum: (CDCl$_3$) 1.4–1.55 (m, 2H), 1.9–2.1 (m, 5H), 2.3 (s, 3H), 2.88 (s, 3H), 2.93 (s, 3H), 2.9 (m, partially obscured by DMF signal), 3.72 (s, 3H), 3.85 (s, 3H), 3.91 (s, 3H), 4.01 (d, 2H), 6.6 (m, 1H), 6.86 (d, 1H), 7.28 (s, 1H), 7.36 (s, 1H), 7.98 (d, 1H), 8.02 (s, 1H), 8.55 (s, 1H), 8.87 (s, 1H), 12.75 (s, 1H); Mass Spectrum: M+H$^+$ 482 (relating to the parent ion).

[29] The product gave the following data: NMR Spectrum: (CDCl$_3$) 1.4–1.55 (m, 2H), 1.85–2.1 (m, 5H), 2.29 (s, 3H), 2.9 (d, 2H), 3.8 (s, 3H), 3.82 (s, 3H), 3.96 (s, 3H), 4.03 (d, 2H), 6.48 (m, 1H), 6.56 (d, 1H), 7.25 (s, 1H), 7.38 (s, 1H), 8.08 (d, 1H), 8.72 (s, 1H), 9.07 (s, 1H), 12.4 (s, 1H); Mass Spectrum: M+H$^+$ 482.

[30] Methylene chloride was used as the reaction solvent. The product gave the following data: NMR Spectrum: (CDCl$_3$) 1.17 (br s, 12H), 1.4–1.6 (m, 2H), 1.7 (br s, 2H), 1.85–2.1 (m, 5H), 2.3 (s, 3H), 2.91 (d, 2H), 3.3 (s, 3H), 4.01 (d, 2H), 7.2–7.22 (m, 3H), 7.3–7.4 (m, 1H), 7.5 (s, 1H), 8.62 (s, 1H), 9.7 (s, 1H), 11.4 (s, 1H); Mass Spectrum: M+H$^+$ 506.

[31] The product gave the following data: NMR Spectrum: (CDCl$_3$) 1.4–1.55 (m, 2H), 1.85–2.1 (m, 5H), 2.28 (s, 6H), 2.3 (s, 3H), 2.34 (s, 3H), 2.9 (d, 2H), 3.37 (s, 3H), 4.01 (d, 2H), 6.91 (s, 2H), 7.22 (s, 1H), 7.3 (s, 1H), 8.64 (s, 1H), 8.7 (s, 1H), 11.8 (s, 1H); Mass Spectrum: M+H$^+$ 464.

[32] The product gave the following data: NMR Spectrum: (CDCl$_3$) 1.44–1.59 (m, 2H), 1.86–2.08 (m, 5H), 2.32 (d, 6H), 2.41 (s, 3H), 2.94 (d, 2H), 3.68 (s, 3H), 4.02 (d, 2H), 6.92 (d, 1H), 7.14 (d, 1H), 7.26 (m, 1H), 7.46 (s, 1H), 7.77 (s, 1H), 8.69 (s, 1H), 9.31 (s, 1H), 12.27 (s, 1H); Mass Spectrum: M+H$^+$ 450.

[33] The product gave the following data: NMR Spectrum: (CDCl$_3$) 1.18 (t, 6H), 1.4–1.55 (m, 2H), 1.85–2.06 (m, 5H), 2.3 (s, 3H), 2.69 (q, 4H), 2.9 (d, 2H), 3.3 (s, 3H), 4.03 (d, 2H), 7.1–7.3 (m, 4H), 7.51 (s, 1H), 8.63 (s, 1H), 9.73 (s, 1H), 11.87 (s, 1H); Mass Spectrum: M+H$^+$ 478.

[34] The product gave the following data: NMR Spectrum: (CDCl$_3$) 1.2 (t, 3H), 1.4–1.6 (m, 2H), 1.85–2.06 (m, 5H), 2.3 (s, 6H), 2.7 (q, 2H), 2.92 (d, 2H), 3.32 (s, 3H), 4.02 (d, 2H), 7.1–7.3 (m, 4H), 7.51 (s, 1H), 8.65 (s, 1H), 9.77 (s, 1H), 11.97 (s, 1H); Mass Spectrum: M+H$^+$ 464.

[35] The product gave the following data: NMR Spectrum: (CDCl$_3$) 1.51 (m, 2H), 1.9–2.1 (m, 5H), 2.3 (s, 9H), 2.95 (d, 2H), 3.52 (s, 3H), 4.02 (d, 2H), 7.23 (s, 1H), 7.25 (s, 2H), 7.37 (s, 1H), 8.67 (s, 1H), 9.32 (s, 1H), 11.82 (s, 1H); Mass Spectrum: M+H$^+$ 528 and 530.

[36] The product gave the following data: NMR Spectrum: (CDCl$_3$) 1.4–1.56 (m, 2H), 1.84–2.05 (m, 5H), 2.3 (s, 3H), 2.38 (s, 3H), 2.9 (d, 2H), 3.44 (s, 3H), 4.03 (d, 2H), 7.19 (d, 2H), 7.22 (s, 1H), 7.33 (t, 1H), 7.47 (s, 1H), 8.70 (s, 1H), 9.67 (s, 1H), 12.21 (s, 1H); Mass Spectrum: M+H$^+$ 470.

[37] The product gave the following data: NMR Spectrum: (CDCl$_3$) 1.81 (s, 4H), 2.17 (m, 2H), 2.57 (s, 4H), 2.7 (t, 2H), 3.77 (s, 3H), 4.26 (t, 2H), 7.23–7.45 (m, 2H), 7.38–7.45 (m, 2H), 8.7 (s, 1H), 8.96 (s, 1H), 12.23 (s, 1H); Mass Spectrum: M+H$^+$ 524 and 526.

The 4-amino-6-methoxy-7-(3-pyrrolidin-1-ylpropoxy) quinazoline used as a starting material was prepared as follows:

4-(4-Bromo-2-fluorophenoxy)-7-hydroxy-6-methoxyquinazoline was reacted with 3-pyrrolidin-1-ylpropyl chloride (Chemical Abstacts, volume 128. no. 227441; PCT Patent Application WO 98/13354) using an analogous procedure to that described in the second last paragraph of Note [38] below to give 4-(2-bromo-4-fluorophenoxy)-6-methoxy-7-(3-pyrrolidin-1-ylpropoxy) quinazoline; NMR Spectrum: (CDCl$_3$) 1.8 (m, 4H), 2.18 (m, 2H), 2.57 (s, 4H), 2.69 (t, 2H), 4.05 (s, 3H), 4.3 (t, 2H), 7.16 (m, 1H), 7.28–7.36 (m, 2H), 7.44 (m, 1H), 7.57 (s, 1H), 8.6 (s, 1H); Mass Spectrum: M+H$^+$ 476 & 478.

The material so obtained was reacted with ammonia using an analogous procedure to that described in the last paragraph of Note [38] below to give the required starting material; NMR Spectrum: (CDCl$_3$) 1.8 (m, 4H), 2.14 (m, 2H), 2.54 (t, 4H), 2.67 (t, 2H), 3.96 (s, 3H), 4.23 (t, 2H), 5.54 (s, 2H), 6.91 (s, 1H), 7.23 (s, 1H), 8.52 (s, 1H); Mass Spectrum: M+H$^+$ 303.

[38] The product gave the following data: NMR Spectrum: (CDCl$_3$) 1.68 (s, 4H), 2.11 (m, 2H), 2.3 (s, 3H), 2.4–2.6 (m, 6H), 3.72 (s, 3H), 4.24 (t, 2H), 7.31 (s, 2H), 7.43 (s, 2H), 8.71 (s, 1H), 9.07 (s, 1H), 12.27 (s, 1H); Mass Spectrum: M+H$^+$ 553, 555 and 557.

The 4-amino-6-methoxy-7-[3-(4-methylpiperazin-1-yl) propoxy]quinazoline used as a starting material was prepared as follows:

A mixture of 7-acetoxy-6-methoxyquinazolin-4-one (international Patent Application WO 96/15118, Example 17 thereof; 15 g), thionyl chloride (225 ml) and DMF (5 ml) was stirred and heated to 90° C. for 4 hours. The mixture was cooled to ambient temperature and the thionyl chloride was evaporated. The material so obtained was dissolved in toluene and the solution was washed with a saturated aqueous sodium bicarbonate solution. The organic solution was dried over magnesium sulphate and evaporated. There was thus obtained 7-acetoxy-4-chloro-6-methoxyquinazoline (13.2 g) which was used without further purification.

A mixture of the material so obtained was reacted with 2-bromo-4-fluorophenol using an analogous procedure to that described in the second last paragraph of the portion of Example 1 above which is concerned with the preparation of starting materials. There was thus obtained 7-acetoxy-4-(2-bromo-4-fluorophenoxy)-6-methoxyquinazoline (14.7 g).

A mixture of a portion (3 g) of the material so obtained, concentrated ammonium hydroxide solution (0.88 g/ml. approximately 14M; 60 ml) and methanol (120 ml) was stirred at ambient temperature for 16 hours. The mixture was evaporated and the residue was triturated under diethyl ether. There was thus obtained 4-(2-bromo-4-fluorophenoxy)-7-hydroxy-6-methoxyquinazoline (2.2 g); NMR Spectrum: (DMSOd$_6$) 3.99 (s, 3H), 7.25 (s, 1H), 7.39 (m, 1H), 7.54 (m, 2H), 7.78 (m, 1H), 8.47 (s, 1H), 10.82 (s, 1H); Mass Spectrum: M−H⁻ 363 & 365.

A mixture of 4-(2-bromo-4-fluorophenoxy)-7-hydroxy-6-methoxyquinazoline (0.94 g), 3-(4-methylpiperazin-1-yl)propyl chloride (0.5 g), potassium carbonate (1.42 g) and DMF (20 ml) was stirred and heated to 65° C. for 16 hours. The mixture was filtered and evaporated. The resulting oil was purified by column chromatography on silica using increasingly polar mixtures of methylene chloride and a 2M methanolic ammonia solution as eluent. There was thus obtained 4-(2-bromo-4-fluorophenoxy)-6-methoxy-7-[3-(4-methylpiperazin-1-yl)propoxy]quinazoline (0.84 g); NMR Spectrum: (CDCl$_3$) 1.72 (s, 4H), 2.13 (m, 2H), 2.31 (s, 3H), 2.4–2.6 (m, 6H), 4.05 (s, 3H), 4.29 (t, 2H), 7.16 (m, 1H), 7.3 (s, 1H), 7.35 (s, 1H), 7.44 (m, 1H), 7.57 (s, 1H), 8.6 (s, 1H); Mass Spectrum: M+H⁺ 505 & 507.

A mixture of the material so obtained, liquid ammonia (1 ml) and a 2M solution of ammonia in isopropanol (15 ml) was sealed in a Carius tube and heated to 120° C. for 16 hours. The mixture was cooled and evaporated. The residue was stirred under a 2N aqueous sodium hydroxide solution (200 ml) for 1 hour. The resultant solid was isolated and washed in turn with water (400 ml) and with methyl tert-butyl ether. There was thus obtained the required starting material (0.55 g); NMR Spectrum: (CDCl$_3$) 1.81 (s, 4H), 2.1 (m, 2H), 2.29 (s, 3H), 2.4–2.6 (m, 6H), 3.96 (s, 3H), 4.22 (t, 2H), 5.46 (s, 2H), 6.9 (s, 1H), 7.22 (s, 1H), 8.51 (s, 1H); Mass Spectrum: M+H⁺ 332.

The 3-(4-methylpiperazin-1-yl)propyl chloride used as an intermediate was prepared by the reaction of 1-methylpiperazine with 1-bromo-3-chloropropane using an analogous procedure to that described in Note [42] hereinafter for the preparation of 3-morpholinopropyl chloride.

[39] The product gave the following data: NMR Spectrum: (CDCl$_3$) 1.42 (q, 2H), 1.58 (m, 4H), 2.09 (m, 2H), 2.38 (s, 4H), 2.49 (t, 2H), 3.63 (s, 3H), 4.23 (t, 2H), 7.18–7.27 (m, 2H), 7.37 (m, 2H), 7.41 (s, 1H), 8.71 (s, 1H), 9.3 (s, 1H), 12.34 (s, 1H); Mass Spectrum: M+H⁺ 504 and 506.

[40] The product gave the following data: NMR Spectrum: (CDCl$_3$) 1.84 (m, 4H), 2.17 (m, 2H), 2.56 (s, 4H), 2.68 (t, 2H), 3.69 (s, 3H), 4.28 (t, 2H), 6.99 (t, 2H), 7.2–7.3 (m, 2H), 7.38 (s, 1H), 8.71 (s, 1H), 9.3 (s, 1H), 12.04 (s, 1H); Mass Spectrum: M+H⁺ 458.

[41] The produce gave the following data: NMR Spectrum: (CDCl$_3$) 1.43 (m, 2H), 1.57–1.76 (m, 4H), 2.12 (m, 2H), 2.47 (s, 4H), 2.54 (t, 2H), 3.7 (s, 3H), 4.23 (t, 2H), 6.94–7.03 (m, 2H), 7.2–7.31 (m, 2H), 7.37 (s, 1H), 8.71 (s, 1H), 9.26 (s, 1H), 12.03 (s, 1H); Mass Spectrum: M+H⁺ 472.

[42] The product gave the following data: NMR Spectrum: (CDCl$_3$) 2.11 (m, 2H), 2.49 (br s, 4H), 2.57 (t, 2H), 3.73 (m, 7H), 4.26 (t, 2H), 7.0 (t, 2H), 7.27 (m, 1H), 7.3 (s, 1H), 7.38 (s, 1H), 8.73 (s, 1H), 9.24 (s, 1H), 12.04 (s, 1H); Mass Spectrum: M+H⁺ 474.

The 4-amino-6-methoxy-7-(3-morpholinopropoxy)quinazolin used as a starting material was prepared as follows:

4-(4-Bromo-2-fluorophenoxy)-7-hydroxy-6-methoxyquinazoline was reacted with 3-morpholinopropyl chloride using an analogous procedure to that described in the second last paragraph of Note [38] above to give 4-(2-bromo-4-fluorophenoxy)-6-methoxy-7-(3-morpholinopropoxy)quinazoline; NMR Spectrum: (CDCl$_3$) 2.13 (m, 2H), 2.49 (t, 4H), 2.58 (t, 2H), 3.74 (t, 4H), 4.06 (s, 3H), 4.29 (t, 2H), 7.15 (m, 1H), 7.31 (m, 1H), 7.37 (s, 1H), 7.43 (m, 1H), 8.58 (s, 1H), 8.6 (s, 1H); Mass Spectrum: M+H⁺ 492 & 494.

The material so obtained was reacted with ammonia using an analogous procedure to that described in the last paragraph of Note [38] above to give the required starting material; NMR Spectrum: (CDCl$_3$) 2.09 (m, 2H), 2.48 (t, 4H), 2.55 (t, 2H), 3.61 (t, 4H), 3.96 (s, 3H), 4.24 (t, 2H), 5.44 (s, 2H), 6.9 (s, 1H), 7.24 (s, 1H), 8.52 (s, 1H).

The 3-morpholinopropyl chloride used as an intermediate was prepared as follows:

Morpholine (52.2 ml) and 1-bromo-3-choropropane (30 ml) were taken up in dry toluene (180 ml) and stirred and heated to 70° C. for 3 hours. The resultant precipitate was filtered off and the filtrate was evaporated to give an orange oil which was purified by vacuum distillation collecting fractions at 62° C./5 mmHg and 58° C./2 mmHg. The required compound was obtained as an oil (37.9 g); NMR Spectrum: 1.85 (m, 2H), 2.3 (t, 4H), 2.38 (t, 2H), 3.53 (t, 4H), 3.65 (t, 2H); M/s: M+H⁺ 164.

[43] The product gave the following data: NMR Spectrum: (CDCl$_3$) 1.71 (s, 4H), 2.12 (m, 2H), 2.31 (s, 3H), 2.42–2.62 (m, 6H), 3.7 (s, 3H), 4.27 (t, 2H), 7.0 (m, 2H), 7.21–7.32 (m, 2H), 7.38 (s, 1H), 8.73 (s, 1H), 9.62 (s, 1H), 12.08 (s, 1H); Mass Spectrum: M+H⁺ 487.

[44] The product gave the following data: NMR Spectrum: (CDCl$_3$) 1.46 (m, 2H), 1.64 (m, 4H), 2.55 (t, 4H), 2.9 (t, 2H), 3.68 (s, 3H), 4.3 (t, 2H), 6.95–7.04 (m, 3H), 7.28 (m, 1H), 7.4 (s, 1H), 8.73 (s, 1H), 9.38 (s, 1H), 12.1 (s, 1H); Mass Spectrum: M+H⁺ 458.

[45] The product gave the following data: NMR Spectrum: (CDCl$_3$) 1.49 (m, 2H), 1.63 (m, 4H), 2.56 (t, 4H), 2.8 (t, 2H), 3.7 (s, 3H), 4.32 (t, 2H), 7.3 (s, 1H), 7.34 (s, 1H), 7.43 (s, 2H), 8.72 (s, 1H), 9.22 (s, 1H), 12.32 (s, 1H); Mass Spectrum: M+H⁺ 524 and 526.

[46] The product gave the following data: NMR Spectrum: (CDCl$_3$) 1.8 (m, 4H), 2.15 (m, 2H), 2.53 (s, 4H), 2.66 (t, 2H), 3.58 (s, 3H), 4.25 (t, 2H), 7.29 (s, 1H), 7.32–7.45 (m, 3H), 7.54 (d, 1H), 8.68 (s, 1H), 9.38 (s, 1H), 12.55 (s, 1H); Mass Spectrum: M+H⁺ 507.

[47] The product gave the following data: NMR Spectrum: (CDCl$_3$) 2.38 (s, 6H), 2.88 (t, 2H), 3.57 (s, 3H), 4.27 (t, 2H), 6.98 (t, 3H), 7.27 (s, 1H), 7.51 (s, 1H), 8.71 (s, 1H), 9.81 (s, 1H), 12.25 (s, 1H); Mass Spectrum: M+H⁺ 418.

The 4-amino-6-methoxy-7-(2-dimethylaminoethoxy)quinazoline used as a starting material was prepared as follows:

4-(4-Bromo-2-fluorophenoxy)-7-hydroxy-6-methoxyquinazoline was reacted with 2-dimethylaminoethyl chloride using an analogous procedure to that described in the second last paragraph of Note [38] above to give 4-(2-bromo-4-fluorophenoxy)-7-(2-dimethylaminoethoxy)-6-methoxyquinazoline; NMR Spectrum: (CDCl$_3$) 2.39 (s, 6H), 2.9 (t, 2H), 4.04 (s, 3H), 4.31 (t, 2H), 7.22 (t, 1H), 7.32 (s, 1H), 7.41 (m, 2H), 7.52 (s, 1H), 8.6 (s, 1H); Mass Spectrum: M+H⁺ 436 & 438.

The material so obtained was reacted with ammonia using an analogous procedure to that described in the last paragraph of Note [38] above to give the required starting material; NMR Spectrum: (DMSOd$_6$) 2.21 (s, 6H), 2.68 (t, 2H), 3.87 (s, 3H), 4.14 (t, 2H), 7.07 (s, 1H), 7.37 (s, 2H), 7.55 (s, 1H), 8.22 (s, 1H); Mass Spectrum: M+H⁺ 263.

[48] The product gave the following data: NMR Spectrum: (CDCl$_3$) 2.38 (s, 6H), 2.87 (t, 2H), 3.49 (s, 3H), 4.26 (t, 2H), 7.24 (s, 2H), 7.4 (d, 2H), 7.53 (s, 1H), 8.72 (s, 1H), 9.8 (s, 1H), 12.47 (s, 1H); Mass Spectrum: M+H⁺ 450 and 452.

[49] The product gave the following data: NMR Spectrum: (CDCl$_3$) 3.47 (t, 2H), 3.74 (m, 4H), 3.89 (s, 3H), 4.33 (t, 2H), 4.42 (s, 1H), 7.01 (t, 3H), 7.28 (m, 2H), 8.0 (s, 1H), 8.73 (s, 1H), 11.9 (s, 1H); Mass Spectrum: M+H$^+$ 459.

The 4-amino-6-methoxy-7-[2-(2-oxoimidazolidin-1-yl)ethoxy]quinazoline used as a starting material was prepared as follows:

4-(4-Bromo-2-fluorophenoxy)-7-hydroxy-6-methoxyquinazoline was reacted with 2-(2-oxoimidazolidin-1-yl)ethyl chloride (*Indian J. Chem. Sect. B*, 1982, 21B, 928–940) using an analogous procedure to that described in the second last paragraph of Note [38] above to give 4-(2-bromo-4-fluorophenoxy)-6-methoxy-7-[2-(2-oxoimidazolidin-1-yl)ethoxy]quinazoline; NMR Spectrum: (CDCl$_3$) 3.47 (t, 2H), 3.75 (m, 4H), 4.05 (s, 3H), 4.35 (t, 2H), 4.47 (s, 1H), 7.21 (t, 1H), 7.30 (s, 1H), 7.41 (t, 2H), 7.54 (s, 1H), 8.6 (s, 1H); Mass Spectrum: M+H$^+$ 477 & 479.

The material so obtained was reacted with ammonia using an analogous procedure to that described in the last paragraph of Note [38] above to give the required starting material; NMR Spectrum: (DMSOd$_6$) 3.23 (t, 2H), 3.48 (m, 4H), 3.87 (s, 3H), 4.2 (t, 2H), 6.4 (s, 1H), 7.1 (s, 1H), 7.4 (s, 2H), 7.58 (s, 1H), 8.23 (s, 1H); Mass Spectrum: M+H$^+$ 304.

[50] The product gave the following data: NMR Spectrum: (CDCl$_3$) 3.48 (t, 2H), 3.73 (m, 7H), 4.32 (t, 2H), 4.48 (s, 1H), 7.13 (m, 2H), 7.44 (t, 3H), 8.74 (s, 3H), 9.1 (s, 1H), 12.27 (s, 1H); Mass Spectrum: M+H$^+$ 491 and 493.

[51] The product gave the following data: NMR Spectrum: (CDCl$_3$) 1.87 (m, 4H), 2.71 (s, 4H), 3.06 (t, 2H), 3.58 (s, 3H), 4.33 (t, 2H), 7.1–7.27 (m, 2H), 7.36–7.46 (m, 3H), 8.73 (s, 1H), 9.5 (s, 1H), 12.37 (s, 1H); Mass Spectrum: M+H$^+$ 476 and 478.

The 4-amino-6-methoxy-7-(2-pyrrolidin-1-ylethoxy)quinazoline used as a starting material was prepared as follows:

4-(4-Bromo-2-fluorophenoxy)-7-hydroxy-6-methoxyquinazoline was reacted with 2-pyrrolidin-1-ylethyl chloride using an analogous procedure to that described in the second last paragraph of Note [38] above to give 4-(2-bromo-4-fluorophenoxy)-6-methoxy-7-(2-pyrrolidin-1-ylethoxy)quinazoline; NMR Spectrum: (CDCl$_3$) 1.83 (m, 4H), 2.69 (m, 4H), 3.06 (t, 2H), 4.04 (s, 3H), 4.34 (t, 2H), 7.21 (t, 1H), 7.31 (s, 1H), 7.4 (t, 2H), 7.53 (s, 1H), 8.6 (s, 1H). Mass Spectrum: M+H$^+$ 462 & 464.

The material so obtained was reacted with ammonia using an analogous procedure to that described in the last paragraph of Note [38] above to give the required starting material; NMR Spectrum: (CDCl$_3$) 1.7 (s, 4H), 2.35 (m, 4H), 2.83 (t, 2H), 3.87 (s, 3H), 4.19 (t, 2H), 7.07 (s, 1H), 7.39 (s, 2H), 7.56 (s, 1H), 8.23 (s, 1H); Mass Spectrum: M+H$^+$ 289.

[52] The product give the following data: NMR Spectrum: (CDCl$_3$) 1.87 (s, 4H), 2.73 (s, 4H), 3.07 (t, 2H), 3.65 (s, 3H), 4.34 (t, 2H), 6.99 (t, 3H), 7.28 (m, 1H), 7.43 (s, 1H), 8.75 (s, 1H), 9.47 (s, 1H), 12.11 (s, 1H); Mass Spectrum: M+H$^+$ 444.

[53] The product gave the following data: NMR Spectrum: (CDCl$_3$) 2.6 (t, 4H), 2.92 (t, 2H), 3.58 (s, 3H), 3.74 (t, 4H), 4.28 (t, 2H), 7.11–7.27 (m, 2H), 7.37–7.45 (m, 3H), 8.73 (s, 1H), 9.47 (s, 1H), 12.36 (s, 1H); Mass Spectrum: M+H$^+$ 492 and 494.

The 4-amino-6-methoxy-7-(2-morpholinoethoxy)quinazoline used as a starting material was prepared as follows:

4-(4-Bromo-2-fluorophenoxy)-7-hydroxy-6-methoxyquinazoline was reacted with 2-morpholinoethyl chloride using an analogous procedure to that described in the second last paragraph of Note [38] above to give 4-(2-bromo-4-fluorophenoxy)-6-methoxy-7-(2-morpholinoethoxy)quinazoline; NMR Spectrum: (CDCl$_3$) 2.63 (t, 4H), 2.98 (t, 2H), 3.76 (t, 4H), 4.06 (s, 3H), 4.34 (t, 2H), 7.22 (t, 1H), 7.32 (s, 1H), 7.41 (t, 2H), 7.52 (s, 1H), 8.61 (s, 1H); Mass Spectrum: M+H$^+$ 478 & 480.

The material so obtained was reacted with ammonia using an analogous procedure to that described in the last paragraph of Note [38] above to give the required starting material; NMR Spectrum: (DMSOd$_6$) 2.5 (m, 4H), 2.75 (t, 2H), 3.58 (t, 4H), 3.87 (s, 3H), 4.2 (t, 2H), 7.09 (s, 1H), 7.39 (s, 2H), 7.58 (s, 1H), 8.24 (s, 1H); Mass Spectrum: M+H$^+$ 305.

[54] The product gave the following data: NMR Spectrum: (CDCl$_3$) 2.63 (t, 4H), 3.04 (t, 2H), 3.61 (s, 3H), 3.76 (t, 4H), 4.33 (t, 2H), 6.99 (t, 2H), 7.27 (m, 2H), 7.45 (s, 1H), 8.74 (s, 1H), 9.57 (s, 1H), 12.15 (s, 1H); Mass Spectrum: M+H$^+$ 460.

[55] The product gave the following data: NMR Spectrum: (CDCl$_3$) 1.8 (m, 4H), 2.15 (m, 2H), 2.33 (s, 6H), 2.57 (br s, 4H), 2.69 (t, 2H), 3.41 (s, 3H), 4.26 (t, 2H), 7.14 (m, 3H), 7.28 (s, 1H), 7.5 (s, 1H), 8.66 (s, 1H), 9.66 (s, 1H), 11.95 (s, 1H); Mass Spectrum: M+H$^+$ 450.

[56] The product gave the following data: NMR Spectrum: (CDCl$_3$) 2.09 (m, 2H), 2.32 (s, 6H), 2.46 (t, 4H), 2.55 (t, 2H), 3.4 (s, 3H), 3.71 (t, 2H), 4.25 (t, 2H), 7.11 (m, 3H), 7.28 (s, 1H), 7.49 (s, 1H), 8.66 (s, 1H), 9.61 (s, 1H), 11.91 (s, 1H); Mass Spectrum: M+H$^+$ 466.

[57] The product gave the following data: NMR Spectrum: (CDCl$_3$) 1.72 (s, 4H), 2.1 (m, 2H), 2.3 (s, 3H), 2.33 (s, 6H), 2.4–2.6 (m, 6H), 3.4 (s, 3H), 4.23 (t, 2H), 7.16 (m, 3H), 7.28 (s, 1H), 7.49 (s, 1H), 8.66 (s, 1H), 9.64 (s, 1H), 11.91 (s, 1H); Mass Spectrum: M+H$^+$ 479.

[58] The product gave the following data: NMR Spectrum: (CDCl$_3$) 1.85 (m, 4H), 2.34 (s, 6H), 2.68 (s, 4H), 3.05 (t, 2H), 3.31 (s, 3H), 4.3 (t, 2H), 7.14 (m, 3H), 7.26 (s, 1H), 7.56 (s, 1H), 8.65 (s, 1H), 9.87 (s, 1H), 11.98 (s, 1H); Mass Spectrum: M+H$^+$ 436.

[59] The product gave the following data: NMR Spectrum: (CDCl$_3$) 1.47 (s, 2H), 1.64 (m, 4H), 2.32 (s, 6H), 2.55 (s, 4H), 2.91 (t, 2H), 3.36 (s, 3H), 4.32 (t, 2H), 7.14 (m, 3H), 7.26 (s, 1H), 7.54 (s, 1H), 8.66 (s, 1H), 9.79 (s, 1H), 11.98 (s, 1H); Mass Spectrum: M+H$^+$ 450.

[60] The product gave the following data: NMR Spectrum: (CDCl$_3$) 2.31 (s, 6H), 2.61 (m, 4H), 2.94 (t, 2H), 3.27 (s, 3H), 3.76 (t, 4H), 4.31 (t, 2H), 7.15 (m, 3H), 7.26 (s, 1H), 7.59 (s, 1H), 8.67 (s, 1H), 9.97 (s, 1H), 12.01 (s, 1H); Mass Spectrum: M+H$^+$ 452.

[61] The product gave the following data: NMR Spectrum: (CDCl$_3$) 2.33 (s, 6H), 3.35 (s, 3H), 3.46 (t, 2H), 3.72 (m, 4H), 4.28 (t, 2H), 4.67 (s, 1H), 7.14 (m, 3H), 7.25 (s, 1H), 7.61 (s, 1H), 8.67 (s, 1H), 9.91 (s, 1H), 11.98 (s, 1H); Mass Spectrum: M+H$^+$ 451.

[62] The product gave the following data: NMR Spectrum: (CDCl$_3$) 2.33 (s, 6H), 2.39 (s, 6H), 2.87 (t, 2H), 3.28 (s, 3H), 4.26 (t, 2H), 7.12 (m, 3H), 7.26 (s, 1H), 7.58 (s, 1H), 8.66 (s, 1H), 9.97 (s, 1H), 12.02 (s, 1H); Mass Spectrum: M+H$^+$ 410.

[63] The product gave the following data: NMR Spectrum: (CDCl$_3$) 1.81 (m, 4H), 2.16 (m, 2H), 2.31 (s, 6H), 2.59 (s, 4H), 2.7 (t, 2H), 3.52 (s, 3H), 4.26 (t, 2H), 7.27 (m, 3H), 7.39 (s, 1H), 8.67 (s, 1H), 9.34 (s, 1H), 11.83 (s, 1H); Mass Spectrum: M+H$^+$ 528 and 530.

[64] The product gave the following data: NMR Spectrum: (CDCl$_3$) 1.45 (q, 2H), 1.6 (m, 4H), 2.13 (m, 2H), 2.3 (s, 6H), 2.44 (s, 4H), 2.54 (t, 2H), 3.53 (s, 3H), 4.25 (t, 2H), 7.29 (m, 3H), 7.37 (s, 1H), 8.68 (s, 1H), 9.27 (s, 1H), 11.81 (s, 1H); Mass Spectrum: M+H⁺ 542 and 544.

[65] The product gave the following data: NMR Spectrum: (CDCl₃) 2.12 (m, 2H), 2.3 (s, 6H), 2.5 (t, 4H), 2.58 (t, 2H), 3.5 (s, 3H), 3.5 (t, 4H), 4.27 (t, 2H), 7.22–7.29 (m, 3H), 7.41 (s, 1H), 8.67 (s, 1H), 9.44 (s, 1H), 11.87 (s, 1H); Mass Spectrum: M+H⁺ 544 and 546.

[66] The product gave the following data: NMR Spectrum: (CDCl₃) 1.66 (s, 10H), 2.11 (m, 2H), 2.3 (s, 3H), 2.4–2.6 (m, 6H), 3.58 (s, 3H), 4.24 (t, 2H), 7.25 (s, 3H), 7.34 (s, 1H), 8.67 (s, 1H), 9.2 (s, 1H), 11.79 (s, 1H); Mass Spectrum: M+H⁺ 557 and 559.

[67] The product gave the following data: NMR Spectrum: (CDCl₃) 1.49 (m, 2H), 1.66 (m, 4H), 2.31 (s, 6H), 2.54 (t, 4H), 2.9 (t, 2H), 3.5 (s, 3H), 4.32 (t, 2H), 7.28 (m, 3H), 7.41 (s, 1H), 8.69 (s, 1H), 9.44 (s, 1H), 11.9 (s, 1H); Mass Spectrum: M+H⁺ 528 and 530.

[68] The product gave the following data: NMR Spectrum: (CDCl₃) 2.3 (s, 6H), 2.64 (t, 4H), 2.95 (t, 2H), 3.41 (s, 3H), 3.77 (t, 4H), 4.33 (t, 2H), 7.27 (s, 3H), 7.48 (s, 1H), 8.69 (s, 1H), 9.71 (s, 1H), 11.97 (s, 1H); Mass Spectrum: M+H⁺ 530 and 532.

[69] The product gave the following data: NMR Spectrum: (CDCl₃) 2.29 (s, 6H), 3.47 (t, 2H), 3.62 (s, 3H), 3.75 (m, 4H), 4.33 (t, 2H), 4.44 (s, 1H), 7.28 (m, 3H), 7.39 (s, 1H), 8.68 (s, 1H), 9.18 (s, 1H), 11.77 (s, 1H); Mass Spectrum: M+H⁺ 529 and 531.

[70] The product gave the following data: NMR Spectrum: (CDCl₃) 3.39 (s, 3H), 3.54 (s, 3H), 3.6 (m, 2H), 3.75 (m, 2H), 3.98 (t, 2H), 4.33 (t, 2H), 7.24 (m, 2H), 7.41 (m, 2H), 7.48 (s, 1H), 8.73 (s, 1H), 9.68 (s, 1H), 12.46 (s, 1H); Mass Spectrum: M+H⁺ 481 and 483.

The 4-amino-6-methoxy-7-[2-(2-methoxyethoxy)ethoxy] quinazoline used as a starting material was prepared as follows:

4-(4-Bromo-2-fluorophenoxy)-7-hydroxy-6-methoxyquinazoline was reacted with 2-(2-methoxyethoxy) ethyl tosylate (prepared from 2-(2-methoxyethoxy)ethanol and tosyl chloride) using an analogous procedure to that described in the second last paragraph of Note [38] above to give 4-(2-bromo-4-fluorophenoxy)-6-methoxy-7-[2-(2-methoxyethoxy)ethoxy]quinazoline; NMR Spectrum: (CDCl₃) 3.4 (s, 3H), 3.6 (m, 2H), 3.76 (m, 2H), 4.03 (m, 5H), 4.39 (t, 2H), 7.21 (m, 1H), 7.34 (s, 1H), 7.41 (t, 2H), 7.51 (s, 1H), 8.6 (s, 1H); Mass Spectrum: M+H⁺ 467 & 469.

The material so obtained was reacted with ammonia using an analogous procedure to that described in the last paragraph of Note [38] above to give the required starting material; NMR Spectrum: (DMSOd₆) 3.23 (s, 3H), 3.46 (m, 2H), 3.6 (m, 2H), 3.79 (t, 2H), 3.88 (s, 3H), 4.2 (t, 2H), 7.08 (s, 1H), 7.39 (s, 2H), 7.57 (s, 1H), 8.23 (s, 1H); Mass Spectrum: M+H⁺ 294.

[71] The product gave the following data: NMR Spectrum: (CDCl₃) 3.39 (s, 3H), 3.6 (m, 5H), 3.77 (m, 2H), 4.01 (t, 2H), 4.36 (s, 1H), 7.01 (t, 3H), 7.26 (m, 2H), 7.46 (s, 1H), 8.72 (s, 1H), 9.58 (s, 1H), 12.16 (s, 1H); Mass Spectrum: M+H⁺ 449.

[72] The product gave the following data: NMR Spectrum: (CDCl₃) 2.31 (s, 6H), 3.27 (s, 3H), 3.4 (s, 3H), 3.6 (m, 2H), 3.75 (m, 2H), 3.97 (t, 2H), 4.34 (t, 2H), 7.14 (m, 3H), 7.26 (s, 1H), 7.57 (s, 1H), 8.66 (s, 1H), 9.95 (s, 1H), 12.03 (s, 1H); Mass Spectrum: M+H⁺ 441.

[73] The product gave the following data: NMR Spectrum: (CDCl₃) 1.4–1.54 (m, 2H), 1.82–2.03 (m, 5H), 2.3 (s, 3H), 2.91 (d, 2H), 3.53 (s, 3H), 4.02 (d, 2H), 7.26 (m, 1H), 7.31–7.47 (m, 3H), 7.55 (d, 1H), 8.68 (s, 1H), 9.49 (s, 1H), 12.6 (s, 1H); Mass Spectrum: M+H⁺ 508.

[74] The product gave the following data: NMR Spectrum: (CDCl₃) 1.82 (m, 4H), 2.66 (m, 4H), 3.0 (t, 2H), 4.27 (t, 2H), 7.2–7.4 (m, 3H), 7.5 (d, 2H), 8.05 (d, 1H), 8.78 (s, 1H), 9.1 (br s, 1H), 12.07 (br s, 1H); Mass Spectrum: M+H⁺ 446 and 448.

The 4-amino-7-(2-pyrrolidin-1-ylethoxy)quinazoline used as a starting material was prepared as follows:

A mixture of 7-hydroxy-4-methylthioquinazoline (6 g) and a saturated solution of ammonia gas in methanol (225 ml) was sealed in a pressure vessel and heated at 120° C. for 40 hours. The mixture was cooled to ambient temperature and evaporated. The residue was purified by column chromatography on silica using increasingly polar mixtures of methylene chloride and methanol as eluent. There was thus obtained 4-amino-7-hydroxyquinazoline (4.9 g); NMR Spectrum: (DMSOd₆) 6.9 (s, 1H), 6.9 (d, 1H), 9.5 (br s, 2H), 8.04 (d, 1H), 8.24 (s, 1H).

Diethyl azodicarboxylate (3.3 ml) was added dropwise to a stirred mixture of 4-amino-7-hydroxyquinazoline (5.16 g), triphenylphosphine (16.8 g) and methylene chloride (260 ml) which had been cooled to 0° C. The mixture was stirred at ambient temperature for 16 hows. The mixture was evaporated and the residue was purified by column chromatography on silica using a 50:45:5 mixture of methylene chloride, ethyl acetate and methanol as eluent. There was thus obtained triphenylphosphine N-(7-hydroxyquinazolin-4-yl)imide (9.7 g); NMR Spectrum: (DMSOd₆) 6.85 (s, 1H), 7.05 (m, 1H), 7.5–7.95 (m, 15H), 8.12 (s, 1H), 8.5 (d, 1H), 10.3 (br s, 1H).

3,3-Dimethyl-1,2,5-thiadiazolidine-1,1-dioxide (*J. Med. Chem.*, 1994, 37, 3023; 0.39 g) was added portionwise to a stirred mixture of triphenylphosphine N -(7-hydroxyquinazolin-4-yl)imide (0.2 g), N-(2-hydroxyethyl) pyrrolidine (0.081 g) and methylene chloride (5 ml) and the mixture was stirred at ambient temperature for 1 hour. Diethyl ether (10 ml) was added and the mixture was filtered through diatomaceous earth. The filtrate was evaporated and the residue was purified by column chromatography on silica using as eluent a 48:50:2 mixture of methylene chloride, ethyl acetate and a saturated ammonia solution in methanol. There was thus obtained triphenylphosphine N-[7-(2-pyrrolidin-1-ylethoxy)quinazolin-4-yl]imide (0.084 g); NMR Spectrum: (DMSOd₆+CF₃CO₂D) 1.93 (m, 2H), 2.08 (m, 2H), 3.2 (m, 2H), 3.66 (m, 2H), 3.73 (m, 2H), 4.5 (m, 2H), 7.16 (s, 1H), 7.42 (m, 1H), 7.6–8.0 (m, 15H), 8.62 (s, 1H), 8.71 (d, 1H); Mass Spectrum: M+H⁺ 519.

A mixture of a portion (0.42 g) of the material so obtained, a 1N aqueous acetic acid solution (2 ml) and ethanol (2 ml) was stirred and heated to 100° C. for 15 hours. The mixture was evaporated and the residue was dried under vacuum. There was thus obtained 4-amino-7-(2-pyrrolidin-1-ylethoxy)quinazoline in quantitative yield and this was used directly without future purification.

[75] The product gave the following data: Mass Spectrum: M+H⁺ 426 and 428.

[76] The product gave the following data: Mass Spectrum: M+H⁺ 412 and 414.

[77] The product gave the following data: Mass Spectrum: M+H⁺ 480 and 482.

[78] The product gave the following data: NMR Spectrum: (CDCl₃) 1.4–1.7 (m, 6H), 2.55 (br s, 4H), 2.85 (t, 2H), 4.25 (t, 2H), 7.1–7.38 (m, 4H), 7.48 (d, 2H), 8.05 (d, 2H), 8.8 (s, 1H), 9.02 (br s, 1H); Mass Spectrum: M+H⁺ 460 and 462.

The 4-amino-7-(2-piperidinoethoxy)quinazoline used as a starting material was prepared as follows:

Triphenylphosphine N-(7-hydroxyquinazolin-4-yl)imide was reacted with N-(2-hydroxyethyl)piperidine using an analogous procedure to that described in the second last paragraph of Note [74] above to give triphenylphosphine N-[7-(2-piperidinoethoxy)quinazolin-4-yl]imide in 21% yield; Mass Spectrum: M+H$^+$ 533. The material so obtained was reacted with aqueous acetic acid using an analogous procedure to that described in the last paragraph of Note [74] above to give the required starting material; Mass Spectrum: M+H$^+$ 273.

[79] The product gave the following data: NMR Spectrum: (CDCl$_3$) 1.45 (br m, 2H), 1.55–1.75 (m, 4H), 2.55 (br s, 4H), 2.85 (t, 2H), 4.28 (t, 2H), 7.05 (m, 2H), 7.12–7.4 (m, 4H), 8.15 (d, 1H), 8.8 (s, 1H), 9.2 (s, 1H); Mass Spectrum: M+H$^+$ 428.

[80] The product gave the following data: NMR Spectrum: (CDCl$_3$) 1.4–1.72 (m, 6H), 2.42 (s, 3H), 2.55 (br s, 4H), 2.85 (t, 2H), 4.3 (t, 2H), 7.12–7.32 (m, 5H), 8.35 (d, 1H), 7.95 (d, 1H), 8.6 (s, 1H), 8.8 (s, 1H); Mass Spectrum: M+H$^+$ 440 and 442.

[81] The product gave the following data: Mass Spectrum: M+H$^+$ 426 and 428.

[82] The product gave the following data: Mass Spectrum: M+H$^+$ 494 and 496.

[83] The product gave the following data: NMR Spectrum: (CDCl$_3$) 2.32 (s, 3H), 2.5 (br s, 4H), 2.7 (br s, 4H), 2.9 (t, 2H), 4.3 (t, 2H), 7.2 (d, 1H), 7.25–7.4 (m, 3H), 7.47 (d, 2H), 8.05 (d, 1H), 8.8 (s, 1H), 9.05 (s, 1H); Mass Spectrum: M+H$^+$ 475 and 477.

The 4-amino-7-[2-(4-methylpiperazin-1-yl)ethoxy]quinazoline used as a starting material was prepared as follows:

Triphenylphosphine N-(7-hydroxyquinazolin-4-yl)imide was reacted with 1-(2-hydroxyethyl)-4-methylpiperazine using an analogous procedure to that described in the second last paragraph of Note [74] above to give triphenylphosphine N-{7-[2-(4-methylpiperazin-1-yl)ethoxy]quinazolin-4-yl}imide in 30% yield; Mass Spectrum: M+H$^+$ 548. The material so obtained was reacted with aqueous acetic acid using an analogous procedure to that described in the last paragraph of Note [74] above to give the required starting material; Mass Spectrum: M+H$^+$ 288.

The 1-(2-hydroxyethyl)-4-methylpiperazine used as a stating material was prepared as follows:

A mixture of 2-bromoethanol (2.36 g), N-methylpiperzine (1.26 g), potassium carbonate (5.0 g) and ethanol (150 ml) was stirred and heated to reflux for 1.8 hours. The mixture was cooled to ambient temperature and filtered. The filtrate was evaporated and the residue was triturated under a mixture of methylene chloride and acetone. The resultant mixture was filtered and the filtrate was evaporated to give the required starting material as an oil (0.87 g); NMR Spectrum: (CDCl$_3$) 2.18 (s, 3H), 2.3–2.7 (br m, 8H), 2.56 (t, 2H), 3.61 (t, 2H).

[84] The product gave the following data: Mass Spectrum: M+H$^+$ 455 and 457.

[85] The product gave the following data: NMR Spectrum: (CDCl$_3$) 2.3 (s, 3H), 2.48 (br s, 4H), 2.65 (br s, 4H), 2.9 (t, 2H), 4.3 (t, 2H), 7.1 (m, 1H), 7.2–7.4 (m, 4H), 7.45 (d, 1H), 7.97 (d, 1H), 8.35 (br s, 1H), 8.45 (d, 1H), 8.85 (s, 1H); Mass Spectrum: M+H$^+$ 441 and 443.

[86] The product gave the following data: Mass Spectrum: M+H$^+$ 509 and 511.

[87] The product gave the following data: Mass Spectrum: M+H$^+$ 460 and 462.

The 4-amino-7-M-methylpiperidin-3-ylmethoxy)quinazoline used as a starting material was prepared as follows:

Triphenylphosphine N-(7-hydroxyquinazolin-4-yl)imide was reacted with 3-hydroxymethyl-N-methylpiperidine using an analogous procedure to that described in the second last paragraph of Note [74] above to give triphenylphosphine N-[7-(N-methylpiperidin-3-ylmethoxy)quinazolinyl]imide in 49% yield; Mass Spectrum: M+H$^+$ 533. The material so obtained was reacted with aqueous acetic acid using an analogous procedure to that described in the last paragraph of Note [74] above to give the required starting material; Mass Spectrum: M+H$^+$ 273.

[88] The product gave the following data: Mass Spectrum: M+H$^+$ 428.

[89] The product gave the following data: Mass Spectrum: M+H$^+$ 440 and 442.

[90] The product gave the following data: Mass Spectrum: M+H$^+$ 426 and 428.

[91] The product gave the following data: Mass Spectrum: M+H$^+$ 494 and 496.

[92] The product gave the following data: NMR Spectrum: (CDCl$_3$) 1.85 (br s, 4H), 2.1 (m, 2H), 2.6 (br s, 4H), 2.7 (t, 2H), 4.2 (t, 2H), 7.15 (d, 1H), 7.2–7.4 (m, 3H), 7.5 (d, 2H), 8.1 (d, 1H), 8.8 (s, 1H), 9.2 (br s, 1H); Mass Spectrum: M+H$^+$ 460 and 462.

The 4-amino-7-(3-pyrrolidin-1-ylpropoxy)quinazoline used as a starting material was prepared as follows:

Triphenylphosphine N-(7-hydroxyquinazolinyl)imide was reacted with N-(3-hydroxypropyl)pyrrolidine using an analogous procedure to that described in the second last paragraph of Note [74] above to give triphenylphosphie N-[7-(3-pyrrolidin-1-ylpropoxy)quinazolin-4-yl]imide in 42% yield; Mass Spectrum: M+H$^+$ 533. The material so obtained was reacted with aqueous acetic acid using an analogous procedure to that described in the last paragraph of Note [74] above to give the required starting material; Mass Spectrum: M+H$^+$ 273.

The N-(3-hydroxypropyl)pyrrolidine used as a starting material was prepared as follows:

A mixture of 3-chloropropanol (66 g), pyrrolidine (50 g), potassium carbonate (145 g) and acetonitrile (1 L) was stirred and heated to reflux for 20 hours. The mixture was cooled to ambient temperature and filtered. The filtrate was evaporated and the residue was purified by distillation to give the required starting material as an oil (62 g); NMR Spectrum: (CDCl$_3$) 1.6–1.8 (m, 6H), 2.55 (br s, 4H), 2.75 (t, 2H), 3.85 (t, 2H), 5.5 (br s, 1H).

[93] The product gave the following data: Mass Spectrum: M+H$^+$ 428.

[94] The product gave the following data: Mass Spectrum: M+H$^+$ 440 and 442.

[95] The product gave the following data: NMR Spectrum: (CDCl$_3$) 1.82 (br s, 4H), 2.1 (m, 2H), 2.55 (br s, 4H), 2.65 (t, 4H), 4.25 (t, 2H), 7.1 (m, 1H), 7.2–7.45 (m, 4H), 7.5 (d, 1H), 7.95 (d, 1H), 8.15 (s, 1H), 8.45 (d, 1H), 8.85 (s, 1H); Mass Spectrum: M+H$^+$ 426 and 428.

[96] The product gave the following data: NMR Spectrum: (CDCl$_3$) 7.2 (m, 1H), 7.25–7.4 (m, 3H), 7.5 (s, 1H), 8.0 (d, 1H), 8.8 (s, 1H), 8.95 (br s, 1H); Mass Spectrum: M+H$^+$ 494 and 496.

[97] The product gave the following data: Mass Spectrum: M+H$^+$ 444.

The 4-amino-7-(3-morpholinopropoxy)quinazoline used as a starting material was prepared as follows:

Triphenylphosphine N-(7-hydroxyquinazolin-4-yl)imide was reacted with N-(3-hydroxypropyl)morpholine using an analogous procedure to that described in the second last paragraph of Note [74] above to give triphenylphosphine N-[7-(3-morpholinopropoxy)quinazolin-4-yl]imide and the material so obtained was reacted with aqueous acetic acid using an analogous procedure to that described in the last paragraph of Note [74] above to give the required starring material; Mass Spectrum: M+H⁺ 289.

[98] The product gave the following data: Mass Spectrum: M+H⁺ 456 and 458.

[99] The product gave the following data: Mass Spectrum: M+H⁺ 510 and 512.

[100] The product gave the following data: NMR Spectrum: (CDCl₃) 2.1 (m, 2H), 2.35 (s, 3H), 2.35–2.75 (m, 8H), 2.6 (t, 2H), 4.22 (t, 2H), 7.12 (m, 1H), 7.2–7.38 (m, 3H), 7.5 (d, 2H), 8.15 (d, 1H), 8.8 (s, 1H), 9.5 (br s, 1H); Mass Spectrum: M+H⁺ 489 and 491.

The 4-amino-7-[3-(4-methylpiperazin-1-yl)propoxy]quinazoline used as a starting material was prepared as follows:

Triphenylphosphine N-(7-hydroxyquinazolin-4-yl)imide was reacted with 1-(3-hydroxypropyl)-4-methylpiperazine using an analogous procedure to that described in the second last paragraph of Note [74] above to give triphenylphosphine N-{7-[3-(4-methylpiperazin-1-yl)propoxy]quinazolin-4-yl}imide in 44% yield; Mass Spectrum: M+H⁺ 562. The material so obtained was reacted with aqueous acetic acid using an analogous procedure to that described in the last paragraph of Note [74] above to give the required starting material; Mass Spectrum: M+H⁺ 302.

The 1-(3-hydroxypropy)-4-methylpiperazine used as a stating material was prepared as follows:

A mixture of 3-bromopropanol (20 ml), N-methylpiperzine (29 ml), potassium carbonate (83 g) and ethanol (200 ml) was stirred and heated to reflux for 20 hours. The mixture was cooled to ambient temperature and filtered. The filtrate was evaporated and the residue was triturated under diethyl ether. The resultant mixture was filtered and the filtrate was evaporated. The residue was purified by distillation to give the required starting material as an oil; NMR Spectrum: (CDCl₃) 1.72 (m, 2H), 2.3 (s, 3H), 2.2–2.8 (m, 8H), 2.6 (t, 2H), 3.8 (t, 2H), 5.3 (br s, 1H).

[101] The product gave the following data: NMR Spectrum: (CDCl₃) 2.07 (t, 2H), 2.32 (s, 3H), 2.3–2.75 (m, 8H), 2.6 (t, 2H), 4.22 (t, 2H), 7.1 (m, 1H), 7.2–7.45 (m, 4H), 7.5 (d, 1H), 8.05 (d, 1H), 8.45 (d, 1H), 8.55 (s, 1H), 8.85 (s, 1H); Mass Spectrum: M+H⁺ 455 and 457.

[102] The product gave the following data: NMR Spectrum: (CDCl₃) 2.1 (m, 2H), 2.3 (s, 3H), 2.35–2.7 (m, 8H), 2.6 (t, 2H), 4.2 (t, 2H), 7.15 (m, 1H), 7.2–7.4 (m, 3H), 7.5 (s, 1H), 8.05 (d, 1H), 8.8 (s, 1H), 9.02 (br s, 1H); Mass Spectrum: M+H⁺ 523 and 525.

[103] The product gave the following data: Mass Spectrum: M+H⁺ 492.

[104] The product gave the following data: Mass Spectrum: M+H⁺ 504 and 506.

[105] The product gave the following data: Mass Spectrum: M+H⁺ 558 and 560.

[106] The product gave the following data: NMR Spectrum: (CDCl₃) 2.55 (m, 2H), 4.15 (t, 2H), 4.7 (t, 2H), 7.2–7.4 (m, 4H), 7.5 (s, 1H), 7.58 (s, 1H), 7.65 (s, 1H), 7.95 (d, 1H), 8.55 (d, 1H), 8.8 (s, 1H); Mass Spectrum: M+H⁺ 492 and 494.

The 4-amino-7-[3-(1,2,3-triazol-1-yl)propoxy]quinazoline used as a starting material was prepared as follows:

Triphenylphosphine N-(7-hydroxyquinazolin-4-yl)imide was reacted with N¹-(3-hydroxypropyl)-1,2,3-triazole using an analogous procedure to that described in the second last paragraph of Note [74] above to give triphenylphosphine N-(7-[3-(1,2,3-triazol-1-yl)propoxy]quinazolin-4-yl)imide in 18% yield; Mass Spectrum: M+H⁺ 531. The material so obtained was reacted with aqueous acetic acid using an analogous procedure to that described in the last paragraph of Note [74] above to give the required starting material; Mass Spectrum: M+H⁺ 271.

The N¹-(3-hydroxypropyl)-1,2,3-triazole used as a starting material was prepared as follows:

A mixture of 1,2,3-triazole (5 g), ethyl acrylate (7.8 ml) and pyridine (50 drops) was stirred and heated to 90° C. for 4 hours. The mixture was cooled to ambient temperature and evaporated. The residue was purified by column chromatography on silica using increasingly polar mixtures of methylene chloride and diethyl ether as eluent. There was thus obtained ethyl 1,2,3-triazol-1-ylpropanoate (8.96 g); NMR Spectrum: (CDCl₃) 1.25 (t, 3H), 2.95 (t, 2H), 4.15 (q, 2H), 4.7 (t, 2H), 7.65 (s, 1H), 7.7 (s, 1H).

A solution of the material so obtained in THF (50 ml) was added dropwise to a suspension of lithium aluminium hydride (3 g) in THF (250 ml) which had been cooled to 0° C. The mixture was stirred at 5° C. for 1 hour and at ambient temperature for a further hour. The mixture was cooled to 0° C. and 4N aqueous sodium hydroxide solution (30 ml) was added dropwise. The mixture was filtered and the filtrate was dried over magnesium sulphate and evaporated. The residue was purified by column chromatography on silica using a 47:3 mixture of methylene chloride and methanol as eluent. There was thus obtained N¹-(3-hydroxypropyl)-1,2,3-triazole (6.2 g); NMR Spectrum: (CDCl₃) 2.1–2.2 (m, 3H), 3.65 (m, 2H), 4.6 (t, 2H), 7.6 (s, 1H), 7.72 (s, 1H).

[107] The product gave the following data: Mass Spectrum: M+H⁺ 440.

The 4-amino-7-[(E)-4-pyrrolidin-1-ylbut-2-en-1-yloxy]quinazoline used as a starting material was prepared as follows:

Triphenylphosphine N-(7-hydroxyquinazolin-4-yl)imide was reacted with (E)-4-pyrrolidin-1-ylbut-2-en-1-ol using an analogous procedure to that described in the second last paragraph of Note [74] above to give triphenylphosphine N-{7-[(E)-4-pyrrolidin-1-ylbut-2-en-1-yloxy]quinazolin-4-yl}imide in 38% yield; Mass Spectrum: M+H⁺ 545. The material so obtained was reacted with aqueous acetic acid using an analogous procedure to that described in the last paragraph of Note [74] above to give the required stating material; Mass Spectrum: M+H⁺ 285.

The (E)-4-pyrrolidin-1-ylbut-2-en-1-ol used as a starting material was prepared as follows:

Thionyl chloride (9.3 ml) was added portionwise to a stirred mixture of 2-butyne-1,4-diol (10 g), pyridine (10.3 ml) and toluene (15 ml) which had been cooled to 0° C. The mixture was stirred at ambient temperature for 3.5 hours and then poured onto a mixture of ice and water. The mixture was extracted with diethyl ether. The organic extract was washed with a saturated aqueous sodium bicarbonate solution and with brine, dried over magnesium sulphate and evaporated. The residue was purified by column chromatography on silica using a 7:3 mixture of petroleum ether (b.p. 40–60° C.) and diethyl ether as eluent. There was thus obtained 4-chlorobut-2-yn-1-ol (4.74 g); NMR Spectrum: (CDCl₃) 1.68 (t, 1H), 4.18 (d, 2H), 4.33 (d, 2H).

Pyrrolidine (7.8 ml) was added dropwise to a solution of 4-chlorobut-2-yn-1-ol (4.74 g) in toluene (40 ml) and the resultant mixture was saline and heated to 60° C. for 1 hour. The mixture was evaporated and the residue was purified by column chromatography on silica using a 24:1 mixture of methylene chloride and methanol as eluent. There was thus obtained 4-pyrrolidin-1-ylbut-2-yn-1-ol (4.3 g); NMR Spectrum: (CDCl₃) 1.82 (t, 4H), 2.63 (t, 4H), 3.44 (t, 2H), 4.29 (t, 2H).

A solution of the material so obtained in THF (20 ml) was added dropwise to a suspension of lithium aluminium hydride (2.35 g) in THF (8 ml) and the mixture was stirred and heated to 60° C. for 2 hours. The mixture was cooled to 5° C. and 2N aqueous sodium hydroxide solution (28 ml) was slowly added. The resulting suspension was filtered and the filtrate was evaporated. The residue was dissolved in a mixture of methylene chloride and ethyl acetate, dried over magnesium sulphate and evaporated. The residue was purified by column chromatography on aluminium oxide using a 97:3 mixture of methylene chloride and methanol as eluent. There was thus obtained (E)-4-pyrrolidin-1-ylbut-2-en-1-ol (3.09 g); NMR Spectrum: (CDCl$_3$) 1.82 (m, 4H), 2.61 (m, 4H), 3.17 (m, 2H), 4.13 (s, 2H), 5.84 (m, 2H).

[108] The product gave the following data: Mass Spectrum: M+H$^+$ 452 and 454.

[109] The product gave the following data: Mass Spectrum: M+H$^+$ 438 and 440.

[110] DMF was used as the reaction solvent. The product gave the following data: NMR Spectrum: (DMSOd$_6$) 1.5–1.65 (m, 2H), 1.68–1.74 (m, 2H), 1.92 (t, 2H), 1.97 (t, 2H), 2.05 (m, 1H), 2.45 (t, 2H), 2.88 (d, 2H), 3.98 (s, 3H), 4.22 (t, 2H), 6.68 (s, 1H), 7.18 (s, 1H), 7.3 (s, 1H), 7.4 (t, 1H), 7.61 (d, 2H), 8.07 (s, 1H), 8.7 (s, 1H), 10.62 (s, 1H), 12.08 (s, 1H); Mass Spectrum: M+H$^+$ 547 and 549.

The 4-amino-7-[3-(4-carbamoylpiperidin-1-yl)propoxy]-6-methoxyquinazoline used as a starting material was prepared as follows:

A mixture of 2-amino-4-benzyloxy-5-methoxybenamide (*J. Med. Chem.*, 1977, 20, 146–149; 10 g) and Gold's reagent (7.4 g) in dioxane (100 ml) was stirred and heated at reflux for 24 hours. Sodium acetate (3.02 g) and acetic acid (1.65 ml) were added to the reaction mixture and it was heated for a further 3 hours. The mixture was evaporated to dryness, water was added to the residue and the solid was filtered off, washed with water and dried. Recrystallisation of the solid from acetic acid gave 7-benzyloxy-6-methoxy-3,4-dihydroquinazolin-4-one (8.7 g, 84%).

7-Benzyloxy-6-methoxy-3,4-dihydroquinazolin-4-one (20.3 g) was taken up in thionyl chloride (440 ml) and DMF (1.75 ml) and heated to reflux for 4 hours. The thionyl chloride was evaporated under vacuum and the residue was azeotroped with toluene three times. There was thus obtained 7-benzyloxy-4-chloro-6-methoxyquinazoline which was used without further purification; NMR Spectrum: 4.88 (s, 3H), 5.25 (s, 2H), 7.44 (s, 1H), 7.49 (s, 1H), 7.32–7.52 (m, 5H), 8.83 (s, 1H).

A mixture of the crude 7-benzyloxy-4-chloro-6-methoxyquinazoline, potassium carbonate (50 g) and 4-bromo-2-fluorophenol (10 ml) in DMF (500 ml) was stirred and heated to 100° C. for 5 hours. The mixture was allowed to cool to ambient temperature and was poured into water (2 L). The resultant solid was isolated and washed with water. The solid was dissolved in methylene chloride and filtered. The filtrate was treated with decolourising charcoal, boiled for a few minutes then filtered. The filtrate was evaporated to give a solid residue which was triturated under diethyl ether. There was thus obtained 7-benzyloxy-4-(4-bromo-2-fluorophenoxy)-6-methoxyquinazoline.

A mixture of the material so obtained and trifluoroacetic acid (15 ml) was stirred and heated to reflux for 3 hours. The reaction mixture was allowed to cool, toluene was added and the mixture was evaporate. The residue was triturated under diethyl ether. The precipitate was collected by filtration and dried to give 4-(4-bromo-2-fluorophenoxy)-7-hydroxy-6-methoxyquinazoline (20.3 g) which was used without further purification.

A mixture of 4-(4-bromo-2-fluorophenoxy)-7-hydroxy-6-methoxyquinazoline (18.2 g), 1,3-dibromopropane (80 ml), potassium carbonate (42 g) and DMF (1.2 L) was stirred and heated to 45° C. for 16 hours. The mixture was cooled to ambient temperature and filtered. The filtrate was evaporated and the residue was purified by column chromatography on silica using increasingly polar mixtures of methylene chloride and methanol as eluent. The product so obtained was stirred under diethyl ether (150 ml) and the resultant solid was isolated. There was thus obtained 4-(4-bromo-2-fluorophenoxy)-7-(3-bromopropoxy)-6-methoxyquinazoline (14.4 g); NMR Spectrum: (DMSOd$_6$) 2.35 (m, 2H), 3.69 (t, 2H), 3.98 (s, 3H), 4.31 (t, 2H), 7.4–7.6 (m, 4H), 7.78 (d, 1H), 8.78 (s, 1H); Mass Spectrum: M+H$^+$ 485, 487 and 489.

A mixture of a portion (2.4 g) of the material so obtained, pipeidine carboxamide (0.82 g), potassium carbonate (3.46 g) and DMF (40 ml) was stirred and heated to 45° C. for 20 hours. The resultant solid was isolated, washed in turn with DMF and with water and dried. There was thus obtained 4-(4-bromo-2-fluorophenoxy)-7-[3-(4-carbamoylpiperidin-1-yl)propoxy]-6-methoxyquinazoline (2.5 g); NMR Spectrum: (DMSOd$_6$) 1.45–1.7 (m, 4H), 1.82–2.1 (m, 5H), 2.22 (t, 2H), 2.86 (m, 2H), 3.96 (s, 3H), 4.03 (t, 2H), 6.65 (s, 1H), 7.14 (s, 1H), 7.38 (s, 1H), 7.42–7.55 (m, 3H), 7.78 (d, 1H), 8.53 (s, 1H); Mass Spectrum: M+H$^+$ 533 and 535.

A mixture of the material so obtained and a saturated solution of ammonia in isopropanol (100 ml) was sealed in a Carius tube and heated at 130° C. for 20 hours. The mixture was cooled and the solvent was evaporated. The residue was stirred with 2N aqueous sodium hydroxide solution (20 ml) for 1 hour. The solid was isolated and washed in turn with water and with methanol. There was thus obtained 4-amino-7-[3-(4-carbamoylpiperidin-1-yl) propoxy]-6-methoxyquinazoline (0.85 g); NMR Spectrum: (DMSOd$_6$) 1.4–1.7 (m, 4H), 1.8–2.1 (m, 5H), 2.4 (t, 2H), 2.68 (d, 2H), 3.86 (s, 3H), 4.1 (t, 2H), 6.66 (s, 1H), 7.03 (s, 1H), 7.15 (s, 1H), 7.33 (s, 2H), 7.53 (s, 1H), 8.23 (s, 1H); Mass Spectrum: M+H$^+$ 360.

[111] The product gave the following data: NMR Spectrum: (DMSOd$_6$) 1.5–1.7 (m, 4H), 1.8–2.1 (m, 5H), 2.4 (t, 2H), 2.88 (d, 2H), 2.94 (s, 3H), 4.0 (t, 2H), 6.65 (s, 1H), 7.1–7.5 (m, 5H), 8.05 (s, 1H), 8.66 (s, 1H), 10.6 (s, 1H), 11.8 (s, 1H); Mass Spectrum: M+H$^+$ 515.

[112] THF was added as a co-solvent. The product gave the following data: NMR Spectrum: (CDCl$_3$) 1.6–2.3 (m, 9H), 2.35 (s, 6H), 2.53 (t, 2H), 2.99 (d, 2H), 3.42 (s, 3H), 4.25 (t, 2H), 5.55 (s, 2H), 7.11 (s, 3H), 7.29 (s, 1H), 7.55 (s, 1H), 8.64 (s, 1H), 9.7 (s, 1H), 11.9 (s, 1H); Mass Spectrum: M+H$^+$ 507.

[113] DMF was used as the reaction solvent. The product was precipitated from the reaction mixture as a 1:1 adduct with DMF. This gave the following data: NMR Spectrum: (CDCl$_3$) 1.7–2.3 (m, 9H), 2.37 (s, 3H), 2.54 (t, 2H), 2.88 (s, 3H), 2.95 (s, 3H), 3.0 (m, partially obscured by DMF), 3.5 (s, 3H), 4.25 (t, 2H), 5.61 (broad d, 2H), 7.16–7.32 (m, 4H), 7.55 (s, 1H), 8.02 (s, 1H), 8.67 (s, 1H), 9.8 (s, 1H), 12.4 (s, 1H); Mass Spectrum: M+H$^+$ 527 and 529.

[114] Acetonitrile plus a few drops of DMF was used as the reaction solvent and the reaction mixture was heated to 45° C. for 3 hours. The product which was precipitated from the reaction mixture was isolated, washed with acetonitrile and diethyl ether and dried under vacuum. The product gave the following data: Mass Spectrum: M+H$^+$ 440 and 442.

The 4-amino-7-[3-(pyrrolidin-1-yl)-1-propynyl] quinazoline used as a starting material was prepared as follows:

Trifluoromethanesulphonic anhydride (0.05 ml) was added dropwise to a stirred mixture of triphenylphosphine N-(7-hydroxyquinazolin-4-yl)imide (0.1 g), pyridine (0.5 ml) and methylene chloride (1 ml) which had been cooled to 0° C. The reaction mixture was stirred at 0° C. for 2 hours. A second portion (0.012 ml) of trifluoromethanesulphonic anhydride was added and the mixture was stirred at ambient temperature for 15 hours. The mixture was evaporated and the residue was partitioned between ethyl acetate and water. The organic solution was dried over magnesium sulphate and evaporated. The residue was purified by column chromatography on silica using increasingly polar mixtures of methylene chloride and ethyl acetate as eluent. There was thus obtained triphenylphosphine N-(7-trifluoromethanesulphonyloxyquinazolin-4-yl)imide (0.078 g).

A solution of 3-(pyrrolidin-1-yl)-1-propyne (*J. Amer. Chem. Soc.*, 1958, 80, 4609; 0.08 g) in DMF (0.2 ml) was added to a mixture of triphenylphosphine N-(7-trifluoromethanesulphonyloxyquinazolin-4-yl)imide (0.2 g), cuprous iodide (0.004 g), tetrakis(triphenylphosphine)palladium(0) (0.02 g), triethylamine (0.201 ml) and DMF (8 ml). The mixture was degassed carefully and placed under an atomsphere of argon. The reaction mixture was stirred and heated to 60° C. for 2.5 hours. The mixture was cooled to ambient temperature and evaporated. The residue was partitioned between ethyl acetate and water. The organic phase was dried over magnesium sulphate and evaporated. The residue was purified by column chromatography on silica using a 9:1 mixture of methylene chloride and methanol as eluent. There was thus obtained triphenylphosphine N-{7-[3-(pyrolidin-1-yl-propynyl]quinazolin-4-yl}imide (0.18 g).

A mixture of the material so obtained, acetic acid (4 ml) and water (4 ml) was stirred and heated at 100° C. for 15 hours. The solvent was evaporated and the residue was partitioned between ethyl acetate and a saturated aqueous sodium bicarbonate solution. The organic solution was washed with water and brine, dried over magnesium sulphate and evaporated. The residue was purified by column chromatography on silica using initially a 9:1 mixture of methylene chloride and methanol and then a 19:1 mixture of methylene chloride and a saturated solution of ammonia in methanol as eluent. There was thus obtained 4-amino-7-[3-(pyrrolidin-1-yl)-1-propynyl]quinazoline (0.038 g); NMR Spectrum: (DMSOd$_6$) 1.75 (m, 4H), 2.6 (m, 4H), 3.65 (s, 2H), 7.45 (m, 1H), 7.25 (d, 1H), 7.85 (br s, 2H), 8.2 (d, 1H), 8.4 (s, 1H); Mass Spectrum: M+H$^+$ 253.

[115] DMF was used as the reaction solvent and 4-dimethylaminopyridine (0.1 equivalents) was added to catalyse the reaction. The product was precipitated from the reaction mixture by the addition of a mixture of diethyl ether and water. The product was isolated and dried under vacuum and gave the following data: NMR Spectrum: (DMSOd$_6$) 1.72 (m, 4H), 2.6 (m, 4H), 3.69 (s, 2H), 3.97 (s, 3H), 7.4 (m, 1H), 7.58 (m, 2H), 7.9 (s, 1H), 8.15 (s, 1H), 8.75 (s, 1H), 10.8 (s, 1H), 11.95 (s, 1H); Mass Spectrum: M+H$^+$ 470 and 472.

The 4-amino-6-methoxy-7-[3-(pyrrolidin-1-yl)-1-propynyl]quinazoline used as a starting material was prepared as follows:

Pyridine (1.13 ml) and a solution of trifluoromethanesulphonic anhydride (2.36 ml) in methylene chloride (10 ml) were added in turn to a stirred mixture of 4-(2-bromo-4-fluorophenoxy)-7-hydroxy-6-methoxyquinazoline (2.6 g) and methylene chloride (40 ml) which had been cooled in an ice bath to 0–5° C. The resultant mixture was stirred at ambient temperature for 4 hours. The mixture was washed in turn with dilute aqueous citric acid, water and a saturated aqueous sodium bicarbonate solution. The organic solution was dried over magnesium sulphate and evaporated. The residue was triturated under a 1:1 mixture of isohexane and diethyl ether. There was thus obtained 4-(2-bromo-4-fluorophenoxy)-6-methoxy-7-trifluoromethanesulphonyloxyquinamoline (2.58 g); NMR Spectrum: (CDCl$_3$) 4.13 (s, 3H), 7.14–7.5 (m, 3H), 7.81 (s, 1H), 7.91 (s, 1H), 8.7 (s, 1H); Mass Spectrum: M+H$^+$ 497 and 499.

A mixture of a portion (0.8 g) of the material so obtained, 3-(pyrrolidin-1-yl)-1-propyne (0.57 g), triethylamine (0.8 ml), triphenylphosphine (0.03 g), bis(triphenylphosphine)palladium(II) chloride (0.06 g), cuprous iodide (0.06 g) and THF (5 ml) was stirred and heated to reflux for 3 hours. Dilute aqueous potassium carbonate solution was added and the mixture was extracted with ethyl acetate. The organic solution was dried over sodium sulphate and evaporated. The residue was purified by column chromatography on silica using a 10:1 mixture of methylene chloride and ethanol as eluent. There was thus obtained 4-(2-bromo-4-fluorophenoxy)-6-methoxy-7-[3-(pyrrolidin-1-yl)-1-propynyl]quinazoline (0.55 g); NMR Spectrum: (DMSOd$_6$) 1.75 (m, 4H), 2.64 (m, 4H), 3.71 (s, 2H), 4.01 (s, 3H), 7.38–7.81 (m, 3H), 7.66 (s, 1H), 8.0 (s, 1H), 8.62 (s, 1H); Mass Spectrum: M+H$^+$ 456 & 458.

A mixture of the material so obtained and a 2M solution of ammonia in isopropanol (10 ml) was sealed in a Carius tube and heated to 130° C. for 38 hours. The reaction mixture was evaporated. The residue was partitioned between ethyl acetate and a 1N aqueous potassium carbonate solution. The organic solution was washed with brine, dried over anhydrous sodium sulphate and evaporated. The residue was triturated under a 1:1 mixture of isohexane and diethyl ether. The resultant solid was isolated and dried. There was thus obtained 4-amino-6-methoxy-7-[3-(pyrrolidin-1-yl)-1-propynyl]quinazoline (0.24 g); Mass Spectrum: M+H$^+$ 283.

[116] DMF was used as the reaction solvent and 4-dimethylaminopyridine (0.1 equivalents) was added to catalyse the reaction. The product gave the following data: NMR Spectrum: (DMSOd$_6$) 1.6 (m, 4H), 2.35 (m, 6H), 2.55 (m, 2H), 3.6 (m, 4H), 3.97 (s, 3H), 7.3–7.6 (m, 3H), 7.83 (s, 1H), 8.11 (s, 1H), 8.72 (s, 1H), 10.78 (s, 1H), 11.95 (s, 1H); Mass Spectrum: M+H$^+$ 528 and 530.

The 4-amino-6-methoxy-7-(6-morpholino-1-hexynyl)quinazoline used as a starting material was prepared as follows:

Using an analogous procedure to that described in the second last paragraph of Note [115] above, 6-morpholino-1-hexyne was reacted with 4-(2-bromo-4-fluorophenoxy)-6-methoxy-7-trifluoromethanesulphonyloxyquinazoline to give 4-(2-bromo-4-fluorophenoxy)-6-methoxy-7-(6-morpholino-1-hexynyl)quinazoline; NMR Spectrum: (DMSOd$_6$) 1.63 (m, 4H), 2.33 (m, 6H), 2.55 (m, 2H), 3.56 (m, 4H), 4.0 (s, 3H), 7.35–7.8 (m, 3H), 7.65 (s, 1H), 7.96 (s, 1H), 8.6 (s, 1H); Mass Spectrum: M+H$^+$ 514 and 516.

The material so obtained was reacted with ammonia using an analogous procedure to that described in the last paragraph of Note [115] above to give the required starting material.

6-Morpholino-1-hexyne was obtained by the reaction of 6-mesyloxy-1-hexyne with morpholine using an analogous procedure to that described in *J. Heterocyclic Chemistry*, 1994, 31, 1421.

[117] DMF was used as the reaction solvent and 4-dimethylaminopyridine (0.1 equivalents) was added to catalyse the reaction. The product gave the following data NMR Spectrum: (DMSOd$_6$) 1.6 (m, 4H), 2.32 (m, 6H), 2.55 (m, 2H), 3.55 (m, 4H), 3.98 (s, 3H), 7.1–7.4 (m, 3H), 7.82 (s, 1H), 8.11 (s, 1H), 8.7 (s, 1H), 10.78 (s, 1H), 11.68 (s, 1H); Mass Spectrum: M+H$^+$ 496.

[118] DMF was used as the reaction solvent and 4-dimethylaminopyridine (0.1 equivalents) was added to catalyst the reaction. The product gave the following data: NMR Spectrum: (DMSOd$_6$) 1.55 (m, 2H), 1.85 (m, 2H), 2.28 (s, 3H), 2.56 (m, 2H), 3.9 (m, 2H), 3.96 (s, 3H), 6.7 (s, 1H), 7.07 (s, 1H), 7.36–7.62 (m, 3H), 7.85 (s, 1H), 8.13 (s, 1H), 8.71 (s, 1H) 10.8 (s, 1H), 11.95 (s, 1H); Mass Spectrum: M+H$^+$ 523 and 525.

The 4-amino-6-methoxy-7-[6-(2-methylimidazol-1-yl)-1-hexynyl]quinazoline used as a starting material was prepared as follows:

Using an analogous procedure to that described in the second last paragraph of Note [115] above, 6-(2-methylimidazol-1-yl)-1-hexyne was reacted with 4-(2-bromo-4-fluorophenoxy)-6-methoxy-7-trifluoromethanesulphonyloxyquinazoline to give 4-(2-bromo-4-fluorophenoxy)-6-methoxy-7-[6-(2-methylimidazol-1-yl)-1-hexynyl]quinazoline; NMR Spectrum: (DMSOd$_6$) 1.56 (m, 2H), 1.85 (m, 2H), 2.28 (s, 3H), 2.56 (m, 2H), 3.9 (m, 2H), 3.98 (s, 3H), 6.75 (br m, 1H), 7.1 (br m, 1H), 7.36–7.82 (m, 3H), 7.63 (s, 1H), 7.98 (s, 1H), 8.61 (s, 1H); Mass Spectrum: M+H$^+$ 509 and 511.

The material so obtained was reacted with ammonia using an analogous procedure to that described in the last paragraph of Note [115] above to give the required starting material.

6-(2-Methylimidazol-1-yl)-1-hexyne was obtained by the reaction of 6-mesyloxy-1-hexyne with 2-methylimidazole using an analogous procedure to that described in *J. Heterocyclic Chemistry*, 1994, 31, 1421.

[119] DMF was used as the reaction solvent and 4-dimethylaminopyridine (0.1 equivalents) was added to catalyse the reaction: The product gave the following data: NMR Spectrum: (DMSOd$_6$) 1.58 (m, 2H), 1.82 (m, 2H), 2.28 (s, 3H), 2.55 (m, 2H), 3.95 (m, 5H), 6.7 (s, 1H), 7.05 (s, 1H), 7.1–7.4 (m, 3H), 7.85 (s, 1H), 8.12 (s, 1H), 8.74 (s, 1H), 10.79 (s, 1H), 11.69 (s, 1H); Mass Spectrum: M+H$^+$ 491.

[120] DMF was used as the reaction solvent and 4-dimethylaminopyridine (0.1 equivalents) was added to catalyse the reaction. The product gave the following data: NMR Spectrum: (DMSOd$_6$) 2.28 (s, 6H), 3.54 (s, 2H), 3.98 (s, 3H), 7.18–7.47 (m, 3H), 7.92 (s, 1H), 8.15 (s, 1H), 8.74 (s, 1H), 10.8 (s, 1H), 11.68 (s, 1H); Mass Spectrum: M+H$^+$ 412.

The 4-amino-6-methoxy-7-(3-dimethylamino-1-propynyl)quinazoline used as a starting material was prepared as follows:

Using an analogous procedure to that described in the second last paragraph of Note [115] above, 3-dimethylamino-1-propyne was reacted with 4-(2-bromo-4-fluorophenoxy)-6-methoxy-7-trifluoromethanesulphonyloxyquinazoline to give 4-(2-bromo-4-fluorophenoxy)-6-methoxy-7-(3-dimethylamino-1-propynyl)quinazoline; NMR Spectrum: (DMSOd$_6$) 2.29 (s, 6H), 3.55 (s, 2H), 4.0 (s, 3H), 7.38–7.83 (m, 3H), 7.67 (s, 1H), 8.05 (s, 1H), 8.63 (s, 1H); Mass Spectrum: M+H$^+$ 430 and 432.

The material so obtained was reacted with ammonia using an analogous procedure to that described in the last paragraph of Note [115] above to give the required starting material.

[121] The product gave the following data: Mass Spectrum: M+H$^+$ 467.

[122] The product gave the following data: Mass Spectrum: M+H$^+$ 454.

[123] The product gave the following data: NMR Spectrum: (CDCl$_3$) 1.42–1.56 (m, 2H), 1.84–2.06 (m, 5H), 2.3 (s, 3H), 2.86–2.99 (m, 2H), 3.92 (s, 3H), 4.04 (d, 2H), 7.02 (m, 1H), 7.22 (s, 1H), 7.28 (s, 1H), 7.36 (d, 1H), 8.44 (d, 1H), 8.64 (s, 1H), 8.76 (s, 1H), 13.12 (s, 1H); Mass Spectrum: M+H$^+$ 490 and 492.

[124] The product gave the following data: NMR Spectrum: (CDCl$_3$) 1.42–1.58 (m, 2H), 1.84–2.06 (m, 5H), 2.3 (s, 3H), 2.58 (s, 3H), 2.86–2.96 (m, 2H), 3.86 (s, 3H), 4.04 (d, 2H), 7.22–7.28 (m, 2H), 7.36 (d, 1H), 7.92 (m, 1H), 8.6 (s, 1H), 8.76 (s, 1H), 9.06 (d, 1H), 12.62 (s, 1H); Mass Spectrum: M+H$^+$ 481.

[125] The product gave the following data: NMR Spectrum: (CDCl$_3$) 1.42–1.56 (m, 2H), 1.84–2.04 (m, 5H), 2.3 (s, 3H), 2.84–2.94 (m, 2H), 3.94 (s, 3H), 4.06 (d, 2H), 7.1 (s, 1H), 7.76–7.36 (m, 2H), 7.56 (d, 1H), 8.22 (s, 1H), 8.78 (m, 2H), 13.16 (s, 1H); Mass Spectrum: M+H$^+$ 524 and 526.

[126] The product gave the following data: NMR Spectrum: (CDCl$_3$) 1.42–1.56 (m, 2H), 1.86–2.06 (m, 5H), 2.3 (s, 3H), 2.84–2.96 (m, 2H), 3.94 (s, 3H), 3.98 (s, 3H), 4.04 (d, 2H), 6.84 (d, 1H), 7.04 (m, 1H), 7.2 (s, 1H), 7.28 (s, 1H), 8.3–8.38 (m, 2H), 8.76 (s, 1H), 12.74 (s, 1H); Mass Spectrum: M+H$^+$ 486 and 488.

[127] The product gave the following data: NMR Spectrum: (CDCl$_3$) 1.44–1.56 (m, 2H), 1.86–2.06 (m, 5H), 2.3–2.34 (m, 6H), 2.84–2.96 (m, 2H), 3.86 (s, 3H), 3.98 (s, 3H), 4.04 (d, 2H), 6.82–6.9 (m, 2H), 7.24 (s, 1H), 7.36 (s, 1H), 8.06 (s, 1H), 8.76 (s, 1H), 8.9 (s, 1H), 12.64 (s, 1H); Mass Spectrum: M+H$^+$ 466.

[128] The product gave the following data: NMR Spectrum: (CDCl$_3$) 1.4–1.4 (m, 2H), 1.84–2.04 (m, 5H), 2.3 (s, 3H), 2.44 (s, 3H), 2.84–2.96 (m, 2H), 3.8 (s, 3H), 4.04 (d, 2H), 7.04 (m, 1H), 7.16 (d, 1H), 7.26 (s, 1H), 7.38 (s, 1H), 8.1 (s, 1H), 8.7 (s, 1H), 9.08 (s, 1H), 12.46 (s, 1H); Mass Spectrum: M+H$^+$ 470 and 472.

[129] The product gave the following data: NMR Spectrum: (CDCl$_3$) 1.42–1.56 (m, 2H), 1.84–2.04 (m, 5H), 2.3 (s, 3H), 2.44 (s, 3H), 2.86–2.96 (m, 2H), 3.86 (s, 3H), 4.04 (d, 2H), 6.8 (m, 1H), 7.18–7.22 (m, 1H), 7.24 (s, 1H), 7.28 (s, 1H), 7.96 (m, 1H), 8.58 (s, 1H), 8.72 (s, 1H), 12.4 (s, 1H); Mass Spectrum: M+H$^+$ 454.

[130] The product gave the following data: NMR Spectrum: (CDCl$_3$) 1.42–1.56 (m, 2H), 1.84–2.04 (m, 5H), 2.28 (s, 3H), 2.34 (s, 3H), 2.86–2.96 (m, 2H), 3.86 (s, 3H), 4.04 (d, 2H), 6.88 (m, 1H), 7.22–7.32 (m, 3H), 8.12 (s, 1H), 8.76 (m, 2H), 12.78 (s, 1H); Mass Spectrum: M+H$^+$ 470 and 472.

[131] The product gave the following data: NMR Spectrum: (CDCl$_3$) 1.78–1.84 (m, 4H), 2.16 (m, 2H), 2.5–2.58 (m, 4H), 2.66 (t, 2H), 3.98 (s, 3H), 4.28 (t, 2H), 6.72–6.8 (m, 1H), 7.16–7.18 (m, 1H), 7.2 (s, 1H), 7.34 (s, 1H), 8.06–8.16 (m, 1H), 8.38 (s, 1H), 8.76 (s, 1H), 12.76 (s, 1H); Mass Spectrum: M+H$^+$ 458.

[132] The product gave the following data: NMR Spectrum: (CDCl$_3$) 1.78–1.84 (m, 4H), 2.16 (m, 2H), 2.48–2.58 (m, 4H), 2.66 (t, 2H), 3.96 (s, 3H), 4.28 (t, 2H), 7.02 (m, 1H), 7.14 (s, 1H), 7.32–7.4 (m, 2H), 8.3 (s, 1H), 8.46 (d, 1H), 8.78 (s, 1H), 13.06 (s, 1H); Mass Spectrum: M+H$^+$ 490 and 492.

[133] The product gave the following data: NMR Spectrum: (CDCl$_3$) 1.78–1.84 (m, 4H), 2.16 (m, 2H), 2.44 (s, 3H), 2.54–2.6 (m, 4H), 2.68 (t, 2H), 3.84 (s, 3H), 4.28 (t, 2H), 7.04 (m, 1H), 7.16 (d, 1H), 7.3 (s, 1H), 7.34 (s, 1H), 8.14 (d, 1H), 8.7 (s, 1H), 8.8 (s, 1H), 12.4 (s, 1H); Mass Spectrum: M+H$^+$ 470 and 472.

[134] The product gave the following data: NMR Spectrum: (CDCl$_3$) 1.78–1.84 (m, 4H), 2.16 (m, 2H), 2.44 (s, 3H), 2.5–2.6 (m, 4H), 2.66 (t, 2H), 3.86 (s, 3H), 4.28 (t, 2H), 6.72–6.8 (m, 1H), 7.16–7.2 (m, 2H), 7.34 (s, 1H), 7.96 (m, 1H), 8.46 (s, 1H), 8.72 (s, 1H), 12.4 (s, 1H); Mass Spectrum: M+H$^+$ 454.

[135] The product gave the following data: NMR Spectrum: (CDCl$_3$) 1.78–1.84 (m, 4H), 2.06–2.22 (m, 2H), 2.46–2.6 (m, 7H), 2.68 (t, 2H), 3.84 (s, 3H), 4.28 (t, 2H), 7.28 (m, 2H), 7.36 (d, 1H), 7.92 (d, 1H), 8.7 (s, 1H), 8.8 (s, 1H), 9.08 (s, 1H), 12.66 (s, 1H); Mass Spectrum: M+H$^+$ 481.

[136] The product gave the following data: NMR Spectrum: (CDCl$_3$) 1.78–1.84 (m, 4H), 2.14 (m, 2H), 2.3 (s, 3H), 2.3–2.6 (m, 4H), 2.64 (t, 2H), 3.84 (s, 3H), 4.28 (t, 2H), 6.88 (m, 1H), 7.28–7.36 (m, 3H), 8.14 (d, 1H), 8.78 (s, 1H), 8.88 (s, 1H), 12.9 (s, 1H); Mass Spectrum: M+H$^+$ 470 and 472.

[137] DMF was used as the reaction solvent. The product was obtain as a dihydrochloride salt and gave the following data: NMR Spectrum: (DMSOd$_6$) 1.6–1.7 (m, 2H), 1.82–1.96 (m, 2H), 2.58–2.62 (t, 2H), 2.8 (s, 3H), 3.3–3.9 (m, 10H), 4.02 (s, 3H), 7.4–7.6 (m, 3H), 7.95 (s, 1H), 8.21 (s, 1H), 8.8 (s, 1H), 11.6–12.0 (m, 2H); Mass Spectrum: M+H$^+$ 541 and 543.

The 4-amino-6-methoxy-7-[6-(N-methylpiperazin-1-yl)-1-hexynyl]quinazoline used as a starting material was prepared as follows:

Using an analogous procedure to that described in the second last paragraph of Note [115] above, 6-(N-methylpiperazin-1-yl)-1-hexyne was reacted with 4-(2-bromo-4-fluorophenoxy)-6-methoxy-7-trifluoromethanesulphonyloxyquinamoline to give 4-(2-bromo-4-fluorophenoxy)-6-methoxy-7-[6-(N-methylpiperazin-1-yl)-1-hexynyl]quinazoline; NMR Spectrum: (DMSOd$_6$) 1.55–1.65 (m, 4H), 2.16 (s, 3H), 2.3–2.45 (m, 10H), 2.5–2.6 (m, 2H), 4.0 (s, 3H), 7.4–7.8 (m, 3H), 7.65 (s, 1H), 7.98 (s, 1H), 8.6 (s, 1H); Mass Spectrum: M+H$^+$ 527and 529.

The material so obtained was reacted with ammonia using an analogous procedure to that described in the last paragraph of Note [115] above to give the required starting material.

6-(N-Methylpiperazin-1-yl)-1-hexyne was obtained by the reaction of 6-mesyloxy-1-hexyne with N-methylpiperzine using an analogous procedure to that described in J. Heterocyclic Chemistry, 1994, 31, 1421.

[138] The reactants were heated to 45° C. for 20 hours. The product gave the following data: NMR Spectrum: (CDCl$_3$) 2.24 (s, 3H), 2.34 (s, 3H), 2.78 (s, 3H), 3.08 (s, 3H), 3.58 (s, 3H), 5.3 (s, 2H), 7.06 (d, 1H), 7.18 (d, 1H), 7.3–7.52 (m, 7H), 8.64 (s, 1H), 9.4 (s, 1H), 11.87 (s, 1H); Mass Spectrum: M+H$^+$ 500.

The 3-(N,N-dimetylcarbamoyl)-2,6-dimethylphenylsocyanate used as a starting material was prepared as follows:

A solution of di-tert-butyl dicarbonate (0.081 g) in methylene chloride (1.6 ml) and a solution of 3-amino-N,N,2,4-tetramethylbenzamide (J. Chem. Soc., Perkin Trans, I. 1973, 1–4; 0.072 g) in methylene chloride (1.0 ml) were added in turn to a solution of 4-diethylaminopyridine (0.004 g) in methylene chloride (0.4 ml). The resultant mixture was stirred at ambient temperature for 20 minutes. There was thus obtained a solution of 3-(N,N-dimethylcarbamoyl)-2,6-dimethylphenylisocyanate which was used without further purification.

[139] The product gave the following data: NMR Spectrum: (DMSOd$_6$) 0.37 (m, 2H), 0.62 (m, 2H), 1.32 (m, 1H), 2.25 (s, 6H), 3.94 (s, 3H), 4.03 (d, 2H), 7.12 (s, 3H), 7.22 (s, 1H), 8.07 (s, 1H), 8.66 (s, 1H), 10.38 (s, 1H), 11.68 (s, 1H); Mass Spectrum: M+H$^+$ 393.

The 4-amino-7-cyclopropylmethoxy-6-methoxyquinazoline used as a starting material was prepared as follows:

A mixture of 4-(4-bromo-2-fluorophenoxy)-7-hydroxy-6-methoxyquinazoline (6.99 g), cyclopropylmethyl chloride (2.16 g), potassium iodide (0.043 g), potassium carbonate (12 g) and DMF (200 ml) was stirred and heated to 45° C. for 16 hours. The mixture was cooled to ambient temperature and filtered. The filtrate was evaporated and the residue was purified by column chromatography on silica using increasingly polar mixtures of methylene chloride and methanol as eluent. There was thus obtained 4-(4-bromo-2-fluorophenoxy)-7-cyclopropylmethoxy-6-methoxyquinazoline (7.6 g); NMR Spectrum: (DMSOd$_6$) 0.43 (m, 2H), 0.68 (m, 2H), 1.37 (m, 1H), 4.0 (s, 3H), 4.1 (d, 2H), 7.4 (s, 1H), 7.45 (m, 1H), 7.57 (m, 2H), 7.82 (m, 1H), 8.58 (s, 1H); Mass Spectrum: M+H$^+$ 421 and 423.

Using an analogous procedure to that described in the last paragraph of the portion of Example 1 that is concerned with starting materials, 4-(4-bromo-2-fluorophenoxy)-7-cyclopropylmethoxy-6-methoxyquinazoline (1.75 g) was reacted with ammonia in isopropanol. There was thus obtained 4-amino-7-cyclopropylmethoxy-6-methoxyquinazoline (1.75 g); NMR Spectrum: (DMSOd$_6$) 0.36 (m, 2H), 0.58 (m, 2H), 1.3 (m, 1H), 3.88 (s, 3H), 3.94 (d, 2H), 6.97 (s, 1H), 7.39 (br s, 2H), 7.55 (s, 1H), 8.25 (s, 1H); Mass Spectrum: M+H$^+$ 246.

[140] The product gave the following data: NMR Spectrum: (DMSOd$_6$) 1.23–1.46 (m, 6H), 1.55–1.69 (m, 2H), 2.1 (s, 3H), 2.1–2.4 (m, 10H), 2.7–2.8 (m, 2H), 3.97 (s, 3H), 7.3–7.6 (m, 3H), 7.65 (s, 1H), 8.05 (s, 1H), 8.7 (s, 1H), 10.7 (s, 1H), 12.05 (s, 1H); Mass Spectrum: M+H$^+$ 545 and 547.

The 4-amino-6-methoxy-7-[6-(N-methylpiperazin-1-yl)hexyl]quinazoline used as a starting material was prepared as follows:

A mixture of 4-amino-6-methoxy-7-[6-(N-methylpiperazin-1-yl)-1-hexynyl]quinazoline (0.145 g), 10% palladium-on-charcoal catalyst (0.02 g) and ethanol (10 ml) was stirred at ambient temperature under 5 atmospheres pressure of hydrogen until uptake of hydrogen ceased. The reaction mixture was filtered and the filtrate was evaporated. There was thus obtained the title compound as a solid (0.142 g); Mass Spectrum: M+H$^+$ 358.

[141] The product gave the following data: NMR Spectrum: (CDCl$_3$) 1.8–2.0 (m, 6H), 2.5–2.7 (m, 6H), 2.79–2.85 (t, 2H), 3.6 (s, 3H), 7.2–7.4 (m, 3H), 7.4 (s, 1H), 7.73 (s, 1H), 8.72 (s, 1H), 9.3–9.45 (s, 1H), 12.3 (s, 1H); Mass Spectrum: M+H$^+$ 474 and 476.

The 4-amino-6-methoxy-7-[3-(pyrrolidin-1-yl)propyl]quinazoline used as a starting material was prepared by the hydrogenation of 4-amino-6-methoxy-7-[3-(pyrrolidin-1-yl)-1-propynyl]quinazoline using an analogous procedure to that described in Note [139] above.

[142] The product gave the following data: NMR Spectrum: (DMSOd$_6$) 1.6–1.75 (m, 2H), 2.1 (s, 3H), 2.2–2.4 (m, 10H), 3.3 (m, 2H), 4.0 (s, 3H), 7.25–7.6 (m, 3H), 7.94 (s, 1H), 8.19 (s, 1H), 8.5 (br t, 1H), 8.77 (s, 1H), 10.87 (s, 1H), 11.96 (s, 1H); Mass Spectrum: M+H$^+$ 546 and 548.

The 4-amino-6-methoxy-7-{N-[3-(N-methylpiperazin-1-yl)propyl]carbamoyl}quinazoline used as a starting material was prepared as follows:

A mixture of 4-(2-bromo-4-fluorophenoxy)-6-methoxy-7-trifluoromethanesulphonyloxyquinazoline (9.7 g), palladium acetate (0.137 g), 1,3-bis(diphenylphosphino)propane (0.402 g ), triethylamine (5.5 ml), DMF (60 ml) and methanol (1.2 L) was stirred and heated to 70° C. under 10 atmospheres pressure of carbon monoxide for 2 hours. The reaction mixture was cooled to ambient temperature and the solid was isolated, washed with methanol and dried under vacuum. There was thus obtained 4-(2-bromo-4-fluorophenoxy)-6-methoxy-7-methoxycarbonylquinazoline (5.96 g); NMR Spectrum: ($DMSOd_6$) 3.91 (s, 3H), 4.02 (s, 3H), 7.4–7.8 (m, 3H), 7.8 (s, 1H), 8.2 (s, 1H), 8.69 (s, 1H); Mass Spectrum: $M+H^+$ 407 & 409.

A mixture of a portion (2 g) of the product so obtained, 2,4,6-trimethoxybenzylamine hydrochloride (2.34 g), anhydrous potassium carbonate (2.76 g) and DMF (20 ml) was stirred and heated to 70° C. for 2 hours. The mixture was cooled to ambient temperature and diluted with water. The resultant solid was isolated, washed in turn with water and diethyl ether and dried under vacuum at 80° C. There was thus obtained 6-methoxy-7-methoxycarbonyl-4-(2,4,6-trirmethoxybenzylamino)quinazoline (1.9 g); NMR Spectrum: ($DMSOd_6$) 3.75–3.85 (m, 15H), 4.55 (d, 2H), 6.3 (s, 2H), 7.8 (m, 2H), 7.9 (m, 1H), 8.45 (s, 1H); Mass Spectrum: $M+H^+$ 414.

A portion (1.8 g) of the material so obtained was suspended in a mixture of THF (27 ml), methanol (14 ml) and water (14 ml) and lithium hydroxide (0.945 g) was added portionwise. The resultant mixture was stirred at ambient temperature for 2 hours. The mixture was concentrated by evaporation and acidified to pH4 by the addition of 2N aqueous hydrochloride acid. The resultant solid was isolated, washed in turn with water and diethyl ether and dried at 80° C. The was thus obtained 7-carboxy-6-methoxy-4-(2,4,6-trimethoxybenzylamino)quinazoline (1.68 g); NMR Spectrum: ($DMSOd_6$) 3.7–3.9 (m, 12H), 4.55 (s, 2H), 6.28 (s, 2H), 7.7–7.9 (m, 3H), 8.42 (s, 1H); Mass Spectrum: $M+H^+$ 400.

A mixture of a portion (0.3 g) of the material so obtained, 3-(N-methylpiperazin-1-yl)propylamine (0.33 g), N-hydroxybenzotriazole (0.13 g), 1-(3-dimethylaminopropyl)-3-ethylcarbodiimide hydrochloride (0.287 g) and DMF (3 ml) was stirred at ambient temperature for 16 hours. Dilute aqueous potassium carbonate solution was added and the resultant solid was isolated, washed in turn with water and diethyl ether and dried at 60° C. under vacuum. There was thus obtained 6-methoxy-7-{N-[3-(N-methylpiperazin-1-yl)propyl]carbamoyl}-4-(2,4,6-trimethoxybenzylamino)quinazoline (0.285 g); NMR Spectrum: ($DMSOd_6$) 1.58–1.7 (m, 2H), 2.11 (s, 3H), 2.2–2.4 (m, 10H), 3.2–3.4 (m, 2H), 3.7–3.92 (m, 12H), 4.51 (m, 2H), 6.3 (s, 2H), 7.7–7.86 (m, 3H), 8.3–8.4 (br t, 1H), 8.42 (s, 1H); Mass Spectrum: $M+H^+$ 539.

A mixture of the material so obtained, trifluoroacetic acid (2 ml), anisole (0.2 ml) and concentrated sulphuric acid (0.2 ml) was stirred at ambient temperature for 2 hours. The mixture was evaporated and the residue was partitioned between diethyl ether and a 2M aqueous potassium carbonate solution. The aqueous solution was evaporated and the residue was extracted with methanol. The methanolic extracts were evaporated and the resultant solid was dried under vacuum. There was thus obtained 4-amino-6-methoxy-7-{N-[3-(N-methylpiperazin-1-yl)propyl]carbamoyl}quinazoline (0.086 g), Mass Spectrum: $M+H^+$ 359.

[143] The product gave the following data: NMR Spectrum: ($DMSOd_6$) 1.88–2.02 (m, 2H), 3.18–3.25 (m, 2H), 4.0 (s, 3H), 4.0–4.08 (m, 2H), 6.88 (s, 1H), 7.22 (s, 1H), 7.3–7.6 (m, 4H), 7.98 (s, 1H), 8.22 (s, 1H), 8.55–8.6 (br t, 1H), 8.8 (s, 1H), 10.9 (s, 1H), 11.98 (s, 1H); Mass Spectrum: $M+H^+$ 514 and 516.

The 4-amino-6-methoxy-7-{N-[3-(N-methylpiperazin-1-yl)propyl]carbamoyl}quinazoline used as a starting material was prepared by the reaction of 7-carboxy-6-methoxy-4-(2,4,6-trimethoxybenzylamino)quinazoline and 3-(1-imidazolyl)propylamine and subsequent cleavage of the 2,4,6-trimethoxybenzyl group using analogous procedures to those described in Note [142] above.

[144] The product gave the following data: NMR Spectrum: ($DMSOd_6$) 2.2 (s, 3H), 3.18–3.24 (m, 4H), 3.3–3.4 (m, 4H), 3.97 (s, 3H), 7.18 (s, 1H), 7.3–7.6 (m, 3H), 7.98(s, 1H), 8.65 (s, 1H), 10.6 (s, 1H), 12.12 (s, 1H); Mass Spectrum: $M+H^+$ 461 and 463.

The 4-amino-6-methoxy-7-(N-methylpiperazin-1-yl)quinazoline used as a starting material was prepared as follows:

A mixture of 4-(2-bromo-4-fluorophenoxy)-6-methoxy-7-trifluoromethanesulphonyloxyquinazoline (0.8 g), 1-methylpiperazine (0.35 ml), caesium carbonate (0.78 g), 1,1'-bis(diphenylphosphino)ferrocene (0.088 g), bis(dibenzylideneacetone)palladium (0.046 g) and toluene (12 ml) was stirred and heated to 100° C. for 6 hours. The mixture was cooled to ambient temperature and partitioned between ethyl acetate and water. The organic extract was washed with a saturated aqueous sodium chloride solution, dried over anhydrous sodium sulphate and evaporated. The residue was purified by column chromatography on silica using increasingly polar mixtures of methylene chloride and methanol as eluent. There was thus obtained 4-(2-bromo-4-fluorophenoxy)-6-methoxy-7-(N-methylpiperazin-1-yl)quinazoline (0.26 g); NMR Spectrum: ($CDCl_3$) 2.4 (s, 3H), 2.66–2.68 (m, 4H), 3.34–3.38 (m, 4H), 4.05 (s, 3H), 7.1–7.44 (m, 3H), 7.38 (s, 1H), 7.55 (s, 1H), 8.58 (s, 1H); Mass Spectrum: $M+H^+$ 447 and 449.

The material so obtained was reacted with ammonia using an analogous procedure to that described in the last paragraph of Note [115] above to give the required starting material.

[145] The product gave the following data: NMR Spectrum: ($DMSOd_6$) 1.43 (s, 9H), 3.13–3.19 (m, 4H), 3.45–3.55 (m, 4H), 4.0 (s, 3H), 7.2 (s, 1H), 7.35–7.6 (m, 3H), 8.02 (s, 1H), 8.65 (s, 1H), 10.65 (s, 1H), 12.1 (s, 1H); Mass Spectrum: $M+H^+$ 547 and 549.

The 4-amino-7-[N-(tert-butoxycarbonyl)piperazin-1-yl]-6-methoxyquinazoline used as a starting material was prepared from as follows:

The procedure described in the first paragraph of the portion of Note [144] above which is concerned with the preparation of stating materials was repeated except that 1-(tert-butoxycarbonyl)piperazine was used in place of 1-methylpiperazine. There was thus obtained 4-(2-bromo-4-fluorophenoxy)-6-methoxy-7-[N-(tert-butoxycarbonyl)piperazin-1-yl]quinazoline; NMR Spectrum: ($CDCl_3$) 1.5 (s, 9H), 3.22 (m, 4H), 3.66 (m, 4H), 4.08 (s, 3H), 7.1–7.46 (m, 3H), 7.35 (s, 1H), 7.57 (s, 1H), 8.58 (s, 1H); Mass Spectrum: $M+H^+$ 533 and 535.

The material so obtained was reacted with ammonia using an analogous procedure to that described in the last paragraph of Note [115] above to give the required starting material.

[146] The product gave the following data: NMR Spectrum: ($DMSOd_6$) 1.75–1.85 (m, 2H), 2.3–2.45 (m, 6H), 3.25–3.35 (m, 2H), 3.6–3.68 (m, 4H), 4.0 (s, 3H), 6.7 (s, 1H), 6.89 (t, 1H), 7.35–7.6 (m, 3H), 7.88 (s, 1H), 8.51 (s, 1H), 10.3 (s, 1H), 12.25 (s, 1H); Mass Spectrum: $M+H^+$ 505 and 507.

The 4-amino-6-methoxy-7-(3-morpholiopropylamino) quinazoline used as a starting material was prepared from as follows:

The procedure described in the first paragraph of the portion of Note [144] above which is concerned with the preparation of starting materials was repeated except that 3-morpholinopropylamine was used in place of 1-methylpiperazine. There was thus obtained 4-(2-bromo-4-fluorophenoxy)-6-methoxy-7-(3-morpholiopropylamino) quinoline; NMR Spectrum: (CDCl$_3$) 1.9–2.0 (m, 2H), 2.48–2.6 (m, 6H), 3.35–3.42 (m, 2H), 3.78–3.82 (m, 4H), 4.07 (s, 3H), 6.4–6.48 (t, 1H), 6.86 (s, 1H), 7.1–7.42 (m, 3H), 7.43 (s, 1H), 8.5 (s, 1H); Mass Spectrum: M+H$^+$ 491 and 493.

The material so obtained was reacted with ammonia using an analogous procedure to that described in the last paragraph of Note [151] above to give the required starting material.

[147] The product gave the following data: NMR Spectrum: (DMSOd$_6$) 2.0–2.12 (m, 2H), 3.15–3.25 (m, 2H), 4.0 (s, 3H), 4.05–4.12 (m, 2H), 6.45–6.5 (t, 1H), 6.68 (s, 1H), 6.9 (s, 1H), 7.22 (s, 1H), 7.35–7.6 (m, 3H), 7.65 (s, 1H), 7.88 (s, 1H), 8.5 (s, 1H), 10.35 (s, 1H), 12.22 (s, 1H); Mass Spectrum: M+H$^+$ 486 and 488.

The 4-amino-7-(3-imidazol-1-ylpropylamino)-6-ethoxyquinazoline used as a starting material was prepared from as follows:

The procedure described in the first paragraph of the portion of Note [144] above which is concerned with the preparation of starting materials was repeated except that 3-imidazol-1-ylpropylamine was used in place of 1-methylpiperazin. There was thus obtained 4-(2-bromo-4-fluorophenoxy)-7-(3-imidazol-1-ylpropylamino)-6-methoxyquinazoline; NMR Spectrum: (CDCl$_3$) 2.2–2.3 (m, 2H), 3.3–3.4 (m, 2H), 4.05 (s, 3H), 4.1–4.15 (m, 2H), 5.04–5.13 (br t, 1H), 6.88 (s, 1H), 6.96 (s, 1H), 7.1 (s, 1H), 7.15–7.5 (m, 3H), 7.45 (s, 1H), 7.52 (s, 1H), 8.55 (s, 1H); Mass Spectrum: M+H$^+$ 472 and 474.

The material so obtained was reacted with ammonia using an analogous procedure to that described in the last paragraph of Note [115] above to give the required starting material.

[148] The reactants were heated to 45° C. for 20 hours. The product gave the following data: NMR Spectrum: (CDCl$_3$) 1.2–1.4 (m, 2H), 1.66–1.94 (m, 5H), 2.14 (s, 3H), 2.16 (s, 3H), 2.26 (s, 3H), 2.7 (m, 2H), 2.78 (s, 3H), 2.98 (s, 3H), 3.94 (s, 3H), 4.04 (d, 2H), 7.0 (d, 1H), 7.18 (d, 1H), 7.24 (s, 1H), 8.02 (s, 1H), 8.64 (s, 1H), 10.36 (s, 1H), 11.72 (s, 1H); Mass Spectrum: M+H$^+$ 521.

[149] The product gave the following data: NMR Spectrum: (CDCl$_3$) 1.73 (m, 4H), 2.09 (m, 2H), 2.28 (s, 3H), 2.48 (br m, 4H), 2.57 (t, 2H), 3.35 (s, 3H), 4.18 (t, 2H), 5.24 (s, 1H), 7.08 (d, 2H), 7.19 (s, 1H), 7.27 (t, 1H), 7.42 (s, 1H), 8.61 (s, 1H), 9.72 (s, 1H), 12.19 (s, 1H); Mass Spectrum: M+H$^+$ 470 and 472.

[150] The product gave the following data: Mass Spectrum: M+H$^+$ 450 and 452.

The 4-amino-7-(3-methoxypropylamino)-6-methoxyquinazoline used as a starting material was prepared from as follows:

The procedure described in the first paragraph of the portion of Note [144] above which is concerned with the preparation of starting materials was repeated except that 3-methoxypropylamine was used in place of 1-methylpiperazine. There was thus obtained 4-(2-bromo-4-fluorophenoxy)-7-(3-methoxypropylamino)-6-methoxyquinazoline.

The material so obtained was reacted with ammonia using an analogous procedure to that described in the last paragraph of Note [115] above to give the required starting material.

[151] The product gave the following data: Mass Spectrum: M+H$^+$ 421 and 423.

The 4-amino-7-(2-aminoethylamino)-6-methoxyquinazoline used as a starting material was prepared from as follows:

The procedure described in the first paragraph of the portion of Note [144] above which is concerned with the preparation of starting materials was repeated except that ethylenediamine was used in place of 1-methylpiperazin. There was thus obtained 7-(2-aminoethylamino)-4-(2-bromo-4-fluorophenoxy)-6-methoxyquinazoline.

The material so obtained was reacted with ammonia using an analogous procedure to that described in the last paragraph of Note [115] above to give the required starting material.

[152] The product gave the following data: Mass Spectrum: M+H$^+$ 491 and 493.

The 4-amino-7-[N-(2-diethylaminoethyl)-N-methylamino]-6-methoxyquinazoline used as a starting material was prepared from as follows:

The procedure described in the first paragraph of the portion of Note [144] above which is concerned with the preparation of starting materials was repeated except that N-(2-diethylaminoethyl)-N-methylamine was used in place of 1-methylpiperzine. There was thus obtained 4-(2-bromo-4-fluorophenoxy)-7-[N-(2-diethylaminoethyl)-N-methylamino]-6-methoxyquinazoline.

The material so obtained was reacted with ammonia using an analogous procedure to that described in the last paragraph of Note [115] above to give the required starting material.

EXAMPLE 3

1-(7-benzyloxy-6-methoxyquinazolin-4-yl)-3-(2,6-dichlorophenyl)urea 2,6-Dichlorophenyl isocyanate (0.745 g) was added to a solution of 4-amino-7-benzyloxy-6-methoxyquinazoline (0.279 g) in chloroform (10 ml) and the reaction mixture was stirred at ambient temperature for 16 hours. The resultant precipitate was isolated by filtration. There was thus obtained the title compound (0.343 g); NMR Spectrum: (DMSOd$_6$) 3.96 (s, 3H), 5.32 (s, 2H), 7.35–7.60 (m, 10H), 8.1 (s, 1H), 8.69 (s, 1H), 10.65 (s, 1H), 12.09 (s, 1H); Mass Spectrum: M+H$^+$ 467 & 469.

EXAMPLE 4

1-(2,6-dichlorophenyl)-3-(6,7-dimethoxyquinazolin-4-yl)urea

Using an analogous procedure to that described in Example 3, 2,6-dichlorophenyl isocyanate was reacted with 4-amino-6,7-dimethoxyquinazoline (European Patent Application No. 30156, Chemical Abstract volume 95, abstract 187290) to give the title compound; NMR Spectrum: (DMSOd$_6$) 3.96 (s, 3H), 7.31 (m, 2H), 7.38 (t, 1H), 7.5 (d, 2H), 7.6 (d, 2H), 8.43 (s, 1H), 8.7 (s, 1H), 10.61 (s, 1H), 12.09 (s, 1H); Mass Spectrum: M+H$^+$ 393 & 395.

EXAMPLE 5

1-(2,6-dichlorophenyl)-3-[6-methoxy-7-(N-methylpiperidin-4-ylmethoxy)quinazolin-4-yl]-3-methylurea 6-Methoxy-4-methylamino-7-(N-methylpiperidin-4-ylmethoxy)quinazoline (0.195 g) was added to 2,6- dichlorophenyl isocyanate (0.3 g) under argon and the solids were mixed together using a spatula. The mixture was heated to 85° C. with gentle mixing for 40 minutes. The mixture was cooled to ambient temperature, dissolved in a mixture of chloroform (15 ml) and methanol (5 ml) and purified by column chromatography on silica using increasingly polar mixtures of methylene chloride and a 1% aqueous ammonium hydroxide solution as eluent. There was thus obtained the title compound (0.016 g); NMR Spectrum: (CDCl$_3$) 1.5 (m, 2H), 1.98 (m, 5H), 2.3 (s, 3H), 2.91 (d, 2H), 3.6 (s, 3H), 4.02 (s, 3H), 4.03 (d, 2H), 7.1 (t, 1H), 7.28 (s, 2H), 7.37 (d, 2H), 8.61 (s, 1H), 8.96 (s, 1H); Mass Spectrum: M+H$^+$ 504.

The 6-methoxy-4-methylamino-7-(N-methylpiperidin-4-ylmethoxy)quinazoline used as a starting material was obtained as follows:

A mixture of 4-chloro-6-methoxy-7-(N-methylpiperidin-4-ylmethoxy)quinazoline (1 g) and methylamine (1M solution in THF; 20 ml) was heated with agitation in a Carius tube at 120° C. for 16 hours. The Carius tube was cooled and opened and the reaction mixture was evaporated. The residue was partitioned between chloroform and a 2N aqueous sodium hydroxide solution. The chloroform solution was dried over magnesium sulphate and evaporated and the resultant solid was washed with methyl tert-butyl ether (20 ml). There was thus obtained the required starting material (0.48 g); NMR Spectrum: (DMSOd$_6$) 1.33 (m, 2H), 1.8 (m, 5H), 2.14 (s, 3H), 2.76 (d, 2H), 2.96 (d, 3H), 3.85 (s, 3H), 3.92 (d, 2H), 7.03 (s, 1H), 7.51 (s, 1H), 7.84 (q, 1H), 8.31 (s, 1H).

EXAMPLE 6

1-[6-methoxy-7-(N-methylpiperidin-4-ylmethoxy)quinazolin-4-yl]-3-(2-methylbenzyl)urea Using an analogous procedure to that described in Example 3, 2-methylbenzyl isocyanate was reacted with 4-amino-6-methoxy-7-(N-methylpiperidin-4-ylmethoxy)quinazoline. The resultant solid was purified by column chromatography on silica using increasingly polar mixtures of methylene chloride, methanol and a 1% aqueous ammonium hydroxide solution as eluent. There was thus obtained the title compound; NMR Spectrum: (CDCl$_3$) 1.39–1.56 (m, 2H), 1.84–2.04 (m, 5H), 2.29 (s, 3H), 2.39 (s, 3H), 2.9 (d, 2H), 3.92 (s, 3H), 4.03 (d, 2H), 4.66 (d, 2H), 7.21 (m, 4H), 7.34 (m, 2H), 8.6 (s, 1H), 8.74 (s, 1H), 10.44 (t, 1H); Mass Spectrum: M+H$^+$ 450.

EXAMPLE 7

1-(2,6-dichlorophenyl)-3-(thieno[3,2-d]pyrimidin-4-yl)urea 2,6-Dichlorophenyl isocyanate (0.075 g) was added to a mixture of 4-aminothieno[3,2-d]pyridine (*Tetrahedron*, 1971, 27, 487; 0.201 g) and acetonitrile (16 ml) and the resultant mixture was stirred at ambient temperature for 16 hours. The precipitate was isolated and washed in turn with diethyl ether and methanol. There was thus obtained the title compound (0.31 g); NMR Spectrum: (DMSOd$_6$) 7.25 (t, 1H), 7.45 (d, 1H), 7.55 (d, 1H), 7.95 (d, 1H), 8.4 (s, 1H), 8.8 (s, 1H), 11.7 (br s, 1H); Mass Spectrum: M+H$^+$ 339 and 341; Elemental Analysis: Found C, 45.8; H, 2.4; N, 16.5; C$_{13}$H$_8$Cl$_2$N$_4$OS requires C, 46.03; H, 2.38; N, 16.52%.

EXAMPLE 8

(E)-3-{4-[3-(2,6-chlorophenyl)ureido]thieno[3,2-d]pyrimidin-6-yl}acrylic acid

Hydrogen chloride gas was bubbled during 3 hours through a stirred solution of tert-butyl (E)-3-{4-[3-(2,6-dichlorophenyl)ureido]thieno[3,2-d]pyrimidin-6-yl}acrylate (1.4 g) in methylene chloride (200 ml) which had been cooled in an ice-bath to 0° C. The mixture was evaporated and there was thus obtained the title compound as its hydrochloride salt; (1.3 g); NMR Spectrum: (DMSOd$_6$ and CF$_3$COOD) 6.6 (d, 1H, J=16 Hz), 7.4 (t, 1H), 7.65 (d, 2H), 7.95 (d, 1H), 7.96 (s, 1H), 8.9 (s, 1H); Mass Spectrum: M+H$^+$ 409, 411 and 413.

The tert-butyl (E)-3-{4-[3-(2,6-dichlorophenyl)ureido]thieno[3,2-d]pyrimidin-6-yl}acrylate used as a starting material was obtained as follows:

A mixture of methyl 3-aminothiophene-2-carboxylate (94 g), formamidine acetic acid salt (187 g) and 2-hydroxyethyl methyl ether (1 L) was stirred and heated to reflux for 3 hours. The mixture was cooled to ambient temperature and water (400 ml) was added. The resultant solid was isolated, washed thoroughly with water and with diethyl ether and dried under vacuum. There was thus obtained 3,4-dihydrothieno[3,2-d]pyrimidin-4-one (65 g); NMR Spectrum: (DMSOd$_6$) 7.4 (d, 1H), 8.15 (s, 1H), 8.18 (d, 2H); Mass Spectrum: M+Na$^+$ 175.

A mixture of a portion (20 g) of the material so obtained, thionyl chloride (250 ml) and DMF (1 ml) was heated to reflux for 2 hours. The mixture was evaporated. Toluene was added and the mixture was evaporated. The residual solid was partitioned between ethyl acetate and a saturated aqueous sodium bicarbonate solution. The organic layer was washed in turn with water and brine, dried over magnesium sulphate and evaporated. The solid so obtained was triturated under petroleum ether (b.p. 60–80° C.), re-isolated and dried under vacuum. There was thus obtained 4-chlorothieno[3,2-d]pyrimidine (18.5 g); NMR Spectrum: (CDCl$_3$) 7.65 (d, 1H), 8.1 (d, 1H), 9.0 (s, 1H); Mass Spectrum: M$^+$ 170 and 172.

A portion (17 g) of the material so obtained was dissolved in DMF (100 ml). Sodium methylthiolate (9.1 g) was added and the mixture was stirred at ambient temperature for 1.5 hours. The mixture was partitioned between ethyl acetate and water. The organic layer was washed with brine, dried over magnesium sulphate and purified by column chromatography on silica using a 9:1 mixture of methylene chloride and ethyl acetate as eluent. There was thus obtained 4-methylthiothieno[3,2-]pyrimidine (16.5 g); NMR Spectrum: (CDCl$_3$) 2.76 (s, 3H), 7.5 (d, 1H), 7.85 (d, 1H), 8.97 (s, 1H).

A portion (5.5 g) of the material so obtained was dissolved in THF (20 ml) and cooled to −78° C. A solution of lithium diisopropylamide [prepared using diisopropylamide (10.5 ml) and n-butyllithium (2.5M in THF; 30 ml)] was added and the mixture was stirred at −78° C. for 1 hour. DMF (7 ml) was added and the mixture was allowed to warm to ambient temperature and was stirred for 16 hours. The resultant mixture was partitioned between ethyl acetate and a saturated aqueous ammonium chloride solution. The organic layer was evaporated and the residue was purified by column chromatography on silica using a 9:1 mixture of methylene chloride and ethyl acetate as eluent. There was thus obtained 6-formyl-4-methylthiothieno[3,2-d]pyrimidine (4.1 g); NMR Spectrum: (CDCl$_3$) 2.78 (s, 3H), 8.13 (s, 1H), 9.04 (s, 1H), 10.23 (s, 1H); Mass Spectrum: M+H$^+$ 211.

tert-Buloxycarbonylmethylenetriphenylphosphorane (20.6 g) was added portionwise to a solution of 6-formyl-4-methylthiothieno[3,2-d]pyrimidine (9.6 g) in methylene chloride (500 ml) and the mixture was stirred at ambient temperature for 16 hours. The mixture was concentrated to half of its original volume and poured onto a column of silica. The column was eluted initially with methylene chloride followed by a 19:1 mixture of methylene chloride and ethyl acetate. The material so obtained was triturated under petroleum ether (b.p. 60–80° C.), re-isolated and dried under vacuum. There was thus obtained tert-butyl (E)-3-(4-methylthiothieno[3,2-d]pyrimidin-6-yl)acrylate (12 g); NMR Spectrum: (CDCl$_3$) 1.54 (s, 9H), 2.76 (s, 3H), 6.42 (d, 1H, J=15 Hz), 7.53 (s, 1H), 7.8 (d, 1H), 8.94 (s, 1H); Mass Spectrum: M+H$^+$ 308.

A portion (2.9 g) of the material so obtained was dissolved in methylene chloride (200 ml) and M-chloroperoxybenzoic acid (70%; 9.25 g) was added. The resultant mixture was stirred at ambient temperature for 2 hours. The mixture was washed with an aqueous sodium bisulphite solution. The organic layer was washed with a dilute (5%) aqueous sodium bicarbonate solution and with brine, dried over magnesium sulphate and evaporated. There was thus obtained tert-butyl (E)-3-(4-methylsulphonylthieno[3,2-d]pyrimidin-6-yl)acrylate (3.1 g); NMR Spectrum: (CDCl$_3$) 1.55 (s, 9H), 3.39 (s, 3H), 6.6 (d, 1H, J=16 Hz), 7.71 (s, 1H), 7.85 (d, 1H), 9.3 (s, 1H).

A solution of the sulphone so obtained (3 g) in THF (100 ml) was cooled at 0° C. and gaseous ammonia was bubbled through the solution for 2 hours. The mixture was evaporated and the residue was triturated under diethyl ether. The solid so obtained was purified by column chromatography on silica using a 49:1 mixture of methylene chloride and methanol as eluent. There was thus obtained tert-butyl (E)-3-(4-aminothieno[3,2-d]pyrimidin-6-yl)acrylate (1.7 g); NMR Spectrum: (CDCl$_3$) 1.55 (s, 9H), 5.25 (br s, 2H), 6.38 (d, 1H, J=16 Hz), 7.51 (s, 1H), 7.76 (d, 1H), 8.6 (s, 1H); Mass Spectrum: M+H$^+$ 277.

A mixture of the material so obtained, 2,6-dichlorophenyl isocyanate (1.41 g) and methylene chloride (250 ml) was stirred at ambient temperate for 3 hours. Water was added and the organic layer was separated, washed with water and brine, dried over magnesium sulphate and evaporated. The residue was purified by column chromatography on silica using a 49:1 mixture of methylene chloride and methanol as eluent. There was thus obtained tert-butyl (E)-3-{4-[3-(2,6-dichlorophenyl)ureido]thieno[3,2-d]pyrimidin-6-yl}acrylate (1.5 g); NMR Spectrum: (CDCl$_3$) 1.57 (s, 9H), 6.29 (d, 1H, J=16 Hz), 7.3 (t, 1H), 7.53 (d, 2H), 7.55 (s, 1H), 7.74 (d, 1H), 8.8 (s, 1H), 9.95 (br s, 1H), 11.8 (br s, 1H); Mass Spectrum: M+H$^+$ 465, 467 & 469.

EXAMPLE 9

(E)-3-{4-[3-(2,6-dichlorophenyl)ureido]thieno[3,2-d]pyrimidin-6-yl}-N-(2-piperidinoethyl)acrylamide Diphenylphosphoryl azide (0.085 ml) was added to a mixture of (E)-3-{4-[3-(2,6-dichlorophenyl)ureido]thieno[3,2-d]pyrimidin-6-yl)acrylic acid hydrochloride salt (0.11 g), 2-piperidinoethylamine (0.064 g), triethylamine (0.07 ml) and DMF (1.5 ml). The mixture was stirred at ambient temperature for 16 hours. The mixture was evaporated and the residue was purified by column chromatography on silica using increasingly polar mixtures of methylene chloride and methanol as eluent. The material so obtained was triturated under diethyl ether, isolated, washed with diethyl ether and dried under vacuum. There was thus obtained the title compound (0.087 g); NMR Spectrum: (DMSOd$_6$ and CF$_3$COOD) 1.3–1.5 (m, 1H), 1.6–1.8 (m, 4H), 1.85 (d, 2H), 2.95 (t, 2H), 3.2 (t, 2H), 3.55 (d, 2H), 3.6 (t, 2H), 6.82 (d, 1H, J=16 Hz), 7.4 (t, 1H), 7.6 (d, 1H), 7.86 (s, 1H), 7.86 (d, 1H), 8.95 (s, 1H); Mass Spectrum: M+H$^+$ 519 and 521.

EXAMPLE 10

Using an analogous procedure to that described in Example 9, the appropriate amine was reacted with (E)-3-{4-[3-(2,6-dichlorophenyl)ureido]thieno[3,2-d]pyrimidin-6-yl}acrylic acid to give the compounds described in Table II.

TABLE II

| No. | R$^a$ | R$^b$ | Note |
|-----|-------|-------|------|
| 1 | 2-dimethylaminoethyl | hydrogen | (a) |
| 2 | 3-dimethylaminopropyl | hydrogen | (b) |
| 3 | 2-pyrrolidin-1-ylethyl | hydrogen | (c) |
| 4 | 3-(2-oxopyrrolidin-1-yl)propyl | hydrogen | (d) |
| 5 | 3-morpholinopropyl | hydrogen | (e) |
| 6 | 3-(4-methylpiperazin-1-yl)propyl | hydrogen | (f) |
| 7 | 3-imidazol-1-ylpropyl | hydrogen | (g) |
| 8 | 4-pyridylmethyl | hydrogen | (h) |
| 9 | 2-(2-pyridyl)ethyl | hydrogen | (i) |
| 10 | 2-(2-pyridyl)ethyl | methyl | (j) |

Notes (a) The product gave the following data: NMR Spectrum: (DMSOd$_6$ and CF$_3$COOD) 2.9 (s, 6H), 3.25 (t, 2H), 3.6 (t, 2H), 6.9 (d, 1H, J=16 Hz), 7.42 (t, 1H), 7.65 (d, 2H), 7.85 (d, 1H), 7.88 (s, 1H), 9.05 (s, 1H); Mass Spectrum: M+H$^+$ 479 and 481.

(b) The product gave the following data: NMR Spectrum: (DMSOd$_6$ and CF$_3$COOD) 1.8–1.9 (m, 2H), 2.81 (s, 3H), 3.15 (m, 2H), 3.3 (t, 2H), 6.84 (d, 1H, J=19 Hz), 7.45 (t, 1H), 7.6 (d, 2H), 7.81 (d, 1H), 7.85 (s, 1H), 9.02 (s, 1H); Mass Spectrum: M+H$^+$ 493 and 495.

(c) The product gave the following data: NMR Spectrum: (DMSOd$_6$ and CF$_3$COOD) 1.8–1.95 (m, 2H), 1.95–2.1 (m, 2H), 3.0–3.15 (m, 2H), 3.3 (t, 2H), 3.55 (t, 2H), 3.55–3.7 (m, 2H), 6.8 (d, 1H), 7.42 (t, 1H), 7.6 (d, 2H), 7.82 (d, 1H), 7.84 (s, 1H), 8.9 (s, 1H); Mass Spectrum: M+H$^+$ 505 and 507.

(d) The product gave the following data: NMR Spectrum: (DMSOd$_6$ and CF$_3$COOD) 1.65–1.75 (m, 2H), 1.9–2.0 (m, 2H), 2.3 (t, 2H), 3.25 (t, 2H), 3.3 (t, 2H), 3.4 (t, 2H), 6.25 (d, 1H, J=16 Hz), 7.42 (t, 1H), 7.62 (d, 2H), 7.81 (d, 1H), 7.85 (s, 1H), 9.12 (s, 1H); Mass Spectrum: M+H$^+$ 533 and 535.

(e) The product gave the following data: NMR Spectrum: (DMSOd$_6$ and CF$_3$COOD) 1.85–2.0 (m, 2H), 3.0–3.25 (m, 4H), 3.3 (t, 2H), 3.5 (d, 2H), 3.7 (t, 2H), 4.0 (d, 2H), 6.9 (d, 1H, J=16 Hz), 7.45 (t, 1H), 7.61 (d, 2H), 7.85 (d, 1H), 7.87 (s, 1H), 9.08 (s, 1H); Mass Spectrum: M+H$^+$ 535 and 537.

(f) The product gave the following data: NMR Spectrum: (DMSOd$_6$ and CF$_3$COOD) 1.85–2.0 (m, 2H), 2.95 (s, 3H), 3.2–3.4 (m, 6H), 3.4–4.0 (br m, 6H), 6.85 (d, 1H, J=14 Hz), 7.42 (t, 1H), 7.65 (d, 2H), 7.82 (d, 1H), 7.85 (s, 1H), 9.0 (s, 1H); Mass Spectrum: M+H$^4$ 548 and 550.

(g) The product gave the following data: NMR Spectrum: (DMSOd$_6$ and CF$_3$COOD) 2.0–2.1 (m, 2H), 3.25 (t, 2H), 4.25 (t, 2H), 6.75 (d, 1H, J=15 Hz), 7.2–7.3 (d, 1H), 7.4 (t, 2H), 7.6 (d, 2H), 7.85 (m, 2H), 8.9 (s, 1H), 9.2 (s, 1H); Mass Spectrum: M+H$^+$ 516.

(h) The product gave the following data: NMR Spectrum: (DMSOd$_6$ and CF$_3$COOD) 4.75 (br s, 2H), 6.95 (d, 1H, J=15 Hz), 7.4 (t, 1H), 7.6 (d, 1H), 7.85 (s, 1H), 7.87 (d, 1H), 8.05 (d, 2H), 8.9 (d, 2H), 8.93 (s, 1H); Mass Spectrum: M+H$^+$ 499 and 501.

(i) The product gave the following data: NMR Spectrum: (DMSOd$_6$ and CF$_3$COOD) 3.25 (t, 2H), 3.7 (t, 2H), 6.8 (d, 1H, J=15 Hz), 7.42 (t, 1H), 7.62 (d, 2H), 7.75 (d, 1H), 7.83 (s, 1H), 8.0 (t, 1H), 8.05 (d, 1H), 8.58 (t, 1H), 8.9 (d, 1H), 9.0 (s, 1H); Mass Spectrum: M+H$^+$ 513 and 515.

(j) The product gave the following data: NMR Spectrum: (DMSOd$_6$ and CF$_3$COOD) 3.4 (s, 3H), 5.0 (s, 2H), 7.35–7.5 (m, 2H), 7.61 (d, 2H), 7.8 (d, 1H), 7.98 (s, 1H), 7.85–8.1 (m, 2H), 8.6 (t, 1H), 8.9 (d, 1H), 9.0 (s, 1H); Mass Spectrum: M+H$^+$ 513 and 515.

EXAMPLE 11

1-benzyl-3-[6-methoxy-7-(N-methylpiperidin-4-ylmethoxy)quinazolin-4-yl]urea

Using an analogous procedure to that described in Example 1 except that the reaction mixture was heated to 35° C. for 16 hours, benzyl isocyanate was reacted with 4-amino-6-methoxy-7-(N-methylpiperidin-4-ylmethoxy) quinazoline to give the title compound; NMR Spectrum: (DMSOd$_6$): 1.3–1.5 (m, 2H), 1.8–1.9 (m, 4H), 1.95 (t, 1H), 2.2 (s, 3H), 2.8 (br d, 2H), 3.9 (br s, 3H), 4.0 (br d, 2H), 4.5 (br d, 2H), 7.2–7.3 (m, 2H), 7.3–7.4 (m, 4H), 8.0 (br s, 1H), 8.55 (br s, 1H), 10.2–10.5 (br s, 1H), 10.4 (t, 1H); Mass Spectrum: M+H$^+$ 436.

EXAMPLE 12

1-[6-methoxy-7-(N-methylpiperidin-4-ylmethoxy)quinazolin-4-yl]-3-phenethylura

Using an analogous procedure to that described in Example 3, phenethyl isocyanate was reacted with 4-amino-6-methoxy-7-(N-methylpiperidin-4-ylmethoxy)quinazoline to give the title compound; NMR Spectrum: (CDCl$_3$) 1.48 (m, 2H), 1.98 (m, 5H), 2.29 (s, 3H), 2.91 (m, 4H), 3.7 (q, 2H), 4.02 (d, 5H), 7.28 (m, partially obscured by CHCl$_3$ peak), 8.47 (s, 1H), 8.65 (s, 1H), 10.1 (s, 1H); Mass Spectrum: M+H$^+$ 450.

EXAMPLE 13

Using an analogous procedure to that described in Example 1 except that, unless otherwise stated, chloroform was used in place of methylene chloride as the reaction solvent, the appropriate 4-aminoquinazoline was reacted with the appropriate isocyanate to give the compounds described in Table III.

TABLE III

| No. | R$^6$ | R$^7$ | (R$^2$)$_n$ | Note |
|---|---|---|---|---|
| 1 | methoxy | N-methylpiperidin-4-ylmethoxy | 4-chloro | (a) |
| 2 | methoxy | N-methylpiperidin-4-ylmethoxy | 3,4-dichloro | (b) |
| 3 | methoxy | N-methylpiperidin-4-ylmethoxy | 3,5-dichloro | (c) |
| 4 | methoxy | N-methylpiperidin-4-ylmethoxy | 4-bromo | (d) |
| 5 | methoxy | N-methylpiperidin-4-ylmethoxy | 4-nitro | (e) |

Notes (a) DMF was used in place of methylene chloride as the reaction solvent. The product gave the following data: NMR Spectrum: (CDCl$_3$) 1.48 (m, 2H), 1.97 (m, 5H), 2.29 (s, 3H), 2.91 (m, 2H), 3.81 (s, 3H), 4.04 (d, 2H), 7.25 (s, 2H), 7.3 (d, 2H), 7.57 (d, 2H), 8.73 (s, 1H), 8.91 (s, 1H), 12.5 (s, 1H); Mass Spectrum: M+H$^+$ 456 and 458.

(b) The product gave the following data: NMR Spectrum: (CDCl$_3$) 1.51 (m, 2H), 1.92 (m, 5H), 2.3 (s, 3H), 2.92 (d, 2H), 3.9 (s, 3H), 4.03 (d, 2H), 7.2 (s, 1H), 7.24 (s, partially obscured by CHCl$_3$ peak), 7.41 (m, 2H), 7.82 (s, 1H), 8.55 (s, 1H), 8.74 (s, 1H), 12.55 (s, 1H); Mass Spectrum: M+H$^+$ 490 and 492.

(c) DMF was used in place of methylene chloride as the reaction solvent. The product gave the following data: NMR Spectrum: (CDCl$_3$) 1.48 (m, 2H), 1.95 (m, 5H), 2.28 (s, 3H), 2.95 (d, 2H), 3.91 (s, 3H), 4.03 (d, 2H), 7.11 (s, 1H), 7.26 (s, 2H), 7.58 (s, 2H), 8.63 (s, 1H), 8.75 (s, 1H), 12.7 (s, 1H); Mass Spectrum: M+H$^+$ 490 and 492.

(d) Methylene chloride was used as the reaction solvent and the reaction mixture was heated to 35° C. for 16 hours. The product gave the following data: NMR Spectrum: (DMSOd$_6$) 1.2–1.4 (m, 2H), 1.7–1.8 (m, 4H), 1.85 (t, 1H), 2.1 (s, 3H), 2.8 (d, 2H), 3.9 (br s, 3H), 4.0 (br d, 2H), 7.2 (s, 1H), 7.4–7.45 (m, 2H), 7.5–7.55 (m, 2H), 7.6–7.7 (m, 2H), 8.0 (br s, 1H), 8.7 (br s, 1H); Mass Spectrum: M+H$^+$ 500 and 502.

(e) Methylene chloride was used as the reaction solvent and the reaction mixture was heated to 35° C. for 16 hours. The product gave the following data: NMR Spectrum: (DMSOd$_6$) 1.3–1.4 (m, 2H), 1.7–1.8 (m, 4H), 1.85 (t, 1H), 2.1 (s, 3H), 2.7 (d, 2H), 3.9 (s, 3H), 4.0 (br d, 2H), 7.2 (s, 1H), 7.8 (d, 2H), 7.9 (s, 1H), 8.1 (d, 2H), 8.6 (br s, 1H), 10.2–10.5 (br s, 1H), 12.3–12.7 (br s, 1H); Mass Spectrum: M+H$^+$ 467.

EXAMPLE 14

1-[6-methoxy-7-(N-methylpiperidin-4-ylmethoxy)quinazolin-4-yl]-3-(trans-2-phenylcyclopropyl)urea trans-2-Phenylcyclopropyl isocyanate (0.2 ml) was added to a stirred mixture of 4-amino-6-methoxy-7-(1-methylpiperidin-4-ylmethoxy)quinazoline (0.1 g) and chloroform (3 ml) and the resultant mixture was stirred at ambient temperature for 20 hours. The reaction mixture was diluted with chloroform (3 ml) and tris-(2-aminoethyl)amine polystyrene resin (0.5 g) was added. The mixture was stirred at ambient temperature for 1 hour. The mixture was filtered and the filtrate was evaporated. The residue was purified by column chromatography, on silica using increasingly polar mixtures of methylene chloride and 2M methanolic ammonia as eluent. There was thus obtained the title compound (0.11 g); NMR Spectrum: (CDCl$_3$) 1.24–1.38 (m, 2H), 1.41–1.57 (m, 2H), 1.87–2.05 (m, 5H), 2.21 (m, 1H), 2.3 (s, 3H), 2.91 (d, 2H), 3.05 (m, 1H), 3.97 (s, 3H), 4.04 (d, 2H), 7.1–7.26 (m, 6H partially obscured by CHCl$_3$ peak), 7.34 (m, 1H), 8.66 (s, 1H), 8.72 (s, 1H), 10.31 (s, 1H); Mass Spectrum: M+H$^+$ 462.

EXAMPLE 15

1-[6-methoxy-7-(N-methylpiperidin-4-ylmethoxy) quinazolin-4-yl]-3-[(S)-(-)-α-methylbenzyl]urea Using an analogous procedure to that described in Example 14, (S)-(-)-α-methylbenzyl isocyanate was reacted with 4-amino-6-methoxy-7-(N-methylpiperidin-4-ylmethoxy)quinazoline to give the title compound; NMR Spectrum: (CDCl$_3$) 1.4–1.56 (m, 2H), 1.61 (d, 3H), 1.84–2.05 (m, 5H), 2.31 (s, 3H), 2.91 (d, 2H), 3.88 (s, 3H), 4.04 (d, 2H), 5.2 (m, 1H), 7.23 (d, 2H), 7.3–7.41 (m, 5H), 8.66 (s, 1H), 8.7 (s, 1H), 10.58 (s, 1H); Mass Spectrum: M+H$^+$ 450.

EXAMPLE 16

1-[6-methoxy-7-(N-methylpiperidin-4-ylmethoxy) quinazolin-4-yl]-3-[(R)-(+)-α-methylbenzyl]urea Using an analogous procedure to that described in Example 14, (R)-(+)-α-methylbenzyl isocyanate was reacted with 4-aminomethoxy-7-(N-methylpiperidin-4-ylmethoxy)quinazoline to give the title compound; NMR Spectrum: (CDCl$_3$) 1.39–1.56 (m, 2H), 1.64 (d, 3H), 1.86–2.05 (m, 5H), 2.3 (s, 3H), 2.9 (d, 2H), 3.9 (s, 3H), 4.01 (d, 2H), 5.19 (m, 1H), 7.24 (d, 2H), 7.32–7.41 (m, 5H), 8.44 (s, 1H), 8.67 (s, 1H), 10.5 (s, 1H); Mass Spectrum: M+H$^+$ 450.

EXAMPLE 17

1-[6-methoxy-7-(N-methylpiperidin-4-ylmethoxy) quinazolin-4-yl]-3-[1-(1-naphthyl)ethyl]urea Using an analogous procedure to that described in Example 14, 1-(1-naphthyl)ethyl isocyanate was reacted with 4-amino-6-methoxy-7-(N-methylpiperidin-4-ylmethoxy)quinazoline to give the title compound; NMR Spectrum: (CDCl$_3$) 1.41–1.57 (m, 2H), 1.76 (m, partially obscured by water peak), 1.86–2.05 (m, 5H), 2.02 (s, 3H), 2.91 (s, 2H), 3.87 (s, 3H), 4.02 (d, 2H), 5.95 (s, 1H), 7.19 (s, 1H), 7.23 (s, 1H), 7.39–7.52 (m, 3H), 7.6 (d, 1H), 7.71 (d, 1H), 7.84 (m, 1H), 8.12 (m, 1H), 8.57 (s, 1H), 8.64 (s, 1H), 10.67 (t, 1H); Mass Spectrum: M+H$^+$ 500.

EXAMPLE 18

1-(3-cyano-6,7-dimethoxyquinolin-4-yl)-3-(2,6-dichlorophenyl)urea

A solution of 4-amino-3-cyano-6,7-ethoxyquinoline (0.115 g) in DMF (2 ml) was added to a stirred mixture of sodium hydride (50% dispersion in mineral oil; 0.04 g) and DMF (3 ml) and the mixture was stirred at ambient temperature for 20 minutes. 2,6-Dichlorophenyl isocyanate (0.17 g) was added and the mixture was stirred at ambient temperature for 20 hours. A second portion of sodium hydride dispersion (0.08 g) was added followed, after 20 minutes, by more 2,6-dichlorophenyl isocyanate (0.3 g). The reaction mixture was stirred for a further 2 hours. Methanol (1 ml) was added and the mixture was partitioned between ethyl acetate (50 ml) and water (10 ml). The organic layer was evaporated. The residue was purified by column chromatography on silica using increasingly polar mixtures of ethyl acetate and methanol as eluent. There was thus obtained the title compound (0.03 g); NMR Spectrum: (DMSOd$_6$) 4.05 (s, 6H), 7.4–7.8 (m, 4H), 8.08 (s, 2H), 9.22 (s, 1H); Mass Spectrum: M+H$^+$ 417 & 419.

The 4-amino-3-cyano-6,7-dimethoxyquinoline used as a starting material was prepared as follows:

A mixture of 4-chloro-3-cyano-6,7-dimethoxyquinoline (International Patent Application WO 98/43960; 1.24 g) and a 1M solution of ammonia gas in isopropanol (20 ml) was sealed in a Carius tube and heated to 120° C. for 16 hours. The mixture was cooled to ambient temperature. A saturated aqueous sodium bicarbonate solution (50 ml) was added and the mixture was stirred for 15 minutes. The precipitate was isolated, washed with water (50 ml) and dried. There was thus obtained the required starting material (0.93 g); NMR Spectrum: (DMSOd$_6$) 3.88 (s, 3H), 3.9 (s, 3H), 7.2 (s, 1H), 7.63 (s, 2H), 7.69 (s, 1H), 8.38 (s, 1H); Mass Spectrum: M+H$^+$ 230.

EXAMPLE 19

Using an analogous procedure to that described in Example 14, the appropriate 4-aminoquinazoline was, unless otherwise stated, reacted with (R)-(+)-α-methylbenzyl isocyanate to give the compounds described in Table IV.

TABLE IV

| No. | R$^6$ | R$^7$ | Z | Note |
|---|---|---|---|---|
| 1 | methoxy | 2-pyrrolidin-1-ylethoxy | O | (a) |
| 2 | methoxy | 2-piperidinoethoxy | O | (b) |
| 3 | methoxy | 2-piperidinoethoxy | O | (c) |
| 4 | methoxy | 2-morpholinoethoxy | O | (d) |
| 5 | methoxy | 2-(2-oxoimidazolidin-1-yl)ethoxy | O | (e) |
| 6 | methoxy | 3-pyrrolidin-1-ylpropoxy | O | (f) |
| 7 | methoxy | 3-piperidinopropoxy | O | (g) |
| 8 | methoxy | 3-morpholinopropoxy | O | (h) |
| 9 | methoxy | 3-(4-methylpiperazin-1-yl)propoxy | O | (i) |
| 10 | methoxy | 2-(2-methoxyethoxy)ethoxy | O | (j) |
| 11 | 3-piperidinopropoxy | methoxy | O | (k) |
| 12 | methoxy | N-methylpiperidin-4-ylmethoxy | S | (l) |

Notes (a) The product gave the following data: NMR Spectrum: (CDCl$_3$) 1.63 (d, 3H), 1.87 (s, 4H), 2.74 (s, 4H), 3.07 (t, 2H), 3.98 (s, 3H), 4.34 (t, 2H), 5.18 (m, 1H), 7.19–7.4 (m, 7H), 8.68 (d, 2H), 10.54 (d, 1H); Mass Spectrum: M+H$^+$ 436.

(b) The product gave the following data: NMR Spectrum: (CDCl₃) 1.47 (m, 2H), 1.66 (d, 7H), 2.54 (t, 4H), 2.9 (t, 2H), 3.89 (s, 3H), 4.3 (t, 2H), 5.19 (m, 1H), 7.2–7.4 (m, 7H), 8.68 (s, 1H), 8.8 (s, 1H), 10.55 (d, 1H); Mass Spectrum: M+H⁺ 450.

(c) (S)-(−)-α-Methylbenzyl isocyanate was used in place of (R)-(+)-α-methylbenzyl isocyanate. The product gave the following data: NMR Spectrum: (CDCl₃) 1.47 (m, 2H), 1.62 (m, 7H), 2.56 (s, 4H), 2.9 (t, 2H), 3.88 (s, 3H), 4.31 (t, 2H), 5.17 (m, 1H), 7.19–7.41 (m, 7H), 8.68 (s, 1H), 8.8 (s, 1H), 10.55 (d, 1H); Mass Spectrum: M+H⁺ 450.

(d) The product gave the following data: NMR Spectrum: (CDCl₃) 1.4 (d, 3H), 2.65 (t, 4H), 3.05 (t, 2H), 3.75 (t, 4H), 3.87 (s, 3H), 4.31 (t, 2H), 5.18 (m, 1H), 7.14 (d, 2K), 7.19–7.41 (m, 5H), 8.68 (s, 1H), 8.85 (s, 1H), 10.54 (d, 1H); Mass Spectrum: M+H⁺ 452.

(e) The product gave the following data: NMR Spectrum: (CDCl₃) 1.63 (d, 3H), 3.46 (t, 2H), 3.75 (m, 4H), 3.93 (s, 3H), 4.29 (t, 2H), 4.61 (s, 1H), 5.17 (m, 1H), 7.2–7.41 (m, 7H), 1H), 8.67 (s, 1H), 10.5 (d, 1H); Mass Spectrum: M+H⁺ 451.

(f) The product gave the following data: NMR Spectrum: (CDCl₃) 1.62 (d, 3H), 1.87 (s, 4H), 2.2 (m, 2H), 2.7 (s, 4H), 2.8 (t, 2H), 3.91 (s, 3H), 4.24 (t, 2H), 5.18 (m, 1H), 7.2–7.27 (m, 2H), 7.29–7.32 (m, 5H), 8.44 (s, 1H), 8.67 (s, 1H), 10.47 (d, 1H); Mass Spectrum: M+H⁺ 450.

(g) The product gave the following data: NMR Spectrum: (CDCl₃) 1.39 (m, 2H), 1.62 (d, 3H), 1.9 (s, 4H), 2.39 (t, 2H), 2.8–3.01 (br m, 6H), 3.9 (s, 3H), 4.24 (t, 2H), 5.14 (m, 1H), 7.1–7.44 (m, 7H), 8.45 (s, 1H), 8.65 (s, 1H), 10.45 (d, 1H); Mass Spectrum: M+H⁺ 464.

(h) The product gave the following data: NMR Spectrum: (CDCl₃) 1.62 (d, 3H), 2.13 (m, 2H), 2.59 (m, 6H), 3.85 (t, 4H), 3.91 (s, 3H), 4.26 (t, 2H), 5.18 (m, 1H), 7.2–7.4 (m, 7H), 8.5 (s, 1H), 8.77 (s, 1H), 10.5 (d, 1H); Mass Spectrum: M+H⁺ 466.

(i) The product gave the following data: NMR Spectrum: (CDCl₃) 1:62 (d, 3H), 1.76 (s, 4H), 2.1 (m, 2H), 2.31 (s, 3H), 2.4–2.6 (m, 6H), 3.92 (s, 3H), 4.24 (t, 2H), 5.19 (m, 1H), 7.21–7.41 (m, 7H), 8.49 (s, 1H), 8.68 (s, 1H), 10.5 (d, 1H); Mass Spectrum: M+H⁺ 479.

(j) The product gave the following data: NMR Spectrum: (CDCl₃) 1.59 (d, 3H), 3.39 (s, 3H), 3.6 (m, 2H), 3.76 (m, 2H), 3.87 (s, 3H), 4.0 (t, 2H), 4.36 (t, 2H), 5.21 (m, 1H), 7.19–7.39 (m, 7H), 8.69 (s, 1H), 8.97 (s, 1H), 10.58 (d, 1H); Mass Spectrum: M+H⁺ 441.

(k) The product gave the following data: NMR Spectrum: (DMSOd₆) 1.38 (br s, 2H), 1.53 (m, 6H), 2.0 (m, 2H), 3.3–3.53 (br s, 6H), 3.95 (s, 3H), 4.17 (t, 2H), 5.04 (m, 1H), 7.25 (s, 1H), 7.37 (br m, 5H), 8.02 (s, 1H), 8.65 (s, 1H), 10:1 (s, 1H), 10.5 (d, 1H); Mass Spectrum: M+H⁺ 464.

(l) The 4-aminoquinazoline was reacted with (R)-(+)-α-methylbenzyl isothiocyanate. The product gave the following data: NMR Spectrum: (CDCl₃) 1.42–1.57 (m, 2H), 1.71 (d, 3H), 1.86–2.06 (m, 5H), 2.31 (s, 3H), 2.92 (d, 2H), 4.02 (m, 5H), 5.69 (m, 1H), 6.98 (s, 1H), 7.24–7.31 (m, 2H), 7.34–7.47 (m, 4H), 8.54 (s, 1H), 8.65 (s, 1H), 12.57 (d, 1H); Mass Spectrum: M+H⁺ 466.

EXAMPLE 20

Using an analogous procedure to that described in Example 5, the appropriate 4-aminoquinazoline was reacted with the appropriate isocyanate to give the compounds described in Table V.

TABLE V

| No. | R⁶ | R⁷ | (R²)ₙ | Note |
|---|---|---|---|---|
| 1 | methoxy | 3-(4-tert-butoxycarbonylamino-methylpiperidin-1-yl)propoxy | 2,6-dichloro | (a) |
| 2 | methoxy | 3-(4-tert-butoxycarbonylamino-methylpiperidin-1-yl)propoxy | 2,6-difluoro | (b) |
| 3 | methoxy | 3-(4-tert-butoxycarbonylamino-methylpiperidin-1-yl)propoxy | 2,6-dimethyl | (c) |
| 4 | methoxy | 3-(4-tert-butoxycarbonylamino-methylpiperidin-1-yl)propoxy | 2-chloro-6-methyl | (d) |

The 4-amino-7-[3-(4-tert-butoxycarbonylaminomethylpiperidin-1-yl)propoxy]-6-methoxyquinazoline used as a starting material was prepared as follows:

A mixture of 4-(4-bromo-2-fluorophenoxy)-7-(3-bromopropoxy)-6-methoxyquinazoline (0.486 g), 4-(tert-butoxycarbonylaminomethyl)piperidine (Chemical Abstracts Registry No. 135632-53-0, for example U.S. Pat. No. 5,864,039; 0.252 g), potassium carbonate (0.7 g) and DMF (10 ml) was stirred at 45° C. for 20 hours. The solvent was evaporated and the residue was stirred with water (20 ml). The resultant solid was isolated and purified by column chromatography on silica using increasingly polar mixtures of methylene chloride and a 2N solution of ammonia in methanol as eluent. There was thus obtained 4-(4-bromo-2-fluorophenoxy)-[3-(4-tert-butoxycarbonylaminomethylpiperidin-1-yl)propoxy]-6-methoxyquinazoline as a resinous solid (0.4 g); NMR Spectrum: (CDCl₃) 1.22–1.4 (m, 2H), 1.44 (s, 9H), 1.69 (m, 3H), 1.98 (t, 2H), 2.12 (m, 2H), 2.56 (t, 2H), 2.9–3.1 (m, 4H), 4.04 (s, 3H), 4.26 (t, 2H), 4.6 (br s, 1H), 7.22 (m, 1H), 7.3–7.45 (m, 3H), 7.51 (s, 1H), 8.67 (s, 1H); Mass Spectrum: M+H⁺ 619 and 621.

A mixture of a portion (0.2 g) of the material so obtained and a saturated solution of ammonia in isopropanol (32 ml) was sealed in a Carius tube and heated at 110° C. for 20 hours. The mixture was cooled to ambient temperature and the solvent was evaporated. The residue was stirred with a mixture of a 2N aqueous sodium hydroxide solution (5 ml), methylene chloride (18 ml) and methanol (2 ml) for 1 hour. The solid was isolated and dried. There was thus obtained the required starting material (0.046 g); NMR Spectrum: (DMSOd₆) 1.0–1.15 (m, 2H), 1.4 (m, 1H), 1.45 (s, 9H), 1.56 (d, 2H), 1.75–1.85 (m, 4H), 2.39 (d, 2H), 2.74–2.9 (m, 4H), 3.85 (s, 3H), 4.09 (t, 2H), 6.75 (br s, 1H), 7.02 (s, 1H), 7.32 (s, 2H), 7.54 (s, 1H), 8.24 (s, 1H); Mass Spectrum: M+H⁺ 446.

(b) The product gave the following data: NMR Spectrum: (DMSOd₆) 1.0–1.2 (m, 2H). 1.25–1.3 (m, 1H), 1.35 (s, 9H), 1.58 (d, 2H), 1.8–2.0 (m, 4H), 2.42 (t, 2H), 2.7–2.9 (m, 4H), 3.95 (s, 3H), 4.21 (t, 2H), 6.76 (t, 1H), 7.1–7.5 (m, 4H), 8.04 (s, 1H), 8.67 (s, 1H), 10.6 (s, 1H), 11.8 (s, 1H); Mass Spectrum: M+H⁺ 601.

(c) The product gave the following data: NMR Spectrum: (CDCl₃) 1.2–1.4 (m, 3H), 1.43 (s, 9H), 1.9–2.15 (m, 4H), 2.33 (s, 6H), 2.52 (t, 2H), 2.92 (d, 4H), 3.02 (t, 2H), 3.38 (s, 3H), 4.21 (t, 2H), 4.6 (s, 1H), 7.05–7.15 (m, 4H), 7.48 (s, 1H), 8.66 (s, 1H), 9.64 (s, 1H), 11.9 (s, 1H); Mass Spectrum: M+H⁺ 593.

(d) The product gave the following data: NMR Spectrum: (CDCl₃) 1.22–1.35 (m, 3H), 1.42 (s, 9H), 1.7 (m, 2H), 1.95 (t, 2H), 2.09 (m, 2H), 2.35 (s, 3H), 2.52 (t, 2H), 2.91 (d, 2H), 3.02 (t, 2H), 3.5 (s, 3H), 4.22 (t, 2H), 4.6 (s, 1H), 7.17 (m, 2H), 7.25–7.35 (m, 2H), 7.46 (s, 1H), 8.69 (s, 1H), 9.54 (s, 1H), 12.2 (s, 1H); Mass Spectrum: M+H⁺ 613 and 615.

EXAMPLE 21

1-{7-[3-(4-aminomethylpiperidin-1-yl)propoxy]-6-methoxyquinazolin-4-yl}-3-(2,6-difluorophenyl)urea A mixture of 1-{7-[3-(4-tert-butoxycarbonylaminomethylpiperidin-1-yl)propoxy]-6-methoxyquinazolin-4-yl}-3-(2,6-dichlorophenyl)urea (0.075 g), trifluoroacetic acid (0.35 ml) and chloroform (1.5 ml) was stirred at ambient temperature for 40 minutes. The mixture was evaporated and the residue was stirred under a 1N aqueous sodium hydroxide solution (3 ml) for 1 hour. The resultant solid was isolated and dried. There was thus obtained the title compound (0.037 g); NMR Spectrum: (DMSOd₆) 1.12 (m, 3H), 1.62–1.7 (m, 2H), 1.9 (t, 2H), 2.0 (m, 4H), 2.38–2.54 (m, 4H), 2.92 (m, 2H), 3.3 (m, partially obscured by a water signal), 3.95 (s, 3H), 4.26 (t, 2H), 7.28 (s, 1H), 7.41 (t, 1H), 7.62 (d, 2H), 8.06 (s, 1H), 8.66 (s, 1H); Mass Spectrum: M+H⁺ 533 and 535.

EXAMPLE 22

1-{7-[3-(4-aminomethylpiperidin-1-yl)propoxy]-6-methoxyquinazolin-4-yl}-3-(2,6-difluorophenyl)urea Using an analogous procedure to that described in Example 21, 1-{7-[3-(4-tert-butoxycarbonylaminomethylpiperidin-1-yl)propoxy]-6-methoxyquinazolin-4-yl}-3-(2,6-difluorophenyl)urea was reacted with trifluoroacetic acid to give the title compound; NMR Spectrum: (DMSOd₆) 1.0–1.4 (m, 3H), 1.7 (d, 2H), 1.9–2.1 (m, 6H), 2.4 (m, 2H), 2.9 (d, 2H), 3.3 (s, partially obscured by a water signal), 4.0 (s, 3H), 4.24 (t, 3H), 5.0–7.0 (br m, 1H), 7.2–7.4 (m, 4H), 8.05 (s, 1H), 8.68 (s, 1H), 11.75S(s, 1H); Mass Spectrum: M+H⁺ 501.

EXAMPLE 23

1-{7-[3-(4-aminomethylpiperidin-1-yl)propoxy]-6-methoxyquinazolin-4-yl}-3-(2,6-dimethylphenyl)urea Using an analogous procedure to that described in Example 21, 1-{7-[3-(4-tert-butoxycarbonylaminomethylpiperidin-1-yl)propoxy]-6-methoxyquinazolin-4-yl}-3-(2,6-diethylphenyl)urea was reacted with trifluoroacetic acid to give the title compound; NMR Spectrum: (DMSOd₆) 1.0–2.0 (m, 9H), 2.23 (s, 6H), 2.4 (m, 2H), 2.7–2.9 (m, 4H), 3.1–3.5 (partially obscured by a water signal), 3.93 (s, 3H), 4.18 (t, 2H), 6.9–7.15 (m, 4H), 7.23 (s, 1H), 8.03 (s, 1H), 8.62 (s, 1H), 11.7 (s, 1H); Mass Spectrum: M+H⁺ 493.

EXAMPLE 24

1-{7-[3-(4-aminomethylpiperidin-1-yl)propoxy]-6-methoxyquinazolin-4-yl}-3-(2-chloro-6-methylphenyl)urea Using an analogous procedure to that described in Example 21, 1-{7-[3-(4-tert-butoxycarbonylamino-methylpiperidin-4-yl)propoxy]-6-methoxyquinazolin-4-yl}-3-(2-chloro-6-methylphenyl)urea was reacted with trifluoroacetic acid to give the title compound; NMR Spectrum: (DMSOd₆) 1.0–1.3 (m, 3H), 1.63 (d, 2H), 1.7–2.0 (m, 4H), 2.28 (s, 3H), 2.4 (m, 2H), 2.86 (d, 2H), 3.1–3.5 (partially obscured by a water signal), 3.94 (s, 3H), 4.19 (t, 2H), 7.1–7.4 (m, 4H), 8.06 (s, 1H), 8.66 (s, 1H), 11.85 (s, 1H); Mass Spectrum: M+H⁺ 513 and 515.

EXAMPLE 25

Using an analogous procedure to that described in Example 1, the appropriate 4-aminoquinazoline was reacted with the appropriate isocyanate to give the compounds described in Table VI.

TABLE VI

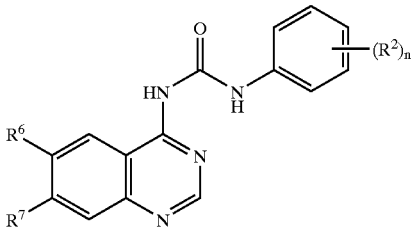

| No. | R⁶ | R⁷ | (R²)ₙ | Note |
|---|---|---|---|---|
| 1 | 3-morpholinopropoxy | methoxy | 2-methyl | (a) |
| 2 | 3-morpholinopropoxy | methoxy | 2,6-dichloro | (b) |
| 3 | 3-morpholinopropoxy | methoxy | 2,6-difluoro | (c) |
| 4 | 3-morpholinopropoxy | methoxy | 2,6-dimethyl | (d) |
| 5 | 3-piperidinopropoxy | methoxy | 2,6-dichloro | (e) |
| 6 | 3-piperidinopropoxy | methoxy | 2,6-difluoro | (f) |
| 7 | 3-piperidinopropoxy | methoxy | 2,6-dimethyl | (g) |
| 8 | 2-pyrrolidin-1-ylethoxy | methoxy | 2,6-dichloro | (h) |
| 9 | N-(3-morpholinopropyl)carbamoyl | methoxy | 2,6-dimethyl | (i) |
| 10 | 2-(2-methoxyethoxy)ethoxy | methoxy | 2,6-dichloro | (j) |
| 11 | 2-(2-methoxyethoxy)ethoxy | methoxy | 2,6-dimethyl | (k) |

The 4-amino-7-methoxy-6-(3-morpholinopropoxy) quinazoline used as a starting material was prepared as follows:

A mixture of 4-(3-chloro-4-fluoroanilino)-7-methoxy-6-(3-morpholinopropoxy)quinazoline (International Patent Application WO 96/33980, Example 1 therein; 6 g) and 6N aqueous hydrochloric acid solution (120 ml) was stirred and heated to reflux for 6 hours. The mixture was cooled to 0° C. and carefully, with cooling, was neutralised by the addition of concentrated aqueous ammonium hydroxide solution. The resultant precipitate was isolated, washed in turn with a dilute aqueous ammonium hydroxide solution and with water and dried under vacuum. There was thus obtained 7-methoxy-6-(3-morpholinopropoxy)-3,4-dihydroquinazolin-4-one (4.2 g); NMR Spectrum: (DMSOd₆) 2.4 (m, 6H), 3.59 (t, 4H), 3.75 (t, 2H), 3.9 (s, 3H), 4.12 (t, 2H), 7.12 (s, 1H), 7.43 (s, 1H), 7.98 (s, 1H), 12.0 (br s, 1H); Mass Spectrum: M+H⁺ 320.

A mixture of a portion (0.99 g) of the material so obtained, thionyl chloride (10 ml) and DMF (0.1 ml) was stirred and heated to 80° C. for 1.5 hours. The mixture was cooled to ambient temperature, toluene (10 ml) was added and the mixture was evaporated. The residue was partitioned between ethyl acetate and water (the acidity of the aqueous layer being adjusted to pH 7.5 by the addition of 2N aqueous sodium hydroxide solution). The organic layer was washed with brine, dried over magnesium sulphate and evaporated. The residue was purified by column chromatography on silica using a 9:1 mixture of methylene chloride and methanol as eluent. The solid so obtained was triturated under hexane, re-isolated and washed with diethyl ether. There was thus obtained 4-chloro-7-methoxy-6-(3-morpholinopropoxy)quinazoline (0.614 g); NMR Spectrum: (CDCl$_3$) 2.12 (m, 2H), 2.5 (br s, 4H), 2.59 (t, 2H), 3.73 (t, 4H), 4.05 (s, 3H), 4.27 (t, 2H), 7.33 (s, 1H), 7.4 (s, 1H), 8.86 (s, 1H).

A mixture of 4-chloro-7-methoxy-6-(3-morpholinopropoxy)quinazoline (1.6 g) and isopropanol (50 ml) was placed in a Carius tube which was cooled to −78° C. prior to the addition of liquid ammonia (10 ml). The Carius tube was sealed and heated to 130° C. for 20 hours. The Carius tube was cooled to ambient temperature, opened and the mixture was evaporated. The residue was triturated under diethyl ether. There was thus obtained 4-amino-7-methoxy-6-(3-morpholinopropoxy)quinazoline (containing 2.9 equivalents of ammonium chloride; 1.54 g) which was used without further purification. A portion of the material was purified by column chromatography on silica using a 19:1 mixture of methylene chloride and methanol as eluent. The purified product gave the following data: NMR Spectrum: (DMSOd$_6$) 1.9 (m, 2H), 2.5 (m, 6H), 3.6 (m, 4H), 3.9 (s, 3H), 4.1 (m, 2H), 7.05 (s, 1H), 7.4 (br s, 2H), 7.6 (s, 1H), 8.25 (s, 1H); Mass Spectrum: M+H$^+$ 319.

(b) The product gave the following data: NMR Spectrum: 2.35 (m, 2H), 3.15 (m, 2H), 3.35 (m, 2H), 3.55 (d, 2H), 3.7 (t, 2H), 4.0 (m, 2H), 4.05 (s, 3H), 4.35 (m, 2H), 7.45 (m, 2H), 7.65 (m, 2H), 8.3 (s, 1H), 9.05 (s, 1H); Mass Spectrum: M+H$^+$ 506 and 508.

(c) The product gave the following data: NMR Spectrum: (DMSOd$_6$+CF$_3$CO$_2$D) 2.3 (m, 2H), 3.15 (m, 2H), 3.35 (m, 2H), 3.55 (d, 2H), 3.7 (t, 2H), 4.0 (m, 2H), 4.05 (m, 5H), 4.3 (m, 2H), 7.25 (m, 2H), 7.4 (m, 2H), 8.25 (s, 1H), 9.0 (s, 1H); Mass Spectrum: M+H$^+$ 474.

(d) The product gave the following data: NMR Spectrum: (DMSOd$_6$+CF$_3$CO$_2$D) 2.35 (m, 8H), 3.15 (m, 2H), 3.35 (m, 2H), 3.55 (d, 2H), 3.7 (t, 2H), 4.0 (m, 2H), 4.05 (s, 3H), 4.35 (m, 2H), 7.2 (m, 2H), 7.5 (s, 1H), 8.3 (s, 1H), 9.05 (s, 1H); Mass Spectrum: M+H$^+$ 466.

(e) The product gave the following data: NMR Spectrum: (DMSOd$_6$) 1.4 (br s, 2H), 1.55 (br s, 4H), 2.04 (br s, 2H), 3.26–3.48 (m, 6H), 3.95 (s, 3H), 4.20 (t, 2H), 7.32 (s, 1H), 7.39 (t, 1H), 7.56 (m, 2H), 8.08 (s, 1H), 8.69 (s, 1H), 10.64 (s, 1H), 12.08 (s, 1H); Mass Spectrum: M+H$^+$ 504 and 506.

The 4-amino-7-methoxy-6-(3-piperidinopropoxy)quinazoline used as a starting material was prepared as follows:

A mixture of 6-acetoxy-7-methoxyquinazolin-4-one (International Patent Application WO 96/15118, Example 39 thereof; 15 g), thionyl chloride (215 ml) and DMF (4.3 ml) was stirred and heated to 90° C. for 4 hours. The mixture was cooled to ambient temperature and the thionyl chloride was evaporated. The material so obtained was dissolved in toluene and the solution was washed with a saturated aqueous sodium bicarbonate solution. The organic solution was dried over magnesium sulphate and evaporated. There was thus obtained 6-acetoxy-4-chloro-7-methoxyquinazoline (14.8 g) which was used without further purification.

A mixture of a portion (5 g) of the material so obtained, diphenylmethyleneamine (3.75 g), cesium carbonate (25.67 g) and xylene (200 ml) was stirred at ambient temperature for 30 minutes. Racemic 2,2'-bis(diphenylphosphino)-1,1'-binaphthyl (1.227 g) and palladium diacetate (0.221 g) were added and the mixture was stirred and heated to 135° C. for 16 hours. The mixture was cooled to ambient temperature and diethyl ether (600 ml) was added. The mixture was filtered and the filtrate was evaporated. There was thus obtained N-diphenylmethylene-6-acetoxy-7-methoxyquinazolin-4-amine (7.12 g); Mass Spectrum: M+H$^+$ 398.

A mixture of a portion (3.09 g) of the material so obtained, concentrated ammonium hydroxide solution (0.88 g/ml, approximately 14M; 60 ml) and methanol (120 ml) was stirred at ambient temperature for 16 hours. The mixture was evaporated. Toluene (200 ml) was added and the mixture was evaporated again. The residue was triturated under diethyl ether (50 ml). There was thus obtained N-diphenylmethylenehydroxy-7-methoxyquinazolin-4-amine (0.938 g); Mass Spectrum: M+H$^+$ 356.

A mixture of the material so obtained, 3-piperidinopropyl chloride (0.55 g), potassium carbonate (1.46 g) and DMF (50 ml) was stirred and heated to 65° C. for 16 hours. The resultant mixture was evaporated and the residue was partitioned between ethyl acetate and water. The organic solution was washed with a saturated aqueous sodium chloride solution, dried over magnesium sulphate and evaporated. The residue was purified by column chromatography on silica using increasingly polar mixtures of methylene chloride and methanol as eluent. There was thus obtained N-diphenylmethylene-6-(3-piperidinopropoxy)-7-methoxyquinazolin-4-amine (0.277 g); NMR Spectrum: (DMSOd$_6$) 1.3 (br s, 2H), 1.42 (br s, 4H), 1.88 (t, 2H), 2.28 (br s, 4H), 2.38 (t, 2H), 3.92 (s, 3H), 4.07 (t, 2H), 7.0 (s, 1H), 7.23 (s, 1H), 7.2–7.65 (br m, 10H), 8.62 (s, 1H); Mass Spectrum: M+H$^+$ 481.

A mixture of the material so obtained, 3N aqueous hydrochloric acid solution (2 ml) and THF (14 ml) was stirred at ambient temperature for 3 hours. The mixture was evaporated and the residue was treated with a 2N aqueous sodium hydroxide solution (10 ml). The resultant precipitate was isolated, washed with water (10 ml) and dried under vacuum. There was thus obtained 4-amino-7-methoxy-6-(3-piperidinopropoxy)quinazoline (0.202 g); NMR Spectrum: (DMSOd$_6$) 1.36 (br s, 2H), 1.47 (br s, 4H), 1.93 (t, 2H), 2.25–2.43 (br m, 6H), 3.88 (s, 3H), 4.05 (t, 2H), 7.04 (s, 1H), 7.35 (br s, 2H), 7.55 (s, 1H), 8.23 (s, 1H); Mass Spectrum: M+H$^+$ 317.

(f) The product gave the following data: NMR Spectrum: (DMSOd$_6$) 1.4 (br s, 2H), 1.53 (br s, 4H), 2.02 (br s, 2H), 3.24–3.47 (br s, 6H), 3.97 (s, 3H), 4.23 (t, 2H), 7.22 (m, 2H), 7.31 (s, 1H), 7.4 (m, 1H), 8.05 (s, 1H), 8.69 (s, 1H), 10.67 (s, 1H), 11.82 (s, 1H); Mass Spectrum: M+H$^+$ 472.

(g) The product gave the following data: NMR Spectrum: (DMSOd$_6$) 1.38 (br s, 2H), 1.5 (br s, 4H), 1.96 (m, 2H), 2.25 (s, 6H), 2.3–2.48 (br m, 6H), 3.96 (s, 3H), 4.15 (t, 2H), 7.14 (m, 3H), 7.3 (s, 1H), 8.07 (s, 1H), 8.67 (s, 1H), 10.38 (s, 1H), 11.69 (s, 1H); Mass Spectrum: M+H$^+$ 464.

(h) The product gave the following data: NMR Spectrum: (DMSOd$_6$) 1.72 (br s, 4H), 2.67 (br s, 4H), 2.97 (br s, 2H), 3.99 (s, 3H), 4.3 (t, 2H), 7.31 (s, 1H), 7.37 (t, 1H), 7.59 (d, 2H), 8.07 (s, 1H), 8.72 (s, 1H), 10.52 (s, 1H), 12.06 (s, 1H); Mass Spectrum: M+H$^+$ 476 and 478.

The 4-amino-7-methoxy-6-(2-pyrrolidin-1-ylethoxy)quinazoline used as a starting material was prepared from N-diphenylmethylene-6-hydroxy-7-methoxyquinazolin-4-amine and 2-pyrrolidin-1-ylethyl chloride using analogous procedures to those described in the last two paragraphs of Note (e) above. The material so obtained gave the following data: NMR Spectrum: (DMSOd$_6$) 1.68 (m, 4H), 2.58 (m, 6H), 3.86 (s, 3H), 4.15 (t, 2H), 7.05 (s, 1H), 7.33 (s, 1H), 8.24 (s, 1H); Mass Spectrum: M+H$^+$ 289.

(i) Chloroform was used as the reaction solvent. Triethylamine (1 equivalent) was also added. The product gave the following data: NMR Spectrum: (CDCl$_3$) 1.99 (t, 2H), 2.37 (s, 6H), 2.7 (m, 4H), 3.63 (q, 2H), 3.79 (m, 6H), 4.15 (s, 3H), 7.13 (s, 3H), 7.4 (s, 1H), 8.0 (t, 1H), 8.2 (s, 1H), 8.79 (s, 1H), 8.9 (s, 1H), 11.2 (s, 1H); Mass Spectrum: M+H$^+$ 493.

The 4-amino-7-methoxy-6-[N-(3-morpholinopropyl) carbamoyl]quinazoline used as a starting material was prepared as follows:

Methyl 4-amino-5-cyano-2-hydroxybenzoate (*J. Chem. Soc. Perkin I.* 1979, 677; 4 g) was added to stirred concentrated sulphuric acid (6 ml) and the mixture was heated to 80° C. for 30 minutes. The mixture was cooled to ambient temperature and poured onto crushed ice. The resultant solid was filtered off, washed well with water and dried to give methyl 4-amino-5-carbamoyl-2-hydroxybenzoate (2.8 g); NMR Spectrum: (DMSOd$_6$) 3.83 (s, 3H), 6.1 (s, 1H), 6.75 (br m, 2H), 8.08 (s, 1H).

A mixture of methyl 4-amino-5-carbamoyl-2-hydroxybenzoate (5.4 g) and formic acid (50 ml) was heated to reflux for 1 hour. The mixture was evaporated. Toluene (75 ml) was added and the mixture was evaporated. The solid residue was washed with methanol and diethyl ether and dried to give methyl 7-hydroxy-4-oxo-3,4-dihydroquinazolin-6-carboxylate (5.2 g); NMR Spectrum: (DMSOd$_6$) 4.9 (s, 3H), 7.09 (s, 1H), 7.39 (s, 1H), 8.5 (s, 1H).

A mixture of methyl 7-hydroxy-4-oxo-3,4-dihydroquinazoline-6-carboxylate (17.7 g) and acetic anhydride (200 ml) was heated to 120° C. for 1.5 hours. The mixture was evaporated. Toluene (75 ml) was added and the mixture was re-evaporated. There was thus obtained methyl 7-acetoxy-4-oxo-3,4-dihydroquinazoline-6-carboxylate (20.7 g); NMR Spectrum: (DMSOd$_6$) 2.33 (s, 3H), 3.86 (s, 3H), 7.5 (s, 1H), 8.28 (s, 1H), 8.68 (s, 1H); Mass Spectrum: M+H$^+$ 263.

A mixture of a portion (7.2 g) of the material so obtained and thionyl chloride (75 ml) was heated to reflux for 1 hour. The excess thionyl chloride was evaporated. Toluene (50 ml) was added and the mixture was re-evaporated. The residue was dissolved in methylene chloride and treated with triethylamine (3.34 g). The mixture was passed through a silica gel column (40 g) using increasingly polar mixtures of methylene chloride and methanol as eluent. There was thus obtained methyl 7-acetoxy-4-chloroquinazoline-6-carboxylate (6.88 g); NMR Spectrum: (CDCl$_3$) 2.43 (s, 3H), 4.0 (s, 3H), 7.8 (s, 1H), 8.99 (s, 1H), 9.12 (s, 1H).

A mixture of a portion (2.74 g) of the material so obtained, 2,4,6-trimethoxybenzylamine (3.86 g) and methylene chloride (90 ml) was allowed to stand at ambient temperature for 16 hours. The mixture was filtered and the filtrate was evaporated. The residue was triturated under diethyl ether. The resultant solid was purified by column chromatography on silica using increasingly polar mixtures of methylene chloride and methanol as eluent. There was thus obtained methyl 7-hydroxy-4-(2,4,6-trimethoxybenzylamino) quinazoline-6-carboxylate (3.25 g); NMR Spectrum: (DMSOd$_6$) 3.85 (s, 9H), 3.98 (s, 3H), 4.82 (d, 2H), 6.2 (s, 1H), 7.25 (s, 1H), 7.27 (s, 1H), 8.27 (s, 1H), 8.67 (s, 1H), 10.73 (s, 1H); Mass Spectrum: M+H$^+$ 400.

(Trimethylsilyl)diazomethane (2M in hexane, 10 ml) was added to a mixture of the material so obtained, di-isopropylethylamine (1.26 g), methanol (10 ml) and methylene chloride (30 ml) and the resultant mixture was stirred at ambient temperature for 3 hours. The reaction mixture was treated with a second aliquot of (trimethylsilyl) diazomethane solution (10 ml) and stirred for a further 8 hours. Silica gel (2 g) was added-cautiously and the mixture was stirred for 5 minutes. The mixture was evaporated and the reaction product (adsorbed onto silica) was purified by column chromatography on silica using increasingly polar mixtures of methylene chloride and methanol as eluent. There was thus obtained methyl 7-methoxy-4-(2,4,6-trimethoxybenzylamino)quinazoline-6-carboxylate (1.244 g); Mass Spectrum: M+H$^+$ 414.

A mixture of a portion (0.295 g) of the material so obtained and N-(3-aminopropyl)morpholine (0.5 ml) was stirred and heated to 150° C. for 1 hour. The mixture was partitioned between methylene chloride and water. The organic solution was dried over magnesium sulphate and evaporated. The residue was purified by column chromatography on silica using increasingly polar mixtures of methylene chloride and methanol as eluent. There was thus obtained 4-(2,4,6-trimethoxybenzylamino)-methoxy-6-[N-(3-morpholinopropyl)carbamoyl]quinazoline (0.144 g) Mass Spectrum: M+H$^+$ 526.

Trifluoroacetic acid (1 ml) was added to a mixture of the material so obtained, triethylsilane (0.093 g) and methylene chloride (0.15 ml) and the reaction mixture was stirred and heated to reflux for 2 minutes. The mixture was evaporated and the residue was partitioned between methylene chloride and water. The organic solution was evaporated to give 4-amino-7-methoxy-6-[N-(3-morpholinopropyl)carbamoyl] quinazoline (0.129 g); Mass Spectrum: M+H$^+$ 346.

(j) The produce gave the following data: NMR Spectrum: (CDCl$_3$) 3.39 (s, 3H), 3.6 (m, 2H), 3.75 (m, 2H), 3.86 (m, 2H), 4.02 (s, 3H), 4.07 (m, 2H), 7.21 (t, 1H), 7.29 (s, 1H), 7.39 (d, 2H), 7.51 (s, 1H), 8.73 (s, 1H), 9.14 (s, 1H), 12.19 (s, 1H); Mass Spectrum: M+H$^+$ 481 and 483.

The 4-amino-7-methoxy-6-[2-(2-methoxyethoxy)ethoxy] quinazoline used as a starting material was prepared from N-diphenylmethylene-6-hydroxy-7-methoxyquinazolin-4-amine and 2-(2-methoxyethoxy)ethyl chloride using analogous procedures to those described in the last two paragraphs of Note (e) above. In a further preparation, 2-(2-methoxyethoxy)ethyl 4-toluenesulphonate was used. The required starting material gave the following data: NMR Spectrum: (CDCl$_3$) 3.4 (s, 3H), 3.61 (m, 2H), 3.72 (m, 2H), 3.93 (m, 2H), 3.99 (s, 3H), 4.34 (m, 2H), 5.67 (br s, 2H), 7.2 (s, 1H), 7.32 (s, 1H), 8.5 (s, 1H); Mass Spectrum: M+H$^+$ 294.

(k) The product gave the following data: NMR Spectrum: (CDCl$_3$) 2.31 (s, 6H), 3.38 (s, 3H), 3.6 (m, 2H), 3.69 (m, 4H), 3.85 (m, 2H), 4.14 (s, 3H), 7.12 (m, 4H), 7.58 (s, 1H), 8.68 (s, 1H), 9.44 (s, 1H), 11.77 (s, 1H); Mass Spectrum: M+H$^+$ 441.

EXAMPLE 26

1-(2,6-dichlorophenyl)-3-[6-methoxy-7-(6-methylamino-1-hexynyl)quinazolin-4-yl]urea A mixture of 1-(2,6-dichlorophenyl)-3-{7-[6-(N-tert-butoxycarbonylamino-N-methylamino)-1-hexynyl]-6-methoxyquinazolin-4-yl}urea (0.1 g), trifluoroacetic acid (1 ml) and methylene chloride (1 ml) was stirred at ambient temperature for 1.5 hours. The mixture was evaporated and a solution of hydrogen chloride gas in ethyl acetate was added. Toluene was added and the mixture was evaporated. The residue was triturated under diethyl ether and the resultant solid was isolated. There was thus obtained the title compound as the hydrochloride salt (0.095 g); NMR Spectrum: (DMSOd$_6$) 1.65 (m, 2H), 1.78 (m, 2H), 2.55 (m, 5H), 2.95 (m, 2H), 4.0 (s, 3H), 7.38 (t, 1H), 7.6 (d, 2H), 7.89 (s, 1H), 8.16 (s, 1H), 8.7 (m, 3H), 10.9 (br, 1H), 11.8 (s, 1H); Mass Spectrum: M+H$^+$ 472 and 474.

The 1-(2,6-dichlorophenyl)-3-{7-[6-(N-tert-butoxycarbonylamino)-N-methylamino-1-hexynyl]-6-methoxyquinazolin-4-yl}urea used as a starting material was prepared as follows:

Using an analogous procedure to that described in the second last paragraph of Note [115] in Example 2 above, 6-(N-tert-butoxycarbonylamino-N-methylamino)-1-hexyne was reacted with 4-(2-bromo-4-fluorophenoxy)-6-methoxy-7-trifluoromethanesulphonyloxyquinazoline to give 4-(2-bromo-4-fluorophenoxy)-6-methoxy-7-[6-(N-tert-butoxycarbonylamino)-N-methylamino-1-hexynyl] quinazoline; NMR Spectrum: (DMSOd$_6$) 1.4 (s, 9H), 1.55 (m, 2H), 1.65 (m, 2H), 2.57 (t, 2H), 2.79 (s, 3H), 3.24 (t, 2H), 4.0 (s, 3H), 7.35–7.82 (m, 3H), 7.65 (s, 1H), 7.95 (s, 1H), 8.6 (s, 1H); Mass Spectrum: M+H$^+$ 558 and 560.

The material so obtained was reacted with ammonia using an analogous procedure to that described in the last paragraph of Note [115] in Example 2 above, except that the ammonia reaction was carried out at 110° C. rather than at 130° C. There was thus obtained 4-amino-6-methoxy-7-[6-(N-tert-butoxycarbonylamino)-N-methylamino-1-hexynyl] quinazoline.

The material so obtained was reacted with 2,6-dichlorophenyl isocyanate using an analogous procedure to that described in Example 1. There was thus obtained the required starting material; NMR Spectrum: (DMSOd$_6$) 1.39 (s, 9H), 1.55 (m, 2H), 1.67 (m, 2H), 2.56 (m, 2H), 2.79 (s, 3H), 3.2 (m, 2H), 3.97 (s, 3H), 7.4 (m, 1H), 7.6 (m, 2H), 7.84 (s, 1H), 8.14 (s, 1H), 8.75 (s, 1H), 10.8 (s, 1H), 11.95 (s, 1H).

The 6-(N-tert-butoxycarbonylamino-N-methylamino)-1-hexyne used as a starting material was, prepared as follows:

6-Mesyloxy-1-hexyne was reacted with methylamine using an analogous procedure to that described in *J. Heterocyclic Chemistry*, 1994, 31, 1421 to give 6-methylamino-1-hexyne which was reacted di-tert-butyl dicarbonate using a conventional procedure.

EXAMPLE 27

1-(2,6-dimethylphenyl)-3-[6-methoxy-7-(N-methylpiperidin-4-ylmethoxy)quinazolin-4-yl] thiourea A solution of 4-amino-4-methoxy-7-(1-methylpiperidin-4-ylmethoxy)quinazoline (150 mg) in DMF (4.5 ml) was added to sodium hydride (60% dispersion in mineral oil, 0.03 g) and the reaction mixture was stirred at ambient temperature for 20 minutes. 2,6-Dimethylphenyl isothiocyanate (0.162 g) was added and the mixture was stirred at ambient temperature for 20 hours. The action mixture was evaporated and the residual solid was purified by column chromatography on silica using increasingly polar mixtures of methylene chloride and a 2M solution of ammonia in methanol as eluent. There was thus obtained the title compound (0.112 g); NMR Spectrum: (CDCl$_3$) 1.44–1.61 (m, 2H), 1.87–2.08 (m, 5H), 2.32 (s, 3H), 2.36 (s, 6H), 2.94 (d, 2H), 4.04 (m, 5H), 7.1 (s, 1H), 7.19 (m, 3H), 7.29 (s, 1H), 8.69 (s, 1H), 8.9 (s, 1H), 13.37 (s, 1H); Mass Spectrum: M+H$^+$ 466.

EXAMPLE 28

Using an analogous procedure to that described in Example 27, the appropriate 4-quinazoline was reacted with the appropriate isothiocyanate to give the compounds described in Table VII.

TABLE VII

| No. | R$^6$ | R$^7$ | (R$^2$)$_n$ | Note |
|---|---|---|---|---|
| 1 | methoxy | N-methylpiperidin-4-ylmethoxy | 2,6-dichloro | (a) |
| 2 | methoxy | N-methylpiperidin-4-ylmethoxy | 2,6-difluoro | (b) |
| 3 | methoxy | N-methylpiperidin-4-ylmethoxy | 2-chloro-6-methyl | (c) |
| 4 | methoxy | N-methylpiperidin-4-ylmethoxy | 2,4,6-trichloro | (d) |
| 5 | methoxy | N-methylpiperidin-4-ylmethoxy | 2,6-dimethyl-4-bromo | (e) |
| 6 | methoxy | N-methylpiperidin-4-ylmethoxy | 2,5-dimethyl | (f) |
| 7 | methoxy | 3-pyrrolidin-1-ylpropoxy | 2,6-dichloro | (g) |
| 8 | methoxy | 3-pyrrolidin-1-ylpropoxy | 2,6-difluoro | (h) |
| 9 | methoxy | 3-pyrrolidin-1-ylpropoxy | 2-chloro-6-methyl | (i) |
| 10 | methoxy | 2-(2-methoxyethoxy)ethoxy | 2,6-dimethyl | (j) |
| 11 | methoxy | 2-morpholinoethoxy | 2,6-dimethyl | (k) |
| 12 | methoxy | 3-morpholinoethoxy | 2,6-dimethyl | (l) |
| 13 | methoxy | cyclopropylmethoxy | 2,6-dimethyl | (m) |
| 14 | methoxy | 2-chloro-2-morpholinoethoxy | (n) 6-methyl | |
| 15 | methoxy | 3-morpholinopropoxy | 2-chloro-6-methyl | (o) |
| 16 | methoxy | N-methylpiperidin-4-ylmethoxy | 2-methyl | (p) |
| 17 | methoxy | 2-pyrrolidin-1-ylethoxy | 2,6-dimethyl | (q) |

Notes
(a) The product gave the following data: Mass Spectrum: M+H$^+$ 506 and 508.
(b) The product gave the following data: NMR Spectrum: (CDCl$_3$) 1.43–1.6 (m, 2H), 1.83–2.09 (m, 5H), 2.33 (s, 3H), 2.94 (d, 2H), 4.04 (m, 5H), 7.0–7.14 (m, 4H), 7.27 (m, 1H), 7.35 (m, 1H), 8.7 (s, 1H), 13.49 (s, 1H); Mass Spectrum: M+H$^+$ 474.
(c) The product gave the following data: NMR Spectrum: (CDCl$_3$) 1.45–1.61 (m, 2H), 1.87–2.11 (m, 5H), 2.31 (s, 3H), 2.42 (s, 2H), 3.97 (d, 2H), 4.02 (m, 5H), 7.07 (s, 1H), 7.2–7.3 (m, 3H), 7.38 (t, 1H), 8.7 (s, 1H), 8.9 (s, 1H), 13.51 (s, 1H); Mass Spectrum: M+H$^+$ 486 and 488.
(d) The product gave the following data: NMR Spectrum: (CDCl$_3$) 1.48–1.61 (m, 2H), 1.88–2.16 (m, 5H), 2.36 (s, 3H), 3.0 (d, 2H), 4.07 (m, 5H), 7.11 (s, 1H), 7.3 (d, 2H), 7.43 (s, 1H), 7.49 (s, 1H), 8.72 (s, 1H), 13.71 (s, 1H); Mass Spectrum: M+H$^+$ 540 and 543.
(e) The product gave the following data: NMR Spectrum: (CDCl$_3$) 1.47–1.61 (m, 2H), 1.87–2.11 (m, 5H), 2.32 (d, 9H), 2.99 (d, 2H), 4.04 (m, 5H), 7.1 (s, 1H), 73 (s, 1H), 7.32 (s, 1H), 8.7 (s, 1H), 8.9 (s, 1H), 13.31 (s, 1H); Mass Spectrum: M+H$^+$ 544 and 546.
(f) The product gave the following data: NMR Spectrum: (CDCl$_3$) 1.44–159 (m, 2H), 1.88–2.07 (m, 5H), 2.31 (s, 3H), 2.35 (d, 6H), 2.94 (d, 2H), 4.04 (m, 5H), 7.08 (d, 1H), 7.2 (d, 1H), 7.29 (s, 1H), 7.55 (s, 1H), 8.68 (s, 1H), 8.77 (s, 1H), 13.63 (s, 1H); Mass Spectrum: M+H$^+$ 466.
(g) The product gave the following data: NMR Spectrum: (CDCl$_3$) 1.83 (s, 4H), 2.21 (m, 2H), 2.63 (s, 4H), 2.76 (t, 2H), 4.03 (s, 3H), 4.29 (t, 2H), 7.08 (t, 1H), 7.27–7.33 (s, 2H), 7.44 (m, 3H), 8.73 (s, 1H), 13.7 (s, 1H); Mass Spectrum: M+H$^+$ 506 and 508.

(h) The product gave the following data: NMR Spectrum: (CDCl$_3$) 1.83 (s, 4H), 2.2 (m, 2H), 2.61 (s, 4H), 2.74 (t, 2H), 4.04 (s, 3H), 4.48 (t, 2H), 6.98–7.11 (m, 3H), 7.27–7.41 (m, 3H), 8.71 (s, 1H), 13.48 (s, 1H); Mass Spectrum: M+H$^+$ 474.

(i) The product gave the following data: NMR Spectrum: (CDCl$_3$) 1.8 (m, 4H), 2.18 (m, 2H), 2.4 (s, 3H), 2.55 (m, 4H), 2.68 (t, 2H), 4.02 (s, 3H), 4.3 (t, 2H), 7.07 (s, 1H), 7.26 (m, 2H), 7.31 (s, 1H), 7.37 (m, 1H), 8.7 (s, 1H), 8.94 (br s, 1H), 13.51 (s, 1H); Mass Spectrum: M+H$^+$ 486 and 488.

(j) The product gave the following data: NMR Spectrum: (CDCl$_3$) 2.35 (s, 6H), 3.4 (s, 3H), 3.6 (m, 2H), 3.87 (m, 2H), 4.03 (t, 2H), 4.05 (s, 3H), 4.37 (t, 2H), 7.09 (s, 1H), 7.14–7.21 (m, 3H), 7.33 (s, 1H), 8.68 (s, 1H), 8.84 (s, 1H), 13.32 (s, 1H); Mass Spectrum: M+H$^+$ 457.

(k) The product gave the following data: NMR Spectrum: (CDCl$_3$) 2.36 (s, 6H), 2.61 (t, 4H), 2.9 (t, 2H), 3.77 (t, 4H), 4.04 (s, 3H), 4.34 (t, 2H), 7.11 (s, 1H), 7.2 (m, 3H), 7.31 (s, 1H), 8.69 (s, 1H), 8.9 (s, 1H), 13.36 (s, 1H); Mass Spectrum: M+H$^+$ 468.

(l) The product gave the following data: NMR Spectrum: (DMSOd$_6$) 2.0 (m, 2H), 2.4 (s, 4H), 2.45 (t, 2H), 3.58 (t, 4H), 4.03 (s, 3H), 4.21 (t, 2H), 7.18 (m, 3H), 7.33 (s, 1H), 8.19 (s, 1H), 8.71 (s, 1H), 11.09 (s, 1H), 13.7 (s, 1H); Mass Spectrum: M+H$^+$ 482.

(m) The product gave the following data: NMR Spectrum: (DMSOd$_6$) 0.39 (m, 2H), 0.61 (m, 2H), 1.32 (m, 1H), 2.25 (s, 6H), 4.0 (m, 5H), 7.17 (s, 3H), 7.25 (s, 1H), 8.17 (s, 1H), 8.72 (s, 1H), 11.08 (br s, 1H), 13.67 (s, 1H); Mass Spectrum: M+H$^4$ 409.

(n) The product gave the following data: Mass Spectrum: M+H$^+$ 488 and 490.

(o) The product gave the following data: Mass Spectrum: M+H$^+$ 502 and 504.

(p) The product gave the following data: Mass Spectrum: M+H$^+$ 452.

(q) The product gave the following data: Mass Spectrum: M+H$^+$ 452.

EXAMPLE 29

1-(2,6-dimethylphenyl)-3-[6-methoxy-7-(N-methylpiperidin-4-ylmethoxy)quinazolin-4-yl]guanidine Mercuric(II) oxide (0.059 g) was added to a mixture of 1-(2,6-dimethylphenyl)-3-[6-methoxy-7-(N-methylpiperidin-4-ylmethoxy)quinazolin-4-yl]thiourea (0.105 g), a 2M solution of ammonia in methanol (3 ml) and chloroform (1 ml) and the reaction mixture was stirred at ambient temperature for 2 hours. The mixture was evaporated and the residue was purified by column chromatography on silica using increasingly polar mixtures of methylene chloride and a 2M solution of ammonia in methanol as eluent. There was thus obtained the title compound (0.074 g); NMR Spectrum: (CDCl$_3$) 1.39–1.53 (m, 2H), 1.87–2.02 (q, 5H), 2.29 (s, 3H), 2.36 (s, 6H), 2.9 (d, 2H), 4.01 (m, 5H), 5.79 (br s, 1H), 7.16 (s, 1H), 7.19 (m, 3H), 7.87 (s, 1H), 8.57 (s, 1H); Mass Spectrum: M+H$^+$ 449.

EXAMPLE 30

Using an analogous procedure to that described in Example 29, the appropriate quinazoline-4-thiourea was reacted with ammonia to give the guanidines described in Table VIII.

TABLE VIII

| No. | R$^6$ | R$^7$ | (R$^2$)$_n$ | Note |
|---|---|---|---|---|
| 1 | methoxy | N-methylpiperidin-4-ylmethoxy | 2,6-dichloro | (a) |
| 2 | methoxy | N-methylpiperidin-4-ylmethoxy | 2,6-difluoro | (b) |
| 3 | methoxy | N-methylpiperidin-4-ylmethoxy | 2-chloro-6-methyl | (c) |
| 4 | methoxy | N-methylpiperidin-4-ylmethoxy | 2,6-di-methyl-4-bromo | (d) |
| 5 | methoxy | N-methylpiperidin-4-ylmethoxy | 2,5-dimethyl | (e) |
| 6 | methoxy | 3-pyrrolidin-1-ylpropoxy | 2,6-dichloro | (f) |
| 7 | methoxy | 3-pyrrolidin-1-ylpropoxy | 2,6-difluoro | (g) |
| 8 | methoxy | 3-pyrrolidin-1-ylpropoxy | 2-chloro-6-methyl | (h) |
| 9 | methoxy | 2-(2-methoxyethoxy)ethoxy | 2,6-dimethyl | (i) |
| 10 | methoxy | 2-morpholinoethoxy | 2,6-dimethyl | (j) |
| 11 | methoxy | cyclopropylmethoxy | 2,6-dimethyl | (k) |
| 12 | methoxy | 2-pyrrolidin-1-ylethoxy | 2,6-dimethyl | (l) |
| 13 | methoxy | N-methylpiperidin-4-ylmethoxy | 2-methyl | (m) |

Notes (a) The product gave the following data: NMR Spectrum: (DMSOd$_6$, 100° C.) 1.4 (m, 2H), 1.78 (m, 3H), 1.96 (t, 2H), 2.2 (s, 3H), 2.8 (m, 2H), 3.76 (s, 3H), 4.0 (d, 2H), 7.11 (s, 1H), 7.28 (t, 2H), 7.47 (s, 1H), 7.54 (d, 2H), 7.98 (s, 1H), 8.5 (s, 1H), 9.0 (br s, 1H); Mass Spectrum: M+H$^+$ 489 and 491.

(b) The product gave the following data: NMR Spectrum: (DMSOd$_6$) 1.34 (m, 2H), 1.73 (d, 3H), 1.88 (t, 2H), 2.16 (s, 3H), 2.79 (d, 2H), 3.3 (s, 2H), 3.69 (s, 3H), 3.95 (d, 2H), 7.07 (s, 1H), 7.2 (t, 2H), 7.34 (br s, 1H), 8.49 (s, 1H), 8.74 (s, 1H); Mass Spectrum: M+H$^+$ 457.

(c) The product gave the following data: NMR Spectrum: (CDCl$_3$) 1.4–1.56 (m, 2H), 1.87–2.05 (q, 5H), 2.3 (s, 3H), 2.4 (s, 3H), 2.9 (d, 2H), 3.98–4.05 (m, 5H), 7.13–7.27 (m, 3H), 7.38 (m, 1H), 7.81 (s, 1H), 8.59 (s, 1H); Mass Spectrum: M+H$^+$ 469 and 471.

(d) The product gave the following data: NMR Spectrum: (CDCl$_3$) 1.38–1.54 (m, 2H), 1.82–2.02 (q, 5H), 2.28 (s, 3H), 2.32 (s, 6H), 2.89 (d, 2H), 4.0 (m, 5H), 5.7 (br s, 1H), 7.03–7.27 (m, 3H), 7.32 (s, 2H), 7.81 (s, 1H), 8.57 (s, 1H); Mass Spectrum: M+H$^+$ 526 and 528

(e) The product gave the following data: NMR Spectrum: (CDCl$_3$) 1.39–1.44 (m, 2H), 1.87–2.04 (q, 5H), 2.29 (s, 3H), 2.34 (d, 6H), 2.89 (d, 2H), 4.02 (m, 5H), 6.19 (br s, 1H), 7.05 (d, 1H), 7.14 (s, 2H), 7.2 (d, 1H), 7.84 (s, 1H), 8.57 (s, 1H); Mass Spectrum: M+H$^+$ 449.

(f) The product gave the following data: NMR Spectrum: (CDCl$_3$) 1.8 (m, 4H), 2.17 (m, 2H), 2.53 (s, 4H), 2.67 (t, 2H), 3.99 (s, 3H), 4.25 (t, 2H), 7.1 (t, 1H), 7.2 (s, 1H), 7.41 (d, 1H), 7.51 (s, 1H), 8.57 (s, 1H); Mass Spectrum: M+H$^+$ 489 and 491.

(g) The product gave the following data: NMR Spectrum: (CDCl$_3$) 1.79 (m, 4H), 2.14 (m, 2H), 2.53 (m, 4H), 2.67 (t, 2H), 3.97 (s, 3H), 4.24 (t, 2H), 7.03 (t, 2H), 7.2 (m, 2H), 7.63 (s, 1H), 8.59 (s, 1H); Mass Spectrum: M+H$^+$ 457.

(h) The product gave the following data: NMR Spectrum: (CDCl$_3$) 1.79 (m, 4H), 2.15 (m, 2H), 2.44 (s, 3H), 2.56 (s, 4H), 2.68 (t, 2H), 3.98 (s, 3H), 4.26 (t, 2H), 6.13 (br s, 1H), 7.14–7.26 (m, 3H), 7.37 (m, 1H), 7.82 (s, 1H), 8.58 (s, 1H); Mass Spectrum: M+H⁺ 469 and 471.

(i) The product gave the following data: NMR Spectrum: (CDCl₃) 2.35 (s, 6H), 3.4 (s, 3H), 3.61 (m, 2H), 3.77 (m, 2H), 3.99 (m, 5H), 4.34 (t, 2H), 5.76 (br s, 1H), 7.17 (m, 4H), 7.87 (s, 1H), 8.56 (s, 1H); Mass Spectrum: M+H⁺ 440.

(j) The product, gave the following data: NMR Spectrum: (DMSOd₆, 100° C.) 2.29 (s, 6H), 2.53 (m, 4H), 2.79 (t, 2H), 3.6 (t, 4H), 3.74 (s, 3H), 4.22 (t, 2H), 7.09 (s, 1H), 7.16 (s, 3H), 7.51 (s, 1H), 7.7 (s, 2H), 8.45 (s, 1H), 8.88 (br s, 1H); Mass Spectrum: M+H⁺ 451.

(k) The product gave the following data: NMR Spectrum: (CDCl₃) 0.34 (m, 2H), 0.63 (m, 2H), 1.37 (m, 1H), 2.28 (s, 6H), 3.93 (d, 2H), 3.97 (s, 3H), 5.9 (br m, 1H), 7.07 (s, 1H), 7.12 (m, 4H), 7.79 (s, 1H), 8.48 (s, 1H); Mass Spectrum: M+H⁺ 392.

(l) The product gave the following data: Mass Spectrum: M+H⁺ 435.

(m) The product gave the following data: Mass Spectrum: M+H⁺ 435.

EXAMPLE 31

1-[6-methoxy-7-(N-methylpiperidin-4-ylmethoxy) quinazolin-4-yl]-3-[(R)-(+)-α-methylbenzyl] guanidine Using an analogous procedure to that described in Example 29, 1-[6-methoxy-7-(N-methylpiperidin-4-ylmethoxy)quinazolin-4-yl]-3-[(R)-(+)-α-methylbenzyl] thiourea was reacted with ammonia to give the title compound; NMR Spectrum: (CDCl₃) 1.38–1.42 (m, 2H), 1.61 (d, 3H), 1.86–2.01 (q, 5H), 2.29 (s, 3H), 2.89 (d, 2H), 3.95 (m, 3H), 4.0 (d, 2H), 4.7 (q, 1H), 6.5 (br s, 1H), 7.12 (s, 1H), 7.29–7.31 (m, 5H), 7.79 (s, 1H), 8.53 (s, 1H); Mass Spectrum: M+H⁺ 449.

EXAMPLE 32

1-(2-aminophenyl)-3-(6,7-dimethoxyquinazolin-4-yl)urea

A mixture of 1-(6,7-dimethoxyquinazolin-4-yl)-3-(2-nitrophenyl)urea (0.18 g), 10% palladium-on-charcoal catalyst (0.023 g) and DMF (10 ml) was stirred at ambient temperature under an atmosphere of hydrogen for 16 hours. The reaction mixture was filtered and the filtrate was evaporated. The resultant gum was triturated under ethyl acetate and there was thus obtained the title compound as a solid (0.137 g); NMR Spectrum: (DMSOd₆) 3.85–3.95 (br s, 8H), 6.63 (t, 1H), 6.81 (d, 1H), 6.91 (t, 1H), 7.25 (s, 1H), 7.47 (d, 1H), 8.05 (s, 1H), 8.64 (s, 1H), 10.28 (br s, 1H), 11.74 (br s, 1H); Mass Spectrum: M+H⁺ 340.

The 1-(6,7-dimethoxyquinazolin-4-yl)-3-(2-nitrophenyl) urea used as a starting material was prepared by the reaction of 2-nitrophenylisocyanate and 4-amino-6,7-dimethoxyquinazoline using an analogous procedure to that described in Example 1. There was thus obtained the required starting material in 62% yield; NMR Spectrum: (DMSOd₆) 3.95 (s, 6H), 7.3 (s, 1H), 7.28–7.35 (t, 1H), 7.74 (t, 1H), 8.05 (s, 1H), 8.13 (m, 1H), 8.51 (m, 1H), 8.72 (s, 1H), 10.61 (s, 1H), 13.67 (br s, 1H); Mass Spectrum: M+H⁺ 370.

EXAMPLE 33

1-(2,6-dchlorophenyl)-3-(6-methoxy-7-piperazin-1-ylquinazolin-4-yl)urea

A mixture of 1-(2,6-dichlorophenyl)-3-(6-methoxy-7-[N-(tert-butoxycarbonyl)piperazin-1-yl]quinazolinyl}urea (0.075 g), trifluoroacetic acid (1 ml) and methylene chloride (1 ml) was stirred at ambient temperature for 1 hour. The resultant mixture was evaporated. A saturated solution of hydrogen chloride gas in ethyl acetate was added and the mixture was evaporated. The resultant solid was triturated under diethyl ether, isolated and dried. There was thus obtained the title compound, as a dihydrochloride salt, (0.042 g); NMR Spectrum: (DMSOd₆) 3.25–3.3 (m, 4H), 3.45–3.5 (m, 4H), 4.03 (s, 3H), 7.3 (s, 1H), 7.36–7.63 (m, 3H), 8.16 (s, 1H), 8.78 (s, 1H), 9.15–9.27 (br s, 2H), 10.9–11.3 (br s, 1H), 10.8 (s, 1H); Mass Spectrum: M+H⁺ 447 and 449.

EXAMPLE 34

Using an analogous procedure to that described in Example 29, except that the appropriate quinazoline-4-thiourea was reacted with ethylamine rather than with ammonia, there were obtained the 2-ethylguanidines described in Table IX.

TABLE IX

| No. | R⁶ | R⁷ | (R²)ₙ | Note |
|---|---|---|---|---|
| 1 | methoxy | N-methylpiperidin-4-ylmethoxy | 2-chloro-6-methyl | (a) |
| 2 | methoxy | N-methylpiperidin-4-ylmethoxy | 2,6-dimethyl | (b) |
| 3 | methoxy | 2-morpholinoethoxy | 2,6-dimethyl | (c) |
| 4 | methoxy | cyclopropylmethoxy | 2,6-dimethyl | (d) |

Notes (a) The product gave the following data: NMR Spectrum: (DMSOd₆, 100° C.) 1.31 (t, 3H), 1.36–1.47 (m, 2H), 1.74–1.84 (m, 3H), 1.95 (t, 2H), 2.2 (s, 3H), 2.33 (s, 3H), 2.79 (d, 2H), 3.57 (m, 2H), 3.72 (s, 3H), 3.99 (t, 2H), 7.06 (s, 1H), 7.29 (m, 2H), 7.41 (m, 2H), 8.35 (br s, 1H), 8.45 (s, 1H), 10.11 (br s, 1H); Mass Spectrum: M+H⁺ 497 and 499.

(b) The product gave the following data: NMR Spectrum: (DMSOd₆, 100° C.) 1.28 (t, 3H), 1.4 (m, 2H), 1.76 (m, 3H), 1.95 (m, 2H), 2.19 (s, 3H), 2.26 (s, 6H), 2.78 (m, 2H), 3.53 (q, 2H), 3.76 (s, 3H), 3.99 (d, 2H), 7.04 (s, 1H), 7.16 (s, 3H), 7.55 (s, 1H), 8.41 (s, 1H), 10.41 (br s, 1H); Mass Spectrum: M+H⁺ 477.

(c) The product gave the following data: NMR Spectrum: (DMSOd₆, 100° C.) 1.27 (t, 3H), 2.27 (s, 6H), 2.54 (m, 4H), 2.8 (t, 2H), 3.54 (m, 2H), 3.61 (t, 4H), 3.78 (s, 3H), 4.26 (t, 2H), 7.11 (s, 1H), 7.19 (s, 3H), 7.59 (s, 1H), 8.42 (s, 1H), 10.42 (br s, 1H); Mass Spectrum: M+H⁺ 479.

(d) The product gave the following data: NMR Spectrum: (DMSOd₆) 0.38 (m, 2H), 0.6 (m, 2H), 1.27 (m, 4H), 2.25 (s, 6H), 3.21 (m), 3.5 (m, 2H), 3.73 (s, 3H), 3.95 (d, 2H), 6.99 (s, 1H), 7.17 (s, 3H), 7.55 (br s, 1H), 8.42 (s, 1H); Mass Spectrum: M+H⁺ 420.

EXAMPLE 35

Pharmaceutical Compositions

The following illustrate representative pharmaceutical dosage forms of the invention as defined herein (the active ingredient being termed "Compound X"), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

| (d) Capsule | mg/capsule |
|---|---|
| Compound X | 10 |
| Lactose Ph.Eur | 488.5 |
| Magnesium | 1.5 |

| (e) Injection I | (50 mg/ml) |
|---|---|
| Compound X | 5.0% w/v |
| 1 M Sodium hydroxide solution | 15.0% v/v |
| 0.1 M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound X | 1.0% w/v |
| Sodium phosphate BP | 3.6% w/v |
| 0.1 M Sodium hydroxide solution | 15.0% v/v |
| Water for injection to 100% | |

| (g) Injection III | (1 mg/ml, buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

-continued

| (k) Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml |
|---|---|
| Compound X | 40 mg |
| Ethanol | 300 μl |
| Water | 300 μl |
| 1-Dodecylazacycloheptan-2-One | 50 μl |
| Propylene glycol | to 1 ml |

Note

The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan tesquioleate, polysorbate 80, polyglycerol oleate or oleic acid.

What is claimed is:

1. A quinazoline derivative of the Formula I

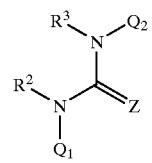

I wherein $Q^1$ is a quinazoline ring of the formula Ia,

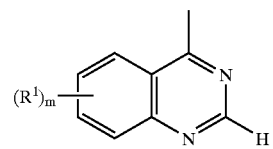

Ia wherein:

m is 0, 1, 2, 3 or 4;

each $R^1$ group, which may be the same or different, is selected from halogeno, trifluoromethyl, cyano, isocyano, nitro, hydroxy, mercapto, amino, formyl, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

wherein $X^1$ is a direct bond or is selected from O, S, SO, $SO_2$, $N(R^4)$, CO, $CH(OR^4)$, $CON(R^4)$, $N(R^4)CO$, $SO_2N(R^4)$, $N(R^4)SO_2$, $OC(R^4)_2$, $SC(R^4)_2$ and $N(R^4)C(R^4)_2$, wherein $R^4$ is hydrogen or (1–6C)alkyl, and $Q^3$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, or $(R^1)_m$ is (1–3C)alkylenedioxy, and wherein adjacent carbon atoms in any (2–6C)alkylene chain within a $R^1$ substituent are optionally separated by the insertion into the chain of a group selected from O, S, SO, $SO_2$, $N(R^5)$, CO, $CH(OR^5)$, $CON(R^5)$, $N(R^5)CO$, $SO_2N(R^5)$, $N(R^5)SO_2$, CH=CH and C≡C wherein $R^5$ is hydrogen or (1–6C)alkyl, and wherein any $CH_2$=CH— or HC≡C— group within a $R^1$ substituent optionally bears at the terminal $CH_2$= or HC≡ position a substituent selected from halogeno, carboxy, carbamoyl, (1–6C)alkoxycarbonyl, N-(1–6C)alkylcarbamoyl, N,N-di-[(1–6C)alkyl]carbamoyl, amino-(1–6C)alkyl, (1–6C)alkylamino-(1–6C)alkyl and di-[(1–6C)alkyl]amino-(1–6C)alkyl or from a group of the formula:

$$Q^4-X^2-$$

wherein $X^2$ is a direct bond or is selected from CO and $N(R^6)CO$, wherein $R^6$ is hydrogen or (1–6C)alkyl, and $Q^4$ is aryl, aryl-(1–6C)alkyl, heteroaryl, heteroaryl-(1–6C)alkyl, heterocyclyl or heterocyclyl-(1–6C)alkyl, and wherein any $CH_2$ or $CH_3$ group within a $R^1$ substituent optionally bears on each said $CH_2$ or $CH_3$ group one or more halogeno substituents or a substituent selected from hydroxy, cyano, amino, carboxy, carbamoyl, (1–6C)alkyl, (1–6C)alkoxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$$-X^3-Q^5$$

wherein $X^3$ is a direct bond or is selected from O, S, SO, $SO_2$, $N(R^7)$, CO, $CH(OR^7)$, $CON(R^7)$, $N(R^7)CO$, $SO_2N(R^7)$, $N(R^7)SO_2$, $C(R^7)_2O$, $C(R^7)_2S$ and $N(R^7)C(R^7)_2$, wherein $R^7$ is hydrogen or (1–6C)alkyl, and $Q^5$ is aryl, aryl-(1–6C)alkyl, (3–7C)cycloalkyl, (3–7C)cycloalkyl-(1–6C)alkyl, (3–7C)cycloalkenyl, (3–7C)cycloalkenyl-(1–6C)alkyl, heteroaryl, heteroaryl-(1–6C)alkyl, heterocyclyl or heterocyclyl-(1–6C)alkyl, and wherein any aryl, heteroaryl or heterocyclyl group within a substituent on $R^1$ optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$$-X^4-R^8$$

wherein $X^4$ is a direct bond or is selected from O and $N(R^9)$, wherein $R^9$ is hydrogen or (1–6C)alkyl, and $R^8$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl, di-[(1–6C)alkyl]amino-(1–6C)alkyl, (2–6C)alkanoylamino-(1–6C)alkyl or (1–6C)alkoxycarbonylamino-(1–6C)alkyl, or from a group of the formula:

$$-X^5-Q^6$$

wherein $X^5$ is a direct bond or is selected from O and $N(R^{10})$, wherein $R^{10}$ is hydrogen or (1–6C)alkyl, and $Q^6$ is aryl, aryl-(1–6C)alkyl, heteroaryl, heteroaryl-(1–6C)alkyl, heterocyclyl or heterocyclyl-(1–6C)alkyl, and any $Q^6$ group optionally bears 1 or 2 substituents, which may be the same or different, selected from halogeno, (1–6C)alkyl and (1–6C)alkoxy, and wherein any heterocyclyl group within a substituent on $R^1$ optionally bears 1 or 2 oxo or thioxo substituents;

$R^2$ is hydrogen or (1–6C)alkyl and $R^3$ is hydrogen or (1–6C)alkyl, or $R^2$ and $R^3$ together form a $CH_2$, $(CH_2)_2$ or $(CH_2)_3$ group;

Z is O, S, N(C≡N) or $N(R^{11})$, wherein $R^{11}$ is hydrogen or (1–6C)alkyl; and $Q^2$ is aryl, aryl-(1–3C)alkyl or aryl-(3–7C)cycloalkyl wherein each aryl group is phenyl or naphthyl, and $Q^2$ is optionally substituted with 1, 2, 3 or 4 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl-(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$$X^6-R^{12}$$

wherein $X^6$ is a direct bond or is selected from O and $N(R^{13})$, wherein $R^{13}$ is hydrogen or (1–6C)alkyl, and $R^{12}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

$$-X^7-Q^7$$

wherein $X^7$ is a direct bond or is selected from O, S, SO, $SO_2$, $N(R^{14})$, CO, $CH(OR^{14})$, $CON(R^{14})$, $N(R^{14})CO$, $SO_2N(R^{14})$, $N(R^{14})SO_2$, $C(R^{14})_2O$, $C(R^{14})_2S$ and $C(R^{14})_2N(R^{14})$, wherein each $R^{14}$ is hydrogen or (1–6C)alkyl, and $Q^7$ is aryl, aryl-(1–6C)alkyl, heteroaryl, heteroaryl-(1–6C)alkyl, heterocyclyl or heterocyclyl-(1–6C)alkyl, or Q² is optionally substituted with a (1–3C)alkylenedioxy group, and wherein any aryl, heteroaryl or heterocyclyl group within a substituent on Q² optionally bears 1, 2 or 3 substituents, which may be the same or different, selected from halogeno, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—X⁸—R¹⁵ wherein X⁸ is a direct bond or is selected from O and N(R¹⁶), wherein R¹⁶ is hydrogen or (1–6C)alkyl, and R¹⁵ is halogeno-(1–6C)alkyl, hydroxyl-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, and wherein any heterocyclyl group within a substituent on Q² optionally bears 1 or 2 oxo or thioxo substituents;

or a pharmaceutically-acceptable salt thereof;

provided that the compounds:

1-(6,7-dimethoxyquinazolin-4-yl)-3-phenylurea,

1-[5-(4-methoxyphenoxy)quinazolin-4-yl]-3-phenylurea,

1-[5-(4-methoxyphenoxy)quinazolin-4-yl]-3-(3-bromophenyl)urea and

1-[5-(4-methoxyphenoxy)quinazolin-4-yl]-3-(3-methoxyphenyl)urea are excluded.

2. A quinazoline derivative of the Formula I according to claim 1 wherein:

m is 1 and the R¹ group is located at the 6- or 7-position and is selected from methoxy, benzyloxy, cyclopropylmethoxy, 2-dimethylaminoethoxy, 2-diethylaminoethoxy, 3-dimethylaminopropoxy, 3-diethylaminopropoxy, 2-(1,2,3-triazol-1-yl)ethoxy, 3-(1,2,3-triazol-1-yl)propoxy, pyrid-2-ylmethoxy, pyrid-3-ylmethoxy, 2-pyrid-2-ylethoxy, 2-pyrid-3-ylethoxy, 2-pyrid-4-ylethoxy, 3-pyrid-2-ylpropoxy, 3-pyrid-3-ylpropoxy, 3-pyrid-4-ylpropoxy, 2-pyrrolidin-1-ylethoxy, 3-pyrrolidin-1-ylpropoxy, pyrrolidin-3-yloxy, N-methylpyrrolidin-3-yloxy, pyrrolidin-2-ylmethoxy, N-methylpyrrolidin-2-ylmethoxy, 2-pyrrolidin-2-ylethoxy, 2-(N-methylpyrrolidin-2-yl)ethoxy, 3-pyrrolidin-2-ylpropoxy, 3-(N-methylpyrrolidin-2-yl)propoxy, 2-(2-oxoimidazolidin-1-yl)ethoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-yloxy, piperidin-4-yloxy, N-methylpiperidin-4-yloxy, piperidin-3-ylmethoxy, N-methylpiperidin-3-ylmethoxy, 2-piperidin-3-ylethoxy, 2-(N-methylpiperidin-3-yl)ethoxy, piperidin-4-ylmethoxy, N-methylpiperidin-4-ylmethoxy, 2-piperidin-4-ylethoxy, 2-(N-methylpiperidin-4-yl)ethoxy, 3-(4-aminomethylpiperidin-1-yl)propoxy, 3-(4-tert-butoxycarbonylaminopiperidin-1-yl)propoxy, 3-(4-carbamoylpiperidin-1-yl)propoxy, 2-piperazin-1-ylethoxy, 3-piperazin-1-ylpropoxy, 2-(4-methylpiperazin-1-yl)ethoxy, 3-(4-methylpiperazin-1-yl)propoxy, 4-morpholinobut-2-en-1-yloxy, 4-morpholinobut-2-yn-1-yloxy, 2-(2-morpholinoethoxy)ethoxy, 2-methylsulphonylethoxy, 3-methylsulphonylpropoxy, 2-[N-(2-methoxyethyl)-N-methylamino]ethoxy, 3-[N-(2-methoxyethyl)-N-methylamino]propoxy, 2-(2-methoxyethoxy)ethoxy, 3-methylamino-1-propynyl, 3-dimethylamino-1-propynyl, 3-diethylamino-1-propynyl, 6-methylamino-1-hexynyl, 6-dimethylamino-1-hexynyl, 3-(pyrrolidin-1-yl)-1-propynyl, 3-(piperidino)-1-propynyl, 3-(morpholino)-1-propynyl, 3-(4-methylpiperazin-1-yl)-1-propynyl, 6-(pyrrolidin-1-yl)-1-hexynyl, 6-(piperidino)-1-hexynyl, 6-(morpholino)-1-hexynyl, 6-(4-methylpiperazin-1-yl)-1-hexynyl, piperazin-1-yl, 4-methylpiperazin-1-yl, 3-imidazol-1-ylpropylamino, 3-pyrrolidin-1-ylpropylamino, 3-morpholinopropylamino, 3-piperidinopropylamino and 3-piperazin-1-ylpropylamino, or m is 2 and the R¹ groups are located at the 6- and 7-positions, one R¹ group is located at the 6- or 7-position and is selected from the groups defined immediately hereinbefore and the other R¹ group is a methoxy group;

R² is hydrogen or methyl;

R³ is hydrogen;

Z is O, S, NH or N(Et); and

Q² is phenyl, benzyl or phenethyl which optionally bears 1, 2 or 3 substituents, which may be the same or different, selected from fluoro, chloro, bromo, trifluoromethyl, nitro, methyl, ethyl and methoxy provided that at least one substituent is located at an ortho position;

or a pharmaceutically-acceptable acid-addition salt thereof; and provided that 1-(6,7-dimethoxyquinazolin-4-yl)-3-phenylurea is excluded.

3. A quinazoline derivative of the Formula I according to claim 1 wherein:

m is 1 and the R¹ group is located at the 7-position and is selected from 3-(1,2,3-triazol-1-yl)propoxy, 2-pyrid-4-ylethoxy, 2-pyrrolidin-1-ylethoxy, 3-pyrrolidin-1-ylpropoxy, 2-morpholinoethoxy, 3-morpholinopropoxy, 2-(1,1-dioxotetrahydro-4H-1,4-thiazin-4-yl)ethoxy, 3-(1,1-dioxotetrahydro-4H-1,4-thiazin-4-yl)propoxy, 2-piperidinoethoxy, 3-piperidinopropoxy, piperidin-3-ylmethoxy, N-methylpiperidin-3-ylmethoxy, piperidin-4-ylmethoxy, N-methylpiperidin-4-ylmethoxy, 2-(4-methylpiperazin-1-yl)ethoxy, 3-(4-methylpiperazin-1-yl)propoxy, 4-pyrrolidin-1-ylbut-2-en-1-yloxy, 4-morpholinobut-2-en-1-yloxy, 4-morpholinobut-2-yn-1-yloxy, 3-methylsulphonylpropoxy and 2-[N-(2-methoxyethyl)-N-methylamino]ethoxy;

or m is 2 and one R¹ group is located at the 7-position and is selected from the groups defined immediately hereinbefore and the other R¹ group is a 6-methoxy group;

R² is hydrogen or methyl;

R³ is hydrogen;

Z is O, S, NH or N(Et); and

Q² is phenyl which bears 1, 2 or 3 substituents, which may be the same or different, selected from fluoro, chloro, bromo, trifluoromethyl, nitro, methyl, ethyl and methoxy provided that at least one substituent is located at an ortho position;

or a pharmaceutically-acceptable acid-addition salt thereof.

4. A quinazoline derivative of the Formula I according to claim 1 wherein:

m is 1 and the $R^1$ group is located at the 7-position and is selected from 3-(1,2,3-triazol-1-yl)propoxy, 2-pyrid-4-ylethoxy, 3-pyrrolidin-1-ylpropoxy, 3-morpholinopropoxy, 3-(1,1-dioxotetrahydro-4H-1,4-thiazin-4-yl)propoxy, 2-piperidinoethoxy, 3-piperidinopropoxy, N-methylpiperidin-4-ylmethoxy, 3-(4-methylpiperazin-1-yl)propoxy, 4-morpholinobut-2-en-1-yloxy, 4-morpholinobut-2-yn-1-yloxy, 3-methylsulphonylpropoxy and 2-[N-(2-methoxyethyl)-N-methylamino]ethoxy;

or m is 2 and one $R^1$ group is located at the 7-position and is selected from the groups defined immediately hereinbefore and the other $R^1$ group is a 6-methoxy group;

$R^2$ is hydrogen or methyl;

$R^3$ is hydrogen;

Z is O; and $Q^2$ is phenyl which bears 1, 2 or 3 substituents, which may be the same or different, selected from fluoro, chloro, bromo and trifluoromethyl provided that at least one substituent is located at an ortho position;

or a pharmaceutically-acceptable acid-addition salt thereof.

5. A quinazoline derivative of the Formula I according to claim 1 selected from:

1-(2,6-dichlorophenyl)-3-[7-(3-morpholinopropoxy)quinazolin-4-yl]urea, 1-(2,6-dichlorophenyl)-3-{7-[3-(1,1-dioxotetrahydro-4H-1,4-thiazin-4-yl)propoxy]quinazolin-4-yl}urea, 1-benzyl-3-[6-methoxy-7-(1-methylpiperidin-4-ylmethoxy)quinazolin-4-yl]urea, 1-phenethyl-3-[6-methoxy-7-(1-methylpiperidin-4-ylmethoxy)quinazolin-4-yl]urea, 1-(2,6-dichlorophenyl)-3-[6-methoxy-7-(1-methylpiperidin-4-ylmethoxy)quinazolin-4-yl]urea, 1-(2,6-difluorophenyl)-3-[6-methoxy-7-(1-methylpiperidin-4-ylmethoxy)quinazolin-4-yl]urea, 1-(2,6-dimethylphenyl)-3-[6-methoxy-7-(N-methylpiperidin-4-ylmethoxy)quinazolin-4-yl]urea, 1-(2-chloro-6-methylphenyl)-3-[6-methoxy-7-(N-methylpiperidin-4-ylmethoxy)quinazolin-4-yl]urea, 1-(2,6-difluorophenyl)-3-[6-methoxy-7-(3-morpholinopropoxy)quinazolin-4-yl]urea, 1-(2,6-difluorophenyl)-3-[6-methoxy-7-[3-(4-methylpiperazin-1-yl)propoxy]quinazolin-4-yl]urea, 1-(2,6-dimethylphenyl)-3-[6-methoxy-7-[3-(4-methylpiperazin-1-yl)propoxy]quinazolin-4-yl]urea, 1-(2,6-dimethylphenyl)-3-[6-methoxy-7-(3-piperidinopropoxy)quinazolin-yl]urea, 1-(2,6-dimethylphenyl)-3-[6-methoxy-7-(N-methylpiperidin-4-ylmethoxy)quinazolin-4-yl]thiourea and 1-(2-chloro-6-methylphenyl)-3-[6-methoxy-7-(3-pyrrolidin-1-ylpropoxy)quinazolin-4-yl]guanidine;

or a pharmaceutically-acceptable acid-addition salt thereof.

6. A pharmaceutical composition which comprises a quinazoline derivative of the Formula I, or a pharmaceutically-acceptable salt thereof, according to claim 1 in association with a pharmaceutically-acceptable diluent or carrier.

7. A method for the treatment of T cell mediated disease which comprises administering to said animal an effective amount of a quinazoline derivative of the Formula I, or a pharmaceutically-acceptable salt thereof, according to claim 1.

* * * * *